(12) United States Patent
Widdison

(10) Patent No.: US 10,792,372 B2
(45) Date of Patent: Oct. 6, 2020

(54) MAYTANSINOID DERIVATIVES WITH SELF-IMMOLATIVE PEPTIDE LINKERS AND CONJUGATES THEREOF

(71) Applicant: IMMUNOGEN, INC., Waltham, MA (US)

(72) Inventor: Wayne C. Widdison, Belmont, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days.

(21) Appl. No.: 15/906,416

(22) Filed: Feb. 27, 2018

(65) Prior Publication Data

US 2018/0296694 A1 Oct. 18, 2018

Related U.S. Application Data

(60) Provisional application No. 62/480,209, filed on Mar. 31, 2017, provisional application No. 62/465,118, filed on Feb. 28, 2017.

(51) Int. Cl.
| | | |
|---|---|---|
| *A61K 47/68* | (2017.01) | |
| *A61K 47/65* | (2017.01) | |
| *A61P 35/00* | (2006.01) | |
| *A61K 9/00* | (2006.01) | |
| *A61K 31/5365* | (2006.01) | |

(52) U.S. Cl.
CPC ........ *A61K 47/6889* (2017.08); *A61K 9/0019* (2013.01); *A61K 31/5365* (2013.01); *A61K 47/65* (2017.08); *A61K 47/6803* (2017.08); *A61K 47/6809* (2017.08); *A61K 47/6851* (2017.08); *A61P 35/00* (2018.01)

(58) Field of Classification Search
None
See application file for complete search history.

(56) References Cited

U.S. PATENT DOCUMENTS

2016/0303254 A1 10/2016 Kolakowski et al.

FOREIGN PATENT DOCUMENTS

| WO | 2012/177837 A2 | 12/2012 |
|---|---|---|
| WO | 2014/176284 A1 | 10/2014 |
| WO | 2015/038426 A1 | 3/2015 |
| WO | 2016/036794 A1 | 3/2016 |
| WO | 2020/014306 A1 | 4/2020 |

OTHER PUBLICATIONS

Kingsbury et al., Portage of various compounds into bacteria by attachment to glycine residues in peptides. Proc Natl Acad Sci U S A. Jul. 1984;81(14):4573-6.

*Primary Examiner* — Noble E Jarrell
(74) *Attorney, Agent, or Firm* — McCarter & English, LLP; Xin Zhang

(57) ABSTRACT

The invention relates to novel cell-binding agent-maytansinoid conjugate having a self-immolative peptide linker and more specifically to conjugates of formula (I). The invention also provides novel maytansinoid compounds of formula (II), (III), (IV) or (V). The invention further provides compositions and methods useful for inhibiting abnormal cell growth or treating a proliferative disorder in a mammal using the compounds or conjugates of the invention.

23 Claims, 31 Drawing Sheets

Specification includes a Sequence Listing.

CBA = anti-folate receptor antibody

M-SPDB-DM4

Ab = ant-folate receptor antibody M9346A-C442
M9346A-C442-mal-SPDB-DM4

SEQUENCE LISTING

```
<160> NUMBER OF SEQ ID NOS: 44

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Leu Ala Leu
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 2

Ala Leu Ala Leu
1
```

```
<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Phe Leu Gly
1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Phe Met Asn
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Lys, Gln, His or Arg
<220> FEATURE:
<221> NAME/KEY: MOD_RES
<222> LOCATION: (16)..(16)
<223> OTHER INFORMATION: Gln, His, Asn or Arg
<220> FEATURE:
<221> NAME/KEY: MOD_RES
<222> LOCATION: (17)..(17)
<223> OTHER INFORMATION: Gly, Glu, Thr, Ser, Ala or Val

<400> SEQUENCE: 5

Arg Ile His Pro Tyr Asp Gly Asp Thr Phe Tyr Asn Gln Xaa Phe Xaa
1               5                   10                  15

Xaa

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Asp Gly Ser Arg Ala Met Asp Tyr
1               5

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 7

Lys Ala Ser Gln Ser Val Ser Phe Ala Gly Thr Ser Leu Met His
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Ser Asn Leu Glu Ala
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Gln Ser Arg Glu Tyr Pro Tyr Thr
1               5

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ile His Pro Tyr Asp Gly Asp Thr Phe Tyr Asn Gln Lys Phe Gln
1               5                   10                  15

Gly

<210> SEQ ID NO 11
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
        50                  55                  60

Gln Gly Lys Ala Thr Leu Thr Val Asp Lys Ser Ser Asn Thr Ala His
65                  70                  75                  80
```

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
                435                 440                 445

<210> SEQ ID NO 12
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 13
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Thr Lys Leu Glu Ile Lys Arg
            100                 105                 110

Thr Val Ala Ala Pro Ser Val Phe Ile Phe Pro Pro Ser Asp Glu Gln
            115                 120                 125
```

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215
```

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115
```

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80
```

```
Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110
```

<210> SEQ ID NO 16
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110
```

<210> SEQ ID NO 17
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Leu Ser Leu Ala Ser Asn
            20                  25                  30

Ser Val Ser Trp Ile Arg Gln Pro Pro Gly Lys Gly Leu Glu Trp Met
        35                  40                  45

Gly Val Ile Trp Asn His Gly Gly Thr Asp Tyr Asn Pro Ser Ile Lys
    50                  55                  60

Ser Arg Leu Ser Ile Ser Arg Asp Thr Ser Lys Ser Gln Val Phe Leu
65                  70                  75                  80

Lys Met Asn Ser Leu Thr Ala Ala Asp Thr Ala Met Tyr Phe Cys Val
                85                  90                  95

Arg Lys Gly Gly Ile Tyr Phe Asp Tyr Trp Gly Gln Gly Val Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly
    435                 440                 445

<210> SEQ ID NO 18
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Thr Val Leu Thr Gln Ser Pro Ser Leu Ala Val Ser Pro Gly Glu
1               5                   10                  15

Arg Ala Thr Ile Ser Cys Arg Ala Ser Glu Ser Val Ser Thr Leu Met
            20                  25                  30

His Trp Tyr Gln Gln Lys Pro Gly Gln Gln Pro Lys Leu Leu Ile Tyr
        35                  40                  45

Leu Ala Ser His Arg Glu Ser Gly Val Pro Ala Arg Phe Ser Gly Ser
    50                  55                  60

Gly Ser Gly Thr Asp Phe Thr Leu Thr Ile Asp Pro Met Glu Ala Glu
65                  70                  75                  80

```
Asp Thr Ala Thr Tyr Tyr Cys Gln Gln Ser Arg Asn Asp Pro Trp Thr
                85                  90                  95

Phe Gly Gln Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 19
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
                20                  25                  30

Trp Met Gln Trp Val Lys Gln Arg Pro Gly Gln Gly Leu Glu Cys Ile
            35                  40                  45

Gly Thr Ile Tyr Pro Gly Asp Gly Asp Thr Thr Tyr Thr Gln Lys Phe
        50                  55                  60

Gln Gly Lys Ala Thr Leu Thr Ala Asp Lys Ser Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 20
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Tyr Gln His Lys Pro Gly Lys Gly Pro Lys Leu Leu Ile
        35                  40                  45

His Tyr Thr Ser Thr Leu His Pro Gly Ile Pro Ser Arg Phe Ser Gly
    50                  55                  60

Ser Gly Ser Gly Arg Asp Tyr Ser Phe Ser Ile Ser Ser Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 21
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Asn Tyr
            20                  25                  30

Leu Ala Trp Tyr Gln His Lys Pro Gly Lys Pro Lys Leu Leu Ile
        35                  40                  45

His Tyr Thr Ser Thr Leu His Pro Gly Ile Pro Ser Arg Phe Ser Gly
    50                  55                  60

Ser Gly Ser Gly Arg Asp Tyr Ser Phe Ser Ile Ser Ser Leu Glu Pro
65                  70                  75                  80

Glu Asp Ile Ala Thr Tyr Tyr Cys Leu Gln Tyr Asp Asn Leu Leu Tyr
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 22
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 22

Gln Val Gln Leu Val Gln Pro Gly Ala Glu Val Val Lys Pro Gly Ala
1               5                   10                  15

Ser Val Lys Leu Ser Cys Lys Thr Ser Gly Tyr Thr Phe Thr Ser Asn
            20                  25                  30

Trp Met His Trp Val Lys Gln Ala Pro Gly Gln Gly Leu Glu Trp Ile
        35                  40                  45

Gly Glu Ile Asp Pro Ser Asp Ser Tyr Thr Asn Tyr Asn Gln Asn Phe
    50                  55                  60

Gln Gly Lys Ala Lys Leu Thr Val Asp Lys Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Arg Gly Ser Asn Pro Tyr Tyr Ala Met Asp Tyr Trp Gly Gln Gly
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 23
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Ile Val Leu Thr Gln Ser Pro Ala Ile Met Ser Ala Ser Pro Gly
1               5                   10                  15

Glu Arg Val Thr Met Thr Cys Ser Ala Ser Ser Gly Val Asn Tyr Met
            20                  25                  30

His Trp Tyr Gln Gln Lys Pro Gly Thr Ser Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Ser Leu Thr Ile Ser Ser Met Glu Pro Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 24
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Ala Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30
```

```
Asn Met His Trp Val Lys Gln Thr Pro Gly Gln Gly Leu Glu Trp Ile
         35                  40                  45

Gly Tyr Ile Tyr Pro Gly Asn Gly Ala Thr Asn Tyr Asn Gln Lys Phe
 50                  55                  60

Gln Gly Lys Ala Thr Leu Thr Ala Asp Thr Ser Ser Ser Thr Ala Tyr
 65                  70                  75                  80

Met Gln Ile Ser Ser Leu Thr Ser Glu Asp Ser Ala Val Tyr Phe Cys
                 85                  90                  95

Ala Arg Gly Asp Ser Val Pro Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

```
<210> SEQ ID NO 25
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Ile Val Leu Thr Gln Ser Pro Ala Thr Met Ser Ala Ser Pro Gly
1               5                   10                  15

Glu Arg Val Thr Ile Thr Cys Ser Ala His Ser Ser Val Ser Phe Met
            20                  25                  30

His Trp Phe Gln Gln Lys Pro Gly Thr Ser Pro Lys Leu Trp Ile Tyr
        35                  40                  45

Ser Thr Ser Ser Leu Ala Ser Gly Val Pro Ala Arg Phe Gly Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Arg Ser Ser Phe Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 26
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

Gln Gly Lys Ala Thr Leu Thr Ala Asp Lys Ser Ser Thr Thr Ala Tyr
65                  70                  75                  80
```

Met Gln Leu Ser Ser Leu Thr Ser Glu Asp Ser Ala Val Tyr Tyr Cys
            85                  90                  95

Ala Arg Glu Val Arg Leu Arg Tyr Phe Asp Val Trp Gly Gln Gly Thr
        100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 27
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Ile Val Leu Thr Gln Ser Pro Gly Ser Leu Ala Val Ser Pro Gly
1               5                   10                  15

Glu Arg Val Thr Met Ser Cys Lys Ser Gln Ser Val Phe Phe Ser
            20                  25                  30

Ser Ser Gln Lys Asn Tyr Leu Ala Trp Tyr Gln Gln Ile Pro Gly Gln
            35                  40                  45

Ser Pro Arg Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 28
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Arg Ser Asn
            20                  25                  30

Leu Ala Trp Tyr Gln Gln Lys Pro Gly Lys Ser Pro Lys Leu Leu Val
            35                  40                  45

Asn Val Ala Thr Asn Leu Ala Asp Gly Val Pro Ser Arg Phe Ser Gly
50                  55                  60

Ser Gly Ser Gly Thr Asp Tyr Ser Leu Lys Ile Asn Ser Leu Gln Pro
65                  70                  75                  80

Glu Asp Phe Gly Thr Tyr Tyr Cys Gln His Tyr Trp Gly Thr Thr Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

```
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 29
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Val Gln Glu Ser Gly Pro Gly Leu Val Ala Pro Ser Gln
1               5                   10                  15
Thr Leu Ser Ile Thr Cys Thr Val Ser Gly Phe Ser Leu Thr Thr Ser
            20                  25                  30
Gly Val Ser Trp Val Arg Gln Pro Pro Gly Lys Gly Leu Glu Trp Leu
        35                  40                  45
Gly Val Ile Trp Gly Asp Gly Ser Thr Asn Tyr His Pro Ser Leu Lys
    50                  55                  60
Ser Arg Leu Ser Ile Lys Lys Asp His Ser Lys Ser Gln Val Phe Leu
65                  70                  75                  80
Lys Leu Asn Ser Leu Thr Ala Ala Asp Thr Ala Thr Tyr Tyr Cys Ala
                85                  90                  95
Lys Gly Gly Tyr Ser Leu Ala His Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
```

```
Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 30
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190
```

```
Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 31
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
            20                  25                  30

His Trp Tyr Gln Gln Lys Pro Gly Gln Ser Pro Lys Arg Trp Ile Tyr
        35                  40                  45

Asp Thr Ser Asn Leu Pro Tyr Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Gln Gly Thr Lys Leu Glu Ile Lys Arg Thr Val Ala Ala Pro
            100                 105                 110
```

```
Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 32
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Gln Val Gln Leu Gln Glu Ser Gly Pro Gly Leu Leu Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln His Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn His Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

-continued

```
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Ser Ile Met His
1               5

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Ile Lys Pro Tyr Asn Asp Gly Thr Lys Tyr Asn Glu Lys Phe Lys
1               5                   10                  15

Gly

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 35

Glu Gly Gly Asn Asp Tyr Tyr Asp Thr Met Asp Tyr
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ala Ser Gln Asp Ile Asn Ser Tyr Leu Ser
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Val Asn Arg Leu Val Asp
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Gln Tyr Asp Ala Phe Pro Tyr Thr
1               5

<210> SEQ ID NO 39
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<223> OTHER INFORMATION: See specification as filed for detailed
      description of substitutions and preferred embodiments

<400> SEQUENCE: 39

Gln Xaa Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Tyr Asn Glu Lys Phe
    50                  55                  60

Lys Gly Arg Ala Thr Leu Thr Ser Asp Arg Ser Thr Ser Thr Ala Tyr
65                  70                  75                  80
```

```
Met Glu Leu Ser Ser Leu Arg Ser Glu Asp Thr Ala Val Tyr Tyr Cys
                 85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120

<210> SEQ ID NO 40
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg
            100                 105

<210> SEQ ID NO 41
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ser Ile Gln Met Thr Gln Ser Pro Ser Ser Leu Ser Ala Ser Val Gly
1               5                  10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg
            100                 105

<210> SEQ ID NO 42
<211> LENGTH: 450
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<223> OTHER INFORMATION: See specification as filed for detailed
      description of substitutions and preferred embodiments

<400> SEQUENCE: 42

Gln Xaa Gln Leu Val Gln Ser Gly Ala Glu Val Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350
```

```
Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Cys Leu Ser
            435                 440                 445

Pro Gly
    450

<210> SEQ ID NO 43
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 44
<211> LENGTH: 450
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<223> OTHER INFORMATION: See specification as filed for detailed
      description of substitutions and preferred embodiments

<400> SEQUENCE: 44
```

Gln Xaa Gln Leu Val Gln Ser Gly Ala Glu Val Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

| | | | | | | | | | | | | |
|---|---|---|---|---|---|---|---|---|---|---|---|---|
| Tyr | Thr | Leu | Pro | Pro | Ser | Arg | Asp | Glu | Leu | Thr | Lys | Asn Gln Val Ser |
| | | 355 | | | | 360 | | | | | 365 | |
| Leu | Thr | Cys | Leu | Val | Lys | Gly | Phe | Tyr | Pro | Ser | Asp | Ile Ala Val Glu |
| | | 370 | | | | 375 | | | | | 380 | |
| Trp | Glu | Ser | Asn | Gly | Gln | Pro | Glu | Asn | Asn | Tyr | Lys | Thr Thr Pro Pro |
| 385 | | | | | 390 | | | | | 395 | | 400 |
| Val | Leu | Asp | Ser | Asp | Gly | Ser | Phe | Phe | Leu | Tyr | Ser | Lys Leu Thr Val |
| | | | 405 | | | | | 410 | | | | 415 |
| Asp | Lys | Ser | Arg | Trp | Gln | Gln | Gly | Asn | Val | Phe | Ser | Cys Ser Val Met |
| | | | 420 | | | | | 425 | | | | 430 |
| His | Glu | Ala | Leu | His | Asn | His | Tyr | Thr | Gln | Lys | Ser | Leu Ser Leu Ser |
| | | 435 | | | | | 440 | | | | | 445 |
| Pro | Gly | | | | | | | | | | | |
| | 450 | | | | | | | | | | | |

MAYTANSINOID DERIVATIVES WITH SELF-IMMOLATIVE PEPTIDE LINKERS AND CONJUGATES THEREOF

RELATED APPLICATIONS

This application claims the benefit of the filing date, under 35 U.S.C. § 119(e), of U.S. Provisional Application No. 62/465,118, filed on Feb. 28, 2017, and U.S. Provisional Application No. 62/480,209, filed on Mar. 31, 2017. The entire contents of each of the above-referenced applications are incorporated herein by reference.

BACKGROUND OF THE INVENTION

Antibody-drug conjugates (ADC) are emerging as a powerful class of anti-tumor agents with efficacy across a range of cancers. ADCs are commonly composed of three distinct elements: a cell-binding agent; a linker; and a cytotoxic agent. The linker component of ADC is an important element in developing targeted anti-cancer agents that possess an optimal therapeutic window, i.e., high activity at a low, non-toxic dose.

Therefore, there is a need for ADCs having new class of linker component.

SUMMARY OF THE INVENTION

The present invention is directed to a cell-binding agent-cytotoxic agent conjugate represented by the following formula:

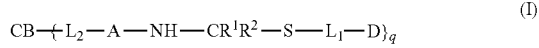

or a pharmaceutically acceptable salt thereof, wherein:
CB is a cell-binding agent;
$L_2$ is absent or a spacer;
A is an amino acid residue or a peptide comprising 2 to 20 amino acid residues;
$R^1$ and $R^2$ are each independently H or a $C_{1-3}$alkyl;
$L_1$ is a spacer;
$D-L_1-SH$ is a cytotoxic agent; and
q is an integer from 1 to 20.

The present invention is also directed to a compound of formula (II):

or a pharmaceutically acceptable salt thereof, wherein:
$L_2'$ is absent or a spacer bearing a reactive moiety that can form a covalent bond with a cell-binding agent;
A' is an amino acid or a peptide comprising 2 to 20 amino acids;
$R^1$ and $R^2$ are each independently H or a $C_{1-3}$alkyl;
$L_1$ is a spacer;
$D-L_1-SH$ is a cytotoxic agent; and
q is an integer from 1 to 20.

Also included in the present invention is a compound of formula (III):

or a pharmaceutically acceptable salt thereof, wherein:
A' is an amino acid or a peptide comprising 2 to 20 amino acids;
$R^1$ and $R^2$ are each independently H or a $C_{1-3}$alkyl;
$L_1$ is a spacer;
$D-L_1-SH$ is a cytotoxic agent; and
q is an integer from 1 to 20.

The present invention is also directed to a compound of formula (IV):

or a pharmaceutically acceptable salt thereof, wherein:
$L_3$ is represented by the following formula:

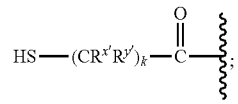

$R^{x'}$ and $R^{y'}$, for each occurrence, are independently H, —OH, halogen, —O—($C_{1-4}$ alkyl), —$SO_3H$, —$NR_{40}R_{41}R_{42}^+$, or a $C_{1-4}$ alkyl optionally substituted with —OH, halogen, $SO_3H$ or $NR_{40}R_{41}R_{42}^+$, wherein $R_{40}$, $R_{41}$ and $R_{42}$ are each independently H or a $C_{1-4}$ alkyl;
k is an integer from 1 to 10;
A is an amino acid or a peptide comprising 2 to 20 amino acids;
$R^1$ and $R^2$ are each independently H or a $C_{1-3}$alkyl;
$L_1$ is a spacer;
$D-L_1-SH$ is a cytotoxic agent; and
q is an integer from 1 to 20.

The present invention also directs to a composition (e.g., a pharmaceutical composition) comprising a conjugate (e.g., a conjugate of formula (I)) or a compound (e.g., a compound of formula (II), (III) or (IV)) and a carrier (a pharmaceutically acceptable carrier). The present invention also includes a composition (e.g., a pharmaceutical composition) comprising a conjugate (e.g., a conjugate of formula (I)) or a compound (e.g., a compound of formula (II), (III) or (IV)) described herein and a carrier (a pharmaceutically acceptable carrier), further comprising a second therapeutic agent. The present compositions are useful for inhibiting abnormal cell growth or treating a proliferative disorder in a mammal (e.g., human) The present compositions are useful for treating conditions such as cancer, rheumatoid arthritis, multiple sclerosis, graft versus host disease (GVHD), transplant rejection, lupus, myositis, infection, immune deficiency such as AIDS, and inflammatory diseases in a mammal (e.g., human).

The present invention also includes a method of inhibiting abnormal cell growth or treating a proliferative disorder in a mammal (e.g., human) comprising administering to said abnormal cell or said mammal a therapeutically effective amount of a conjugate (e.g., a conjugate of formula (I)) or a compound (e.g., a compound of formula (II), (III) or (IV)) or a composition thereof, alone or in combination with a second therapeutic agent.

BRIEF DESCRIPTION OF THE FIGURES

FIG. 18 body weight changes for mice treated with representative conjugates of the present invention having different peptide linkers as compared to mice treated with conjugate 1a.

Figure 25C:
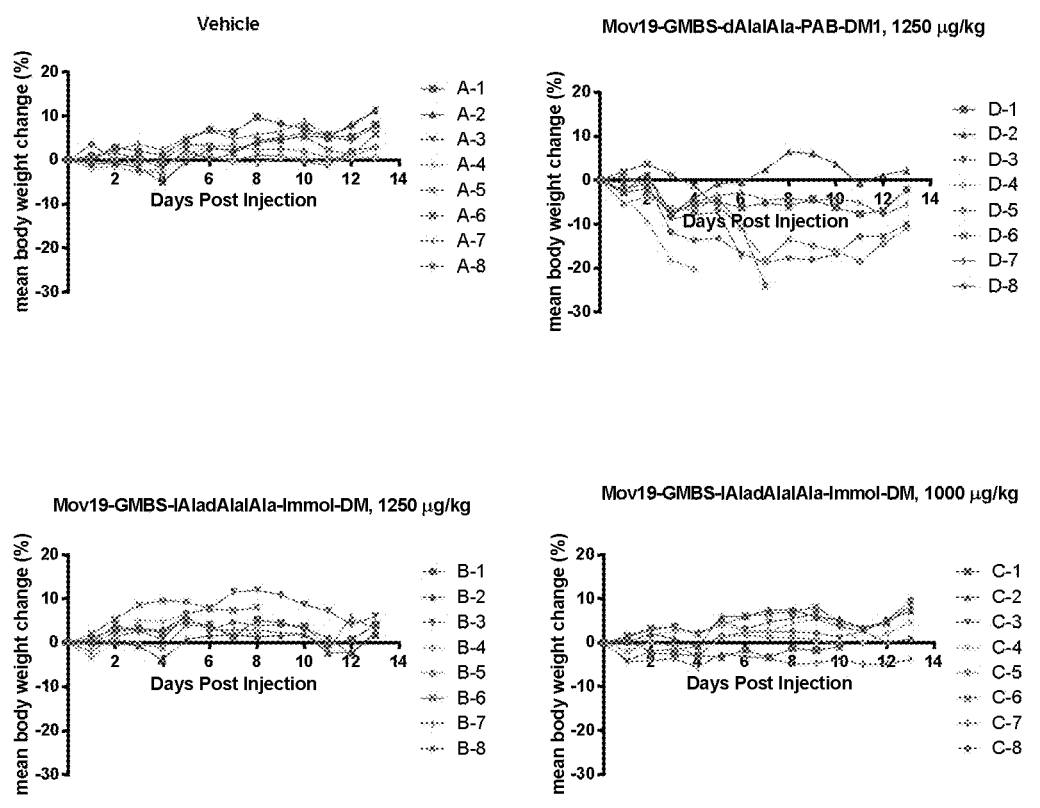
Figure 25D:
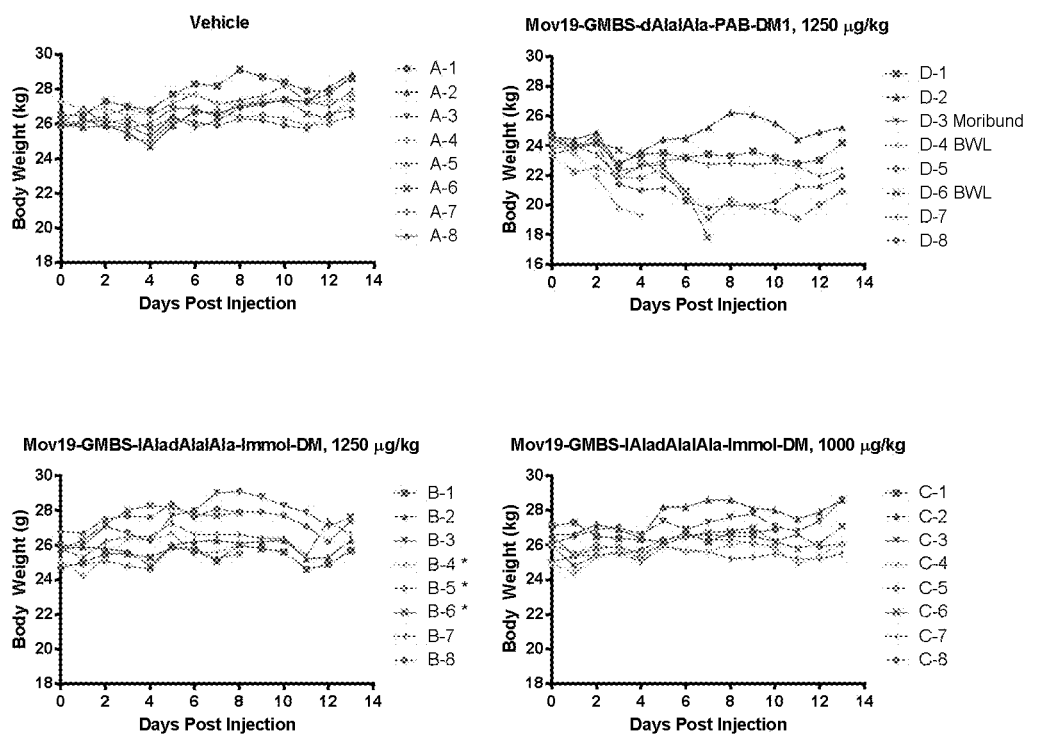

FIG. 25C shows body weight change of individual CD-1 mice dosed with 1000 or 1250 µg/kg Mov19v1.6-GMBS-1AladAlalAla-Immol-DM (conjugate 17c) or 1250 µg/kg Mov19v1.6-GMBS-dAlalAla-PAB-DM1 (conjugate 4b).

FIG. 25D shows individual body weight CD-1 mice dosed with 1000 or 1250 µg/kg Mov19v1.6-GMBS-1AladAlalAla-Immol-DM (conjugate 17c) or 1250 µg/kg Mov19v1.6-GMBS-dAlalAla-PAB-DM1 (conjugate 4b).

DETAILED DESCRIPTION OF THE INVENTION

Figure 1:
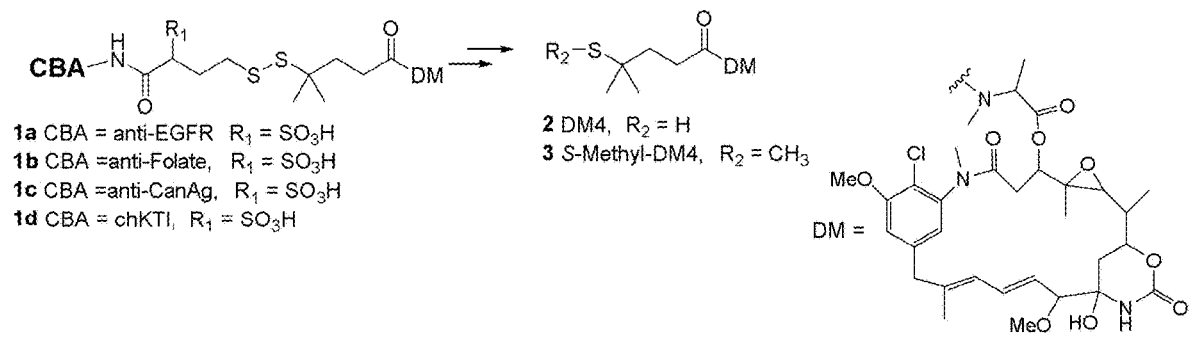
FIG. 1 depicts Ab-sSPDB-DM4 conjugates tested and compared with the conjugates of the present invention.
Figure 2:
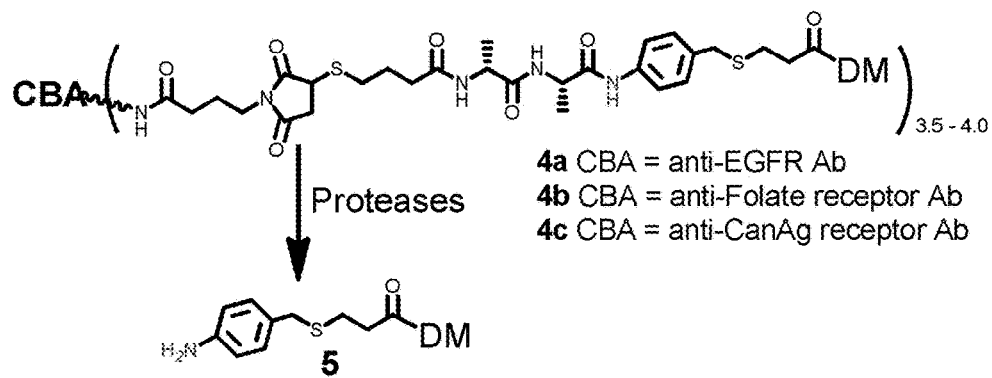
FIG. 2 depicts the peptide anilino maytansinoid ADCs tested and compared with the conjugates of the present invention.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

It should be understood that any of the embodiments described herein, including those described under different aspects of the invention (e.g., compounds, compound-linker molecules, conjugates, compositions, methods of making and using) and different parts of the specification (including embodiments described only in the Examples) can be combined with one or more other embodiments of the invention, unless explicitly disclaimed or improper. Combinations of embodiments are not limited to those specific combinations claimed via the multiple dependent claims.

Definitions

As used herein, the term "treating" or "treatment" includes reversing, reducing, or arresting the symptoms, clinical signs, and underlying pathology of a condition in manner to improve or stabilize a subject's condition. As used herein, and as well understood in the art "treatment" is an approach for obtaining beneficial or desired results, including clinical results. Beneficial or desired clinical results can include, but are not limited to, alleviation, amelioration, or slowing the progression, of one or more symptoms or conditions associated with a condition. e.g., cancer, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Exemplary beneficial clinical results are described herein.

"Optional" or "optionally" means that the subsequently described circumstance may or may not occur, so that the application includes instances where the circumstance occurs and instances where it does not. For example, the phrase "optionally substituted" means that a nonhydrogen substituent may or may not be present on a given atom, and, thus, the application includes structures wherein a nonhydrogen substituent is present and structures wherein a nonhydrogen substituent is not present.

Unless specifically stated as "unsubstituted," references to chemical moieties herein are understood to include substituted variants. For example, reference to an "alkyl" group or moiety implicitly includes both substituted and unsubstituted variants. Examples of substituents on chemical moieties includes but is not limited to, halogen, hydroxyl, carbonyl (such as carboxyl, alkoxycarbonyl, formyl, or acyl), thiocarbonyl (such as thioester, thioacetate, or thioformate), alkoxyl, alkylthio, acyloxy, phosphoryl, phosphate, phosphonate, amino, amido, amidine, imine, cyano, nitro, azido, sulfhydryl, alkylthio, sulfate, sulfonate, sulfamoyl, sulfonamido, sulfonyl, heterocyclyl, aralkyl, or aryl or heteroaryl moiety.

As used herein, the term "cell-binding agent" or "CBA" refers to a compound that can bind a cell (e.g., on a cell-surface ligand) or bind a ligand associated with or proximate to the cell, preferably in a specific manner. In certain embodiments, binding to the cell or a ligand on or near the cell is specific. The CBA may include peptides and non-peptides.

"Alkyl" as used herein refers to a saturated linear or branched-chain monovalent hydrocarbon radical. In preferred embodiments, a straight chain or branched chain alkyl has thirty or fewer carbon atoms in its backbone (e.g., $C_1$-$C_{30}$ for straight chains, $C_3$-$C_{30}$ for branched chains), and more preferably twenty or fewer. Examples of alkyl include, but are not limited to, methyl, ethyl, 1-propyl, 2-propyl, 1-butyl, 2-methyl-1-propyl, —$CH_2CH(CH_3)_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Moreover, the term "alkyl" as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. In certain embodiments, a straight chain or branched chain alkyl has or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) acorns in its backbone. In other embodiments, the chain has six or fewer carbon ($C_1$-$C_6$) atoms in its backbone. In another embodiment, the chain has three of few carbon ($C_1$-$C_3$) atoms in its backbone.

"Alkylene" as used herein refers to a saturated linear or branched-chain divalent hydrocarbon radical. In preferred embodiments, a straight chain or branched chain alkylene has thirty or fewer carbon atoms in its backbone (e.g., $C_1$-$C_{30}$ for straight chains, $C_3$-$C_{30}$ for branched chains), and more preferably twenty or fewer. Moreover, the term "alkylene" as used throughout the specification, examples, and claims is intended to include both "unsubstituted alkylenes" and "substituted alkylenes", the latter of which refers to alkylene moieties having substituents replacing a hydrogen on one or more carbons of the hydrocarbon backbone. In certain embodiments, a straight chain or branched chain alkylene has or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In other embodiments, the chain has six or fewer carbon ($C_1$-$C_6$) atoms in its backbone. In another embodiment, the chain has three of few carbon ($C_1$-$C_3$) atoms in its backbone.

"Alkenyl" refers to linear or branched-chain monovalent hydrocarbon radical of two to twenty carbon atoms with at least one site of unsaturation, i.e., a carbon-carbon double bond, wherein the alkenyl radical includes radicals having "cis" and "trans" orientations, or alternatively, "E" and "Z" orientations. Examples include, but are not limited to, ethylenyl or vinyl (—$CH$=$CH_2$), allyl (—$CH_2CH$=$CH_2$), and the like. Preferably, the alkenyl has two to ten carbon atoms. More preferably, the alkenyl has two to four carbon atoms.

"Alkenylene" refers to linear or branched-chain divalent hydrocarbon radical of two to twenty carbon atoms with at least one site of unsaturation, i.e., a carbon-carbon double bond, wherein the alkenyl radical includes radicals having "cis" and "trans" orientations, or alternatively, "E" and "Z" orientations. Examples include, but are not limited to, ethylenylene or vinylene (—$CH$=$CH$—) allylene (—$CH_2CH$=$CH$—), and the like. Preferably, the alkenylene has two to ten carbon atoms. More preferably, the alkenylene has two to four carbon atoms.

"Alkynyl" refers to a linear or branched monovalent hydrocarbon radical of two to twenty carbon atoms with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like. Preferably, the alkynyl has two to ten carbon atoms. More preferably, the alkynyl has two to four carbon atoms.

"Alkynylene" refers to a linear or branched divalent hydrocarbon radical of two to twenty carbon atoms with at least one site of unsaturation, i.e., a carbon-carbon triple bond. Examples include, but are not limited to, ethynylene, propynylene, 1-butynylene, 2-butynylene, 1-pentynylene, 2-pentynylene, 3-pentynylene, hexynylene, and the like. Preferably, the alkynylene has two to ten carbon atoms. More preferably, the alkynylene has two to four carbon atoms.

The term "carbocycle," "carbocyclyl" and "carbocyclic ring" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6], or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The terms "cyclic alkyl" and "cycloalkyl" can be used interchangeably. As used herein, the term refers to the radical of a saturated ring. In preferred embodiments, cycloalkyls have from 3-10 carbon atoms in their ring structure, and more preferably from 5-7 carbon atoms in the ring structure. In some embodiments, the two cyclic rings can have two or more atoms in common, e.g., the rings are "fused rings." Suitable cycloalkyls include cycloheptyl, cyclohexyl, cyclopentyl, cyclobutyl and cyclopropyl. In some embodiments, the cycloalkyl is a mono-cyclic group. In some embodiments, the cycloalkyl is a hi-cyclic group. In some embodiments, the cycloalkyl is a tri-cyclic group.

The term "cycloalkylene" refers to divalent radical of a saturated carbocycle. In preferred embodiments, cycloalkylenes have from 3-10 carbon atoms in their ring structure, and more preferably from 5-7 carbon atoms in the ring structure. In some embodiments, the two cyclic Sings can have two or more atoms in common, e.g., the rings are "fused rings." Suitable cycloalkylenes include cycloheptylene, cyclohexylene, cyclopentylene, cyclobutylene and cyclopropylene. In some embodiments, the cycloalkylene is a mono-cyclic group. In some embodiments, the cycloalkylene is a hi-cyclic group. In some embodiments, the cycloalkylene is a tri-cyclic group, The term "cyclic alkenyl" refers to a carbocyclic ring radical having at least one double bond in the ring structure.

The term "cyclic alkynyl" refers to a carbocyclic ring radical having at least one triple bond in the ring structure.

The term "aryl" as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, and the like. The terms "aryl" also includes "polycyclyl", "polycycle", and "polycyclic" ring systems having two or more rings in which two or more atoms are common to two adjoining rings, e.g., the rings are "fused rings," wherein at least one of the rings is aromatic, e.g., the other cyclic rings can be cycloalkyls, cycloalkenyls, cycloalkynyls. In some preferred embodiments, polycycles have 2-3 rings. In certain preferred embodiments, polycyclic ring systems have two cyclic rings in which both of the rings are aromatic. Each of the rings of the polycycle can be substituted or unsubstituted. In certain embodiments, each ring of the polycycle contains from 3 to 10 atoms in the ring, preferably from 5 to 7. For example, aryl groups include, but are not limited to, phenyl (benzene), tolyl, anthracenyl, fluorenyl, indenyl, azulenyl, and naphthyl, as well as benzo-fused carbocyclic moieties such as 5,6,7,8-tetrahydronaphthyl, and the like. In some embodiments, the aryl is a single-ring aromatic group. In some embodiments, the aryl is a two-ring aromatic group. In some embodiments, the aryl is a three-ring aromatic group.

"Arylene" as used herein is a divalent radical of an aryl group described above.

The terms "heterocycle," "heterocyclyl," and "heterocyclic ring" as used herein, refers to substituted or unsubstituted non-aromatic ring structures of 3- to 18-membered rings, preferably 3- to 10-membered rings, more preferably 3- to 7-membered rings, whose ring structures include at least one heteroatom, preferably one to four heteroatoms, more preferably one or two heteroatoms. In certain embodiments, the ring structure can have two cyclic rings. In some embodiments, the two cyclic rings can have two or more atoms in common, e.g., the rings are "fused rings." Heterocyclyl groups include, for example, piperidine, piperazine, pyrrolidine, morpholine, lactones, lactams, and the like. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, tetrahydrofurane, dihydrofurane, tetrahydrothiene, tetrahydropyrane, dihydropyrane, tetrahydrothiopyranyl, thiomorpholine, thioxane, homopiperazine, azetidine, oxetane, thietane, homopiperidine, oxepane, thiepane, oxazepine, diazepine, thiazepine, 2-pyrroline, 3-pyrroline, indoline, 2H-pyrane, 4H-pyrane, dioxanyl, 1,3-dioxolane, pyrazoline, dithiane, dithiolane, dihydropyrane, dihydrothiene, dihydrofurane, pyrazolidinylimidazoline, imidazolidine, 3-azabicyco[3.1.0] hexanyl, 3-azabicyclo[4.1.0]heptane, and azabicyclo[2.2.2] hexane. Spiro moieties are also included within the scope of this definition. Examples of a heterocyclic group wherein ring atoms are substituted with oxo (=O) moieties are pyrimidinone and 1,1-dioxo-thiomorpholine.

The term "heterocyclylene" refers to divalent radical of a heterocycle group described above.

The term "heteroaryl" as used herein, refers to substituted or unsubstituted aromatic single ring structures, preferably 5- to 7-membered rings, more preferably 5- to 6-membered rings, whose ring structures include at least one heteroatom (e.g., 0, N, or S), preferably one to four or one to 3 heteroatoms, more preferably one or two heteroatoms. When two or more heteroatoms are present in a heteroaryl ring, they may be the same or different. The term "heteroaryl." also includes "polycyclyl", "polycycle", and "polycyclic" ring systems having two or more cyclic rings in which two or more carbons are common to two adjoining rings, e.g., the rings are "fused rings," wherein at least one of the rings is heteroaromatic, e.g., the other cyclic rings can be cycloalkyls, cycloalkenyls, cycloalkynyls, aryls, and/or heterocyclyls. In some preferred embodiments, preferred polycycles have 2-3 rings. In certain embodiments, preferred polycyclic ring systems have two cyclic rings in which both of the rings are aromatic. In certain embodiments, each ring of the polycycle contains from 3 to 10 atoms in the ring, preferably from 5 to 7. For examples, heteroaryl groups include, but are not limited to, pyrrole, furan, thiophene, imidazole, oxazole, thiazole, pyrazole, pyridine, pyrazine, pyridazine, quinoline, pyrimidine, indolizine, indole, indazole, benzimidazole, benzothiazole, benzofuran, benzothiophene, cinnoline, phthalazine, quinazoline, carbazole, phenoxazine, quinoline, purine and the like. In some embodiments, the heteroaryl is a single-ring aromatic group. In some embodiments, the heteroaryl is a two-ring aromatic group. In some embodiments, the heteroaryl is a three-ring aromatic group.

The term "heteroarylene" refers to divalent radical of a heteroaryl group described above.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocyclyl include the oxidized forms such as NO, SO, and $SO_2$.

The term "halo" or "halogen" refers to fluorine (F), chlorine (Cl), bromine (Br) or iodine (I).

The alkyl, alkylene, alkenylene, alkyne, alkynylene, cyclic alkyl, cycloalkylene, carbocyclyl, aryl, arylene, heterocyclyl, heterocycloalkylene, heteroaryl and heteroarylene described above can be optionally substituted with one more (e.g., 2, 3, 4, 5, 6 or more) substituents.

The term "substituted" refers to moieties having substituents replacing a hydrogen on one or more carbons of the backbone of a chemical compound. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated). "Optional" or "optionally" means that the subsequently described circumstance may or may not occur, so that the application includes instances where the circumstance occurs and instances where it does not. For example, the phrase "optionally substituted" means that a nonhydrogen substituent may or may not be present on a given atom, and, thus, the application includes structures wherein a non-hydrogen substituent is present and structures wherein a nonhydrogen substituent is not present. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent. One exemplary substituent may be depicted as —NR'R", wherein R' and R" together with the nitrogen atom to which they are attached, may form a heterocyclic ring. The heterocyclic ring formed from R' and R" together with the nitrogen atom to which they are attached may be partially or fully saturated. In some embodiments, the heterocyclic ring consists of 3 to 7 atoms. In another embodiment, the heterocyclic ring is selected from the group consisting of pyrrolyl, imidazolyl, pyrazolyl, triazolyl, tetrazolyl, isoxazolyl, pyridyl and thiazolyl.

This specification uses the terms "substituent," and "group" interchangeably.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. Such substituents, in non-limiting examples, can be selected from a linear, branched or cyclic alkyl, alkenyl or alkynyl having from 1 to 10 carbon atoms, aryl, heteroaryl, heterocyclyl, halogen, guanidinium [—NH(C=NH) NH$_2$], —OR$^{100}$, NR$^{101}$R$^{102}$, NO$_2$, —NR$^{101}$COR$^{102}$, —SR$^{100}$, a sulfoxide represented by —SOR$^{101}$, a sulfone represented by —SO$_2$R$^{101}$, a sulfonate —SO$_3$M, a sulfate —OSO$_3$M, a sulfonamide represented by —SO$_2$NR$^{101}$R$^{102}$, cyano, an azido, —COR$^{101}$, —OCOR$^{101}$, —OCONR$^{101}$R$^{102}$ and a polyethylene glycol unit (—CH$_2$CH$_2$O)$_n$R$^{101}$ wherein M is H or a cation (such as Na$^+$ or K$^+$); R$^{101}$, R$^{102}$ and R$^{103}$ are each independently selected from H, linear, branched or cyclic alkyl, alkenyl or alkynyl having from 1 to 10 carbon atoms, a polyethylene glycol unit (—CH$_2$CH$_2$O)$_n$—R$^{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$^{104}$ is H or a linear or branched alkyl having 1 to 4 carbon atoms, wherein the alkyl, alkenyl, alkynyl, aryl, heteroaryl and heterocyclyl in the groups represented by R$^{100}$, R$^{101}$, R$^{102}$, R$^{103}$ and R$^{104}$ are optionally substituted with one or more (e.g., 2, 3, 4, 5, 6 or more) substituents independently selected from halogen, —OH, —CN, —NO$_2$ and unsubstituted linear or branched alkyl having 1 to 4 carbon atoms. Preferably, the substituents for the optionally substituted alkyl, alkenyl, alkynyl, cyclic alkyl, cyclic alkenyl, cyclic alkynyl, carbocyclyl, aryl, heterocyclyl and heteroaryl described above include halogen, —CN, —NR$^{102}$R$^{103}$, —CF$_3$, —OR$^{101}$, aryl, heteroaryl, heterocyclyl, —SR$^{101}$, —SOR$^{101}$, —SO$_2$R$^{101}$ and —SO$_3$M.

The term "compound" or "cytotoxic compound" are used interchangeably. They are intended to include compounds for which a structure or formula or any derivative thereof has been disclosed in the present invention or a structure or formula or any derivative thereof that has been incorporated by reference. The term also includes, stereoisomers, geometric isomers, tautomers, solvates, metabolites, salts (e.g., pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "conjugate" as used herein refers to a compound described herein or a derivative thereof that is linked to a cell binding agent.

The term "linkable to a cell binding agent" as used herein refers to the compounds described herein or derivatives thereof comprising at least one linking group or a precursor thereof suitable to bond these compounds or derivatives thereof to a cell binding agent.

The term "precursor" of a given group refers to any group which may lead to that group by any deprotection, a chemical modification, or a coupling reaction.

The term "linked to a cell binding agent" refers to a conjugate molecule comprising at least one of the compounds described herein, or derivative thereof bound to a cell binding agent via a suitable linking group or a precursor thereof.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds," John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

The term "prodrug" is also meant to include a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by Burger's Medicinal Chemistry and Drug Discovery (1995) 172-178, 949-982 (Manfred E. Wolff ed., 5th ed.); see also Goodman and Gilman's, The Pharmacological basis of Therapeutics, 8th ed., McGraw-Hill, Int. Ed. 1992, "Biotransformation of Drugs."

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound which further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

The terms "abnormal cell growth" and "proliferative disorder" are used interchangeably in this application. "Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells, and/or benign or precancerous cells.

A "therapeutic agent" encompasses both a biological agent such as an antibody, a peptide, a protein, an enzyme or a chemotherapeutic agent.

A "chemotherapeutic agent" is a chemical compound useful in the treatment of cancer.

A "metabolite" is a product produced through metabolism in the body of a specified compound, a derivative thereof, or a conjugate thereof, or salt thereof. Metabolites of a compound, a derivative thereof, or a conjugate thereof, may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds, a derivative thereof, or a conjugate thereof, of the invention, including compounds, a derivative thereof, or a conjugate thereof, produced by a process comprising contacting a compound, a derivative thereof, or a conjugate thereof, of this invention with a mammal for a period of time sufficient to yield a metabolic product thereof.

The phrase "pharmaceutically acceptable" indicates that the substance or composition must be compatible chemically and/or toxicologically, with the other ingredients comprising a formulation, and/or the mammal being treated therewith.

The term "protecting group" or "protecting moiety" refers to a substituent that is commonly employed to block or protect a particular functionality while reacting other functional groups on the compound, a derivative thereof, or a conjugate thereof. For example, an "amine-protecting group" or an "amino-protecting moiety" is a substituent attached to an amino group that blocks or protects the amino functionality in the compound. Such groups are well known in the art (see for example P. Wuts and T. Greene, 2007, Protective Groups in Organic Synthesis, Chapter 7, J. Wiley & Sons, N.J.) and exemplified by carbamates such as methyl and ethyl carbamate, FMOC, substituted ethyl carbamates, carbamates cleaved by 1,6-β-elimination (also termed "self immolative"), ureas, amides, peptides, alkyl and aryl derivatives. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see P. G. M. Wuts & T. W. Greene, Protective Groups in Organic Synthesis, John Wiley & Sons, New York, 2007.

The term "leaving group" refers to an group of charged or uncharged moiety that departs during a substitution or displacement. Such leaving groups are well known in the art and include, but not limited to, halogens, esters, alkoxy, hydroxyl, tosylates, triflates, mesylates, nitriles, azide, carbamate, disulfides, thioesters, thioethers and diazonium compounds.

The term "bifunctional crosslinking agent," "bifunctional linker" or "crosslinking agents" refers to modifying agents that possess two reactive groups; one of which is capable of reacting with a cell binding agent while the other one reacts with the cytotoxic compound to link the two moieties together. Such bifunctional crosslinkers are well known in the art (see, for example, Isalm and Dent in *Bioconjugation* chapter 5, p 218-363, Groves Dictionaries Inc., New York, 1999). For example, bifunctional crosslinking agents that enable linkage via a thioether bond include N-succinimidyl-4-(N-maleimidomethyl)-cyclohexane-1-carboxylate (SMCC) to introduce maleimido groups, or with N-succinimidyl-4-(iodoacetyl)-aminobenzoate (SIAB) to introduce iodoacetyl groups. Other bifunctional crosslinking agents that introduce maleimido groups or haloacetyl groups on to a cell binding agent are well known in the art (see US Patent Applications 2008/0050310, 20050169933, available from Pierce Biotechnology Inc. P.O. Box 117, Rockland, Ill. 61105, USA) and include, but not limited to, bis-maleimidopolyethyleneglycol (BMPEO), BM(PEO)$_2$, BM(PEO)$_3$, N-(β-maleimidopropyloxy) succinimide ester (BMPS), γ-maleimidobutyric acid N-succinimidyl ester (GMBS), ε-maleimidocaproic acid N-hydroxysuccinimide ester (EMCS), 5-maleimidovaleric acid NHS, HBVS, N-succinimidyl-4-(N-maleimidomethyl)-cyclohexane-1-carboxy-(6-amidocaproate), which is a "long chain" analog of SMCC (LC-SMCC), m-maleimidobenzoyl-N-hydroxysuccinimide ester (MBS), 4-(4-N-maleimidophenyl)-butyric acid hydrazide or HCl salt (MPBH), N-succinimidyl 3-(bromoacetamido)propionate (SBAP), N-succinimidyl iodoacetate (SIA), κ-maleimidoundecanoic acid N-succinimidyl ester (KMUA), N-succinimidyl 4-(p-maleimidophenyl)-butyrate (SMPB), succinimidyl-6-(β-maleimidopropionamido) hexanoate (SMPH), succinimidyl-(4-vinylsulfonyl)benzoate (SVSB), dithiobis-maleimidoethane (DTME), 1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimidomethyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MBS), N-(γ-maleimidobutryloxy)sulfosuccinimide ester (sulfo-GMBS), N-(ε-maleimidocaproyloxy)sulfosuccimido ester (sulfo-EMCS), N-(κ-maleimidoundecanoyloxy)sulfosuccinimide ester (sulfo-KMUS), and sulfosuccinimidyl 4-(p-maleimidophenyl)butyrate (sulfo-SMPB).

Heterobifunctional crosslinking agents are bifunctional crosslinking agents having two different reactive groups. Heterobifunctional crosslinking agents containing both an amine-reactive N-hydroxysuccinimide group (NHS group) and a carbonyl-reactive hydrazine group can also be used to link the cytotoxic compounds described herein with a cell-binding agent (e.g., antibody). Examples of such commercially available heterobifunctional crosslinking agents include succinimidyl 6-hydrazinonicotinamide acetone hydrazone (SANH), succinimidyl 4-hydrazidoterephthalate hydrochloride (SHTH) and succinimidyl hydrazinium nicotinate hydrochloride (SHNH). Examples of bifunctional crosslinking agents that can be used include succinimidyl-p-formyl benzoate (SFB) and succinimidyl-p-formylphenoxyacetate (SFPA).

Bifunctional crosslinking agents that enable the linkage of cell binding agent with cytotoxic compounds via disulfide bonds are known in the art and include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to introduce dithiopyridyl groups. Other bifunctional crosslinking agents that can be used to introduce disulfide groups are known in the art and are disclosed in U.S. Pat. Nos. 6,913,748, 6,716,821 and US Patent Publications 20090274713 and 20100129314, all of which are incorporated herein by reference. Alternatively, crosslinking agents such as 2-iminothiolane, homocysteine thiolactone or S-acetylsuccinic anhydride that introduce thiol groups can also be used.

A "reactive moiety" or "reactive group" as defined herein refers to a chemical moiety that forms a covalent bond with another chemical group. For example, a reactive moiety can reactive with certain groups on the cell-binding agent (CBA) to form a covalent bond. In some embodiments, the reactive moiety is an amine reactive group that can form a covalent bond with ε-amine of a lysine residue located on the CBA. In another embodiment, a reactive moiety is an aldehyde reactive group that can form a covalent bond with an aldehyde group located on the CBA. In yet another embodiment, a reactive moiety is a thiol reactive group that can form a covalent bond with the thiol group of a cysteine residue located on the CBA.

A "linker," "linker moiety," or "linking group" as defined herein refers to a moiety that connects two groups, such as a cell binding agent and a cytotoxic compound, together. Typically, the linker is substantially inert under conditions for which the two groups it is connecting are linked. A bifunctional crosslinking agent may comprise two reactive groups, one at each ends of a linker moiety, such that one reactive group can be first reacted with the cytotoxic compound to provide a compound bearing the linker moiety and a second reactive group, which can then react with a cell binding agent. Alternatively, one end of the bifunctional crosslinking agent can be first reacted with the cell binding agent to provide a cell binding agent bearing a linker moiety and a second reactive group, which can then react with a cytotoxic compound. The linking moiety may contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. Other linkers that can be used in the present invention include non-cleavable linkers, such as those described in are described in detail in U.S. publication number 20050169933, or charged linkers or hydrophilic linkers and are described in US 2009/0274713, US 2010/01293140 and WO 2009/134976, each of which is expressly incorporated herein by reference, each of which is expressly incorporated herein by reference.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, selinocystiene and O-phosphoserine Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. One amino acid that may be used in particular is citrulline, which is a derivative of arginine and is involved in the formation of urea in the liver Amino acid mimetics refers to chemical compounds that have a structure that is different from the general chemical structure of an amino acid, but functions in a manner similar to a naturally occurring amino acid. The term "unnatural amino acid" is intended to represent the "D" stereochemical form of the twenty naturally occurring amino acids described above. It is further understood that the term unnatural amino acid includes homologues of the natural amino acids or their D isomers, and synthetically modified forms of the natural amino acids. The synthetically modified forms include, but are not limited to, amino acids having side chains shortened or lengthened by up to two carbon atoms, amino acids comprising optionally substituted aryl groups, and amino acids comprised halogenated groups, preferably halogenated alkyl and aryl groups and also N substituted amino acids e.g. N-methyl-alanine. An amino acid or peptide can be attached to a linker/spacer or a cell binding agent through the terminal amine or terminal carboxylic acid of the amino acid or peptide. The amino acid can also be attached to a linker/spacer or a cell-binding agent through a side chain reactive group, such as but not restricted to the thiol group of cysteine, the epsilon amine of lysine or the side chain hydroxyls of serine or threonine.

In some embodiments, the amino acid is represented by $NH_2$—$C(R^{aa'}R^{aa})$—$C(=O)OH$, wherein $R^{aa}$ and $R^{aa'}$ are each independently H, an optionally substituted linear, branched or cyclic alkyl, alkenyl or alkynyl having 1 to 10 carbon atoms, aryl, heteroaryl or heterocyclyl, or $R^{aa}$ and the N-terminal nitrogen atom can together form a heterocyclic ring (e.g., as in proline). The term "amino acid residue" refers to the corresponding residue when one hydrogen atom is removed from the amine and/or the hydroxyl group is removed from the carboxy end of the amino acid, such as —NH—$C(R^{aa'}R^{aa})$—$C(=O)O$—.

As used herein, the amino acid can be L or D isomers. Unless specified otherwise, the when an amino acid is referenced, it can be L or D isomer or a mixture thereof. In certain embodiments, when a peptide is referenced by its amino acid sequence, each of the amino acid can be L or D isomer unless otherwise specified. If one of the amino acid in a peptide is specified as D isomer, the other amino acid(s) are L isomer unless otherwise specified. For example, the peptide D-Ala-Ala means D-Ala-L-Ala.

Amino acids and peptides may be protected by blocking groups. A blocking group is an atom or a chemical moiety that protects the N-terminus of an amino acid or a peptide from undesired reactions and can be used during the synthesis of a drug-ligand conjugate. It should remain attached to the N-terminus throughout the synthesis, and may be removed after completion of synthesis of the drug conjugate by chemical or other conditions that selectively achieve its removal. The blocking groups suitable for N-terminus protection are well known in the art of peptide chemistry. Exemplary blocking groups include, but are not limited to, methyl esters, tert-butyl esters, 9-fluorenylmethyl carbamate (Fmoc) and carbobenzoxy (Cbz).

The term "peptide cleavable by a protease" refers to peptides containing a cleavage recognition sequence of a protease. As used herein, a protease is an enzyme that can cleave a peptide bond. A cleavage recognition sequence for a protease is a specific amino acid sequence recognized by the protease during proteolytic cleavage. Many protease cleavage sites are known in the art, and these and other cleavage sites can be included in the linker moiety. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al, in AMYLOID PROTEIN PRECURSOR IN DEVELOPMENT, AGING, AND ALZHEIMER'S DISEASE, ed. Masters et al. pp. 190-198 (1994).

The peptide sequence is chosen based on its ability to be cleaved by a protease, non-limiting examples of which include cathepsins B, C, D, H, L and S, and furin. Preferably, the peptide sequence is capable of being cleaved by an appropriate isolated protease in vitro, which can be tested using in vitro protease cleavage assays known in the art.

In another embodiment, the peptide sequence is chosen based on its ability to be cleaved by a lysosomal protease. A lysosomal protease is a protease located primarily in the lysosomes, but can also be located in endosomes. Examples of a lysosomal protease include, but are not limited to, cathepsins B, C, D, H, L and S, and furin In another embodiment, the peptide sequence is chosen based on its ability to be cleaved by a tumor-associated protease, such as a protease that is found on the surface of a cancerous cell or extracellularly in the vicinity of tumor cells, non-limiting examples of such proteases include thimet oligopeptidase (TOP), CD10 (neprilysin), a matrix metalloprotease (such as MMP2 or MMP9), a type II transmembrane serine protease (such as Hepsin, testisin, TMPRSS4 or matriptase/MT-SP1), legumain and enzymes described in the following reference (Current Topics in Developmental Biology: Cell Surface Proteases, vol. 54 Zucker S. 2003, Boston, Mass.). The ability of a peptide to be cleaved by tumor-associated protease can be tested using in vitro protease cleavage assays known in the art.

The term "cation" refers to an ion with positive charge. The cation can be monovalent (e.g., $Na^+$, $K^+$, etc.), bi-valent (e.g., $Ca^{2+}$, $Mg^{2+}$, etc.) or multi-valent (e.g., $Al^{3+}$ etc.). In some embodiments, the cation is monovalent.

The term "therapeutically effective amount" means that amount of active compound or conjugate that elicits the desired biological response in a subject. Such response includes alleviation of the symptoms of the disease or disorder being treated, prevention, inhibition or a delay in the recurrence of symptom of the disease or of the disease itself, an increase in the longevity of the subject compared with the absence of the treatment, or prevention, inhibition or delay in the progression of symptom of the disease or of the disease itself. Determination of the effective amount is well within the capability of those skilled in the art, especially in light of the detailed disclosure provided herein. Toxicity and therapeutic efficacy of compound I can be determined by standard pharmaceutical procedures in cell cultures and in experimental animals. The effective amount of compound or conjugate of the present invention or other therapeutic agent to be administered to a subject will depend on the stage, category and status of the multiple myeloma and characteristics of the subject, such as general health, age, sex, body weight and drug tolerance. The effective amount of compound or conjugate of the present invention or other therapeutic agent to be administered will also depend on administration route and dosage form. Dosage amount and interval can be adjusted individually to provide plasma levels of the active compound that are sufficient to maintain desired therapeutic effects.

Cell-Binding Agent-Cytotoxic Agent Conjugates

In a first aspect, the present invention provides cell-binding agent-cytotoxic agent conjugates comprising a cell-binding agent described herein covalently linked to one or more molecules of the cytotoxic compounds described herein.

In a first embodiment, the conjugate of the present invention is represented by the following formula:

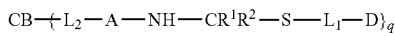
(I)

or a pharmaceutically acceptable salt thereof, wherein:
CB is a cell-binding agent;
L$_2$ is absent or a spacer;
A is an amino acid residue or a peptide comprising 2 to 20 amino acid residues;
R$^1$ and R$^2$ are each independently H or a C$_{1-6}$alkyl (e.g., R$^1$ and R$^2$ are each independently H or a C$_{1-3}$alkyl);
L$_1$ is a spacer;
D-L$_1$-SH is a cytotoxic agent; and
q is an integer from 1 to 20.

In one embodiment, L$_1$ is -L$_1$'-C(=O)—; and L$_1$' is an alkylene, an alkenylene, an alkynylene, a cycloalkylene, a heterocycloalkylene, an arylene, or a heteroarylene, wherein the —C(=O)— group in L$_1$ is connected to D.

In another embodiment, at least one of R$^1$ and R$^2$ is H. In a more specific embodiment, one of R$^1$ and R$^2$ is H and the other one is Me.

In a 1$^{st}$ specific embodiment, for the conjugate of formula (I), R$^1$ and R$^2$ are each independently H or Me. In a more specific embodiment, R$^1$ and R$^2$ are both H.

In a 2$^{nd}$ specific embodiment, for the conjugate for formula (I), L$_1$ is -L$_1$'-C(=O)—; and L$_1$' is an alkylene or a cycloalkylene, wherein the —C(=O)— group in L$_1$ is connected to D; and the remaining variables are as described above in the first embodiment or the 1$^{st}$ specific embodiment. In a more specific embodiment, L$_1$' is C$_{1-10}$alkylene. In another more specific embodiment, L$_1$' is C$_{1-20}$alkylene.

In a 3$^{rd}$ specific embodiment, for the conjugate for formula (I), L$_1$ is —CR$^3$R$^4$—(CH$_2$)$_{1-8}$—C(=O)—; R$^3$ and R$^4$ are each independently H or Me; and the remaining variables are as described above in the first embodiment or the 1$^{st}$ specific embodiment. In a more specific embodiment, R$^3$ and R$^4$ are both Me.

In a 4$^{th}$ specific embodiment, for the conjugate for formula (I), L$_1$ is —CR$^3$R$^4$—(CH$_2$)$_{2-5}$—C(=O)— or —CR$^3$R$^4$—(CH$_2$)$_3$—S—C(=O)—; R$^3$ and R$^4$ are each independently H or Me; and the remaining variables are as described above in the first embodiment or the 1$^{st}$ specific embodiment. In a more specific embodiment, R$^3$ and R$^4$ are both Me. In another more specific embodiment, R$^3$ and R$^4$ are both H.

In a 5$^{th}$ specific embodiment, for the conjugate for formula (I), L$_1$ is —(CH$_2$)$_{4-6}$—C(=O)—; and the remaining variables are as described above in the first embodiment or the 1$^{st}$ specific embodiment.

In a 6$^{th}$ specific embodiment, for the conjugate for formula (I), L$_2$ is represented by the following structural formula:

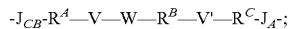

wherein:
R$^A$ is an alkylene, a cycloalkylalkylene, an arylene, heteroarylene or a heterocyclylene;
R$^B$ and R$^C$ are each independently absent, an alkylene, a cyclalkylene, or an arylene;
V and V' are each independently —(O—CH$_2$—CH$_2$)$_p$—, or —(CH$_2$—CH$_2$—O)$_p$—;
p is 0 or an integer from 1 to 10;
W is absent,

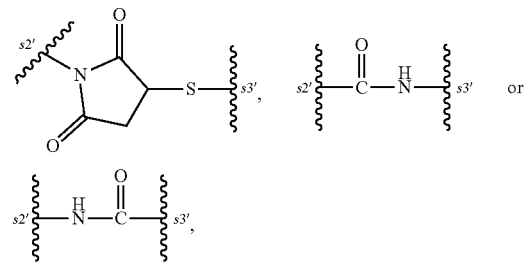

wherein s2' indicates the site connected to V, R$^A$ or J$_{CB}$ and s3' indicates the site connected to R$^B$, V', R$^C$ or J$_A$;
J$_{CB}$ is —C(=O)—,

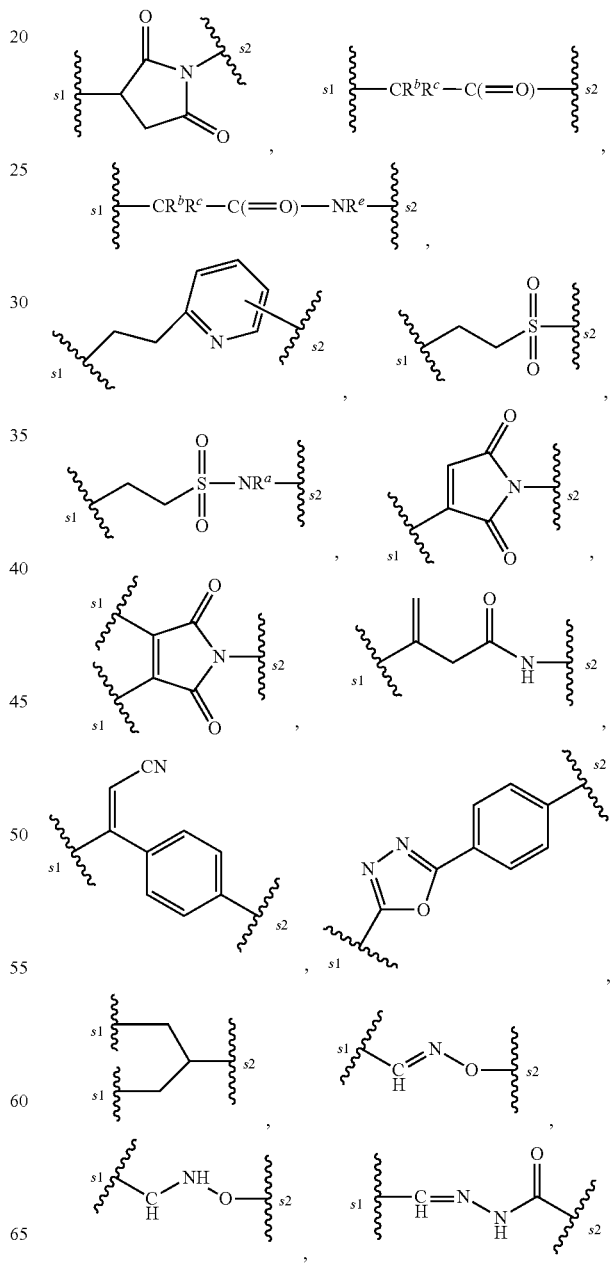

-continued

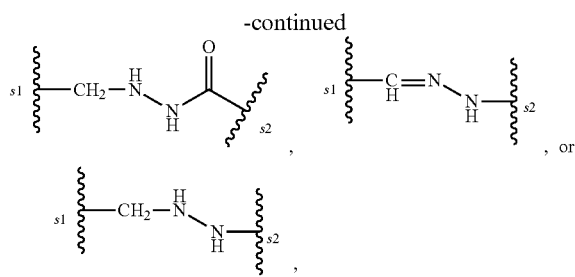
, or wherein s1 indicates the site connected to the cell-binding agent CB and s2 indicates the site connected to $R^A$;

$R^a$, $R^b$, $R^c$, and $R^e$, for each occurrence, are independently H or an alkyl;

$J_A$ is —C(=O)—; and the remaining variables are as described above in the first embodiment or the $1^{st}$, $2^{nd}$, $3^{rd}$, $4^{th}$ or $5^{th}$ specific embodiment.

In a more specific embodiment, for conjugates of the $6^{th}$ specific embodiment, $R^A$ is an alkylene, a cycloalkylalkylene, or an arylene; W is absent, or

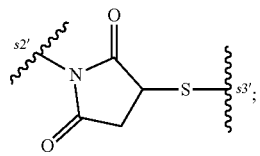 [SMILES: *SC1CC(=O)N(*)C1=O]

and $J_{CB}$ is —C(=O)—,

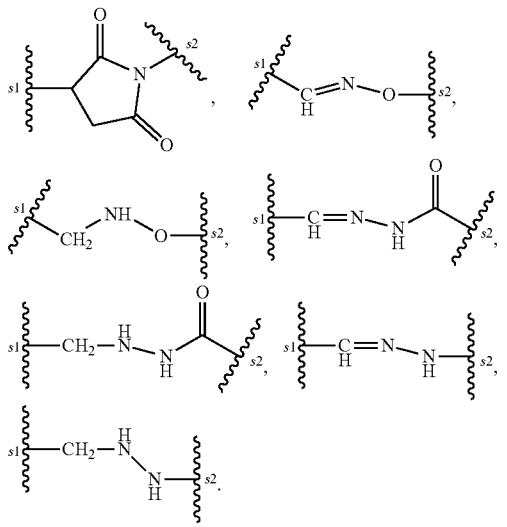

In a more specific embodiment, p is 0 and $R^C$ is absent; and the remaining variables as as described above in the $6^{th}$ specific embodiment.

In another more specific embodiment, $J_{CB}$ is —C(=O)— or

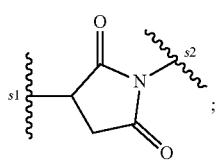 [SMILES: *C1CC(=O)N(*)C1=O]

and the remaining variables as as described above in the $6^{th}$ specific embodiment.

In a $7^{th}$ embodiment, for the conjugate for formula (I), $L_2$ is represented by the following structural formulas:

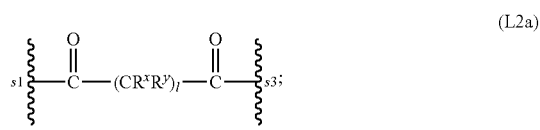
(L2a)

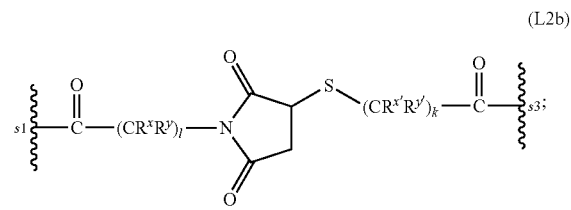
(L2b)

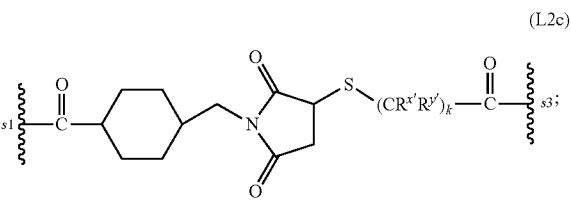
(L2c)

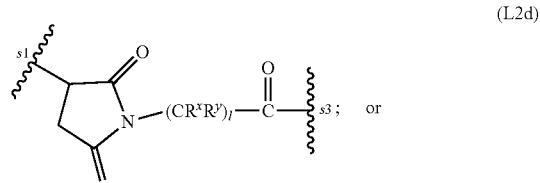
(L2d)

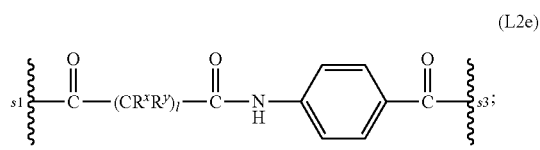
(L2e)

wherein:

$R^x$, $R^y$, and $R^{y'}$, for each occurrence, are independently H, —OH, halogen, —O—($C_{1-4}$ alkyl), —SO$_3$H, —NR$_{40}$R$_{41}$R$_{42}^+$, or a $C_{1-4}$ alkyl optionally substituted with —OH, halogen, —SO$_3$H or NR$_{40}$R$_{41}$R$_{42}^+$, wherein R$_{40}$, R$_{41}$ and R$_{42}$ are each independently H or a $C_{1-4}$ alkyl;

l and k are each independently an integer from 1 to 10;

s1 indicates the site that is connected to CBA and s3 indicates the site that is connected to the group A;

and the remaining variables are as described above in the first embodiment or the $1^{st}$, $2^{nd}$, $3^{rd}$, $4^{th}$ or $5^{th}$ specific embodiment.

In a more specific embodiment, $R^x$, $R^y$, $R^{x'}$ and $R^{y'}$ are all H; and the remaining variables are as described above in the $7^{th}$ specific embodiment.

In another more specific embodiment, 1 and k are each independently an integer an integer from 2 to 6; and the remaining variables are as described above in the 7$^{th}$ specific embodiment.

In an even more specific embodiment, $R^x$, $R^y$, $R^{x'}$ and $R^{y'}$ are all H; 1 and k are each independently an integer an integer from 2 to 6; and the remaining variables are as described above in the 7$^{th}$ specific embodiment.

In another more specific embodiment, $L_2$ is represented by the following structural formula:

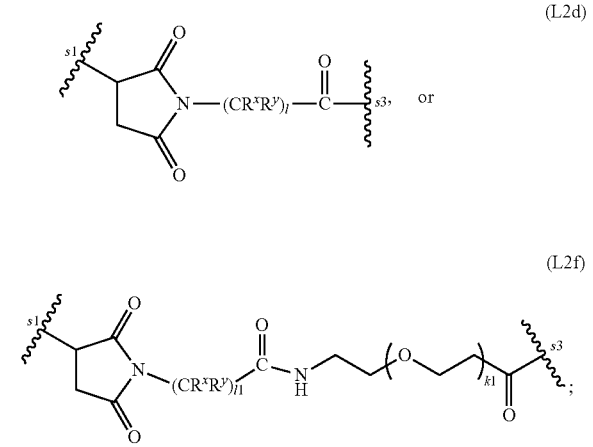

wherein:
$R^x$ and $R^y$ are both H;
1 and 11 are each independently an integer from 1 to 10; and
k1 is an integer from 1 to 12 (e.g., 2, 4, 6, 8, 10 or 12).

In one embodiment, 1 and 11 are each an integer from 2 to 6; and k1 is an integer from 2 to 6 (e.g., 2, 4, or 6)

In a 8$^{th}$ specific embodiment, for the conjugate for formula (I), A is a peptide cleavable by a protease; the remaining variables are as described above in the first embodiment or the 1$^{st}$, 2$^{nd}$, 3$^{rd}$, 4$^{th}$, 5$^{th}$, 6$^{th}$ or 7$^{th}$ in a more specific embodiment, A is a peptide cleavable by a protease expressed in tumor tissue.

In a 9$^{th}$ specific embodiment, for the conjugate for formula (I), A is a peptide having an amino acid that is covalent linked with —NH—CR$^1$R$^2$—S-L$_1$-D selected from the group consisting of Ala, Arg, Asn, Asp, Cit, Cys, selino-Cys, Gln, Glu, Gly, Ile, Leu, Lys, Met, Phe, Pro, Ser, Thr, Trp, Tyr and Val, each independently as L or D isomer; the remaining variables are as described above in the first embodiment or the 1$^{st}$, 2$^{nd}$, 3$^{rd}$, 4$^{th}$, 5$^{th}$, 6$^{th}$ or 7$^{th}$ specific embodiment. In a more specific embodiment, the amino acid connected to —NH—CR$^1$R$^2$—S-L$_1$-D is an L amino acid.

In a 10$^{th}$ specific embodiment, for the conjugate for formula (I), A is selected from the group consisting of Gly-Gly-Gly, Ala-Val, Val-Ala, D-Val-Ala, Val-Cit, D-Val-Cit, Val-Lys, Phe-Lys, Lys-Lys, Ala-Lys, Phe-Cit, Leu-Cit, Ile-Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Ala-Ala, D-Ala-Ala-Ala, Ala-D-Ala-Ala, Ala-Ala-D-Ala, Ala-Leu-Ala-Leu (SEQ ID NO: 1), β-Ala-Leu-Ala-Leu (SEQ ID NO: 2), Gly-Phe-Leu-Gly (SEQ ID NO: 3), Val-Arg, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, Gln-Val, Asn-Ala, Gln-Phe, Gln-Ala, D-Ala-Pro, and D-Ala-tBu-Gly, wherein the first amino acid in each peptide is connected to L$_2$ group and the last amino acid in each peptide is connected to —NH—CR$^1$R$^2$—S-L$_1$-D; and the remaining variables are as described above in the first embodiment or the 1$^{st}$, 2$^{nd}$, 3$^{rd}$, 4$^{th}$, 5$^{th}$, 6$^{th}$ or 7$^{th}$ specific embodiment. In a more specific embodiment, A is Ala-Ala-Ala, Ala-D-Ala-Ala, D-Ala-Ala-Ala, Ala-Ala-D-Ala, Ala-Ala, D-Ala-Ala, Val-Ala, D-Val-Ala, D-Ala-Pro, or D-Ala-tBu-Gly. In another more specific embodiment, A is Ala-Ala-Ala, Ala-D-Ala-Ala, Ala-Ala, D-Ala-Ala, Val-Ala, D-Val-Ala, D-Ala-Pro, or D-Ala-tBu-Gly.

In a 11$^{th}$ specific embodiment, for the conjugate for formula (I), D is a maytansinoid; and the remaining variables are as described above in the first embodiment or the 1$^{st}$, 2$^{nd}$, 3$^{rd}$, 4$^{th}$, 5$^{th}$, 6$^{th}$, 7$^{th}$, 8$^{th}$, 9$^{th}$, or 10$^{th}$ specific embodiment. In a more specific embodiment, D is represented by the following formula:

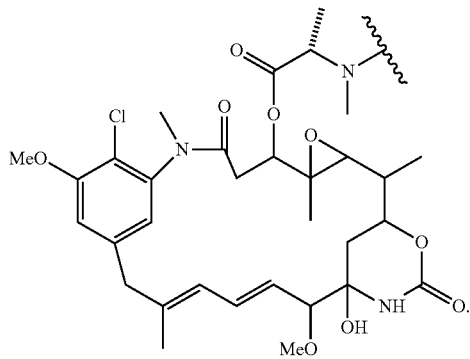 [SMILES: *N(C)[C@@H](C)C(=O)OC1CC(=O)N(C)c2cc(cc(OC)c2Cl)C/C(C)=C/C=C/C(OC)C2(O)CC(OC(=O)N2)C(C)C2OC12C]

In a more specific embodiment, D is represented by the following formula:

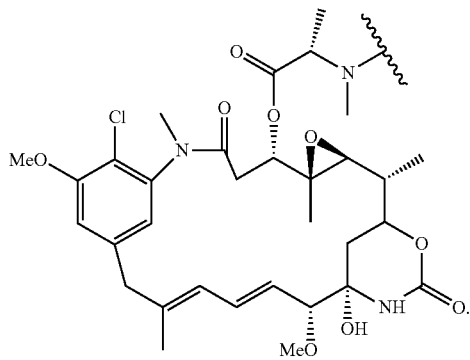 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)CC(OC(=O)N2)[C@@H](C)[C@@H]2O[C@@]12C]

In a 12$^{th}$ specific embodiment, the conjugate of the present invention is represented by the following formula:

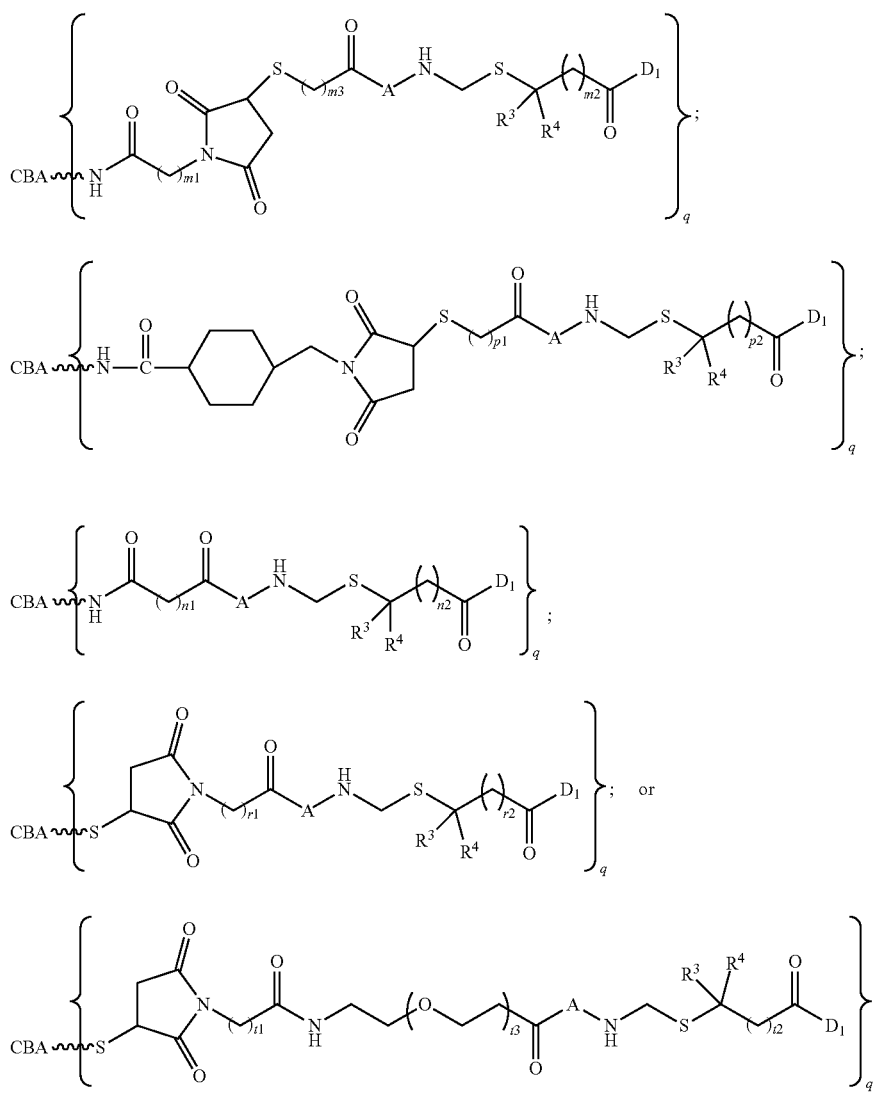

or a pharmaceutically acceptable salt thereof, wherein:

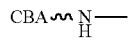

is the cell-binding agent connected to the $L_2$ group through an amine group (e.g., Lys amine group);

is the cell-binding agent connected to the $L_2$ group through a thiol group (e.g., a Cys thiol group);

$R^3$ and $R^4$ are each independently H or Me;

m1, m3, p1, n1, r1 and t1 are each independently an integer from 1 to 10;

m2, n2, p2, r2 and t2 are each independently an integer from 1 to 19;

t3 is an integer from 1 to 12;

$D_1$ is represented by the following formula:

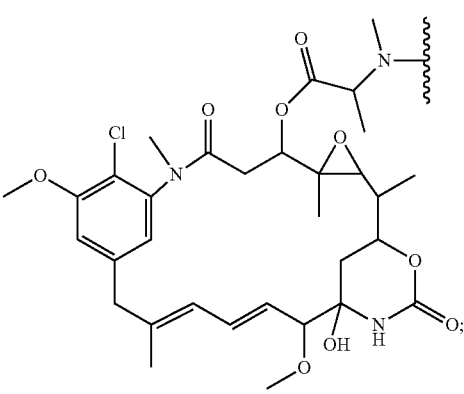 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]

and

A is as described above in the 8th, 9th, or 10th specific embodiment.

In a more specific embodiment, m1, m3, p1, n1, and r1 are each independently an integer from 1 to 6; and m2, n2, p2, and r2 are each independently an integer from 1 to 7.

In a more specific embodiment, $D_1$ is represented by the following formula:

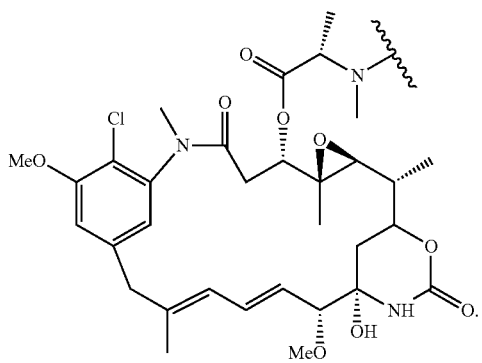 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)CC(OC(=O)N2)[C@@H](C)[C@@H]2O[C@@]12C]

In a more specific embodiment, A is Ala-Ala-Ala, Ala-D-Ala-Ala, D-Ala-Ala-Ala, Ala-Ala-D-Ala, Ala-Ala, D-Ala-Ala, Val-Ala, D-Val-Ala, D-Ala-Pro, or D-Ala-tBu-Gly (more specifically, A is Ala-Ala-Ala, Ala-D-Ala-Ala, Ala-Ala, D-Ala-Ala, Val-Ala, D-Val-Ala, D-Ala-Pro, or D-Ala-tBu-Gly); and the remaining variables are as described above in the 12$^{th}$ specific embodiment.

In another more specific embodiment, m1, r1, n1, p1 and m3 are each independently an integer from 2 to 4; and m2, p2, n2 and r2 are each independently an integer from 3 to 5. In a more specific embodiment, m1, m3, p1, n1, r1 and t1 are each independently an integer from 2 to 10. In a more specific embodiment, m1, m3, p1, n1, r1 and t1 are each independently an integer from 3 to 6.

In a more specific embodiment, m2, n2, p2, r2 and t2 are each independently an integer from 2 to 10. In a more specific embodiment, m2, n2, p2, r2 and t2 are each independently an integer from 3 to 6. In a more specific embodiment, m2, n2, p2, r2 and t2 are each independently 5.

In a more specific embodiment, m1, m3, p1, n1, r1 and t1 are each independently an integer from 2 to 10 and m2, n2, p2, r2 and t2 are each independently an integer from 2 to 10. In a more specific embodiment, m1, m3, p1, n1, r1 and t1 are each independently an integer from 3 to 6 and m2, n2, p2, r2 and t2 are each independently an integer from 2 to 10. In a more specific embodiment, m1, m3, p1, n1, r1 and t1 are each independently an integer from 3 to 6 and m2, n2, p2, r2 and t2 are each independently an integer from 3 to 6.

In a more specific embodiment, r2 and t2 are each independently an integer from 2 to 6, r1 and t1 are each independently an integer from 2 to 6 and t3 is an integer from 1 to 12. In a more specific embodiment, r2 and t2 are each independently an integer from 2 to 6, r1 and t1 are each independently an integer from 2 to 6 and t3 is an integer from 1 to 6. In a more specific embodiment, r2 and t2 are each independently an integer from 2 to 6, r1 and t1 are each independently an integer from 2 to 6 and t3 is an integer from 1 to 4. In a more specific embodiment, r2 and t2 are each independently an integer from 3 to 5, r1 and t1 are each independently an integer from 2 to 6 and t3 is an integer from 1 to 12. In a more specific embodiment, r2 and t2 are each independently an integer from 3 to 5, r1 and t1 are each independently an integer from 2 to 6 and t3 is an integer from 1 to 6. In a more specific embodiment, r2 and t2 are each independently an integer from 3 to 5, r1 and t1 are each independently an integer from 2 to 6 and t3 is an integer from 1 to 4.

In a more specific embodiment, r2 and r1 are each independently an integer from 2 to 6. In a more specific embodiment, r2 is an integer from 3 to 5 and r1 is an integer from 2 to 6. In a more specific embodiment, r2 is an integer from 3 to 5 and r1 is an integer from 2 to 4. In a more specific embodiment, r2 is 4 and r1 is 2. In a more specific embodiment, r2 is 4 and r1 is 3. In a more specific embodiment, r2 is 4 and r1 is 4. In a more specific embodiment, r2 is 4 and r1 is 5. In a more specific embodiment, r2 is 4 and r1 is 6.

In yet another more specific embodiment, $R^3$ and $R^4$ are both Me. Alternatively, $R^3$ and $R^4$ are both H.

In another specific embodiment, the conjugate is represented by the following formula:

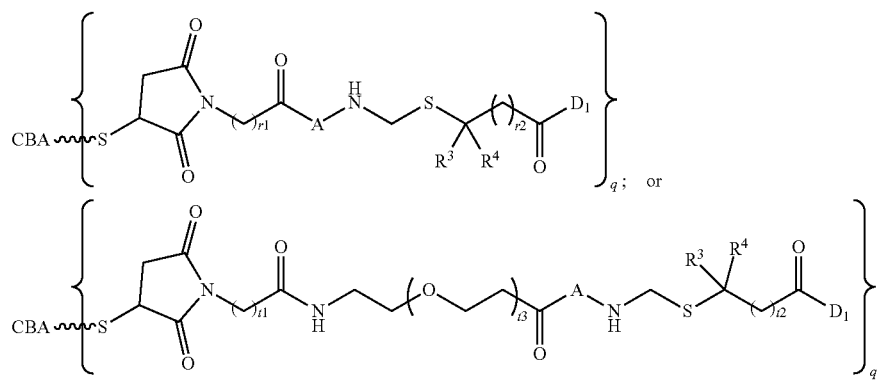

wherein:

r1 and t1 are each an integer from 2 to 10;

r2 and t2 are each an integer from 2 to 19; and t3 is an integer from 2 to 12 (e.g., t3 is 2, 4, 6, 8, 10 or 12).

In a more specific embodiment, r1 and t1 are each an integer from 2 to 6; r2 and t2 are each an integer from 2 to 5; and t3 is an integer from 2 to 6 (e.g. t3 is 2, 4 or 6).

In a 13$^{th}$ specific embodiment, the conjugate of the present invention is represented by the following formula:

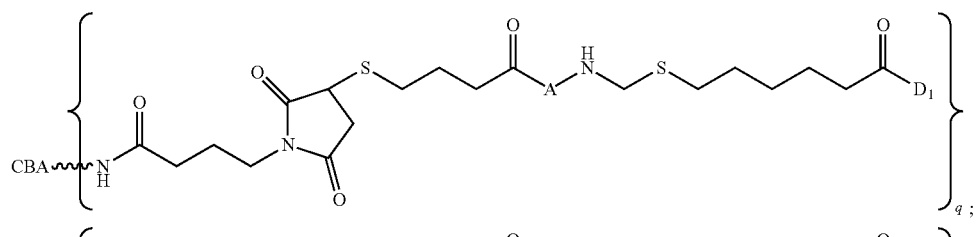
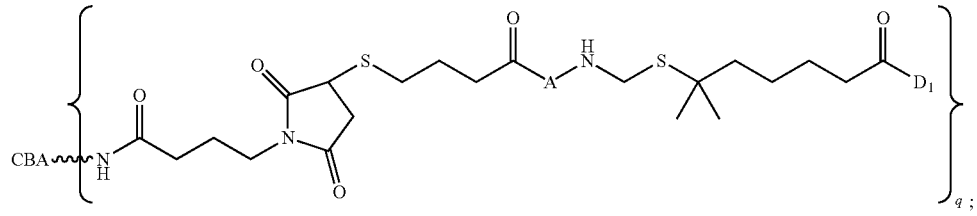
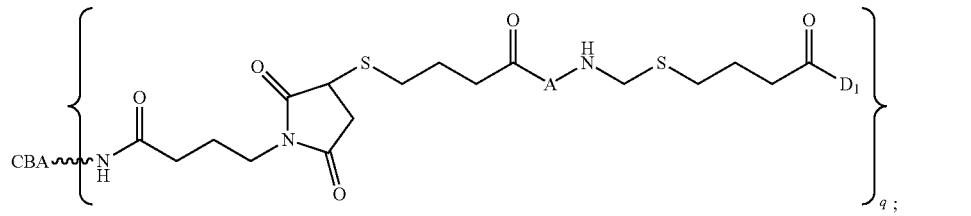
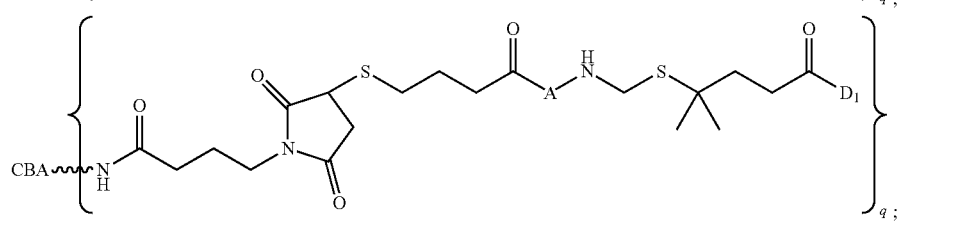
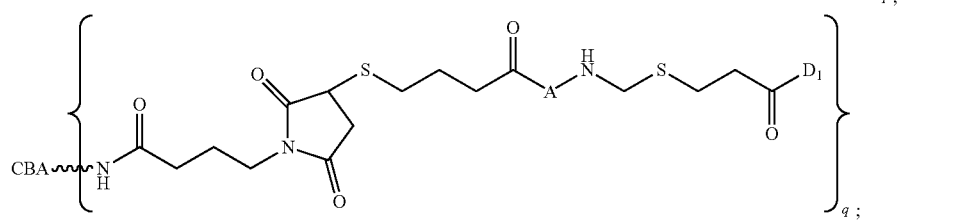
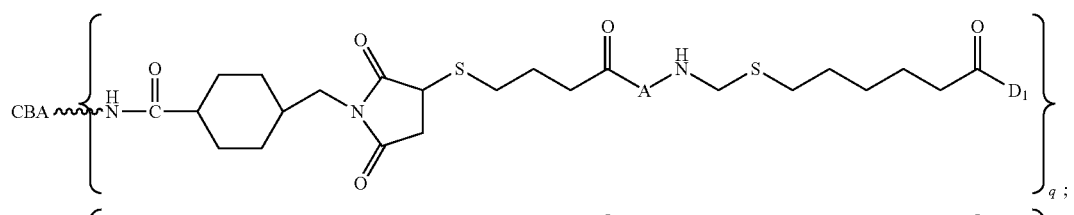
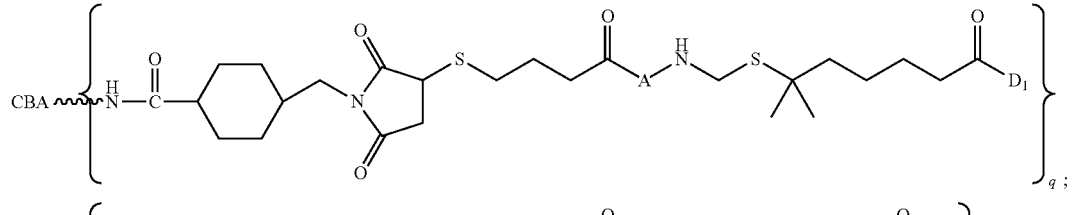
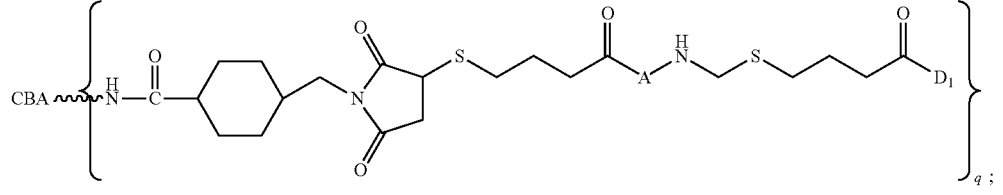

-continued
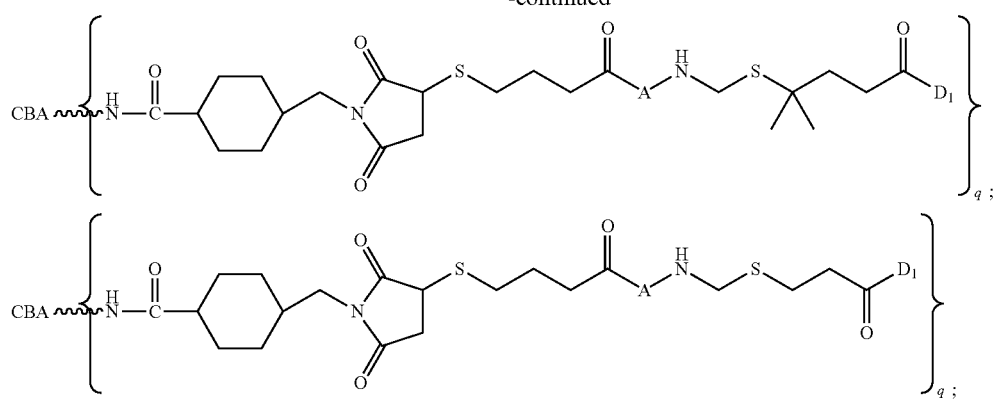
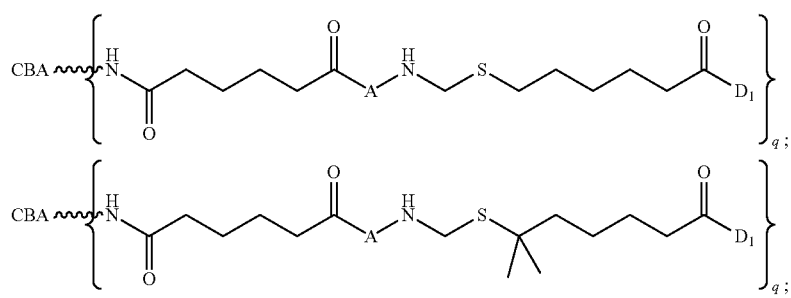
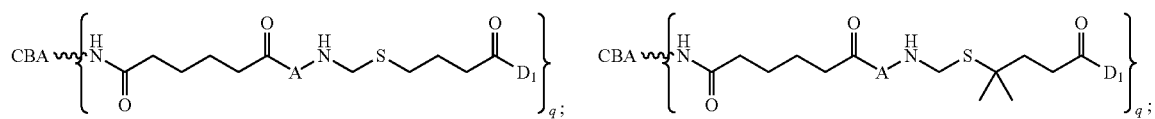
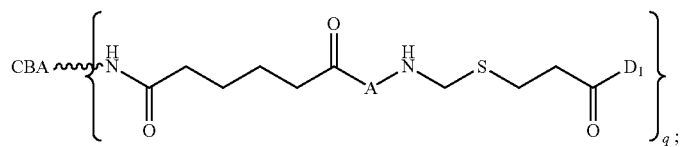
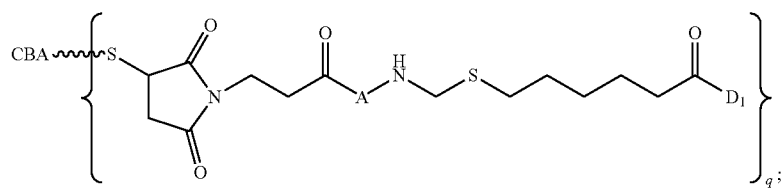
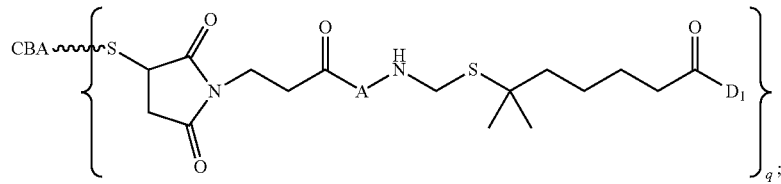
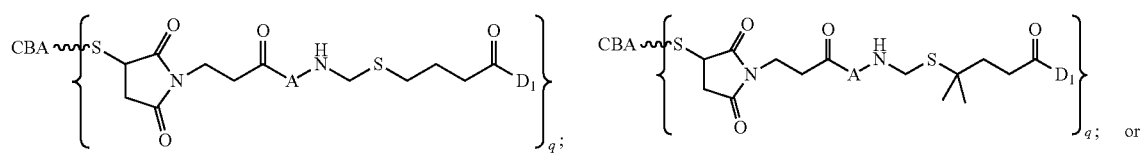
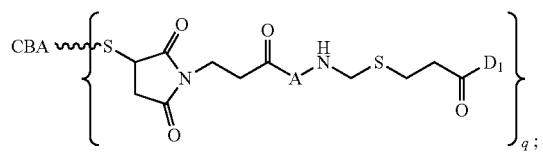

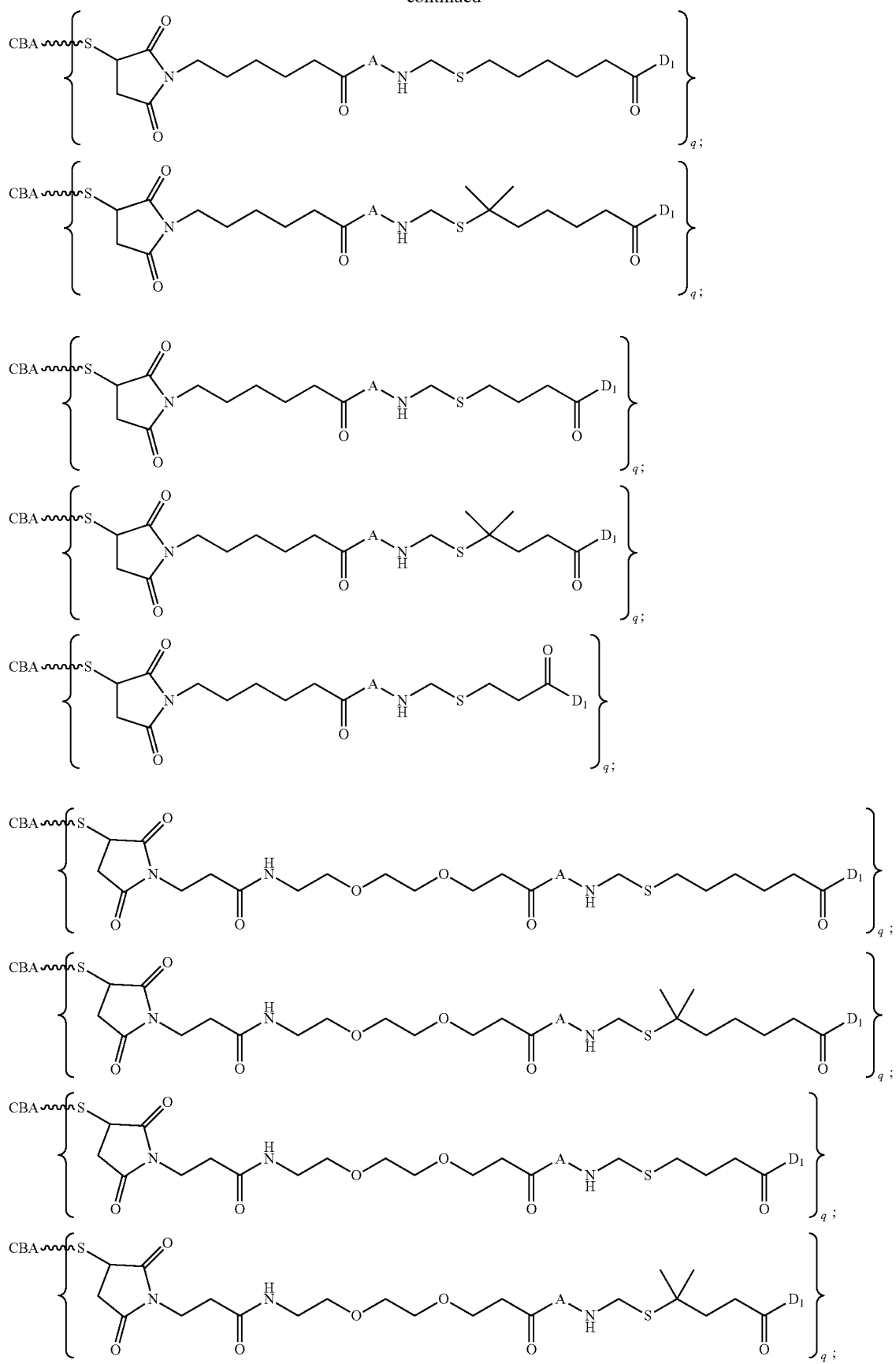

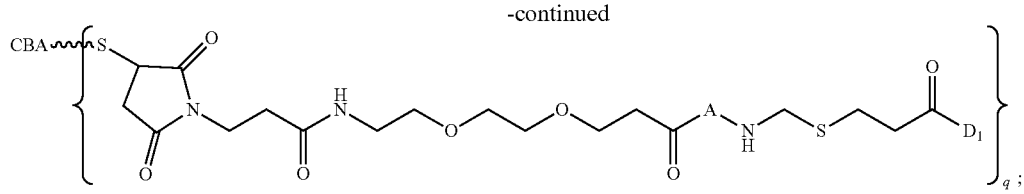

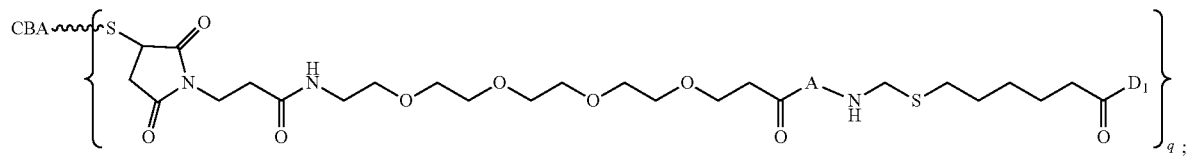

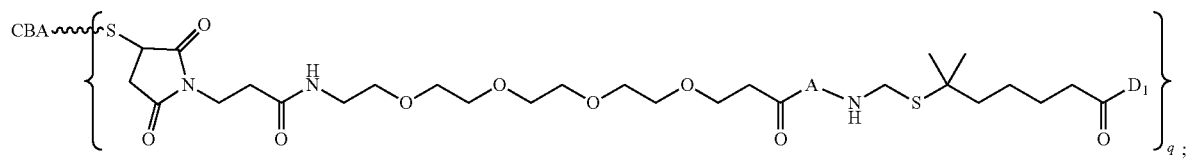

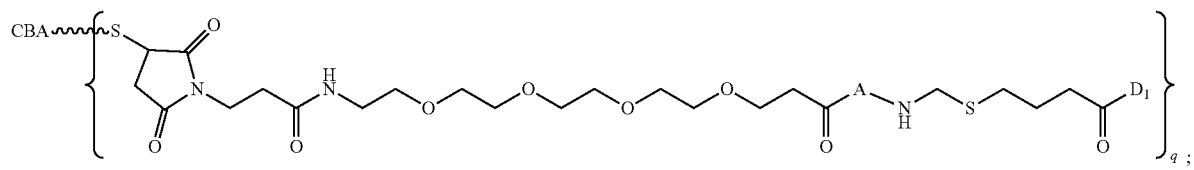

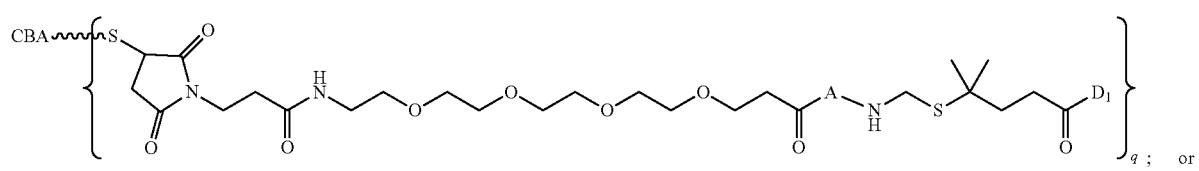

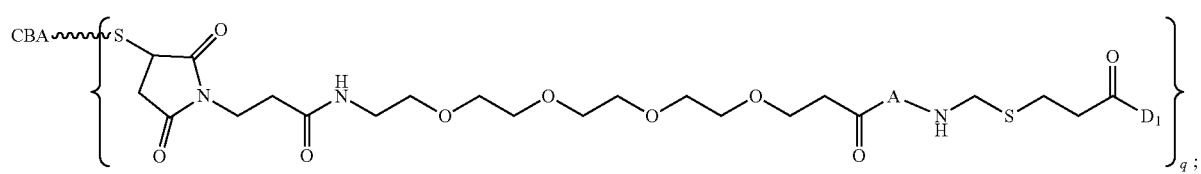

or a pharmaceutically acceptable salt thereof, wherein:

A is Ala-Ala-Ala, Ala-D-Ala-Ala, D-Ala-Ala-Ala, Ala-Ala-D-Ala, Ala-Ala, D-Ala-Ala, Val-Ala, D-Val-Ala, D-Ala-Pro, or D-Ala-tBu-Gly (more specifically, A is Ala-Ala-Ala, Ala-D-Ala-Ala, Ala-Ala, D-Ala-Ala, Val-Ala, D-Val-Ala, D-Ala-Pro, or D-Ala-tBu-Gly), and $D_1$ is represented by the following formula:

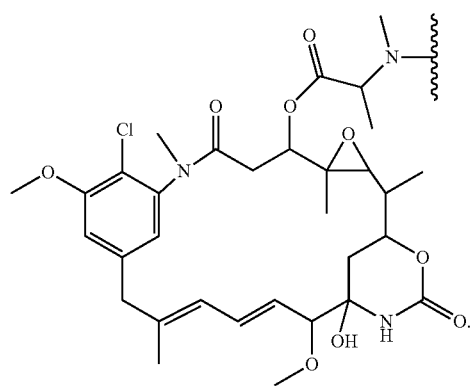 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]

In a more specific embodiment, $D_1$ is represented by the following formula:

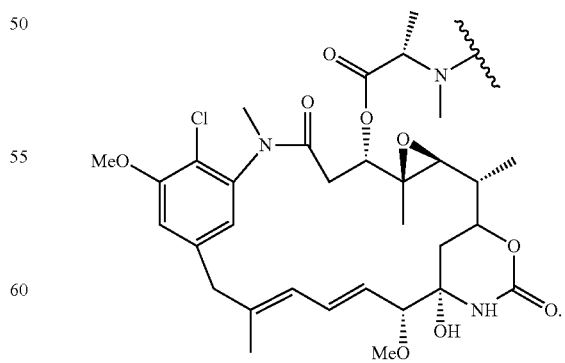

Also in the 13$^{th}$ specific embodiment, the conjugate of the present invention is represented by the following formula:

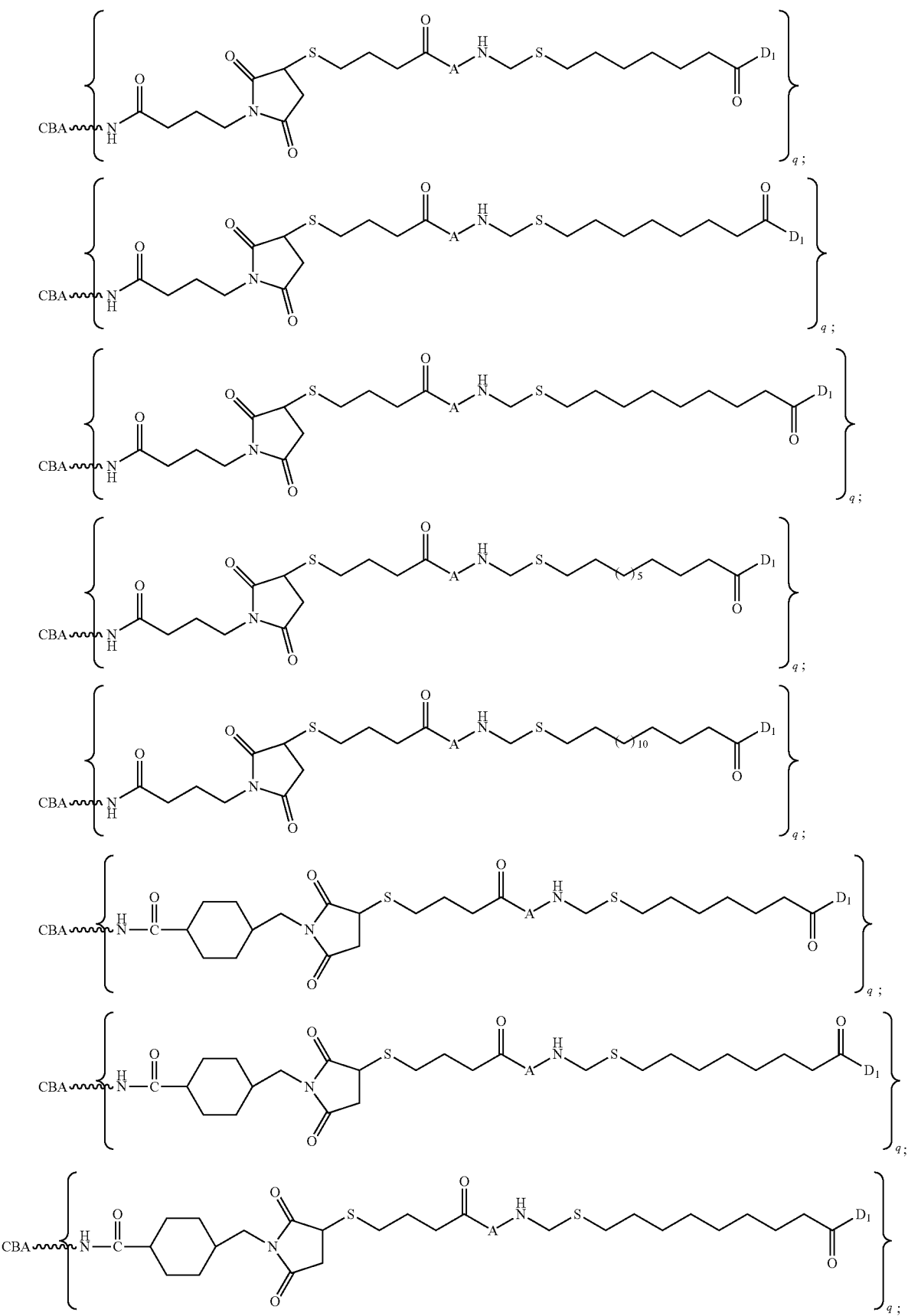

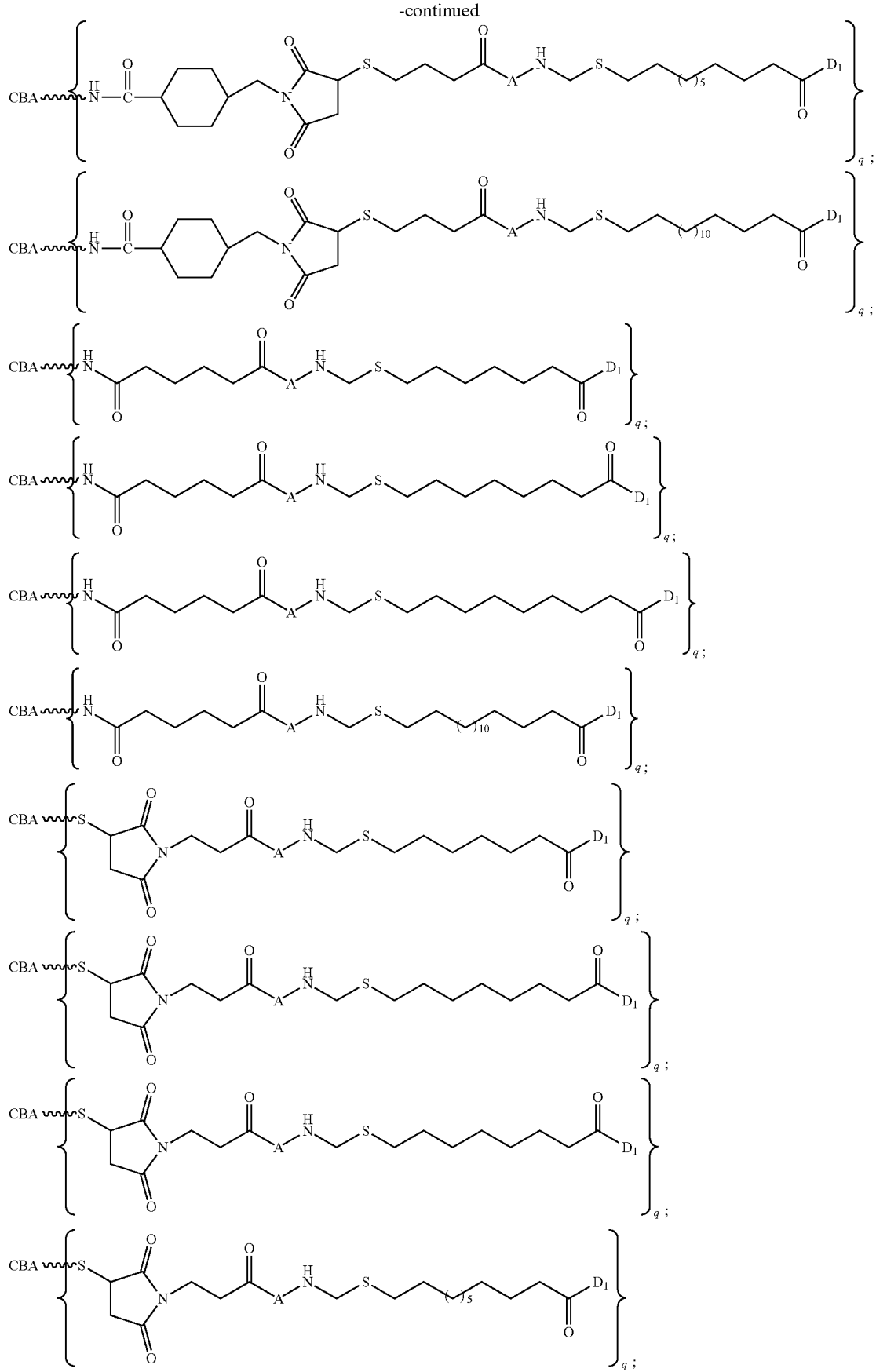

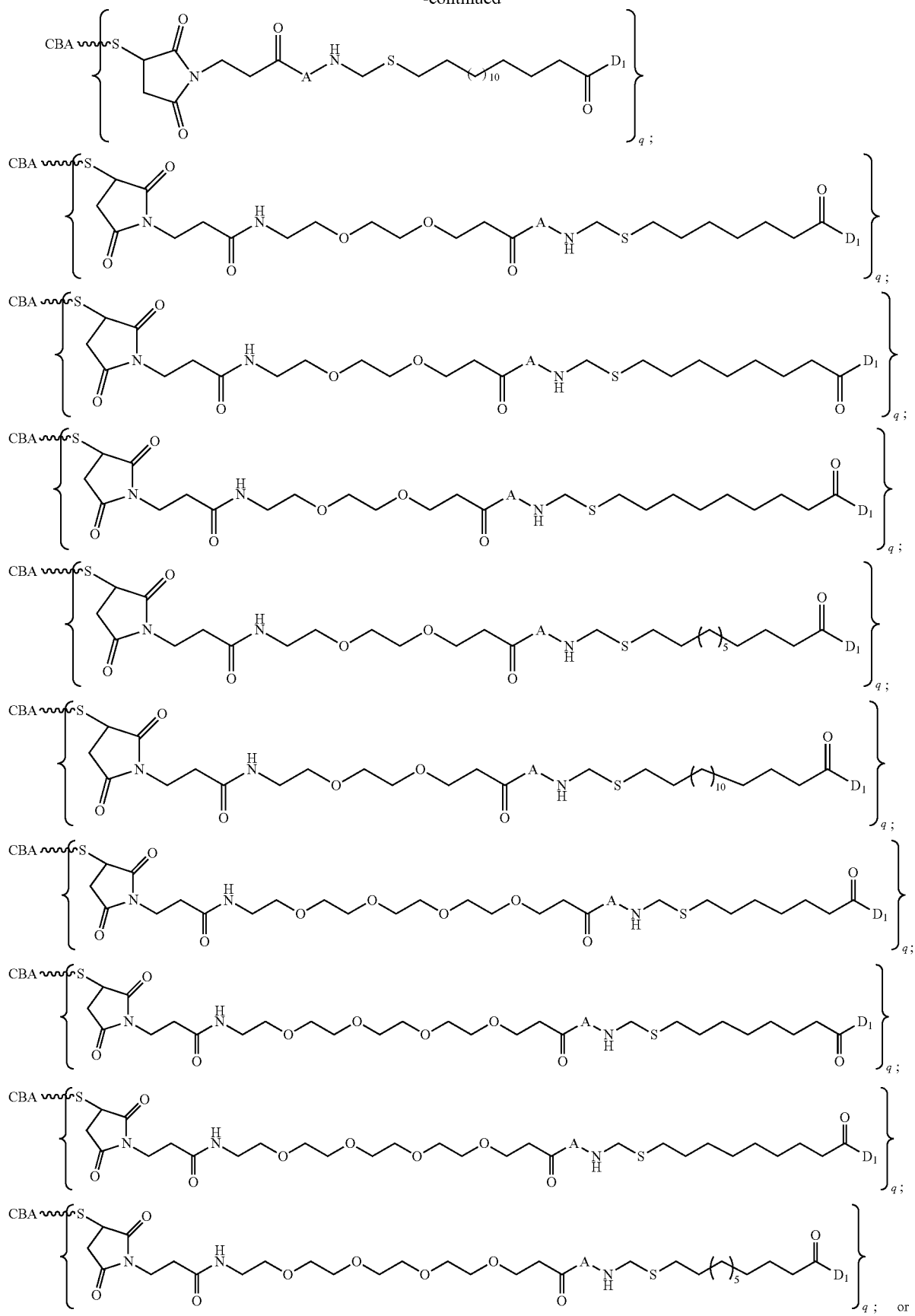

-continued

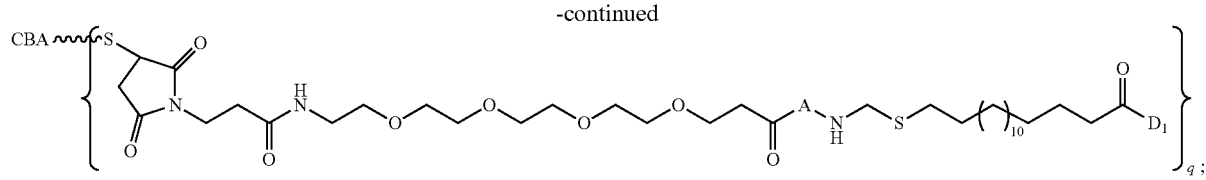

or a pharmaceutically acceptable salt thereof, wherein:
A is Ala-Ala-Ala, Ala-D-Ala-Ala, D-Ala-Ala-Ala, Ala-Ala-D-Ala, Ala-Ala, D-Ala-Ala, Val-Ala, D-Val-Ala, D-Ala-Pro, or D-Ala-tBu-Gly (more specifically, A is Ala-Ala-Ala, Ala-D-Ala-Ala, Ala-Ala, D-Ala-Ala, Val-Ala, D-Val-Ala, D-Ala-Pro, or D-Ala-tBu-Gly), and
$D_1$ is represented by the following formula:

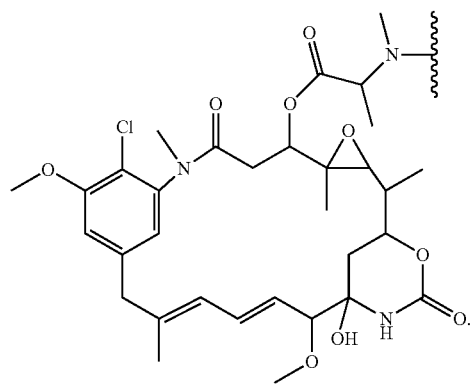 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]

In a more specific embodiment, $D_1$ is represented by the following formula:

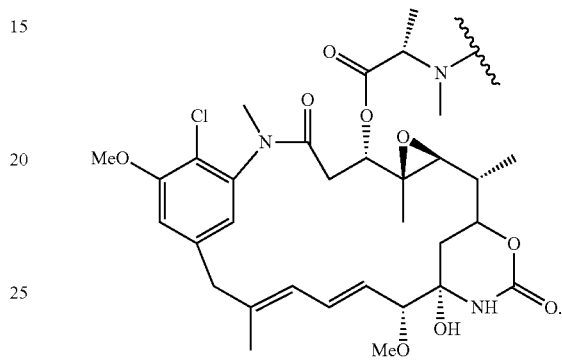

In another more specific embodiment, the conjugate is represented by the following formula:

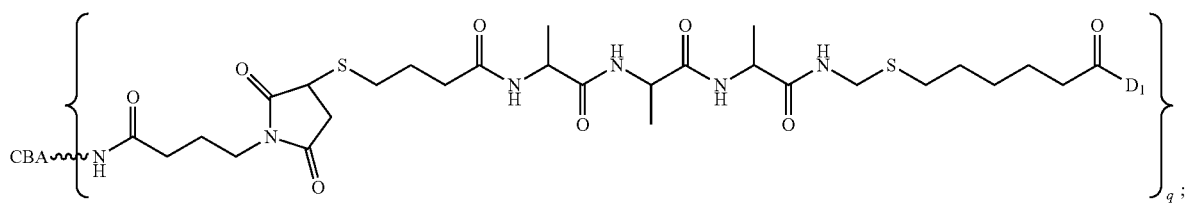

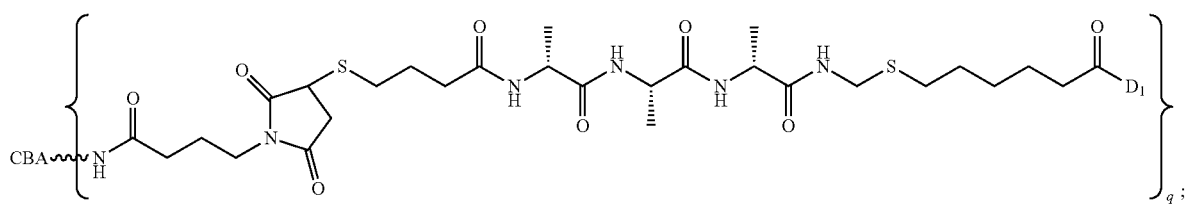

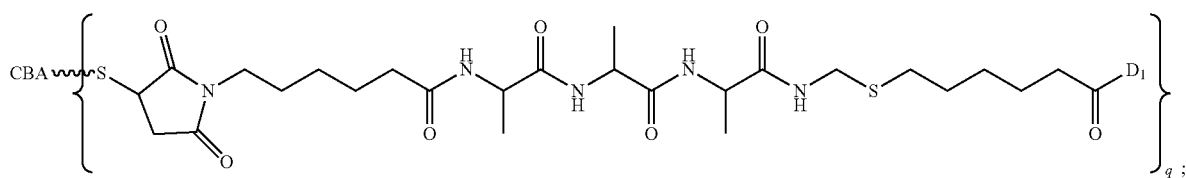

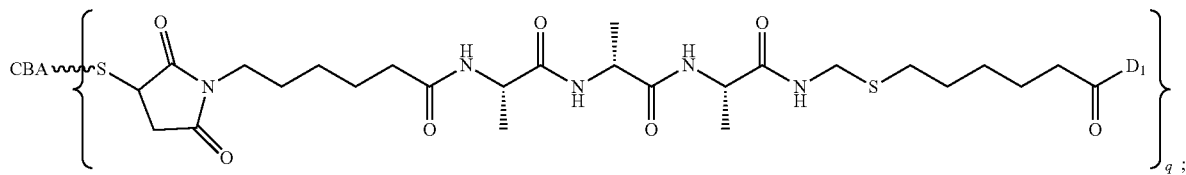

-continued

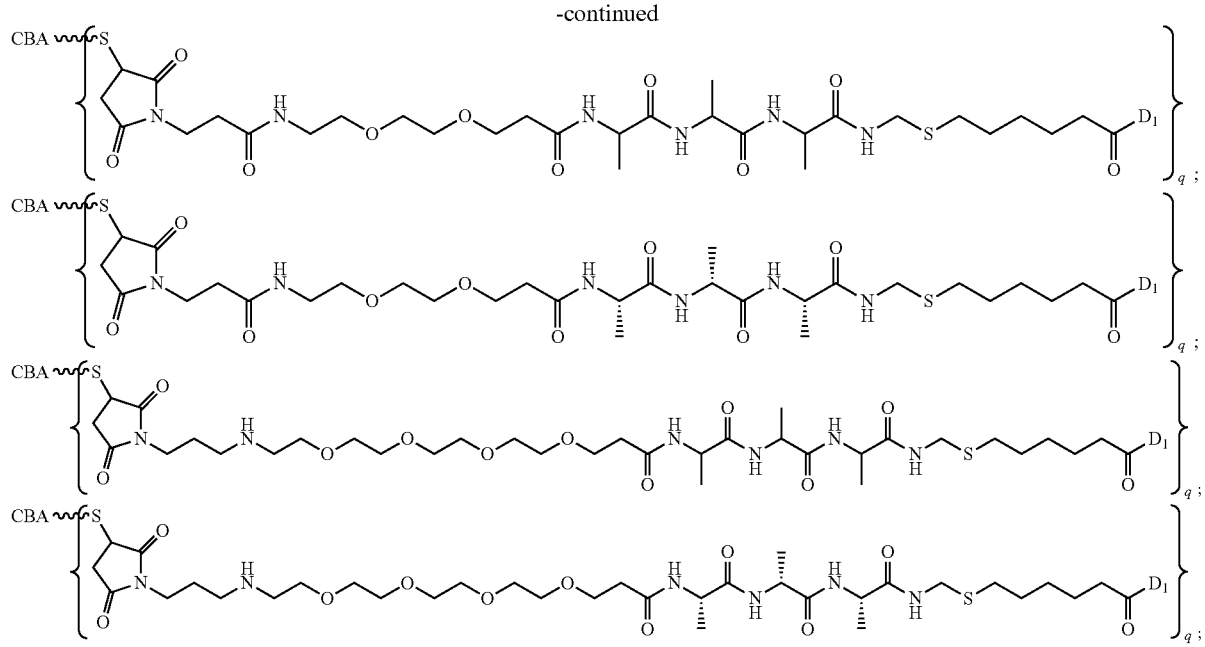

wherein: $D_1$ is represented by the following formula:

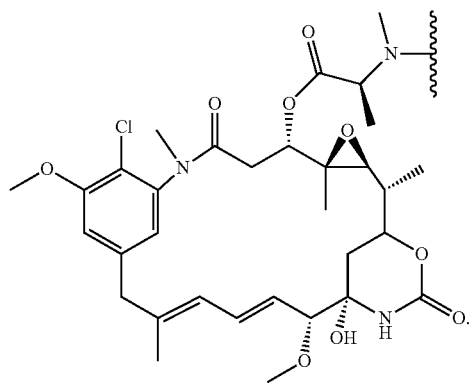 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)CC(OC(=O)N2)[C@@H](C)[C@@H]2O[C@@]12C]

In some embodiments, for the conjugates of the present invention described above (e.g., conjugates described in the first embodiment or the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$ specific embodiment), the cell-binding agents (CBA) can be any one of the cell-binding agents (CBA) described herein.

In some embodiments, for the conjugates of the present invention described above (e.g., conjugates described in the first embodiment or the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, or $13^{th}$ specific embodiment), the cell-binding agent (CBA) binds to target cells selected from tumor cells, virus infected cells, microorganism infected cells, parasite infected cells, autoimmune cells, activated cells, myeloid cells, activated T-cells, B cells, or melanocytes; cells expressing the CA6, CAK1, CD4, CD6, CD19, CD20, CD22, CD30, CD33, CD37, CD38, CD40, CD44, CD56, CD123, CD138, CanAg, CALLA, CEACAM5, FGFR3, LAMP1, p-cadherin, CA6, TROP-2, DLL-3, CDH6, AXL, SLITRK6, ENPP3, BCMA, Tissue Factor (TF), CD352, Her-2 or Her-3 antigens; or cells expressing insulin growth factor receptor, epidermal growth factor receptor, Nectin-4, mesothelin, GD3, prolactin receptor, and folate receptor.

In some embodiments, for the conjugates of the present invention described above (e.g., conjugates described in the first embodiment or the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, or $13^{th}$ specific embodiment), the cell-binding agent is an antibody or an antigen-binding fragment thereof, a single chain antibody, a single chain antibody fragment that specifically binds to a target cell, a monoclonal antibody, a single chain monoclonal antibody, or a monoclonal antibody fragment that specifically binds to a target cell, a chimeric antibody, a chimeric antibody fragment that specifically binds to a target cell, a domain antibody, a domain antibody fragment that specifically binds to a target cell, a probody, a nanobody, a lymphokine, a hormone, a vitamin, a growth factor, a colony stimulating factor, a nutrient-transport molecule, a Bicycles® peptide, or a pentarin.

In some embodiments, for the conjugates of the present invention described above (e.g., conjugates described in the first embodiment or the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, or $13^{th}$ specific embodiment), the cell-binding agent is an antibody or an antigen-binding fragment thereof. In other embodiments, the cell-binding agent is a resurfaced antibody or a resurfaced antibody fragment thereof. In some embodiments, the cell-binding agent is a monoclonal antibody or a monoclonal antibody fragment thereof. In some embodiments, the cell-binding agent is a humanized antibody or a humanized antibody fragment thereof. In other embodiments, the cell-binding agent is a chimeric antibody or a chimeric antibody fragment thereof. In some embodiments, the cell-binding agent is an anti-folate receptor antibody or an antibody fragment thereof, an anti-EGFR antibody or an antibody fragment thereof, an anti-CD33 antibody or an antibody fragment thereof, an anti-CD19 antibody or an antibody fragment thereof, an anti-Muc1 antibody or an antibody fragment thereof, or an anti-CD37 antibody or an antibody fragment thereof.

In one embodiment, the conjugate of the present invention is represented by the following formula:

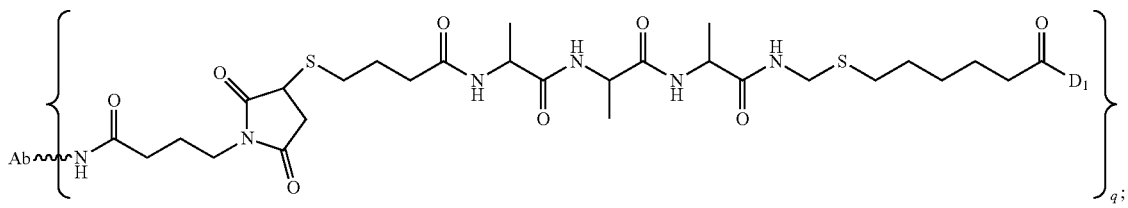

wherein Ab is an anti-folate receptor antibody.

In another embodiment, the conjugate of the present invention is represented by the following formula:

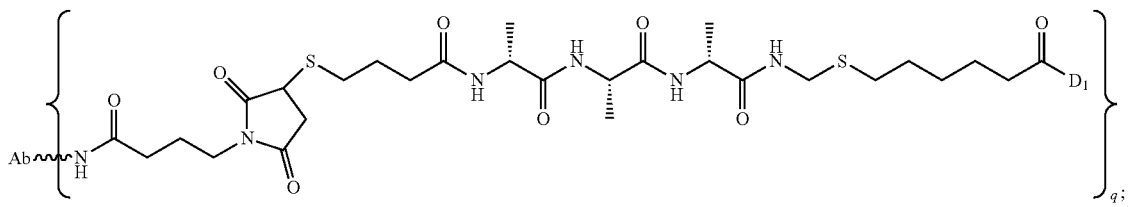

wherein Ab is an anti-folate receptor antibody. In a specific embodiment, the anti-folate receptor antibody comprises (a) a heavy chain CDR1 comprising GYFMN (SEQ ID NO: 4); a heavy chain CDR2 comprising RIHPYDGDTFYNQXaa$_1$FXaa$_2$Xaa$_3$ (SEQ ID NO: 5); and a heavy chain CDR3 comprising YDGSRAMDY (SEQ ID NO: 6); and (b) a light chain CDR1 comprising KASQS-VSFAGTSLMH (SEQ ID NO: 7); a light chain CDR2 comprising RASNLEA (SEQ ID NO: 8); and a light chain CDR3 comprising QQSREYPYT (SEQ ID NO: 9); wherein Xaa$_1$ is selected from K, Q, H, and R; Xaa$_2$ is selected from Q, H, N, and R; and Xaa$_3$ is selected from G, E, T, S, A, and V. Preferably, the heavy chain CDR2 sequence comprises RIHPYDGDTFYNQKFQG (SEQ ID NO: 10). In another specific embodiment, the anti-folate receptor antibody comprises a heavy chain variable domain having the amino acid sequence of SEQ ID NO: 14, and a light chain variable domain having the amino acid sequence of SEQ ID NO: 15 or SEQ ID NO: 16. In another specific embodiment, the anti-folate receptor antibody comprises the heavy chain having the amino acid sequence of SEQ ID NO: 11, and the light chain having the amino acid sequence of SEQ ID NO: 12 or SEQ ID NO: 13. Preferably, the antibody comprises the heavy chain having the amino acid sequence of SEQ ID NO: 11 and the light chain having the amino acid sequence of SEQ ID NO: 13 (huFOLR1). In another specific embodiment, the anti-folate receptor antibody is encoded by the plasmid DNA deposited with the ATCC on Apr. 7, 2010 and having ATCC deposit nos. PTA-10772 and PTA-10773 or 10774. See WO2011/106528, incorporated herein by reference.

In some embodiments, for the conjugates of the present invention described above (e.g., conjugates described in the first embodiment or the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$, 12$^{th}$, or 13$^{th}$ specific embodiment), q is an integer from 1 to 10, from 1 to 8, or from 2 to 5. In some embodiments, for conjugates that is covalently linked to the cytotoxic agent through a Cys thiol group, q is 1 or 2. In one embodiment, q is 2.

In some embodiments, for compositions (e.g., pharmaceutical compositions) comprising the conjugates of the present invention described above (e.g., conjugates described in the first embodiment or the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$, 12$^{th}$, or 13$^{th}$ specific embodiment), the average number of the cytotoxic agent per cell-binding agent (CBA, e.g., antibody) (i.e., average value of q), also known as Drug-Antibody Ratio (DAR) in the compositions is in the range of 1.0 to 8.0. In some embodiments, DAR is in the range of 1.0 to 5.0, 1.0 to 4.0, 1.0 to 3.4, 1.0 to 3.0, 1.5 to 2.5, 2.0 to 2.5, or 1.8 to 2.2.

Compounds of the Present Invention

In a second aspect, the present invention provides maytansinoid derivatives described herein.

In a second embodiment, the compounds of the present invention is represented by formula (II), (III) or (IV):

 (II),

 (III), or

 (IV)

or a pharmaceutically acceptable salt thereof, wherein:

L$_2$' is absent or a spacer bearing a reactive moiety that can form a covalent bond with a cell-binding agent;

A is an amino acid residue or a peptide comprising 2 to 20 amino acid residues;

R$^1$ and R$^2$ are each independently H or a C$_{1-6}$alkyl (e.g., R$^1$ and R$^2$ are each independently H or a C$_{1-3}$alkyl);

L$_1$ is a spacer;

D-L$_1$-SH is a cytotoxic agent;

q is an integer from 1 to 20;

A' is an amino acid or a peptide comprising 2 to 20 amino acids;

L$_3$ is represented by the following formula:

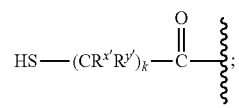

R$^{x'}$ and R$^{y'}$, for each occurrence, are independently H, —OH, halogen, —O—(C$_{1-4}$ alkyl), —SO$_3$H, —NR$_{40}$R$_{41}$R$_{42}^+$, or a C$_{1-4}$ alkyl optionally substituted with —OH, halogen, SO$_3$H or NR$_{40}$R$_{41}$R$_{42}^+$, wherein R$_{40}$, R$_{41}$ and R$_{42}$ are each independently H or a C$_{1-4}$ alkyl; and k is an integer from 1 to 10.

In one embodiment, L$_1$ is -L$_1$'-C(=O)—; and L$_1$' is an alkylene, an alkenylene, an alkynylene, a cycloalkylene, a heterocycloalkylene, an arylene, or a heteroarylene, wherein the —C(=O)— group in L$_1$ is connected to D.

In another embodiment, at least one of R$^1$ and R$^2$ is H. In a more specific embodiment, one of R$^1$ and R$^2$ is H and the other one is Me.

In a 14$^{th}$ specific embodiment, for compounds of formula (II), (III) and (IV), R$^1$ and R$^2$ are each independently H or Me; and the remaining variables are as described above in the second embodiment. In a more specific embodiment, R$^1$ and R$^2$ are both H.

In a 15$^{th}$ specific embodiment, for compounds of formula (II), (III) and (IV), L$_1$ is -L$_1$'C(=O)—; and L$_1$' is an alkylene or a cycloalkylene, wherein the —C(=O)— group in L$_1$ is connected to D; and the remaining variables are as described above in the second embodiment or the 14$^{th}$ specific embodiment. In a more specific embodiment, L$_1$' is C$_{1-10}$alkylene. In another more specific embodiment, L$_1$' is C$_{1-20}$alkylene.

In a 16$^{th}$ specific embodiment, for compounds of formula (II), (III) and (IV), L$_1$ is —CR$^3$R$^4$—(CH$_2$)$_{1-8}$—C(=O)—; R$^3$ and R$^4$ are each independently H or Me; and the remaining variables are as described above in the second embodiment or the 14$^{th}$ specific embodiment. In a more specific embodiment, R$^3$ and R$^4$ are both Me.

In a 17$^{th}$ specific embodiment, for compounds of formula (II), (III) and (IV), L$_1$ is —CR$^3$R$^4$—(CH$_2$)$_{2-5}$—C(=O)— or —CR$^3$R$^4$—(CH$_2$)$_{3-5}$—C(=O)—; R$^3$ and R$^4$ are each independently H or Me; and the remaining variables are as described above in the second embodiment or the 14$^{th}$ specific embodiment. In a more specific embodiment, R$^3$ and R$^4$ are both Me. In another more specific embodiment, R$^3$ and R$^4$ are both H.

In a 18$^{th}$ specific embodiment, for compounds of formula (II), (III) and (IV), L$_1$ is —(CH$_2$)$_{4-6}$—C(=O)—; and the remaining variables are as described above in the second embodiment or the 14$^{th}$ specific embodiment.

In a 19$^{th}$ specific embodiment, for compounds of formula (II), (III) and (IV), A or A' is a peptide cleavable by a protease; the remaining variables are as described above in the second embodiment or the 14$^{th}$, 15$^{th}$, 16$^{th}$, 17$^{th}$ or 18$^{th}$ specific embodiment. In a more specific embodiment, A or A' is a peptide cleavable by a protease expressed in tumor tissue.

In a 20$^{th}$ specific embodiment, for compounds of formula (II), (III) and (IV), A or A' is a peptide having an amino acid that is covalent linked with —NH—CR$^1$R$^2$—S-L$_1$-D selected from the group consisting of Ala, Arg, Asn, Asp, Cit, Cys, selino-Cys, Gln, Glu, Gly, Ile, Leu, Lys, Met, Phe, Pro, Ser, Thr, Trp, Tyr and Val, each independently as L or D isomer; the remaining variables are as described above in the second embodiment or the 14$^{th}$, 15$^{th}$, 16$^{th}$, 17$^{th}$ or 18$^{th}$ specific embodiment. In a more specific embodiment, the amino acid connected to —NH—CR$^1$R$^2$—S-L$_1$-D is an L amino acid.

In a 21$^{st}$ specific embodiment, for compounds of formula (II), (III) and (IV), A or A' is selected from the group consisting of Gly-Gly-Gly, Ala-Val, Val-Ala, D-Val-Ala, Val-Cit, D-Val-Cit, Val-Lys, Phe-Lys, Lys-Lys, Ala-Lys, Phe-Cit, Leu-Cit, Ile-Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Ala-Ala, D-Ala-Ala-Ala, Ala-D-Ala-Ala, Ala-Ala-D-Ala, Ala-Leu-Ala-Leu (SEQ ID NO: 1), β-Ala-Leu-Ala-Leu (SEQ ID NO: 2), Gly-Phe-Leu-Gly (SEQ ID NO: 3), Val-Arg, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, Gln-Val, Asn-Ala, Gln-Phe, Gln-Ala, D-Ala-Pro, and D-Ala-tBu-Gly, wherein the first amino acid in each peptide is connected to L$_2$ group and the last amino acid in each peptide is connected to —NH—CR$^1$R$^2$—S-L$_1$-D; and the remaining variables are as described above in the second embodiment or the 14$^{th}$, 15$^{th}$, 16$^{th}$, 17$^{th}$ or 18$^{th}$ specific embodiment. In a more specific embodiment, A is Ala-Ala-Ala, Ala-D-Ala-Ala, D-Ala-Ala-Ala, Ala-Ala-D-Ala, Ala-Ala, D-Ala-Ala, Val-Ala, D-Val-Ala, D-Ala-Pro, or D-Ala-tBu-Gly. In another more specific embodiment, A is Ala-Ala-Ala, Ala-D-Ala-Ala, Ala-Ala, D-Ala-Ala, Val-Ala, D-Val-Ala, D-Ala-Pro, or D-Ala-tBu-Gly.

For A described herein, when specific amino acid or peptide sequence is referenced, it means the amino acid residue or peptide comprising amino acid residue, in which hydrogen atom is removed from the amino end of the amino acid connected to L$_2$ group and the hydroxyl group is removed from the carboxy end of the amino acid connected to —NH—CR$^1$R$^2$-S-L$_1$-D. For example, when A is represented by Ala-Ala-Ala, it refers to —NH—CH(CH$_3$)—C(=O)—NH—CH(CH$_3$)—C(=O)—NH—CH(CH$_3$)—C(=O)—.

For A' described herein, when specific amino acid or peptide sequence is referenced, it means the amino acid residue or peptide comprising amino acid residue, in which the hydroxyl group is removed from the carboxy end of the amino acid connected to —NH—CR$^1$R$^2$-S-L$_1$-D. For example, when A' is represented by Ala-Ala-Ala, it refers to NH$_2$—CH(CH$_3$)—C(=O)—NH—CH(CH$_3$)—C(=O)—NH—CH(CH$_3$)—C(=O)—.

In a 22$^{nd}$ specific embodiment, for compounds of formula (II), (III) and (IV), D is a maytansinoid; and the remaining variables are as described above in the second embodiment or the 14$^{th}$, 15$^{th}$, 16$^{th}$, 17$^{th}$, 18$^{th}$, 19$^{th}$, 20$^{th}$ or 21$^{st}$ specific embodiment. In a more specific embodiment, D is represented by the following formula:

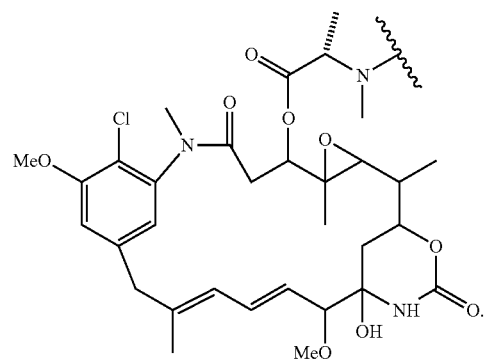 [SMILES: *N(C)[C@@H](C)C(=O)OC1CC(=O)N(C)c2cc(cc(OC)c2Cl)C/C(C)=C/C=C/C(OC)C2(O)CC(OC(=O)N2)C(C)C2OC12C]

In another more specific embodiment, D is represented by the following formula:

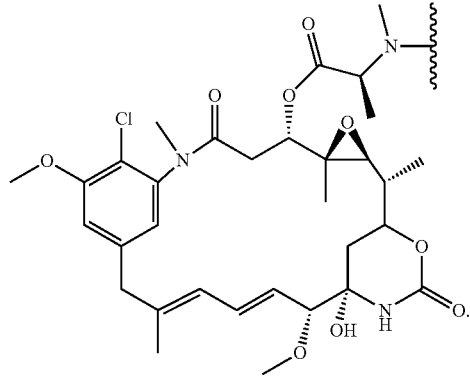 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)CC(OC(=O)N2)[C@@H](C)[C@@H]2O[C@@]12C]

In a 23$^{rd}$ specific embodiment, for compounds of formula (II), L$_2$' is represented by the following structural formula:

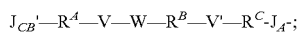

wherein:

R$^A$ is an alkylene, a cycloalkylalkylene, an arylene, heteroarylene or a heterocyclylene;

R$^B$ and R$^C$ are each independently absent, an alkylene, a cyclalkylene, or an arylene;

V and V' are each independently —(O—CH$_2$—CH$_2$)$_p$—, or —(CH$_2$—CH$_2$—O)$_p$—;

p is 0 or an integer from 1 to 10;

W is absent,

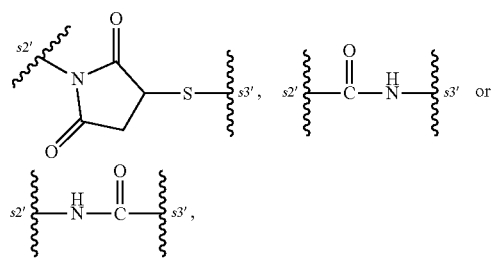

wherein s2' indicates the site connected to V, R$^A$ or J$_{CB}$ and s3' indicates the site connected to R$^B$, V', R$^C$ or J$_A$;

J$_{CB}$ is —C(=O)OH, —COE,

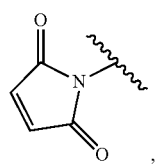

X$^1$—CR$^b$R$^c$—C(=O)—, X$^1$—CR$^b$R$^c$—C(=O)—NR$^e$—,

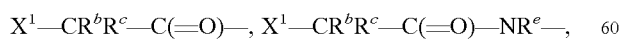

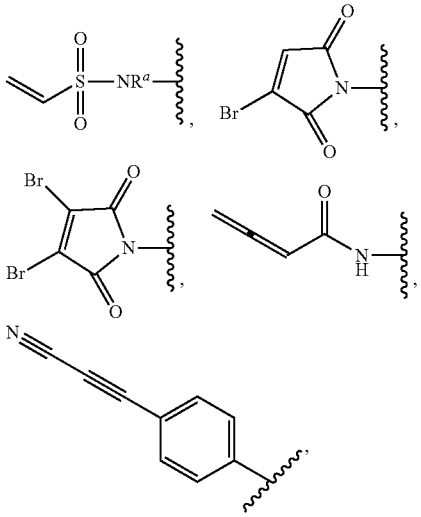

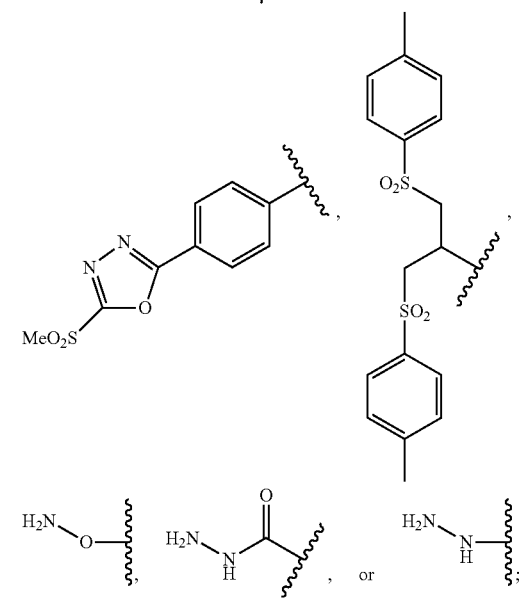

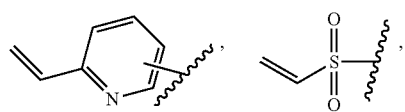

R$^a$, R$^b$, R$^c$, and R$^e$, for each occurrence, are independently H or an alkyl;

X$^1$ is a halogen (e.g., —Cl, —Br or —I);

COE is a reactive ester;

J$_A$ is —C(=O)—; and the remaining variables are as described above in the second embodiment or the 14$^{th}$, 15$^{th}$, 16$^{th}$, 17$^{th}$, 18$^{th}$, 19$^{th}$, 20$^{th}$, 21$^{st}$ or 22$^{nd}$ specific embodiment.

In a more specific embodiment, for compounds of the 23rd specific embodiment, R$^A$ is an alkylene, a cycloalkylalkylene, or an arylene; W is absent, or

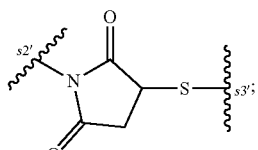

and J$_{CB}$' is —C(=O)OH, —COE,

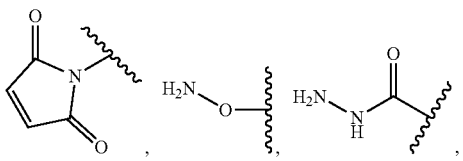

or

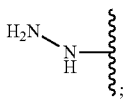

and the remaining variables as as described above in the 23$^{rd}$ specific embodiment.

In a more specific embodiment, p is 0 and R$^c$ is absent; and the remaining variables as as described above in the 23$^{rd}$ specific embodiment.

In another more specific embodiment, J$_{CB}$'' is —C(=O)OH, —COE or

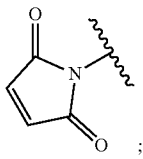

and the remaining variables as as described above in the 23$^{rd}$ specific embodiment.

In a 24$^{th}$ embodiment, for compounds of formula (II), L$_2$' is represented by the following structural formulas:

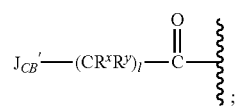
(L2a')

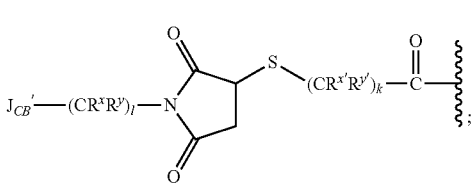
(L2b')

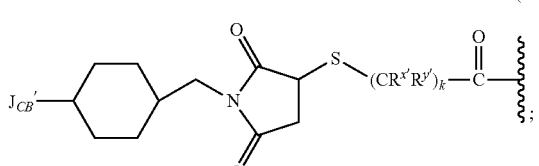
(L2c')

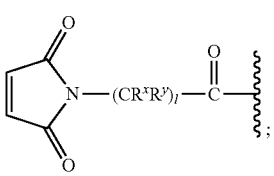
(L2d')

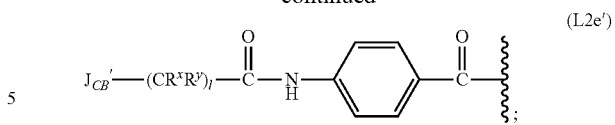
(L2e')

wherein:
R$^x$, R$^y$, and R$^{x'}$ and R$^{y'}$, for each occurrence, are independently H, —OH, halogen, —O—(C$_{1-4}$ alkyl), —SO$_3$H, —NR$_{40}$R$_{41}$R$_{42+}$, or a C$_{1-4}$ alkyl optionally substituted with —OH, halogen, —SO$_3$H or NR$_{40}$R$_{41}$R$_{42}$$^+$, wherein R$_{40}$, R$_{41}$ and R$_{42}$ are each independently H or a C$_{1-4}$ alkyl;
l and k are each independently an integer from 1 to 10;
J$_{CB}$' is —C(=O)OH or —COE;
and the remaining variables are as described above in the second embodiment or the 14$^{th}$, 15$^{th}$, 16$^{th}$, 17$^{th}$, 18$^{th}$, 19$^{th}$, 20$^{th}$, 21$^{st}$, 22$^{nd}$ or 23$^{rd}$ specific embodiment.

In a more specific embodiment, R$^x$, R$^y$, R$^{x'}$ and R$^{y'}$ are all H; and the remaining variables are as described above in the 24$^{th}$ specific embodiment.

In another more specific embodiment, l and k are each independently an integer an integer from 2 to 6; and the remaining variables are as described above in the 24$^{th}$ specific embodiment.

In an even more specific embodiment, R$^x$, R$^y$, R$^{x'}$ and R$^{y'}$ are all H; l and k are each independently an integer from 2 to 6; and the remaining variables are as described above in the 24$^{th}$ specific embodiment.

In another more specific embodiment, L$_2$' is represented by the following structural formula:

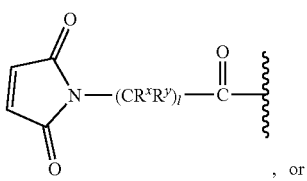
(L2d')

, or

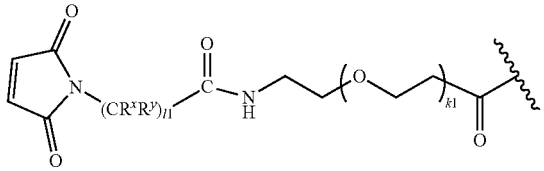
(L2f')

wherein:
R$^x$ and R$^y$ are both H;
l and l1 are each an integer from 1 to 10; and
k1 is an integer from 1 to 12.

In a even more specific embodiment, l and l1 are each an integer from 2 to 6.

In a 25$^{th}$ specific embodiment, for compounds of formula (IV), R$^{x'}$ and R$^{y'}$ are both H; and the remaining variables are as described above in the second embodiment or the 14$^{th}$, 15$^{th}$, 16$^{th}$, 17$^{th}$, 18$^{th}$, 19$^{th}$, 20$^{th}$, 21$^{st}$, or 22$^{nd}$ specific embodiment.

In a more specific embodiment, k is an integer from 2 to 6; and the remaining variables are as described above in 25$^{th}$ specific embodiment.

In another more specific embodiment, k is 3; and the remaining variables are as described above in 25$^{th}$ specific embodiment.

In a 26th specific embodiment, the compounds of formula (II) is represented by the following formula:

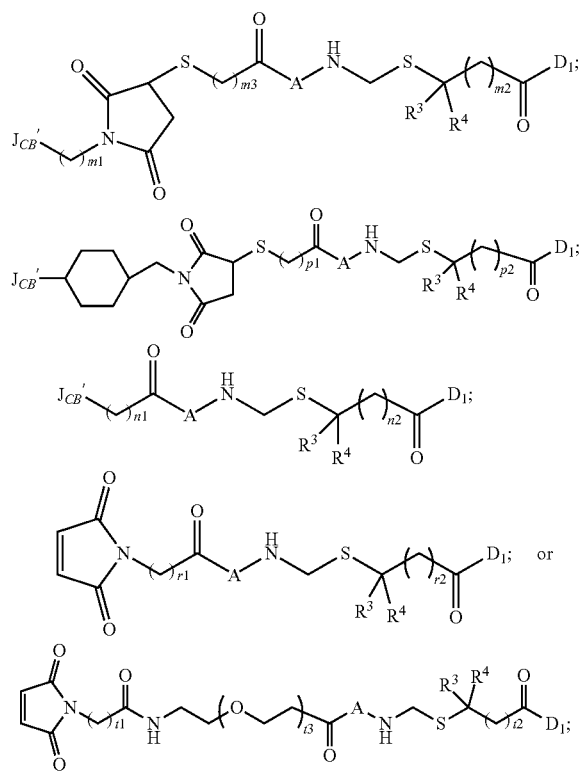

or a pharmaceutically acceptable salt thereof, wherein:
R$^3$ and R$^4$ are each independently H or Me;
m1, m3, n1, r1, p1 and t1 are each independently an integer from 1 to 10;
m2, n2, r2, p2 and t2 are each independently an integer from 1 to 19;
t3 is an integer from 1 to 12;
J$_{CB}$' is —C(=O)OH or —COE;
D$_1$ is represented by the following formula:

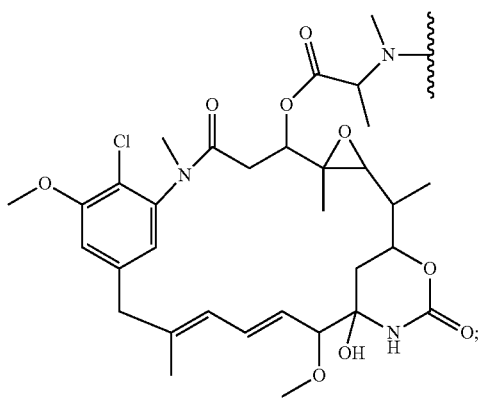 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]

and
the remaining variables are as described in the second embodiment or the 19$^{th}$, 20$^{th}$ or 21$^{st}$ specific embodiment.
In a more specific embodiment, A is Ala-Ala-Ala, Ala-D-Ala-Ala, D-Ala-Ala-Ala, Ala-Ala-D-Ala, Ala-Ala, D-Ala-Ala, Val-Ala, D-Val-Ala, D-Ala-Pro, or D-Ala-tBu-Gly. In another more specific embodiment, A is Ala-Ala-Ala, Ala-D-Ala-Ala, Ala-Ala, D-Ala-Ala, Val-Ala, D-Val-Ala, D-Ala-Pro, or D-Ala-tBu-Gly.

In a more specific embodiment, m1, m3, p1, n1, and r1 are each independently an integer from 1 to 6; and m2, n2, p2, and r2 are each independently an integer from 1 to 7.

In another more specific embodiment, m1, p1, r1, n1 and m3 are each independently an integer from 2 to 4; and m2, p2, n2 and r2 are each independently an integer from 3 to 5. In a more specific embodiment, m1, m3, p1, n1, r1 and t1 are each independently an integer from 2 to 10. In a more specific embodiment, m1, m3, p1, n1, r1 and t1 are each independently an integer from 3 to 6.

In a more specific embodiment, m2, n2, p2, r2 and t2 are each independently an integer from 2 to 10. In a more specific embodiment, m2, n2, p2, r2 and t2 are each independently an integer from 3 to 6. In a more specific embodiment, m2, n2, p2, r2 and t2 are each independently 5.

In a more specific embodiment, m1, m3, p1, n1, r1 and t1 are each independently an integer from 2 to 10 and m2, n2, p2, r2 and t2 are each independently an integer from 2 to 10. In a more specific embodiment, m1, m3, p1, n1, r1 and t1 are each independently an integer from 3 to 6 and m2, n2, p2, r2 and t2 are each independently an integer from 2 to 10. In a more specific embodiment, m1, m3, p1, n1, r1 and t1 are each independently an integer from 3 to 6 and m2, n2, p2, r2 and t2 are each independently an integer from 3 to 6.

In a more specific embodiment, r2 and t2 are each independently an integer from 2 to 6, r1 and t1 are each independently an integer from 2 to 6 and t3 is an integer from 1 to 12. In a more specific embodiment, r2 and t2 are each independently an integer from 2 to 6, r1 and t1 are each independently an integer from 2 to 6 and t3 is an integer from 1 to 6. In a more specific embodiment, r2 and t2 are each independently an integer from 2 to 6, r1 and t1 are each independently an integer from 2 to 6 and t3 is an integer from 1 to 4. In a more specific embodiment, r2 and t2 are each independently an integer from 3 to 5, r1 and t1 are each independently an integer from 2 to 6 and t3 is an integer from 1 to 12. In a more specific embodiment, r2 and t2 are each independently an integer from 3 to 5, r1 and t1 are each independently an integer from 2 to 6 and t3 is an integer from 1 to 6. In a more specific embodiment, r2 and t2 are each independently an integer from 3 to 5, r1 and t1 are each independently an integer from 2 to 6 and t3 is an integer from 1 to 4.

In a more specific embodiment, r2 and r1 are each independently an integer from 2 to 6. In a more specific embodiment, r2 is an integer from 3 to 5 and r1 is an integer from 2 to 6. In a more specific embodiment, r2 is an integer from 3 to 5 and r1 is an integer from 2 to 4. In a more specific embodiment, r2 is 4 and r1 is 2. In a more specific embodiment, r2 is 4 and r1 is 3. In a more specific embodiment, r2 is 4 and r1 is 4. In a more specific embodiment, r2 is 4 and r1 is 5. In a more specific embodiment, r2 is 4 and r1 is 6.

In yet another more specific embodiment, R$^3$ and R$^4$ are both Me. Alternatively, R$^3$ and R$^4$ are both H.

In another more specific embodiment, the compound is represented by the following formula:

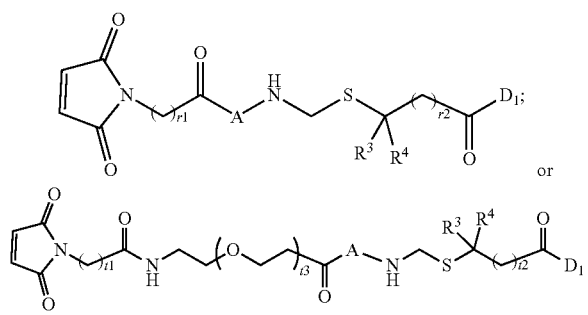
wherein:
r1 and t1 are each an integer from 2 to 10;
r2 and t2 are each an integer from 2 to 19; and
t3 is an integer from 2 to 12 (e.g., t3 is 2, 4, 6, 8, 10 or 12).
In a more specific embodiment, r1 and t1 are each an integer from 2 to 6; r2 and t2 are each an integer from 2 to 5; and t3 is an integer from 2 to 6 (e.g. t3 is 2, 4 or 6).
In a 27$^{th}$ specific embodiment, the compounds of formula (II) is represented by the following formula:
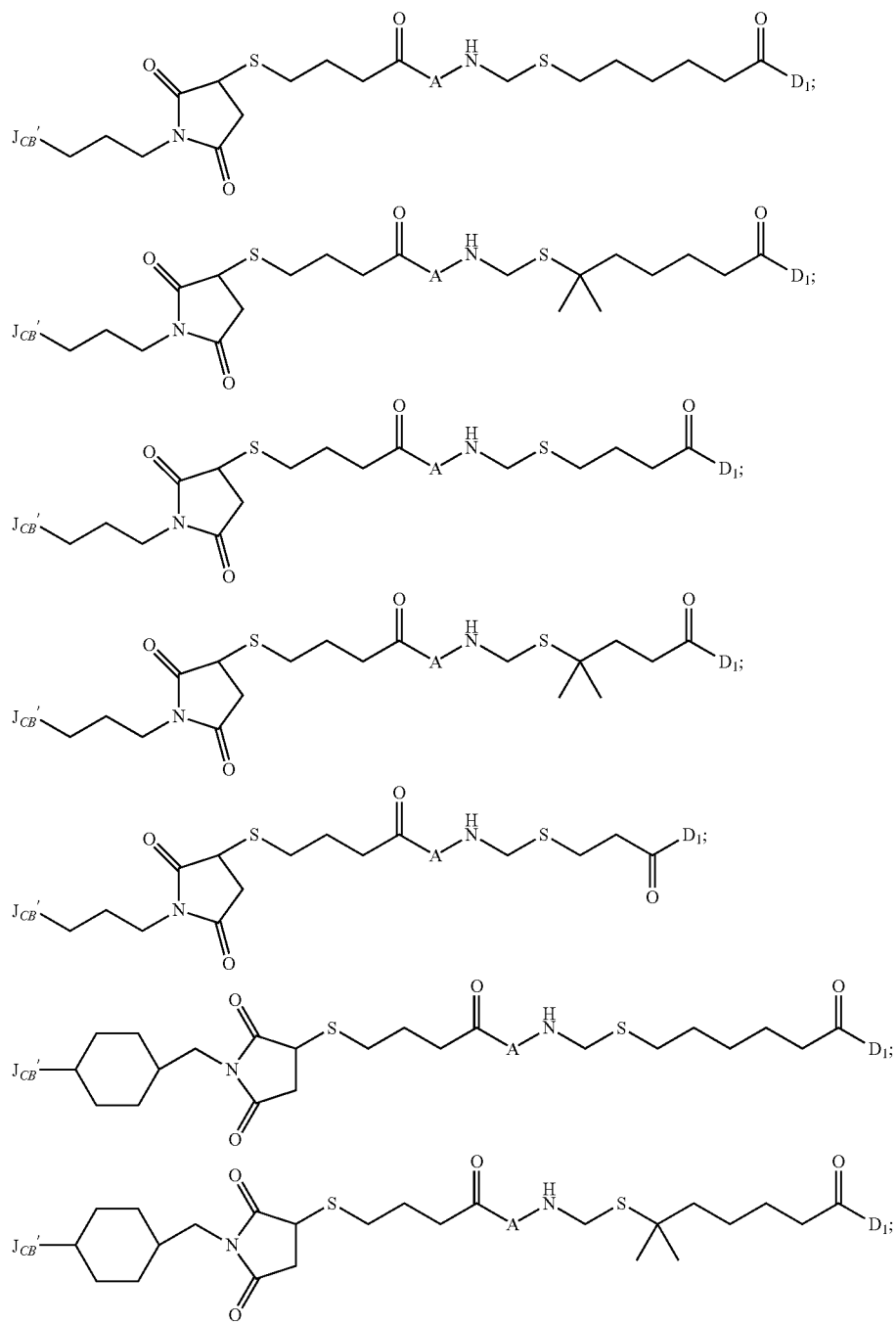

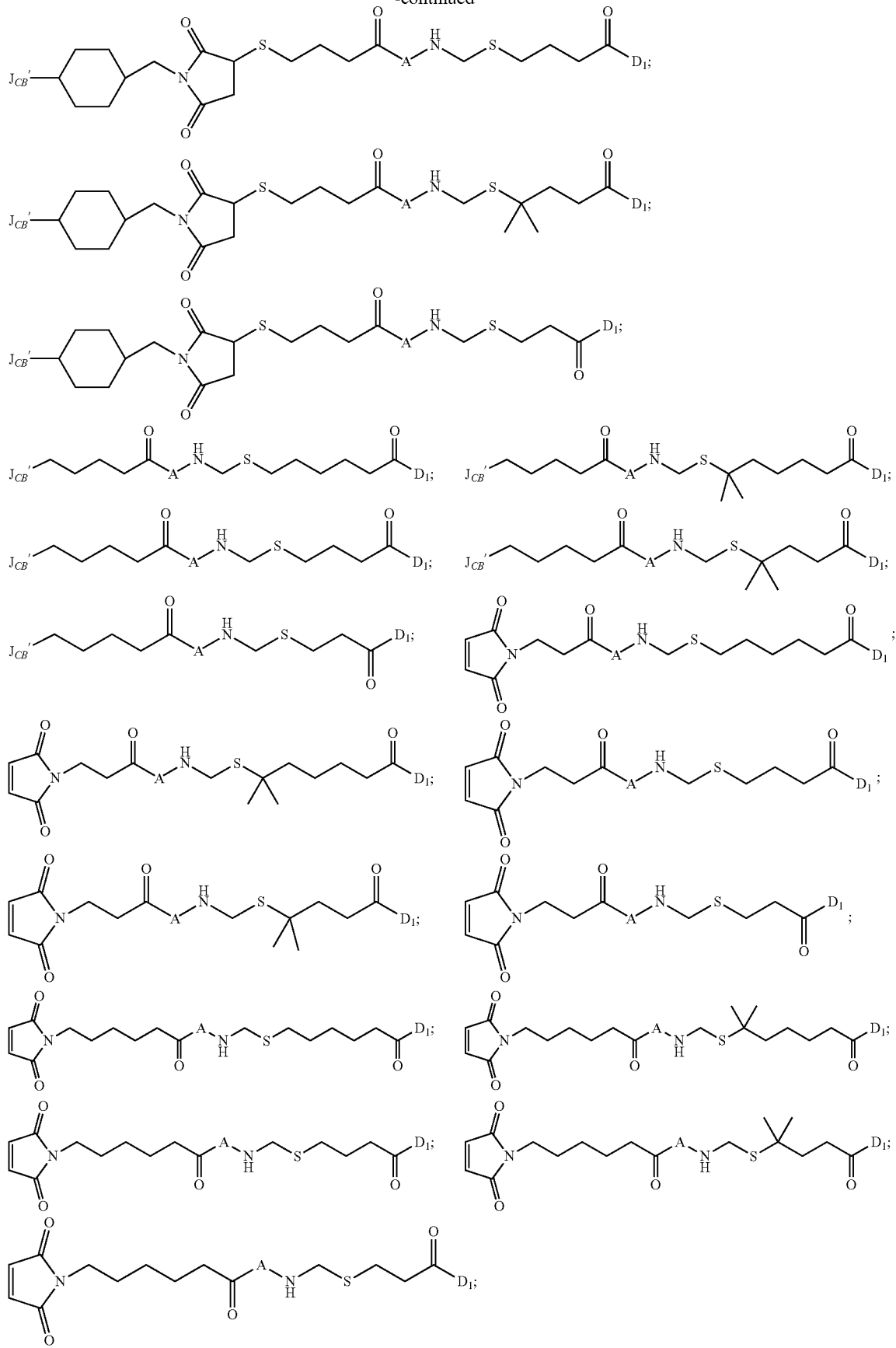

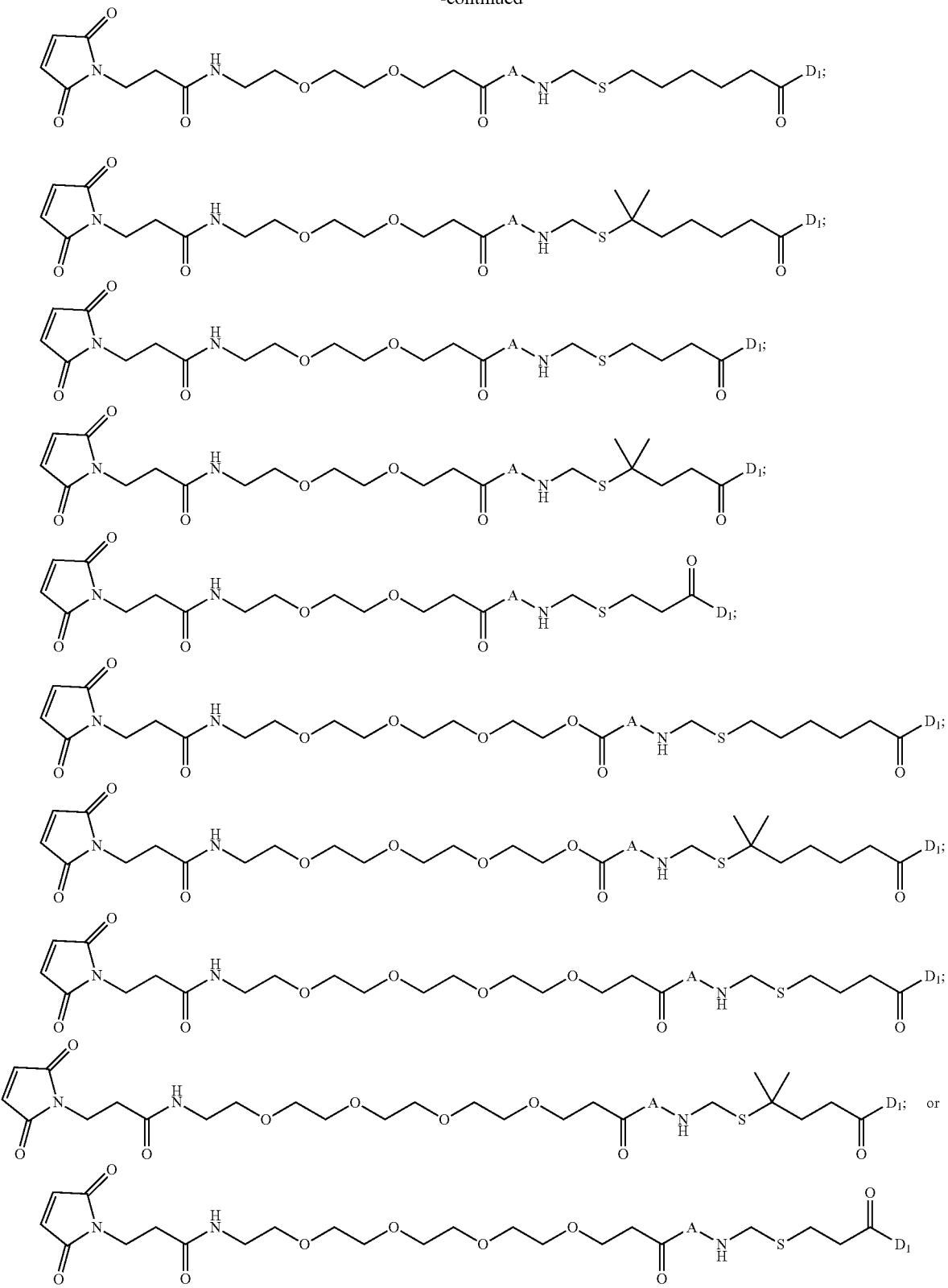
or a pharmaceutically acceptable salt thereof, wherein:
A is Ala-Ala-Ala, Ala-D-Ala-Ala, D-Ala-Ala-Ala, Ala-Ala-D-Ala, Ala-Ala, D-Ala-Ala, Val-Ala, D-Val-Ala, D-Ala-Pro, or D-Ala-tBu-Gly (more specifically, A is Ala-Ala-Ala, Ala-D-Ala-Ala, Ala-Ala, D-Ala-Ala, Val-Ala, D-Val-Ala, D-Ala-Pro, or D-Ala-tBu-Gly),
$J_{CB}'$ is —C(=O)OH or —COE; and $D_1$ is represented by the following formula:
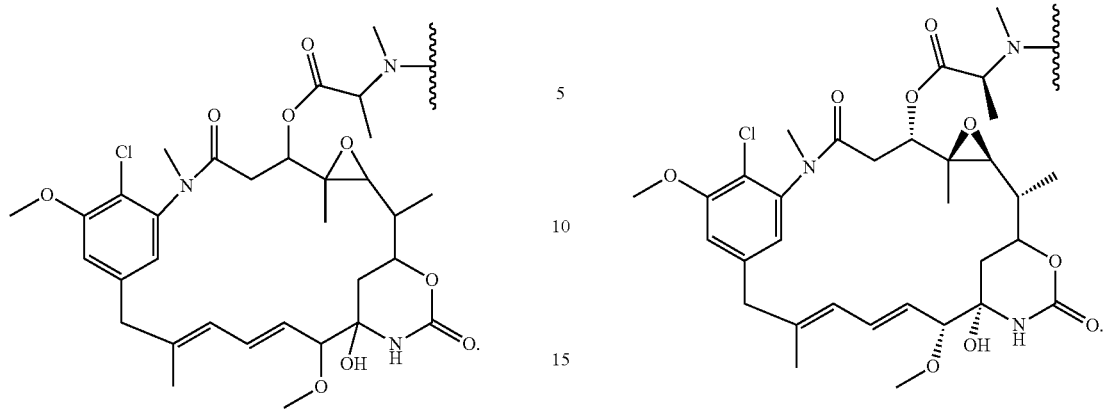
In a even more specific embodiment, $D_1$ is represented by the following formula:
Also in a $27^{th}$ specific embodiment, the compounds of formula (II) is represented by the following formula:
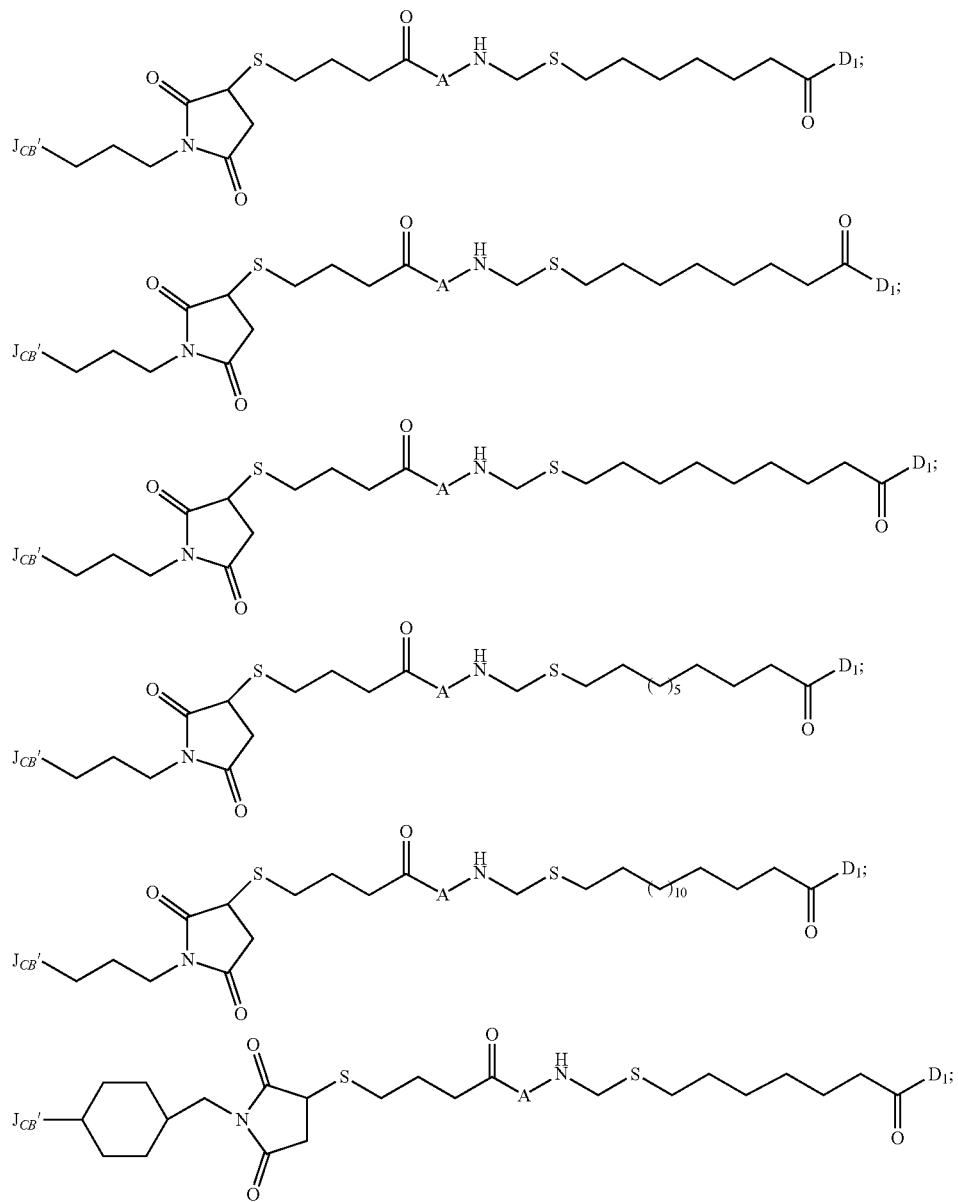

-continued
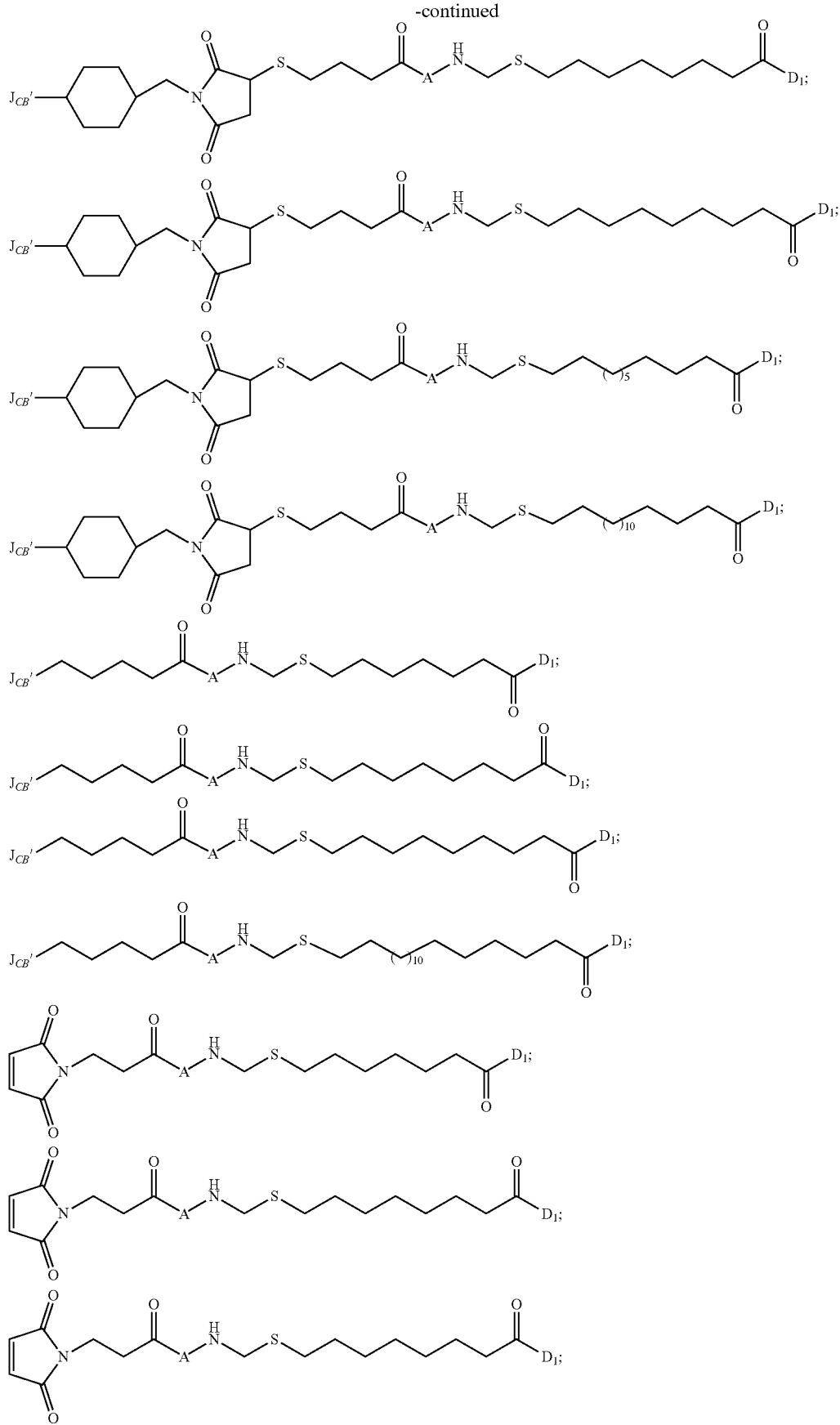

-continued
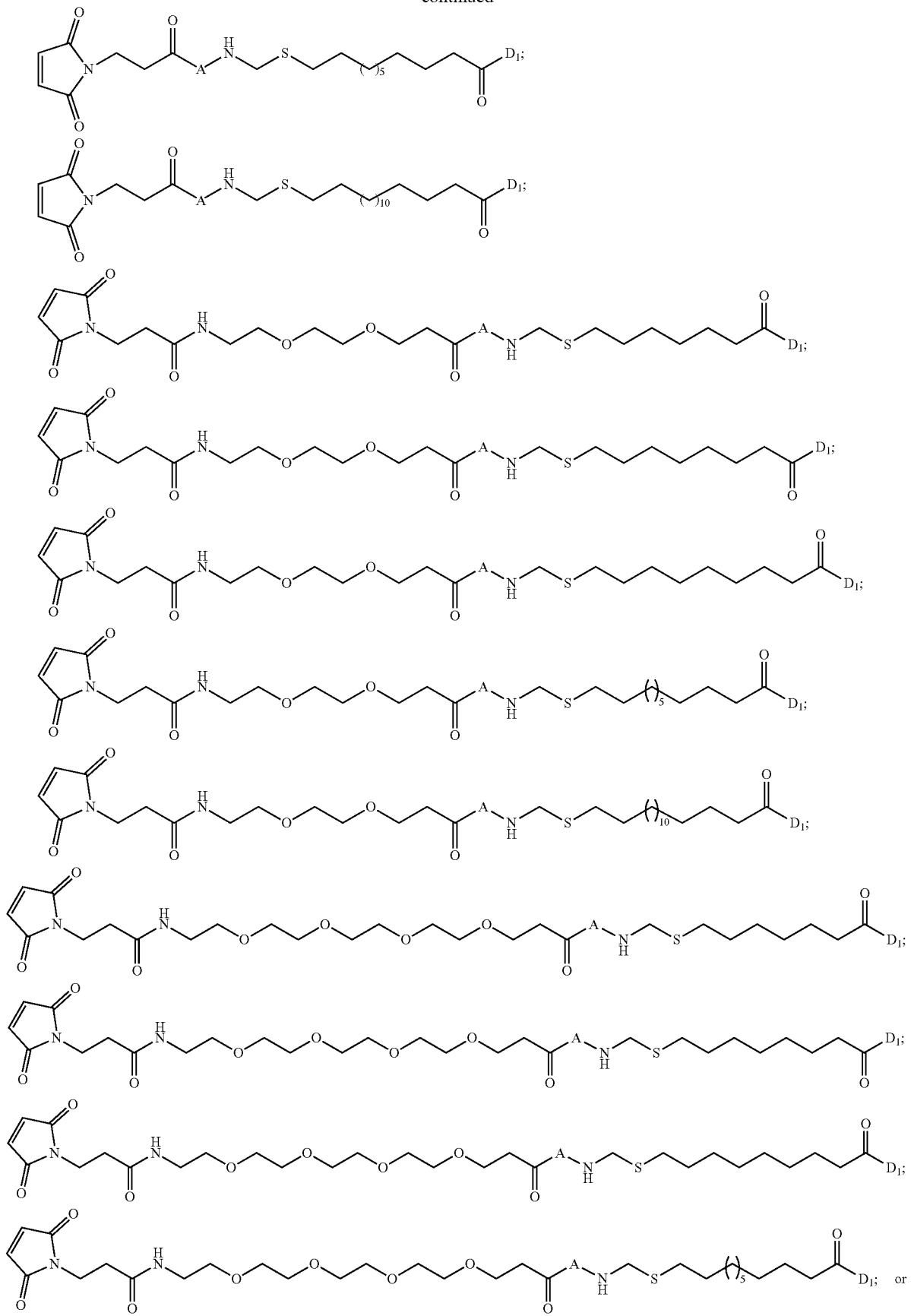

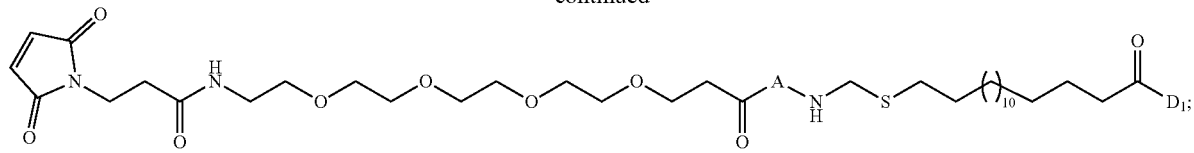

or a pharmaceutically acceptable salt thereof, wherein:

A is Ala-Ala-Ala, Ala-D-Ala-Ala, D-Ala-Ala-Ala, Ala-Ala-D-Ala, Ala-Ala, D-Ala-Ala, Val-Ala, D-Val-Ala, D-Ala-Pro, or D-Ala-tBu-Gly (more specifically, A is Ala-Ala-Ala, Ala-D-Ala-Ala, Ala-Ala, D-Ala-Ala, Val-Ala, D-Val-Ala, D-Ala-Pro, or D-Ala-tBu-Gly), $J_{CB}'$ is —C(═O)OH or —COE; and $D_1$ is represented by the following formula:

In a even more specific embodiment, $D_1$ is represented by the following formula:

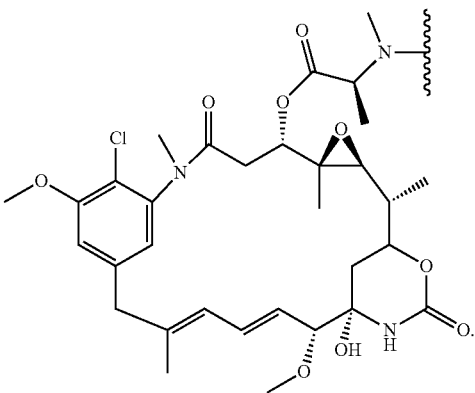 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)CC(OC(=O)N2)[C@@H](C)[C@@H]2O[C@@]12C]

In another more specific embodiment, the compound is represented by the following formula:

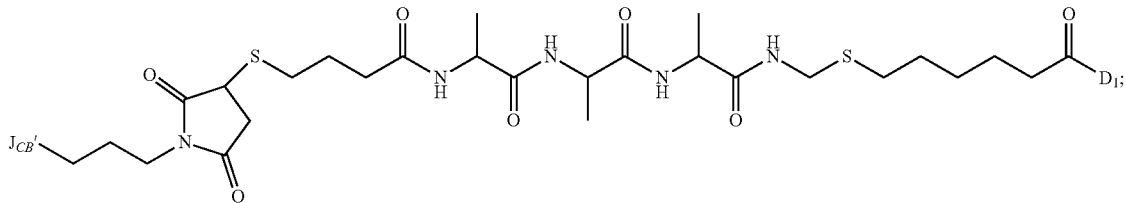

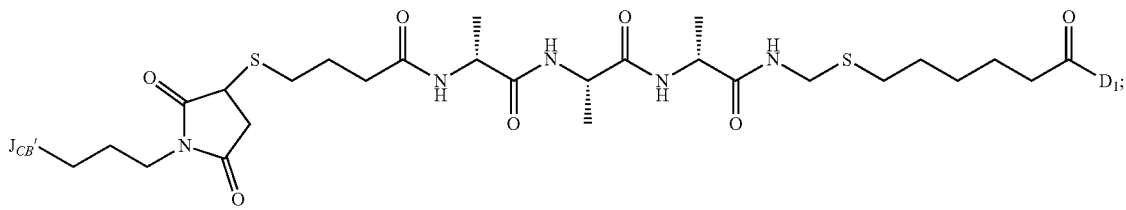

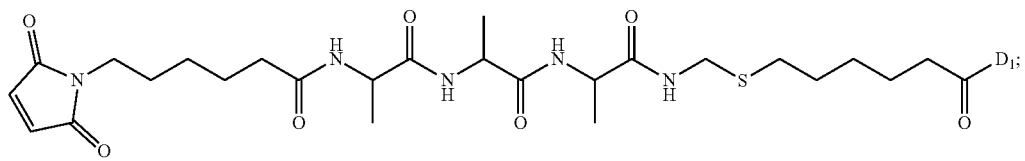

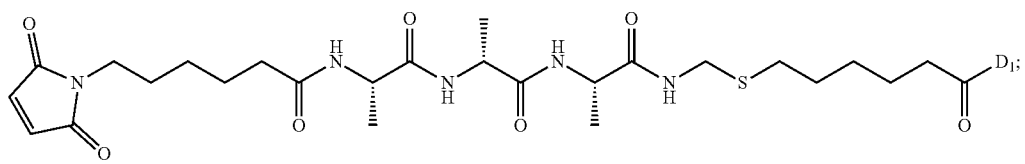

-continued

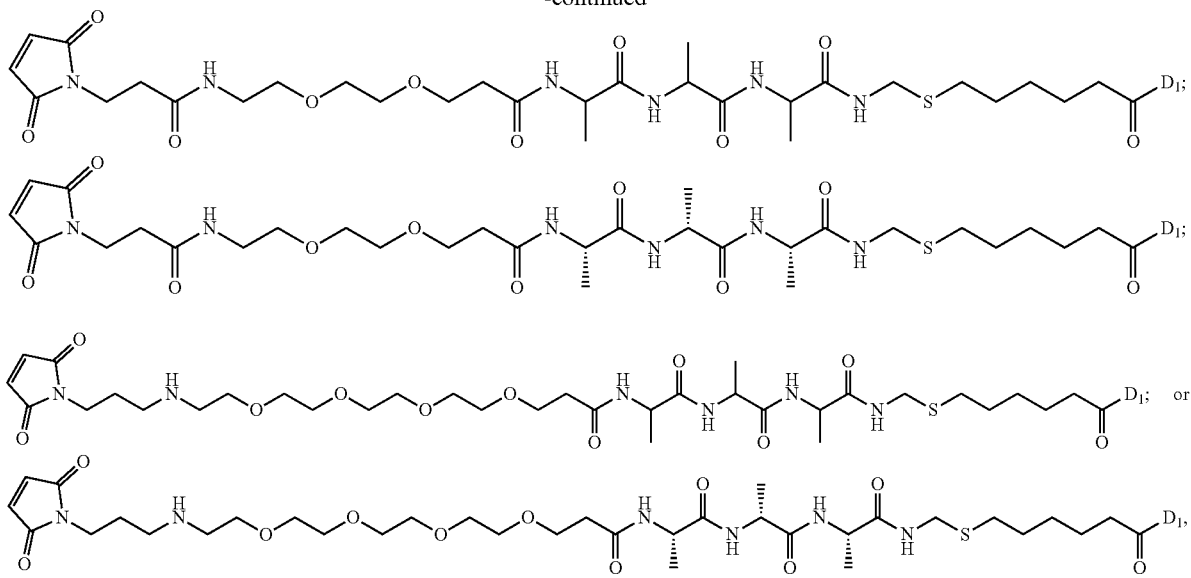

wherein $D_1$ is represented by the following formula:

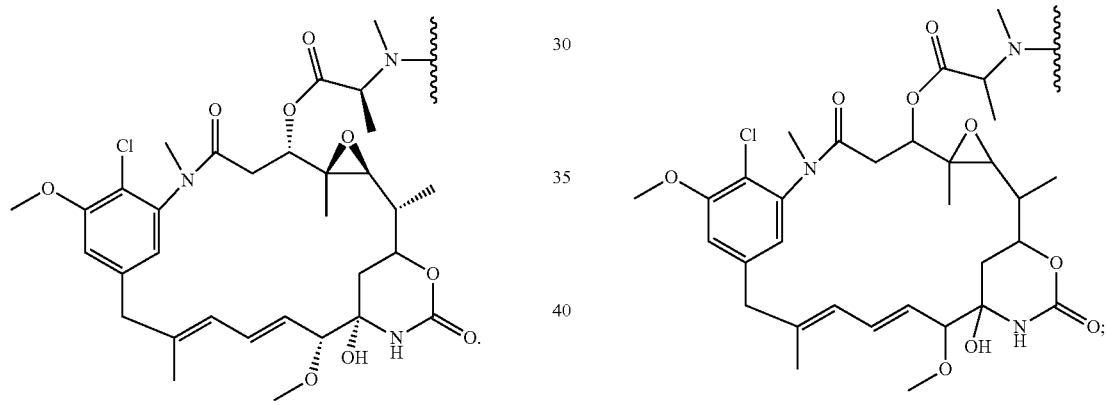

In some embodiments, —COE is a reactive ester selected from N-hydroxysuccinimide ester, N-hydroxy sulfosuccinimide ester, nitrophenyl (e.g., 2 or 4-nitrophenyl) ester, dinitrophenyl (e.g., 2,4-dinitrophenyl) ester, sulfo-tetrafluorophenyl (e.g., 4-sulfo-2,3,5,6-tetrafluorophenyl) ester, and pentafluorophenyl ester. More specifically, —COE is N-hydroxysuccinimide ester or N-hydroxy sulfosuccinimide ester.

In a 28th specific embodiment, the compounds of formula (III) is represented by the following formula:

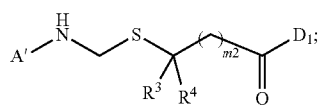

or a pharmaceutically acceptable salt thereof, wherein:
R$^3$ and R$^4$ are each independently H or Me;
m2 is an integer from 1 to 19; and $D_1$ is represented by the following formula:

and
the remaining variables are as described in the second embodiment or the 19th, 20th or 21[4] specific embodiment.

In a more specific embodiment, $D_1$ is represented by the following formula:

In a more specific embodiment, A is Ala-Ala-Ala, Ala-D-Ala-Ala, D-Ala-Ala-Ala, Ala-Ala-D-Ala, Ala-Ala, D-Ala-Ala, Val-Ala, D-Val-Ala, D-Ala-Pro, or D-Ala-tBu-Gly. In a even more specific embodiment, A is Ala-Ala-Ala, Ala-D-Ala-Ala, Ala-Ala, D-Ala-Ala, Val-Ala, D-Val-Ala, D-Ala-Pro, or D-Ala-tBu-Gly.

In a more specific embodiment, m2 is an integer from 2 to 10. In another more specific embodiment, m2 is an integer from 1 to 7. In another more specific embodiment, m2 is an integer from 2 to 6. In another more specific embodiment, m2 is an integer from 2 to 5. In another more specific embodiment, m2 is 4.

In yet another more specific embodiment, $R^3$ and $R^4$ are both Me. Alternatively, $R^3$ and $R^4$ are both H.

In a 29$^{th}$ specific embodiment, the compound of formula (III) is represented by the following formula:

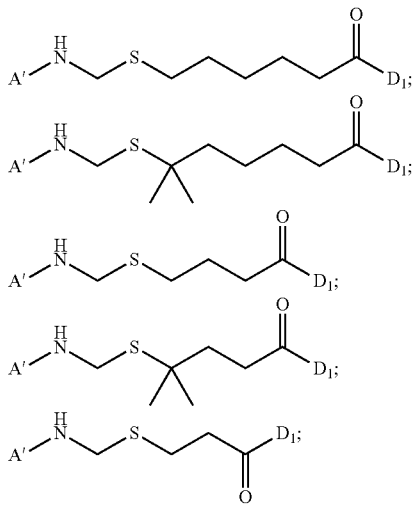

or a pharmaceutically acceptable salt thereof, wherein:
A' is Ala-Ala-Ala, Ala-D-Ala-Ala, D-Ala-Ala-Ala, Ala-Ala-D-Ala, Ala-Ala, D-Ala-Ala, Val-Ala, D-Val-Ala, D-Ala-Pro, or D-Ala-tBu-Gly (more specifically, A is Ala-Ala-Ala, Ala-D-Ala-Ala, Ala-Ala, D-Ala-Ala, Val-Ala, D-Val-Ala, D-Ala-Pro, or D-Ala-tBu-Gly),
$D_1$ is represented by the following formula:

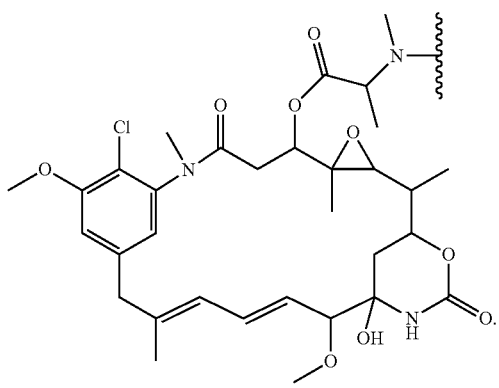 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]

In a more specific embodiment, $D_1$ is represented by the following formula:

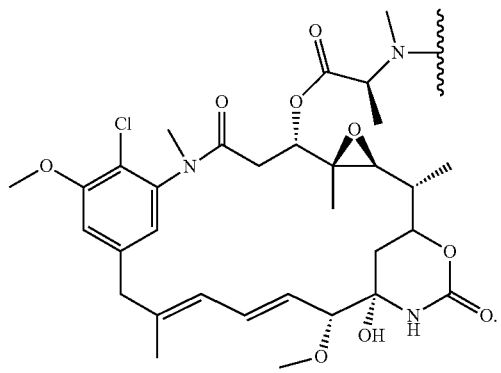 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)CC(OC(=O)N2)[C@@H](C)[C@@H]2O[C@@]12C]

Also in a 29$^{th}$ specific embodiment, the compound of formula (III) is represented by the following formula:

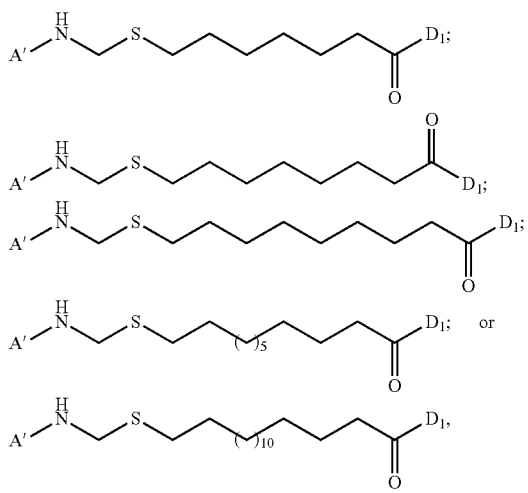

or a pharmaceutically acceptable salt thereof, wherein:
A' is Ala-Ala-Ala, Ala-D-Ala-Ala, D-Ala-Ala-Ala, Ala-Ala-D-Ala, Ala-Ala, D-Ala-Ala, Val-Ala, D-Val-Ala, D-Ala-Pro, or D-Ala-tBu-Gly (more specifically, A is Ala-Ala-Ala, Ala-D-Ala-Ala, Ala-Ala, D-Ala-Ala, Val-Ala, D-Val-Ala, D-Ala-Pro, or D-Ala-tBu-Gly),
$D_1$ is represented by the following formula:

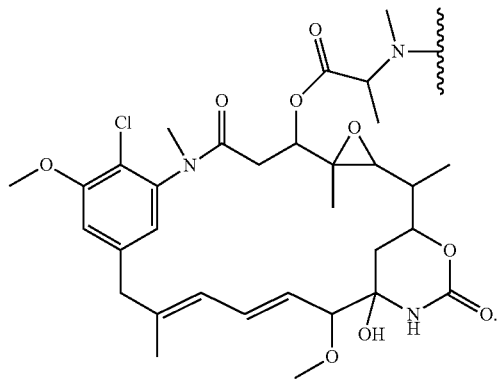 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]

In a more specific embodiment, $D_1$ is represented by the following formula:

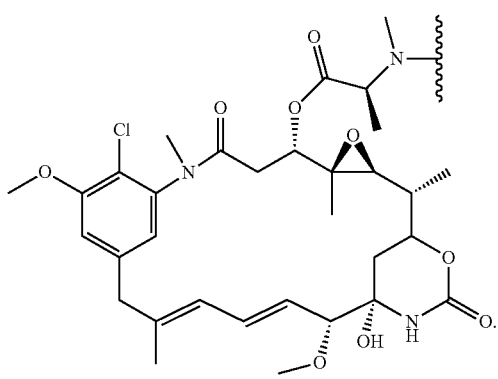 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)CC(OC(=O)N2)[C@@H](C)[C@@H]2O[C@@]12C]

In a 30th specific embodiment, the compound of formula (IV) is represented by the following formula:

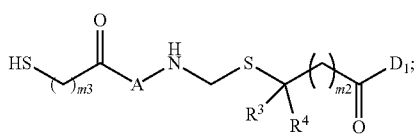

or a pharmaceutically acceptable salt thereof, wherein:
R$^3$ and R$^4$ are each independently H or Me;
m3 is an integer from 1 to 10;
m2 is an integer from 1 to 19;
D$_1$ is represented by the following formula:

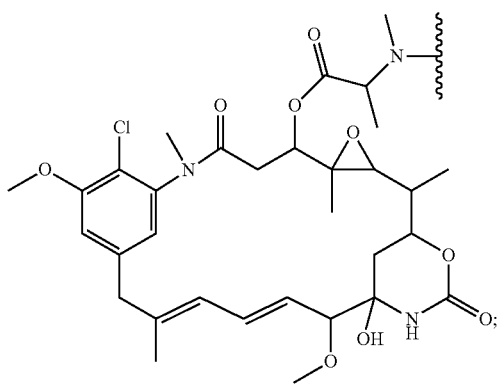 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]

and
the remaining variables are as described in the second embodiment or the 19th, 20th or 21st specific embodiment. In a more specific embodiment, A is Ala-Ala-Ala, Ala-D-Ala-Ala, D-Ala-Ala-Ala, Ala-Ala-D-Ala, Ala-Ala, D-Ala-Ala, Val-Ala, D-Val-Ala, D-Ala-Pro, or D-Ala-tBu-Gly. In another more specific embodiment, A is Ala-Ala-Ala, Ala-D-Ala-Ala, Ala-Ala, D-Ala-Ala, Val-Ala, D-Val-Ala, D-Ala-Pro, or D-Ala-tBu-Gly.

In a more specific embodiment, m3 is an integer from 1 to 6, and m2 is an integer from 1 to 7. In another more specific embodiment, m3 is an integer from 2 to 4; and m2 is an integer from 3 to 5. In a more specific embodiment, m3 is an integer from 2 to 10 and m2 is an integer from 2 to 10. In a more specific embodiment, m3 is an integer from 3 to 6 and m2 is an integer from 2 to 10. In a more specific embodiment, m3 is an integer from 3 to 6 and m2 is an integer from 3 to 6.

In yet another more specific embodiment, R$^3$ and R$^4$ are both Me. Alternatively, R$^3$ and R$^4$ are both H.

In a 31st specific embodiment, the compound of formula (IV) is represented by the following formula:

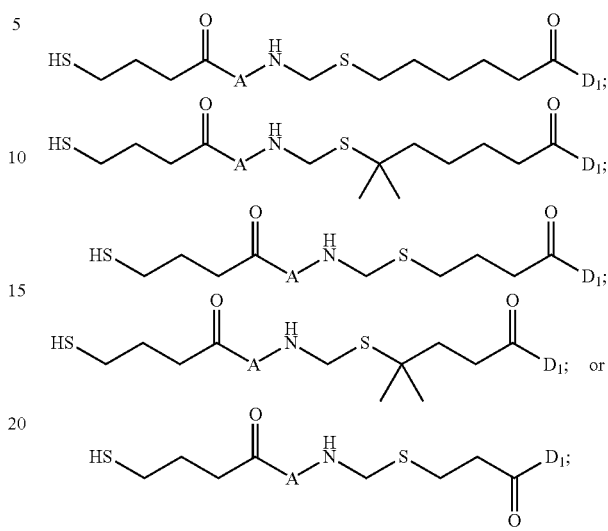

or a pharmaceutically acceptable salt thereof, wherein:
A is Ala-Ala-Ala, Ala-D-Ala-Ala, D-Ala-Ala-Ala, Ala-Ala-D-Ala, Ala-Ala, D-Ala-Ala, Val-Ala, D-Val-Ala, D-Ala-Pro, or D-Ala-tBu-Gly (more specifically, A is Ala-Ala-Ala, Ala-D-Ala-Ala, Ala-Ala, D-Ala-Ala, Val-Ala, D-Val-Ala, D-Ala-Pro, or D-Ala-tBu-Gly) and
D$_1$ is represented by the following formula:

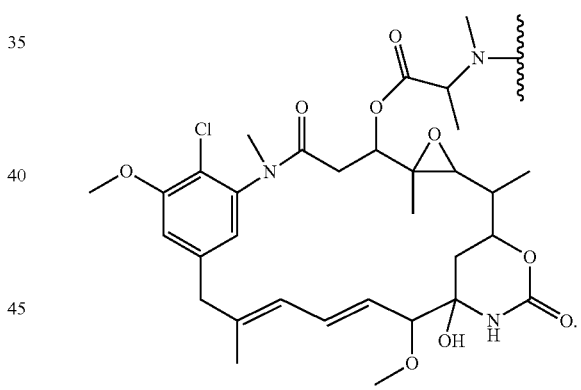

In a more specific embodiment, D$_1$ is represented by the following formula:

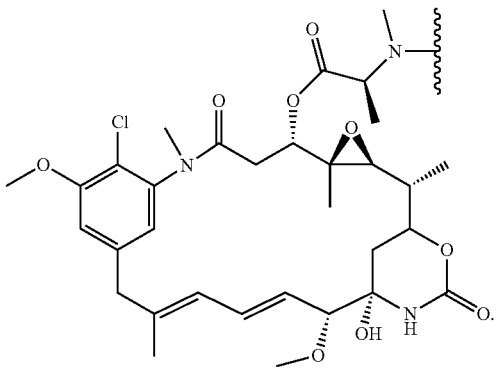 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)CC(OC(=O)N2)[C@@H](C)[C@@H]2O[C@@]12C]

Also a 31$^{st}$ specific embodiment, the compound of formula (IV) is represented by the following formula:

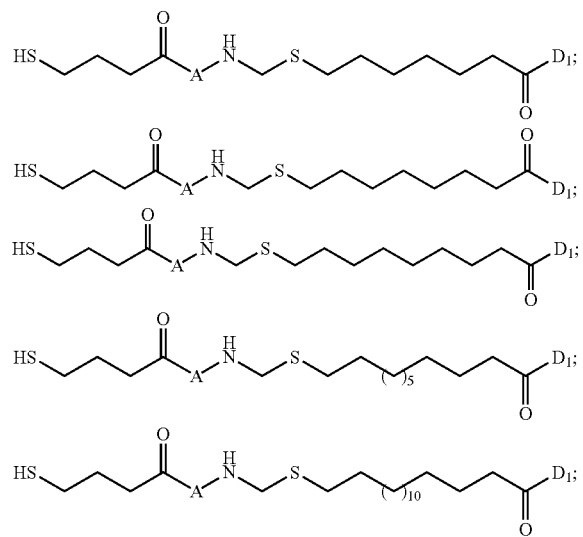

or a pharmaceutically acceptable salt thereof, wherein:

A is Ala-Ala-Ala, Ala-D-Ala-Ala, D-Ala-Ala-Ala, Ala-Ala-D-Ala, Ala-Ala, D-Ala-Ala, Val-Ala, D-Val-Ala, D-Ala-Pro, or D-Ala-tBu-Gly (more specifically, A is Ala-Ala-Ala, Ala-D-Ala-Ala, Ala-Ala, D-Ala-Ala, Val-Ala, D-Val-Ala, D-Ala-Pro, or D-Ala-tBu-Gly) and $D_1$ is represented by the following formula:

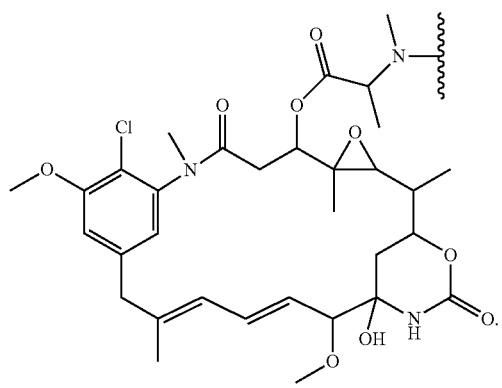 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]

In a more specific embodiment, $D_1$ is represented by the following formula:

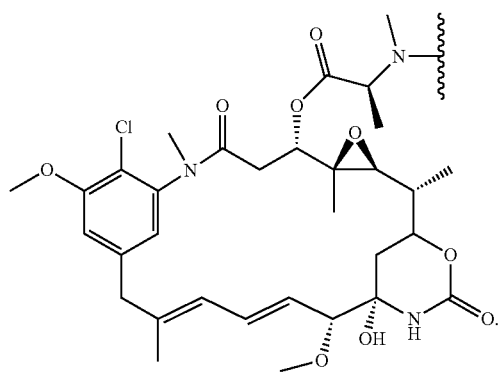 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)CC(OC(=O)N2)[C@@H](C)[C@@H]2O[C@@]12C]

Metabolites

In certain embodiments, the conjugates of the present invention can release free cytotoxic agent (e.g., a maytansinoid) via bond cleavage at the peptide moiety represented by variable A followed by self-immolation of —NH—$CR^1R^2$—S— moiety to release free cytotoxic agent having a thiol group, which can be further methylated.

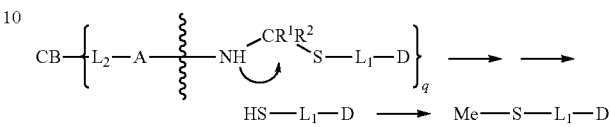

Accordingly, in a third embodiment, the present invention is directed to a compound of formula (V):

$$D\text{-}L_1\text{-}SZ^0 \qquad (V),$$

wherein:

$L_1$ is a spacer;

$Z^0$ is H or Me, provided when $Z^0$ is H, $L_1$ is not —C(=O)—$(CH_2)_q$— or —C(=O)—$CH_2$—$CH_2$—$C(CH_3)_2$—, wherein q is an integer from 1 to 3; and when $Z^0$ is Me, $L_1$ is not —C(=O)—$(CH_2)_2$— or —C(=O)—$CH_2$—$CH_2$—$C(CH_3)_2$—; and D-$L_1$-SH is a cytotoxic agent.

In a 32$^{nd}$ specific embodiment, $L_1$ is -$L_1$'-C(=O)—; and $L_1$' is an alkylene or a cycloalkylene. More specifically, $L_1$' is $C_{1-10}$alkylene. In another more specific embodiment, $L_1$' is $C_{1-20}$alkylene In a 33$^{rd}$ specific embodiment, $L_1$ is —$CR^3R^4$—$(CH_2)_{1-8}$—C(=O)—; and $R^3$ and $R^4$ are each independently H or Me.

In a 34$^{th}$ specific embodiment, $L_1$ is —$CR^3R^4$—$(CH_2)_{2-5}$—C(=O)— or —$CR^3R^4$—$(CH_2)_{3-5}$—C(=O)—. In a more specific embodiment, $R^3$ and $R^4$ are both Me. In another more specific embodiment, $R^3$ and $R^4$ are both H.

In a 35$^{th}$ specific embodiment, $L_1$ is —$(CH_2)_{2-10}$—C(=O)—. In a more specific embodiment, $L_1$ is —$(CH_2)_{4-6}$—C(=O)—. In another more specific embodiment, $L_1$ is —$(CH_2)_5$—C(=O)—. In another more specific embodiment, $L_1$ is —$(CH_2)_6$—C(=O)—. In another more specific embodiment, $L_1$ is —$(CH_2)_7$—C(=O)—. In another more specific embodiment, $L_1$ is —$(CH_2)_8$—C(=O)—. In another more specific embodiment, $L_1$ is —$(CH_2)_{10}$—C(=O)—. In another more specific embodiment, $L_1$ is —$(CH_2)_{15}$—C(=O)—.

In a 36$^{th}$ specific embodiment, for the compound of formula (V), D is represented by the following formula:

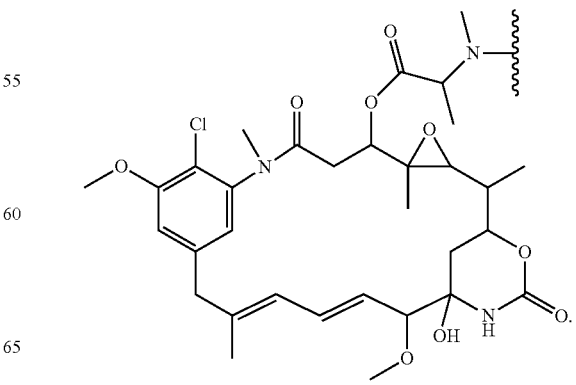

Wherein the definition for the remaining variables are as described in the second embodiment, or the 32$^{nd}$, 33$^{rd}$, 34$^{th}$ or 35$^{th}$ specific embodiment.

More specifically, D is represented by the following formula:

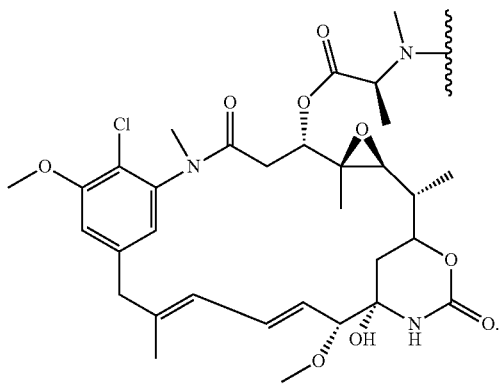 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)CC(OC(=O)N2)[C@@H](C)[C@@H]2O[C@@]12C]

In a 37$^{th}$ specific embodiment, the compound of formula (V) is presented by the following formula:

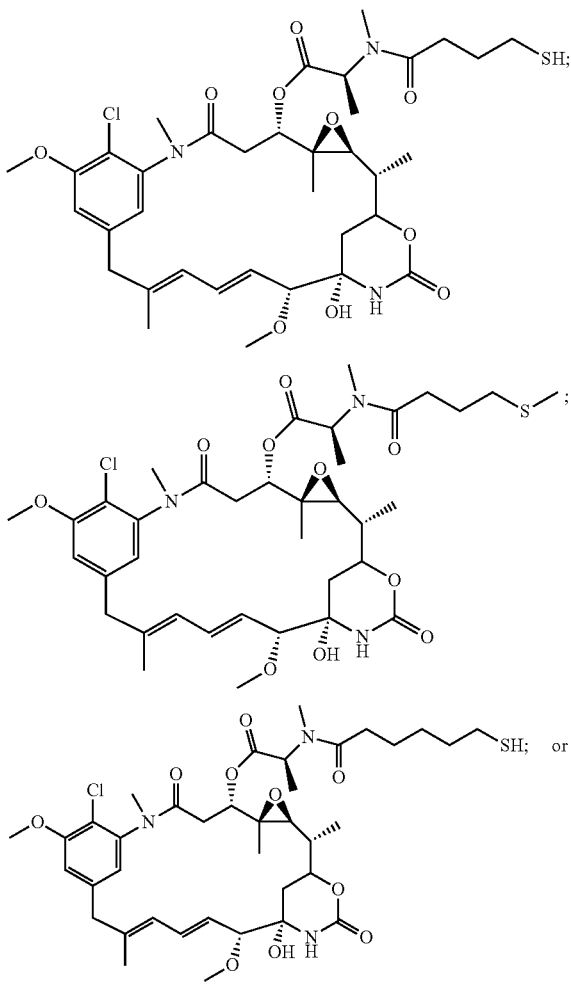

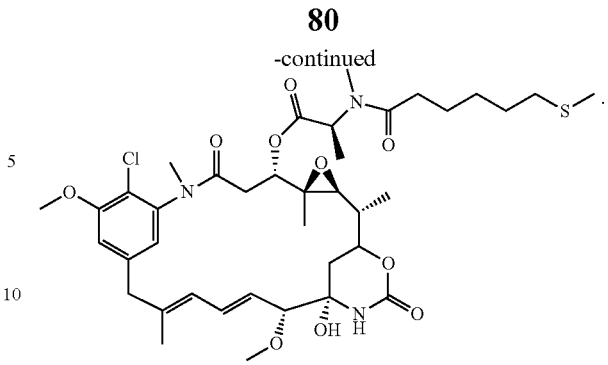

Cell-Binding Agents

The effectiveness of the conjugates of the invention as therapeutic agents depends on the careful selection of an appropriate cell-binding agent. Cell-binding agents can be of any kind presently known, or that become known, including peptides and non-peptides. Generally, these can be antibodies (such as polyclonal antibodies and monoclonal antibodies, especially monoclonal antibodies), lymphokines, hormones, growth factors, vitamins (such as folate etc., which can bind to a cell surface receptor thereof, e.g., a folate receptor), nutrient-transport molecules (such as transferrin), or any other cell-binding molecule or substance.

Selection of the appropriate cell-binding agent is a matter of choice that partly depends upon the particular cell population that is to be targeted, but in many (but not all) cases, human monoclonal antibodies are a good choice if an appropriate one is available. For example, the monoclonal antibody MY9 is a murine IgG$_1$ antibody that binds specifically to the CD33 Antigen (J. D. Griffin et al., Leukemia Res., 8:521 (1984)), and can be used if the target cells express CD33 as in the disease of acute myelogenous leukemia (AML).

In certain embodiments, the cell-binding agent is not a protein. For example, in certain embodiments, the cell binding agent may be a vitamin that binds to a vitamin receptor, such as a cell-surface receptor. In this regard, vitamin A binds to retinol-binding protein (RBP) to form a complex, which complex in turn binds the STRA6 receptor with high affinity and increases vitamin A in-take. In another example, folic acid/folate/vitamin B$_9$ binds the cell-surface folate receptor (FR), for example, FRα, with high affinity. Folic acid or antibodies that bind to FRα can be used to target the folate receptor expressed on ovarian and other tumors. In addition, vitamin D and its analog bind to vitamin D receptor.

In other embodiments, the cell-binding agent is a protein or a polypeptide, or a compound comprising a protein or polypeptide, including antibody, non-antibody protein, or polypeptide. Preferably, the protein or polypeptides comprise one or more Lys residues with side chain —NH$_2$ group. The Lys side chain —NH$_2$ groups can be covalently linked to the bifunctional crosslinkers, which in turn are linked to the dimer compounds of the invention, thus conjugating the cell-binding agents to the dimer compounds of the invention. Each protein-based cell-binding agents can contain multiple Lys side chain —NH$_2$ groups available for linking the compounds of the invention through the bifunctional crosslinkers.

In some embodiments, GM-CSF, a ligand/growth factor which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Epidermal growth factor can be used to target squamous cancers, such as lung and head and neck and gingival squamous cell carcinoma. Somatostatin can be used to target neuroblastomas and other tumor types. Estrogen (or estrogen analogues) can be used to target breast cancer. Androgen (or androgen analogues) can be used to target testes.

In certain embodiments, the cell-binding agent can be a lymphokine, a hormone, a growth factor, a colony stimulating factor, or a nutrient-transport molecule.

In certain embodiments, the cell-binding agent is an antibody mimetic, such as an ankyrin repeat protein, a Centyrin, or an adnectin/monobody.

In other embodiments, the cell-binding agent is an antibody, a single chain antibody, an antibody fragment that specifically binds to the target cell, a monoclonal antibody, a single chain monoclonal antibody, a monoclonal antibody fragment (or "antigen-binding portion") that specifically binds to a target cell, a chimeric antibody, a chimeric antibody fragment (or "antigen-binding portion") that specifically binds to the target cell, a domain antibody (e.g., sdAb), or a domain antibody fragment that specifically binds to the target cell.

In certain embodiments, the cell-binding agent is a humanized antibody, a humanized single chain antibody, or a humanized antibody fragment (or "antigen-binding portion"). In a specific embodiment, the humanized antibody is huMy9-6 or another related antibody, which is described in U.S. Pat. Nos. 7,342,110 and 7,557,189. In another specific embodiment, the humanized antibody is an anti-folate receptor antibody described in WO2011/106528 and U.S. Pat. Nos. 8,557,966, 9,133,275, 9,598,490, 9,657,100, 9,670,278, 9,670,279 and 9,670,280. The teachings of all these applications are incorporated herein by reference in its entirety.

In certain embodiments, the cell-binding agent is a resurfaced antibody, a resurfaced single chain antibody, a resurfaced antibody fragment (or "antigen-binding portion"), or a bispecific antibody.

In certain embodiments, the cell-binding agent is a minibody, an avibody, a diabody, a tribody, a tetrabody, a nanobody, a probody, a domain antibody, or an unibody.

In other words, an exemplary cell binding agent may include an antibody, a single chain antibody, an antibody fragment that specifically binds to the target cell, a monoclonal antibody, a single chain monoclonal antibody, a monoclonal antibody fragment that specifically binds to a target cell, a chimeric antibody, a chimeric antibody fragment that specifically binds to the target cell, a bispecific antibody, a domain antibody, a domain antibody fragment that specifically binds to the target cell, an interferon (e.g., $\alpha, \beta, \gamma$), a lymphokine (e.g., IL-2, IL-3, IL-4, and IL-6), a hormone (e.g., insulin, thyrotropin releasing hormone (TRH), melanocyte-stimulating hormone (MSH), and a steroid hormone (e.g., androgen and estrogen)), a vitamin (e.g., folate), a growth factor (e.g., EGF, TGF-alpha, FGF, VEGF), a colony stimulating factor, a nutrient-transport molecule (e.g., transferrin; see O'Keefe et al. (1985) *J. Biol. Chem.* 260:932-937, incorporated herein by reference), a Centyrin (a protein scaffold based on a consensus sequence of fibronectin type III (FN3) repeats; see U.S. Patent Publication 2010/0255056, 2010/0216708 and 2011/0274623 incorporated herein by reference), an Ankyrin Repeat Protein (e.g., a designed ankyrin repeat protein, known as DARPin; see U.S. Patent Publication Nos. 2004/0132028, 2009/0082274, 2011/0118146, and 2011/0224100, incorporated herein by reference, and also see C. Zahnd et al., *Cancer Res.* (2010) 70:1595-1605; Zahnd et al., *J. Biol. Chem.* (2006) 281(46):35167-35175; and Binz, H. K., Amstutz, P. & Pluckthun, A., *Nature Biotechnology* (2005) 23:1257-1268, incorporated herein by reference), an ankyrin-like repeats protein or synthetic peptide (see e.g., U.S. Patent Publication No. 2007/0238667; U.S. Pat. No. 7,101,675; WO 2007/147213; and WO 2007/062466, incorporated herein by reference), an Adnectin (a fibronectin domain scaffold protein; see US Patent Publication Nos. 2007/0082365; 2008/0139791, incorporated herein by reference), Avibody (including diabodies, triabodies, and tetrabodies; see U.S. Publication Nos. 2008/0152586 and 2012/0171115), dual receptor retargeting (DART) molecules (P. A. Moore et al., *Blood,* 2011; 117(17):4542-4551; Veri M C, et al., *Arthritis Rheum,* 2010 Mar. 30; 62(7):1933-43; Johnson S, et al., *J. Mol. Biol.,* 2010 Apr. 9; 399(3):436-49), cell penetrating supercharged proteins (*Methods in Enzymol.* 502, 293-319 (2012), and other cell-binding molecules or substances.

In certain embodiments, the cell-binding agent may be a ligand that binds to a moiety on the target cell, such as a cell-surface receptor. For example, the ligand may be a growth factor or a fragment thereof that binds to a growth factor receptor; or may be a cytokine or a fragment thereof that binds to a cytokine receptor. In certain embodiments, the growth factor receptor or cytokine receptor is a cell-surface receptor.

In certain embodiments, wherein the cell-binding agent is an antibody or an antigen-binding portion thereof (including antibody derivatives), or certain antibody mimetics, the CBA may bind to a ligand on the target cell, such as a cell-surface ligand, including cell-surface receptors.

Specific exemplary antigens or ligands may include renin; a growth hormone (e.g., human growth hormone and bovine growth hormone); a growth hormone releasing factor; a parathyroid hormone; a thyroid stimulating hormone; a lipoprotein; alpha-1-antitrypsin; insulin A-chain; insulin B-chain; proinsulin; a follicle stimulating hormone; calcitonin; a luteinizing hormone; glucagon; a clotting factor (e.g., factor vmc, factor IX, tissue factor, and von Willebrands factor); an anti-clotting factor (e.g., Protein C); an atrial natriuretic factor; a lung surfactant; a plasminogen activator (e.g., a urokinase, a human urine or tissue-type plasminogen activator); bombesin; a thrombin; hemopoietic growth factor; tumor necrosis factor-alpha and -beta; an enkephalinase; RANTES (i.e., the regulated on activation normally T-cell expressed and secreted); human macrophage inflammatory protein-1-alpha; a serum albumin (human serum albumin); Muellerian-inhibiting substance; relaxin A-chain; relaxin B-chain; prorelaxin; a mouse gonadotropin-associated peptide; a microbial protein (beta-lactamase); DNase; IgE; a cytotoxic T-lymphocyte associated antigen (e.g., CTLA-4); inhibin; activin; a vascular endothelial growth factor; a receptor for hormones or growth factors; protein A or D; a rheumatoid factor; a neurotrophic factor (e.g., bone-derived neurotrophic factor, neurotrophin-3, -4, -5, or -6), a nerve growth factor (e.g., NGF-β); a platelet-derived growth factor; a fibroblast growth factor (e.g., aFGF and bFGF); fibroblast growth factor receptor 2; an epidermal growth factor; a transforming growth factor (e.g., TGF-alpha, TGF-β1, TGF-β2, TGF-β3, TGF-β4, and TGF-β5); insulin-like growth factor-I and -II; des (1-3)-IGF-I (brain IGF-I); an insulin-like growth factor binding protein; melanotransferrin; CA6, CAK1, CALLA, CAECAM5, GD3;

FLT3; PSMA; PSCA; MUC1; STEAP; CEA; TENB2; an EphA receptor; an EphB receptor; a folate receptor; FOLR1; mesothelin; cripto; an alpha$_v$beta$_6$; integrins; VEGF; VEGFR; EGFR; FGFR3; LAMP1, β-cadherin, transferrin receptor; IRTA1; IRTA2; IRTA3; IRTA4; IRTA5; CD proteins (e.g., CD2, CD3, CD4, CD6, CD8, CD11, CD14, CD19, CD20, CD21, CD22, CD26, CD28, CD30, CD33, CD36, CD37, CD38, CD40, CD44, CD52, CD55, CD56, CD59, CD70, CD79, CD80. CD81, CD103, CD105, CD123, CD134, CD137, CD138, and CD152), one or more tumor-associated antigens or cell-surface receptors (see US Publication No. 2008/0171040 or US Publication No. 2008/0305044, incorporated in their entirety by reference); erythropoietin; an osteoinductive factor; an immunotoxin; a bone morphogenetic protein; an interferon (e.g., interferon-alpha, -beta, and -gamma); a colony stimulating factor (e.g., M-CSF, GM-CSF, and G-CSF); interleukins (e.g., IL-1 to IL-10); a superoxide dismutase; a T-cell receptor; a surface membrane protein; a decay accelerating factor; a viral antigen s (e.g., a portion of the HIV envelope); a transport protein, a homing receptor; an addressin; a regulatory protein; an integrin (e.g., CD11a, CD11b, CD11c, CD18, an ICAM, VLA-4, and VCAM;) a tumor associated antigen (e.g., HER2, HER3 and HER4 receptor); endoglin; c-Met; c-kit; 1GF1R; PSGR; NGEP; PSMA; PSCA; TMEFF2; LGR5; B7H4; TROP-2, DLL-3, CDH6, AXL, SLITRK6, ENPP3, BCMA, tissue factor, CD352, and fragments of any of the above-listed polypeptides.

As used herein, the term "antibody" includes immunoglobulin (Ig) molecules. In certain embodiments, the antibody is a full-length antibody that comprises four polypeptide chains, namely two heavy chains (HC) and two light chains (LC) inter-connected by disulfide bonds. Each heavy chain is comprised of a heavy chain variable region (HCVR or VH) and a heavy chain constant region (CH). The heavy chain constant region is comprised of three domains, CH1, CH2, and CH3. Each light chain is comprised of a light chain variable region (LCVR or VL) and a light chain constant region, which is comprised of one domain, CL. The VH and VL regions can be further subdivided into regions of hypervariability, termed complementarity determining regions (CDRs). Interspersed with such regions are the more conserved framework regions (FRs). Each VH and VL is composed of three CDRs and four FRs, arranged from amino-terminus to carboxy-terminus in the following order: FR1, CDR1, FR2, CDR2, FR3, CDR3, and FR4.

In certain embodiments, the antibody is IgG, IgA, IgE, IgD, or IgM. In certain embodiments, the antibody is IgG1, IgG2, IgG3, or IgG4; or IgA1 or IgA2.

In certain embodiments, the cell-binding agent is an "antigen-binding portion" of a monoclonal antibody, sharing sequences critical for antigen-binding with an antibody (such as huMy9-6 or its related antibodies described in U.S. Pat. Nos. 7,342,110 and 7,557,189; huMov19 or its related antibodies described in U.S. Pat. Nos. 8,557,966, 9,133,275, 9,598,490, 9,657,100, 9,670,278, 9,670,279 and 9,670,280, and WO2011106528, all of which are incorporated herein by reference).

As used herein, the term "antigen-binding portion" of an antibody (or sometimes interchangeably referred to as "antibody fragments"), include one or more fragments of an antibody that retain the ability to specifically bind to an antigen. It has been shown that the antigen-binding function of an antibody can be performed by certain fragments of a full-length antibody. Examples of binding fragments encompassed within the term "antigen-binding portion" of an antibody include (without limitation): (i) a Fab fragment, a monovalent fragment consisting of the VL, VH, CL and CH1 domains (e.g., an antibody digested by papain yields three fragments: two antigen-binding Fab fragments, and one Fc fragment that does not bind antigen); (ii) a F(ab')$_2$ fragment, a bivalent fragment comprising two Fab fragments linked by a disulfide bridge at the hinge region (e.g., an antibody digested by pepsin yields two fragments: a bivalent antigen-binding F(ab')$_2$ fragment, and a pFc' fragment that does not bind antigen) and its related F(ab') monovalent unit; (iii) a Fd fragment consisting of the VH and CH1 domains (i.e., that portion of the heavy chain which is included in the Fab); (iv) a Fv fragment consisting of the VL and VH domains of a single arm of an antibody, and the related disulfide linked Fv; (v) a dAb (domain antibody) or sdAb (single domain antibody) fragment (Ward et al., Nature 341:544-546, 1989), which consists of a VH domain; and (vi) an isolated complementarity determining region (CDR). In certain embodiments, the antigen-binding portion is a sdAb (single domain antibody).

In certain embodiments, antigen-binding portion also include certain engineered or recombinant derivatives (or "derivative antibodies") that also include one or more fragments of an antibody that retain the ability to specifically bind to an antigen, in addition to elements or sequences that may not be found in naturally existing antibodies.

For example, although the two domains of the Fv fragment, VL and VH, are coded for by separate genes, they can be joined, using standard recombinant methods, by a synthetic linker that enables them to be made as a single protein chain in which the VL and VH regions pair to form monovalent molecules (known as single chain Fv (scFv); see, e.g., Bird et al. Science 242:423-426, 1988: and Huston et al., Proc. Natl. Acad. Sci. USA 85:5879-5883, 1988).

In all embodiments described herein, the N-terminum of an scFv may be a VH domain (i.e., N—VH-VL-C), or a VL domain (i.e., N—VL-VH—C).

Divalent (or bivalent) single-chain variable fragments (di-scFvs, bi-scFvs) can be engineered by linking two scFvs. This produces a single peptide chain with two VH and two VL regions, yielding a tandem scFvs (tascFv). More tandem repeats, such as tri-scFv, may be similarly produced by linking three or more scFv in a head-to-tail fashion.

In certain embodiments, scFvs may be linked through linker peptides that are too short (about five amino acids) for the two variable regions to fold together, forcing scFvs to dimerize, and form diabodies (see, e.g., Holliger et al., Proc. Natl. Acad. Sci. USA 90:6444-6448, 1993; Poljak et al., Structure 2:1121-1123, 1994). Diabodies may be bi-specific or monospecific. Diabodies have been shown to have dissociation constants up to 40-fold lower than corresponding scFvs, i.e., having a much higher affinity to the target.

Still shorter linkers (one or two amino acids) lead to the formation of trimers, or so-called triabodies or tribodies. Tetrabodies have also been produced similarly. They exhibit an even higher affinity to their targets than diabodies. Diabodies, triabodies, and tetrabodies are sometimes collectively called "AVIBODY™" cell binding agents (or "AVIBODY" in short). That is, AVIBODY having two, three, or four Target Binding Regions (TBRs) are commonly known as Dia-, Tria- and Tetra-bodies. See, for example, U.S. Publication Nos. 2008/0152586 and 2012/0171115 for details, the entire teachings of which are incorporated herein by reference.

All of these formats can be composed from variable fragments with specificity for two or more different antigens, in which case they are types of bi- or multi-specific antibodies. For example, certain bispecific tandem di-scFvs, are known as bi-specific T-cell engagers (BiTEs).

In certain embodiments, each scFv in the tandem scFv or diabody/triabody/tetrabody may have the same or different binding specificity, and each may independently have an N-terminal VH or N-terminal VL.

Single chain Fv (scFv) can also be fused to an Fc moiety, such as the human IgG Fc moiety to obtain IgG-like properties, but nevertheless they are still encoded by a single gene. As transient production of such scFv-Fc proteins in mammalians can easily achieve milligram amounts, this derivative antibody format is particularly suitable for many research applications.

Fcabs are antibody fragments engineered from the Fc constant region of an antibody. Fcabs can be expressed as soluble proteins, or they can be engineered back into a full-length antibody, such as IgG, to create mAb2. A mAb2 is a full-length antibody with an Fcab in place of the normal Fc region. With these additional binding sites, mAb2 bispecific monoclonal antibodies can bind two different targets at the same time.

In certain embodiments, the engineered antibody derivatives have reduced size of the antigen-binding Ig-derived recombinant proteins ("miniaturized" full-size mAbs), produced by removing domains deemed non-essential for function. One of the best examples is SMIPs.

A Small modular immunopharmaceutical, or SMIP, is an artificial protein largely built from parts of antibodies (immunoglobulins), and is intended for use as a pharmaceutical drug. SMIPs have similar biological half-life as antibodies, but are smaller than antibodies and hence may have better tissue penetration properties. SMIPs are single-chain proteins that comprise one binding region, one hinge region as a connector, and one effector domain. The binding region comprises a modified single-chain variable fragment (scFv), and the rest of the protein can be constructed from the Fc (such as CH2, and CH3 as the effector domain) and the hinge region of an antibody, such as IgG1. Genetically modified cells produce SMIPs as antibody-like dimers that are about 30% smaller than real antibodies.

Another example of such engineered miniaturized antibody is "unibody," in which the hinge region has been removed from IgG4 molecules. IgG4 molecules are unstable and can exchange light-heavy chain heterodimers with one another. Deletion of the hinge region prevents heavy chain-heavy chain pairing entirely, leaving highly specific monovalent light/heavy heterodimers, while retaining the Fc region to ensure stability and half-life in vivo.

A single-domain antibody (sdAb, including but not limited to those called nanobody by Ablynx) is an antibody fragment consisting of a single monomeric variable antibody domain. Like a whole antibody, it is able to bind selectively to a specific antigen, but is much smaller due to its molecular weight of only 12-15 kDa. In certain embodiments, the single-domain antibody is engineered from heavy-chain antibodies (hcIgG). The first such sdAb was engineered based on an hcIgG found in camelids, called $V_HH$ fragments. In certain embodiments, the single-domain antibody is engineered from IgNAR ("immunoglobulin new antigen receptor," see below) using a $V_{NAR}$ fragment. Cartilaginous fishes (such as shark) have such heavy-chain IgNAR antibodies. In certain embodiments, the sdAb is engineered by splitting the dimeric variable domains from common immunoglobulin G (IgG), such as those from humans or mice, into monomers. In certain embodiments, a nanobody is derived from a heavy chain variable domain. In certain embodiments, a nanobody is derived from light chain variable domain. In certain embodiments, the sdAb is obtained by screening libraries of single domain heavy chain sequences (e.g., human single domain HCs) for binders to a target antigen.

The single variable new antigen receptor domain antibody fragments ($V_{NAR}$s, or $V_{NAR}$ domains) are derived from cartilaginous fish (e.g., shark) immunoglobulin new antigen receptor antibodies (IgNARs). Being one of the smallest known immunoglobulin-based protein scaffolds, such single domain proteins demonstrate favorable size and cryptic epitope recognition properties. Mature IgNAR antibodies consist of homodimers of one variable new antigen receptor ($V_{NAR}$) domain and five constant new antigen receptor ($C_{NAR}$) domains. This molecule is highly stable, and possesses efficient binding characteristics. Its inherent stability can likely be attributed to both (i) the underlying Ig scaffold, which presents a considerable number of charged and hydrophilic surface exposed residues compared to the conventional antibody VH and VL domains found in murine antibodies; and (ii) stabilizing structural features in the complementary determining region (CDR) loops including inter-loop disulphide bridges, and patterns of intra-loop hydrogen bonds.

A minibody is an engineered antibody fragment comprising an scFv linked to a CH domain, such as the CH3γ1 (CH3 domain of IgG1) or CH4ε (CH4 domain of IgE). For example, an scFv specific for carcinoembryonic antigen (CEA) has been linked to the CH3γ1 to create a minibody, which has previously been demonstrated to possess excellent tumor targeting coupled with rapid clearance in vivo (Hu et al., *Cancer Res.* 56:3055-3061, 1996). The scFv may have a N-terminal VH or VL. The linkage may be a short peptide (e.g., two amino acid linker, such as ValGlu) that results in a non-covalent, hingeless minibody. Alternatively, the linkage may be an IgG1 hinge and a GlySer linker peptide that produces a covalent, hinge-minibody.

Natural antibodies are mono-specific, but bivalent, in that they express two identical antigen-binding domains. In contrast, in certain embodiments, certain engineered antibody derivatives are bi- or multi-specific molecules possess two or more different antigen-binding domains, each with different target specificity. Bispecific antibodies can be generated by fusing two antibody-producing cells, each with distinct specificity. These "quadromas" produced multiple molecular species, as the two distinct light chains and two distinct heavy chains were free to recombine in the quadromas in multiple configurations. Since then, bispecific Fabs, scFvs and full-size mAbs have been generated using a variety of technologies (see above).

The dual variable domain immunoglobulin (DVD-Ig) protein is a type of dual-specific IgG that simultaneously target two antigens/epitopes (DiGiammarino et al., *Methods Mol. Biol.,* 899:145-56, 2012). The molecule contains an Fc region and constant regions in a configuration similar to a conventional IgG. However, the DVD-Ig protein is unique in that each arm of the molecule contains two variable domains (VDs). The VDs within an arm are linked in tandem and can possess different binding specificities.

Trispecific antibody derivative molecules can also been generated by, for example, expressing bispecific antibodies with two distinct Fabs and an Fc. One example is a mouse IgG2a anti-Ep-CAM, rat IgG2b anti-CD3 quadroma, called BiUII, which is thought to permit the co-localization of tumor cells expressing Ep-CAM, T cells expressing CD3, and macrophages expressing FCγRI, thus potentiating the costimulatory and anti-tumor functions of the immune cells.

Probodies are fully recombinant, masked monoclonal antibodies that remain inert in healthy tissue, but are activated specifically in the disease microenvironment (e.g., through protease cleavage by a protease enriched or specific in a disease microenvironment). See Desnoyers et al., *Sci. Transl. Med.*, 5:207, 144, 2013. Similar masking techniques can be used for any of the antibodies or antigen-binding portions thereof described herein.

An intrabody is an antibody that has been modified for intracellular localization, for working within the cell to bind to an intracellular antigen. The intrabody may remain in the cytoplasm, or may have a nuclear localization signal, or may have a KDEL sequence for ER targeting. The intrabody may be a single-chain antibody (scFv), modified immunoglobulin VL domains with hyperstability, selected antibody resistant to the more reducing intracellular environment, or expressed as a fusion protein with maltose binding protein or other stable intracellular proteins. Such optimizations have improved the stability and structure of intrabodies, and may have general applicability to any of the antibodies or antigen-binding portions thereof described herein.

The antigen-binding portions or derivative antibodies of the invention may have substantially the same or identical (1) light chain and/or heavy chain CDR3 regions; (2) light chain and/or heavy chain CDR1, CDR2, and CDR3 regions; or (3) light chain and/or heavy chain regions, compared to an antibody from which they are derived/engineered. Sequences within these regions may contain conservative amino acid substitutions, including substitutions within the CDR regions. In certain embodiments, there is no more than 1, 2, 3, 4, or 5 conservative substitutions. In an alternative, the antigen-binding portions or derivative antibodies have a light chain region and/or a heavy chain region that is at least about 90%, 95%, 99% or 100% identical to an antibody from which they are derived/engineered. These antigen-binding portions or derivative antibodies may have substantially the same binding specificity and/or affinity to the target antigen compared to the antibody. In certain embodiments, the $K_d$ and/or $k_{off}$ values of the antigen-binding portions or derivative antibodies are within 10-fold (either higher or lower), 5-fold (either higher or lower), 3-fold (either higher or lower), or 2-fold (either higher or lower) of an antibody described herein.

In certain embodiments, the antigen-binding portions or derivative antibodies may be derived/engineered from fully human antibodies, humanized antibodies, or chimeric antibodies, and may be produced according to any art-recognized methods.

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969,108; McCafferty et al., WO 92/01047; Liming et al., WO 99/06587). In addition, resurfaced antibodies disclosed in U.S. Pat. No. 5,639,641 may also be used, as may chimeric antibodies and humanized antibodies.

Cell-binding agent can also be peptides derived from phage display (see, for example, Wang et al., *Proc. Natl. Acad. Sci. USA* (2011) 108(17), 6909-6914) or peptide library techniques (see, for example, Dane et al., *Mol. Cancer. Ther.* (2009) 8(5):1312-1318).

In certain embodiments, the CBA of the invention also includes an antibody mimetic, such as a DARPin, an affibody, an affilin, an affitin, an anticalin, an avimer, a Fynomer, a Kunitz domain peptide, a monobody, a nanofitin, a Bicycles® peptide, such as those described in US2014/0163201 (incorporated herein by reference), and a pentarin, such as those described in Abstract 3674, AACR 106th Annual Meeting 2015; Apr. 18-22, 2015; Philadelphia, Pa. (incorporated herein by reference).

As used herein, the terms "DARPin" and "(designed) ankyrin repeat protein" are used interchangeably to refer to certain genetically engineered antibody mimetic proteins typically exhibiting preferential (sometimes specific) target binding. The target may be protein, carbohydrate, or other chemical entities, and the binding affinity can be quite high. The DARPins may be derived from natural ankyrin repeat-containing proteins, and preferably consist of at least three, usually four or five ankyrin repeat motifs (typically about 33 residues in each ankyrin repeat motif) of these proteins. In certain embodiments, a DARPin contains about four- or five-repeats, and may have a molecular mass of about 14 or 18 kDa, respectively. Libraries of DARPins with randomized potential target interaction residues with diversities of over $10^{12}$ variants can be generated at the DNA level, for use in selecting DARPins that bind desired targets (e.g., acting as receptor agonists or antagonists, inverse agonists, enzyme inhibitors, or simple target protein binders) with picomolar affinity and specificity, using a variety of technologies such as ribosome display or signal recognition particle (SRP) phage display. See, for example, U.S. Patent Publication Nos. 2004/0132028, 2009/0082274, 2011/0118146, and 2011/0224100, WO 02/20565 and WO 06/083275 for DARPin preparation (the entire teachings of which are incorporated herein by reference), and also see C. Zahnd et al. (2010) *Cancer Res.*, 70:1595-1605; Zahnd et al. (2006) *J. Biol. Chem.*, 281(46):35167-35175; and Binz, H. K., Amstutz, P. & Pluckthun, A. (2005) *Nature Biotechnology*, 23:1257-1268 (all incorporated herein by reference). Also see U.S. Patent Publication No. 2007/0238667; U.S. Pat. No. 7,101,675; WO 2007/147213; and WO 2007/062466 (the entire teachings of which are incorporated herein by reference), for the related ankyrin-like repeats protein or synthetic peptide.

Affibody molecules are small proteins engineered to bind to a large number of target proteins or peptides with high affinity, thus imitating monoclonal antibodies. An Affibody consists of three alpha helices with 58 amino acids and has a molar mass of about 6 kDa. They have been shown to withstand high temperatures (90° C.) or acidic and alkaline conditions (pH 2.5 or pH 11), and binders with an affinity of down to sub-nanomolar range have been obtained from naïve library selections, and binders with picomolar affinity have been obtained following affinity maturation. In certain embodiments, affibodies are conjugated to weak electrophiles for binding to targets covalently.

Monobodies (also known as Adnectins), are genetically engineered antibody mimetic proteins capable of binding to antigens. In certain embodiments, monobodies consist of 94 amino acids and have a molecular mass of about 10 kDa. They are based on the structure of human fibronectin, more specifically on its tenth extracellular type III domain, which has a structure similar to antibody variable domains, with seven beta sheets forming a barrel and three exposed loops on each side corresponding to the three complementarity determining regions. Monobodies with specificity for different proteins can be tailored by modifying the loops BC (between the second and third beta sheets) and FG (between the sixth and seventh sheets).

A tribody is a self-assembly antibody mimetic designed based on the C-terminal coiled-coil region of mouse and human cartilage matrix protein (CMP), which self-assembles into a parallel trimeric complex. It is a highly stable trimeric targeting ligand created by fusing a specific target-binding moiety with the trimerization domain derived from CMP. The resulting fusion proteins can efficiently self-assemble into a well-defined parallel homotrimer with high stability. Surface plasmon resonance (SPR) analysis of the trimeric targeting ligands demonstrated significantly enhanced target-binding strength compared with the corresponding monomers. Cellular-binding studies confirmed that such tribodies have superior binding strength toward their respective receptors.

A Centyrin is another antibody mimetic that can be obtained using a library built upon the framework of a consensus FN3 domain sequence (Diem et al., *Protein Eng. Des. Sel.*, 2014). This library employs diversified positions within the C-strand, CD-loop, F-strand and FG-loop of the FN3 domain, and high-affinity Centyrin variants can be selected against specific targets.

In some embodiments, the cell-binding agent is an anti-folate receptor antibody. More specifically, the anti-folate receptor antibody is a humanized antibody or antigen binding fragment thereof that specifically binds a human folate receptor 1 (also known as folate receptor alpha (FR-α)). The terms "human folate receptor 1," "FOLR1," or "folate receptor alpha (FR-α)", as used herein, refers to any native human FOLR1, unless otherwise indicated. Thus, all of these terms can refer to either a protein or nucleic acid sequence as indicated herein. The term "FOLR1" encompasses "full-length," unprocessed FOLR1 as well as any form of FOLR1 that results from processing within the cell. The FOLR1 antibody comprises: (a) a heavy chain CDR1 comprising GYFMN (SEQ ID NO: 4); a heavy chain CDR2 comprising RIHPYDGDTFYNQXaa$_1$FXaa$_2$Xaa$_3$ (SEQ ID NO: 5); and a heavy chain CDR3 comprising YDGSRAMDY (SEQ ID NO: 6); and (b) a light chain CDR1 comprising KASQSVSFAGTSLMH (SEQ ID NO: 7); a light chain CDR2 comprising RASNLEA (SEQ ID NO: 8); and a light chain CDR3 comprising QQSREYPYT (SEQ ID NO: 9); wherein Xaa$_1$ is selected from K, Q, H, and R; Xaa$_2$ is selected from Q, H, N, and R; and Xaa$_3$ is selected from G, E, T, S, A, and V. Preferably, the heavy chain CDR2 sequence comprises RIHPYDGDTFYNQKFQG (SEQ ID NO: 10).

In another embodiment, the anti-folate receptor antibody is a humanized antibody or antigen binding fragment thereof that specifically binds the human folate receptor 1 comprising the heavy chain having the amino acid sequence of QVQLVQSGAEVVKPGASVKISCKASGYTFTGYFMN-WVKQSPGQSLEWIGRIHPYD GDTFYNQKFQG-KATLTVDKSSNTAHMELLSLTSEDFAVYYCTRYDG-SRAMDYWG QGTTVTVSSASTKGPSVFPLAPSSKSTSGGTAALG-CLVKDYFPEPVTVSWNSGALTS GVHTFPAVLQSS-GLYSLSSVVTVPSSSLGTQTYICNVNHKPSNTKVDK-KVEPKSCDK THTCPPCPAPELLGGPSVFLFPPKPKDTLMISRTPE-VTCVVVDVSHEDPEVKFNWYVD GVEVHNAKTK-PREEQYNSTYRVVSVLTVLHQDWLNGKEYKCK-VSNKALPAPIEKTI SKAKGQPREPQVYTLPPSRDELTKNQVSLTCLVKGFY PSDIAVEWESNGQPENNYKTTPPVLDSDGSFFLY-SKLTVDKSRWQQGNVFSCSVMH EALHNHYTQK-SLSLSPG (SEQ ID NO: 11). In some embodiments, the heavy chain amino acid sequence has a C-terminal lysine after the last glycine of SEQ ID NO:11.

In another embodiment, the anti-folate receptor antibody is a humanized antibody or antigen binding fragment thereof encoded by the plasmid DNA deposited with the ATCC on Apr. 7, 2010 and having ATCC deposit nos. PTA-10772 and PTA-10773 or 10774. In one embodiment, the anti-folate receptor antibody comprises a heavy chain HC that is encoded by the plasmid DNA having ATCC deposit no. PTA-10772 and a light chain LC that is encoded by the plasmid DNA having ATCC deposit no. PTA-10773 or 10774. In another embodiment, the anti-folate receptor antibody comprises a heavy chain HC that is encoded by the plasmid DNA having ATCC deposit no. PTA-10772 and a light chain LC that is encoded by the plasmid DNA having ATCC deposit no. PTA-10773. In yet another embodiment, the anti-folate receptor antibody comprises a heavy chain HC that is encoded by the plasmid DNA having ATCC deposit no. PTA-10772 and a light chain LC that is encoded by the plasmid DNA having ATCC deposit no. PTA-10774.

In another embodiment, the anti-folate receptor antibody is a humanized antibody or antigen binding fragment thereof that specifically binds the human folate receptor 1 comprising the light chain having the amino acid sequence of DIVLTQSPLSLAVSLGQPAIISCKASQSVSFAGTSLMH-WYHQKPGQQPRLLIYRASN LEAGVPDRFSGSGSK-TDFTLNISPVEAEDAATYYCQQSREYPYTFGGGT-KLEIKRTV AAPSVFIFPPSDEQLKSGTASVVCLLNNFYPREAK-VQWKVDNALQSGNSQESVTEQD SKD-STYSLSSTLTLSKADYEKHKVY-ACEVTHQGLSSPVTKSFNRGEC (SEQ ID NO: 12); or DIVLTQSPLSLAVSLGQPAIISCKASQSVSFAGTSLMH-WYHQKPGQQPRLLIYRASN LEAGVPDRFSGSGSK-TDFTLTISPVEAEDAATYYCQQSREYPYTFGGGT-KLEIKRTV AAPSVFIFPPSDEQLKSGTASVVCLLNNFYPREAK-VQWKVDNALQSGNSQESVTEQD SKD-STYSLSSTLTLSKADYEKHKVY-ACEVTHQGLSSPVTKSFNRGEC (SEQ ID NO: 13).

In another embodiment the anti-folate receptor antibody is a humanized antibody or antigen binding fragment thereof that specifically binds the human folate receptor 1 comprising the heavy chain having the amino acid sequence of SEQ ID NO: 11, and the light chain having the amino acid sequence of SEQ ID NO: 12 or SEQ ID NO: 13. Preferably, the antibody comprises the heavy chain having the amino acid sequence of SEQ ID NO: 11 and the light chain having the amino acid sequence of SEQ ID NO: 13 (hu FOLR1). In some embodiments, the heavy chain sequence of hu FOLR1 (huMov19) comprises a C-terminal lysine after the last glycine of SEQ ID NO:11.

In another embodiment, the anti-folate receptor antibody is a humanized antibody or antigen binding fragment thereof that specifically binds the human folate receptor 1, and comprising a heavy chain variable domain at least about 90%, 95%, 99% or 100% identical to QVQLVQSGAEV-VKPGASVKISCKASGYTFTGYFMN-WVKQSPGQSLEWIGRIHPYDG DTFYNQKFQG-KATLTVDKS SNTAHMELLSLTSEDFAVYYCTRYDGSRAMDY-WGQG TTVTVSS (SEQ ID NO: 14), and a light chain variable domain at least about 90%, 95%, 99% or 100% identical to DIVLTQSPLSLAVSLGQPAIIS CKASQSVSF-AGTSLMHWYHQKPGQQPRLLIYRASNL EAGVPDRF- SGSGSKTDFTLNISPVEAEDAATYYCQQSREYPYTF-GGGTKLEIKR (SEQ ID NO: 15); or DIVLTQSPLSLAVSLGQPAIISCKASQSVSFAGTSLMH-WYHQKPGQQPRLLIYRASNL EAGVPDRFSGSGSK-TDFTLTISPVEAEDAATYYCQQSREYPYTFGGGT-KLEIKR (SEQ ID NO: 16).

In another embodiment, the anti-folated receptor antibody is huMov19 or M9346A or M antibody (see, for example, U.S. Pat. Nos. 8,709,432, 8,557,966, 9,133,275, 9,598,490, 9,657,100, 9,670,278, 9,670,279 and 9,670,280 and WO2011106528, all incorporated herein by reference).

In another embodiment, the cell-binding agent is an anti-EGFR antibody or an antibody fragment thereof. In some embodiments, the anti-EGFR antibody is a non-antagonist antibody, including, for example, the antibodies described in WO2012058592, herein incorporated by reference. In another embodiment, the anti-EGFR antibody is a non-functional antibody, for example, humanized ML66 or EGFR-8. More specifically, the anti-EGFR antibody is huML66.

In yet another embodiment, the anti-EGFR antibody comprising the heavy chain having the amino acid sequence of SEQ ID NO: 17, and the light chain having the amino acid sequence of SEQ ID NO: 18. As used herein, double underlined sequences represent the variable regions (i.e., heavy chain variable region or HCVR, and light chain variable region or LCVR) of the heavy or light chain sequences, while bold sequences represent the CDR regions (i.e., from N-terminal to C-terminal, CDR1, CDR2, and CDR3, respectively, of the heavy chain or light chain sequences).

| Antibody | Full-Length Heavy/Light Chain Amino Acid Sequence |
|---|---|
| huML66HC | QVQLQESGPGLVKPSETLSLTCTVSGLSLASNSVSWIRQPPGKGLEWMGVIWNHGGTDYNPSIKSRLSISRDTSKSQVFLKMNSLTAADTAMYFCVRKGGIYFDYWGQGVLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 17) |
| huML66LC | DTVLTQSPSLAVSPGERATISCRASESVSTLMHWYQQKPGQQPKLLIYLASHRESGVPARFSGSGSGTDFTLTIDPMEAEDTATYYCQQSRNDPWTFGQGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 18) |

In yet another embodiment, the anti-EGFR antibody comprises the heavy chain CDR1-CDR3 of SEQ ID NO: 17, and/or the light chain CDR1-CDR3 of SEQ ID NO: 18, and preferably specifically binds EGFR.

In yet another embodiment, the anti-EGFR antibody comprises a heavy chain variable region (HCVR) sequence at least about 90%, 95%, 97%, 99%, or 100% identical to SEQ ID NO: 17, and/or a light chain variable region (LCVR) sequence at least about 90%, 95%, 97%, 99%, or 100% identical to SEQ ID NO: 18, and preferably specifically binds EGFR.

In another embodiment, the anti-EGFR antibody are antibodies described in U.S. Pat. No. 8,790,649 and WO 2012/058588, herein incorporated by reference. In some embodiments, the anti-EGFR antibody is huEGFR-7R antibody.

In some embodiments, the anti-EGFR antibody comprises an immunoglobulin heavy chain region having the amino acid sequence of (SEQ ID NO: 19)
QVQLVQSGAEVAKPGASVKLSCKASGYTFTSYWMQWVKQRPGQGLECIG

TIYPGDGDTTYTQKFQGKATLTADKSSSTAYMQLSSLRSEDSAVYYCAR

YDAPGYAMDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPG and an immunoglobulin light chain region having the amino acid sequence of (SEQ ID NO: 20)
DIQMTQSPSSLSASVGDRVTITCRASQDINNYLAWYQHKPGKGPKLLIH

YTSTLHPGIPSRFSGSGSGRDYSFSISSLEPEDIATYYCLQYDNLLYTF

GQGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC, or an immunoglobulin light chain region having the amino acid sequence of (SEQ ID NO: 21)
DIQMTQSPSSLSASVGDRVTITCKASQDINNYLAWYQHKPGKGPKLLIH

YTSTLHPGIPSRFSGSGSGRDYSFSISSLEPEDIATYYCLQYDNLLYTF

GQGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

In another embodiment, the anti-EGFR antibody comprises an immunoglobulin heavy chain region having the amino acid sequence set forth in SEQ ID NO:19 and an immunoglobulin light chain region having the amino acid sequence set forth in SEQ ID NO:20.

In another embodiment, the anti-EGFR antibody comprises an immunoglobulin heavy chain region having the amino acid sequence set forth in SEQ ID NO:19 and an immunoglobulin light chain region having the amino acid sequence set forth in SEQ ID NO:21.

In yet another embodiment, the anti-EGFR antibody comprises the heavy chain CDR1-CDR3 of SEQ ID NO: 19, and/or the light chain CDR1-CDR3 of SEQ ID NO: 20 or 21, and preferably specifically binds EGFR.

In yet another embodiment, the anti-EGFR antibody comprises a heavy chain variable region (HCVR) sequence at least about 90%, 95%, 97%, 99%, or 100% identical to SEQ ID NO: 19, and/or a light chain variable region (LCVR) sequence at least about 90%, 95%, 97%, 99%, or 100% identical to SEQ ID NO: 20 or 21, and preferably specifically binds EGFR.

In another embodiment, the cell-binding agent is an anti-CD19 antibody, such as those described in U.S. Pat. No. 8,435,528 and WO2004/103272, herein incorporated by reference. In some embodiments, the anti-CD19 antibody comprises an immunoglobulin heavy chain region having the amino acid sequence of QVQLVQPGAEVVKPGASVKLSCKTSGYTFTSNWMHWVKQAPGQGLEWIGEIDPSD SYTNYNQNFQGKAKLTVDKSTSTAYMEVSSLRSDDTAVYYCARGSNPYYYAMDY WGQGTSVTVSSASTKGPSVFPLAPSSKSTSGGTAALGCLVKDYFPEPVTVSWNSGAL TSGVHTFPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEK TISKAKGQPREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQKSLSLSPGK (SEQ ID NO:22) and an immunoglobulin light chain region having the amino acid sequence of EIVLTQSPAIMSASPGERVTMTCSASSGVNYMHWYQQKPGTSPRRWIYDTSKLASG VPARFSGSGSGTDYSLTISSMEPEDAATYYCHQRGSYTFGGGTKLEIKRTVAAPSVFI FPPSDEQLKSGTASVVCLLNNFYPREAKVQWKVDNALQSGNSQESVTEQDSKDSTY SLSSTLTLSKADYEKHKVYACEVTHQGLSSPVTKSFNRGEC (SEQ ID NO:23).

In another embodiment, the anti-CD19 antibody is huB4 antibody.

In yet another embodiment, the anti-CD19 antibody comprises the heavy chain CDR1-CDR3 of SEQ ID NO: 22, and/or the light chain CDR1-CDR3 of SEQ ID NO: 23, and preferably specifically binds CD19.

In yet another embodiment, the anti-CD19 antibody comprises a heavy chain variable region (HCVR) sequence at least about 90%, 95%, 97%, 99%, or 100% identical to SEQ ID NO: 22, and/or a light chain variable region (LCVR) sequence at least about 90%, 95%, 97%, 99%, or 100% identical to SEQ ID NO: 23, and preferably specifically binds CD19.

In yet another embodiment, the cell-binding agent is an anti-Muc1 antibody, such as those described in U.S. Pat. No. 7,834,155, WO 2005/009369 and WO 2007/024222, herein incorporated by reference. In some embodiments, the anti-Muc1 antibody comprises an immunoglobulin heavy chain region having the amino acid sequence of

```
                                          (SEQ ID NO: 24)
QAQLVQSGAEVVKPGASVKMSCKASGYTFTSYNMHWVKQTPGQGLEWIG

YIYPGNGATNYNQKFQGKATLTADTSSSTAYMQISSLTSEDSAVYFCAR

GDSVPFAYWGQGTLVTVSAASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSL

SLSPGK
``` and an immunoglobulin light chain region having the amino acid sequence of

```
                                          (SEQ ID NO: 25)
EIVLTQSPATMSASPGERVTITCSAHSSVSFMHWFQQKPGTSPKLWIYS

TSSLASGVPARFGGSGSGTSYSLTISSMEAEDAATYYCQQRSSFPLTFG

AGTKLELKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC.
```

In another embodiment, the anti-Muc1 antibody is huDS6 antibody.

In yet another embodiment, the anti-Muc1 antibody comprises the heavy chain CDR1-CDR3 of SEQ ID NO: 24, and/or the light chain CDR1-CDR3 of SEQ ID NO: 25, and preferably specifically binds Muc1.

In yet another embodiment, the anti-Muc1 antibody comprises a heavy chain variable region (HCVR) sequence at least about 90%, 95%, 97%, 99%, or 100% identical to SEQ ID NO: 24, and/or a light chain variable region (LCVR) sequence at least about 90%, 95%, 97%, 99%, or 100% identical to SEQ ID NO: 25, and preferably specifically binds Muc1.

In another embodiment, the cell-binding agent is an anti-CD33 antibody or fragment thereof, such as the antibodies or fragments thereof described in U.S. Pat. Nos. 7,557,189, 7,342,110, 8,119,787 and 8,337,855 and WO2004/043344, herein incorporated by reference. In another embodiment, the anti-CD33 antibody is huMy9-6 antibody.

In some embodiments, the anti-CD33 antibody comprises an immunoglobulin heavy chain region having the amino acid sequence of

```
                                          (SEQ ID NO: 26)
QVQLQQPGAEVVKPGASVKMSCKASGYTFTSYYIHWIKQTPGQGLEWVG

VIYPGNDDISYNQKFQGKATLTADKSSTTAYMQLSSLTSEDSAVYYCAR

EVRLRYFDVWGQGTTVTVSSASTKGPSVFPLAPSSKSTSGGTAALGCLV

KDYFPEPVTVSWNSGALTSGVHTFPAVLQSSGLYSLSSVVTVPSSSLGT
```

-continued
QTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKS

LSLSPG, and an immunoglobulin light chain region having the amino acid sequence of (SEQ ID NO: 27)
EIVLTQSPGSLAVSPGERVTMSCKSSQSVFFSSSQKNYLAWYQQIPGQS

PRLLIYWASTRESGVPDRFTGSGSGTDFTLTISSVQPEDLAIYYCHQYL

SSRTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC.

In yet another embodiment, the anti-CD33 antibody comprises the heavy chain CDR1-CDR3 of SEQ ID NO: 26, and/or the light chain CDR1-CDR3 of SEQ ID NO: 27, and preferably specifically binds CD33.

In yet another embodiment, the anti-CD33 antibody comprises a heavy chain variable region (HCVR) sequence at least about 90%, 95%, 97%, 99%, or 100% identical to SEQ ID NO: 26, and/or a light chain variable region (LCVR) sequence at least about 90%, 95%, 97%, 99%, or 100% identical to SEQ ID NO: 27, and preferably specifically binds CD33.

In another embodiment, the cell-binding agent is an anti-CD37 antibody or an antibody fragment thereof, such as those described in U.S. Pat. No. 8,765,917 and WO 2011/112978, herein incorporated by reference. In some embodiments, the anti-CD37 antibody is huCD37-3 antibody.

In some embodiments, the anti-CD37 antibody comprises an immunoglobulin light chain region having the amino acid sequence of (SEQ ID NO: 28)
DIQMTQSPSSLSVSVGERVTITCRASENIRSNLAWYQQKPGKSPKLLVN

VATNLADGVPSRFSGSGSGTDYSLKINSLQPEDFGTYYCQHYWGTTWTF

GQGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC and an immunoglobulin heavy chain region having the amino acid sequence of (SEQ ID NO: 29)
QVQVQESGPGLVAPSQTLSITCTVSGFSLTTSGVSWVRQPPGKGLEWLG

VIWGDGSTNYHPSLKSRLSIKKDHSKSQVFLKLNSLTAADTATYYCAKG

GYSLAHWGQGTLVTVSSASTKGPSVFPLAPSSKSTSGGTAALGCLVKDY

FPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSL

SPG, or an immunoglobulin heavy chain region having the amino acid sequence of (SEQ ID NO: 30)
QVQVQESGPGLVAPSQTLSITCTVSGFSLTTSGVSWVRQPPGKGLEWLG

VIWGDGSTNYHSSLKSRLSIKKDHSKSQVFLKLNSLTAADTATYYCAKG

GYSLAHWGQGTLVTVSSASTKGPSVFPLAPSSKSTSGGTAALGCLVKDY

FPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSL

SPG

In another embodiment, the anti-CD37 antibody comprises an immunoglobulin light chain region having the amino acid sequence set forth in SEQ ID NO:28 and an immunoglobulin heavy chain region having the amino acid sequence set forth in SEQ ID NO:29.

In yet another embodiment, the anti-CD37 antibody comprises an immunoglobulin light chain region having the amino acid sequence set forth in SEQ ID NO:28 and an immunoglobulin heavy chain region having the amino acid sequence set forth in SEQ ID NO:30.

In yet another embodiment, the anti-CD37 antibody comprises the heavy chain CDR1-CDR3 of SEQ ID NO: 29 or 30, and/or the light chain CDR1-CDR3 of SEQ ID NO: 28, and preferably specifically binds CD37.

In yet another embodiment, the anti-CD37 antibody comprises a heavy chain variable region (HCVR) sequence at least about 90%, 95%, 97%, 99%, or 100% identical to SEQ ID NO: 29 or 30, and/or a light chain variable region (LCVR) sequence at least about 90%, 95%, 97%, 99%, or 100% identical to SEQ ID NO: 28, and preferably specifically binds CD37.

In yet another embodiment, the anti-CD37 antibody comprises an immunoglobulin light chain region having the amino acid sequence of (SEQ ID NO: 31)
EIVLTQSPATMSASPGERVTMTCSATSSVTYMHWYQQKPGQSPKRWIYD

TSNLPYGVPARFSGSGSGTSYSLTISSMEAEDAATYYCQQWSDNPPTFG

QGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC and an immunoglobulin heavy chain region having the amino acid sequence of (SEQ ID NO: 32)
QVQLQESGPGLLKPSQSLSLTCTVSGYSITSGFAWHWIRQHPGNKLEWM

GYILYSGSTVYSPSLKSRISITRDTSKNHFFLQLNSVTAADTATYYCAR

GYYGYGAWFAYWGQGTLVTVSAASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQ

KSLSLSPG.

In yet another embodiment, the anti-CD37 antibody comprises the heavy chain CDR1-CDR3 of SEQ ID NO: 32, and/or the light chain CDR1-CDR3 of SEQ ID NO: 31, and preferably specifically binds CD37.

In yet another embodiment, the anti-CD37 antibody comprises a heavy chain variable region (HCVR) sequence at least about 90%, 95%, 97%, 99%, or 100% identical to SEQ ID NO: 32, and/or a light chain variable region (LCVR) sequence at least about 90%, 95%, 97%, 99%, or 100% identical to SEQ ID NO: 31, and preferably specifically binds CD37.

In yet another embodiment, the anti-CD37 antibody is huCD37-50 antibody.

In one embodiment, the cell-binding agent is an anti-CD123 antibody or an antibody fragment thereof, such as those described in WO2017/004026, herein incorporated by reference.

In one embodiment, the anti-CD123 antibody or antibody fragment thereof comprises: a) a heavy chain variable region CDR1 having the amino acid sequence of SSIMH (SEQ ID NO:33), a heavy chain variable region CDR2 having the amino acid sequence of YIKPYNDGTKYNEKFKG (SEQ ID NO:34), and a heavy chain variable region CDR3 having the amino acid sequence of EGGNDYYDTMDY (SEQ ID NO:35); and b) a light chain variable region CDR1 having the amino acid sequence of RASQDINSYLS (SEQ ID NO:36), a light chain variable region CDR2 having the amino acid sequence of RVNRLVD (SEQ ID NO:37), and a light chain variable region CDR3 having the amino acid sequence of LQYDAFPYT (SEQ ID NO:38).

In another embodiment, the anti-CD123 antibody or antibody fragment thereof comprises a heavy chain variable region having the amino acid sequence of QXQLVQSGAEVKKPGASVKVSCKASGYIFTSSIMH-WVRQAPGQGLEWIGYIKPYND GTKYNEKFK-GRATLTSDRSTSTAYMELSSLRSEDTAVYYCAREGG-NDYYDTMDYW GQGTLVTVSS (SEQ ID NO:39) and a light chain variable region having the amino acid sequence of DIQMTQSPSSLSASVGDRVTITCRASQDIN-SYLSWFQQKPGKAPKTLIYRVNRLVDG VPSRF-SGSGSGNDYTLTISSLQPEDFATYYCLQYDAFPYTF-GQGTKVEIKR (SEQ ID NO:40). In certain embodiments, X (or Xaa), the second residue from the N-terminus of SEQ ID NO:39 is Phe (F). In certain embodiments, X (or Xaa) in SEQ ID NO:39 is Val (V).

In another embodiment, the anti-CD123 antibody or antibody fragment thereof comprises a heavy chain variable region having the amino acid sequence of SEQ ID NO:39 and a light chain variable region having the amino acid sequence of SIQMTQSPSSLSASVGDRVTITCRASQDIN-SYLSWFQQKPGKAPKTLIYRVNRLVDGV PSRF-SGSGSGNDYTLTISSLQPEDFATYYCLQYDAFPYTF-GQGTKVEIKR (SEQ ID NO:41).

In another embodiment, the anti-CD123 antibody comprises a heavy chain having the amino acid sequence of QXQLVQSGAEVKKPGASVKVSCKASGYIFTSSIMH-WVRQAPGQGLEWIGYIKPYND GTKYNEKFK-GRATLTSDRSTSTAYMELSSLRSEDTAVYYCAREG-GNDYYDTMDYW
GQGTLVTVSSASTKGPSVFPLAPSSKSTSGGTAALG-CLVKDYFPEPVTVSWNSGALT SGVHTFPAVLQSS-GLYSLSSVVTVPSSSLGTQTYICNVNHKPSNTKVDK-KVEPKSCD
KTHTCPPCPAPELLGGPSVFLFPPKPKDTLMISRTPE-VTCVVVDVSHEDPEVKFNWY VDGVEVHNAKTK-PREEQYNSTYRVVSVLTVLHQDWLNGKEYKCK-VSNKALPAPIE
KTISKAKGQPREPQVYTLPPSRDELTKNQVSLTCLVK-GFYPSDIAVEWESNGQPENN YKTTPPVLDSDGSFF-LYSKLTVDKSRWQQGNVFSCSVMHEALHNHYTQK-SLCLSPG (SEQ ID NO:42) and a light chain having the amino acid sequence of DIQMTQSPSSLSASVGDRVTIT-CRASQDINSYLSWFQQKPGKAPKTLIYRVNRLVDG VPSRFSGSGSGNDYTLTISSLQPEDFATYYCLQYDAF-PYTFGQGTKVEIKRTVAAPSV FIFPPSDEQLKSGTAS-VVCLLNNFYPREAKVQWKVDNALQSGNSQESVTE-QDSKDST
YSLSSTLTLSKADYEKHKVY-ACEVTHQGLSSPVTKSFNRGEC (SEQ ID NO:43). In some embodiments, X (or Xaa), the second residue from the N-terminus of SEQ ID NO: 42, is Val.

In another embodiment, the anti-CD123 antibody comprises a heavy chain having the amino acid sequence of QXQLVQSGAEVKKPGASVKVSCKASGYIFTSSIMH-WVRQAPGQGLEWIGYIKPYND GTKYNEKFK-GRATLTSDRSTSTAYMELSSLRSEDTAVYYCAREG-GNDYYDTMDYW
GQGTLVTVSSASTKGPSVFPLAPSSKSTSGGTAALG-CLVKDYFPEPVTVSWNSGALT SGVHTFPAVLQSS-GLYSLSSVVTVPSSSLGTQTYICNVNHKPSNTKVDK-KVEPKSCD
KTHTCPPCPAPELLGGPSVFLFPPKPKDTLMISRTPE-VTCVVVDVSHEDPEVKFNWY VDGVEVHNAKTK-PREEQYNSTYRVVSVLTVLHQDWLNGKEYKCK-VSNKALPAPIE
KTISKAKGQPREPQVYTLPPSRDELTKNQVSLTCLVK-GFYPSDIAVEWESNGQPENN YKTTPPVLDSDGSFF-LYSKLTVDKSRWQQGNVFSCSVMHEALHNHYTQK-SLSLSPG (SEQ ID NO:44) and a light chain having the amino acid sequence of SEQ ID NO:43. In some embodiments, X (or Xaa), the second residue from the N-terminus of SEQ ID NO: 44, is Val.

In certain embodiments, the cell-binding agent of the present invention (e.g., antibody) have a N-terminal serine, which can be oxidized with an oxidizing agent to form an oxidized cell-binding agent having a N-terminal aldehyde group.

Any suitable oxidizing agent can be used in step (a) of the methods described above. In certain embodiments, the oxidizing agent is a periodate. More specifically, the oxidizing agent is sodium periodate.

Excess molar equivalents of the oxidizing agent relative to the cell-binding agent can be used. In certain embodiments, about 2-100, 5-80, 10-50, 1-10 or 5-10 molar equivalents of the oxidizing agent can be used. In certain embodiments, about 10 or about 50 equivalents of the oxidizing agent can be used. When large amount of the oxidizing agent is used, short reaction time is used to avoid over-oxidation. For example, when 50 equivalents of the oxidizing agent is used, the oxidation reaction is carried out for about 5 to about 60 minutes. Alternatively, when 10 equivalents of the oxidizing agent is used, the reaction is carried out for about 30 minutes to about 24 hours. In some embodiments, 5-10 molar equivalents of the oxidizing agent is used and the oxidation reaction is carried out for about 5 to about 60 minutes (e.g., about 10 to about 30 minutes, about 20 to about 30 minutes).

In certain embodiments, the oxidation reaction does not lead to significant non-targeted oxidation. For example, no signification extent (e.g., less than 20%, less than 10%, less than 5%, less than 3%, less than 2% or less than 1%) of methionine and/or glycans are oxidized during the oxidation process of N-terminal serine to generate the oxidized cell-binding agent having a N-terminal aldehyde group.

In certain embodiments, the cell-binding agent of the present invention (e.g., antibody) has a recombinantly engineered Cys residue, such as a Cys residue at EU/OU numbering position 442 of the antibody. Thus the term "cysteine engineered antibody" includes an antibody with at least one Cys that is not normally present at a given residue of the antibody light chain or heavy chain. Such Cys, which may also be referred to as "engineered Cys," can be engineered using any conventional molecular biology or recombinant DNA technology (e.g., by replacing the coding sequence for a non-Cys residue at the target residue with a coding sequence for Cys). For example, if the original residue is Ser with a coding sequence of 5'-UCU-3', the coding sequence can be mutated (e.g., by site-directed mutagenesis) to 5'-UGU-3', which encodes Cys. In certain embodiments, the Cys engineered antibody of the invention has an engineered Cys in the heavy chain. In certain embodiments, the engineered Cys is in or near the CH3 domain of the heavy chain. The engineered antibody heavy (or light) chain sequence can be inserted into a suitable recombinant expression vector to produce the engineered antibody having the engineered Cys residue in place of the original Ser residue.

Cytotoxicity of Compounds and Conjugates

The cytotoxic compounds and cell-binding agent-drug conjugates of the invention can be evaluated for their ability to suppress proliferation of various cancer cell lines in vitro. For example, cell lines such as human choriocarcinoma JEG-3 cells, can be used for the assessment of cytotoxicity of these compounds and conjugates. Cells to be evaluated can be exposed to the compounds or conjugates for 1-5 days and the surviving fractions of cells measured in direct assays by known methods. $IC_{50}$ values can then be calculated from the results of the assays. Alternatively or in addition, an in vitro cell line sensitivity screen, such as the one described by the U.S. National Cancer Institute (see Voskoglou-Nomikos et al., 2003, Clinical Cancer Res. 9: 42227-4239, incorporated herein by reference) can be used as one of the guides to determine the types of cancers that may be sensitive to treatment with the compounds or conjugates of the invention.

Examples of in vitro potency and target specificity of antibody-cytotoxic agent conjugates of the present invention are described in Example 6. Antigen negative cell lines remained viable when exposed to the same conjugates.

Compositions and Methods of Use

The present invention includes a composition (e.g., a pharmaceutical composition) comprising novel maytansinoid compounds described herein, derivatives thereof, or conjugates thereof, (and/or solvates, hydrates and/or salts thereof) and a carrier (a pharmaceutically acceptable carrier). The present invention also includes a composition (e.g., a pharmaceutical composition) comprising novel maytansinoid compounds described herein, derivatives thereof, or conjugates thereof, (and/or solvates, hydrates and/or salts thereof) and a carrier (a pharmaceutically acceptable carrier). The present compositions are useful for inhibiting abnormal cell growth or treating a proliferative disorder in a mammal (e.g., human).

The present invention includes a method of inhibiting abnormal cell growth or treating a proliferative disorder in a mammal (e.g., human) comprising administering to said mammal a therapeutically effective amount of novel maytansinoid compounds described herein, derivatives thereof, or conjugates thereof, (and/or solvates and salts thereof) or a composition thereof.

The present invention also provides methods of treatment comprising administering to a subject in need of treatment an effective amount of any of the conjugates described above.

Similarly, the present invention provides a method for inducing cell death in selected cell populations comprising contacting target cells or tissue containing target cells with an effective amount of a cytotoxic agent comprising any of the cytotoxic compound-cell-binding agents of the present invention, a salt or solvate thereof. The target cells are cells to which the cell-binding agent can bind.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/mL to 25 mg/mL human serum albumin, (2) 0.9% saline (0.9% w/v NaCl), and (3) 5% (w/v) dextrose; and may also contain an antioxidant such as tryptamine and a stabilizing agent such as Tween 20.

The method for inducing cell death in selected cell populations can be practiced in vitro, in vivo, or ex vivo.

Examples of in vitro uses include treatments of autologous bone marrow prior to their transplant into the same patient in order to kill diseased or malignant cells: treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 μM to 1

μM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as a solution or a lyophilized powder that are tested for sterility and for endotoxin levels.

In some embodiments, the compounds and conjugates of the present invention can be used for treating cancer (e.g., renal cancer, breast cancer (e.g., triple-negative breast cancer (TNBC)), colon cancer, brain cancer, prostate cancer, endometrial cancer, cervical cancer, kidney cancer, pancreatic cancer, ovarian cancer, head and neck cancer, melanoma, colorectal cancer, gastric cancer, squamous cancer, lung cancer (e.g., non small-cell lung cancer and small-cell lung cancer), testicular cancer, choriocarcinoma, Merkel cell carcinoma, sarcoma (e.g., osteosarcoma, chondrosarcoma, liposarcoma, and leiomyosarcoma), glioblastoma, neuroblastoma, lymphoma (e.g., non-Hodgkin lymphoma), myelodysplastic syndrome (MDS), peritoneal cancer, fallopian tube cancer, uterine cancer or leukemia (e.g., acute myeloid leukemia (AML), acute monocytic leukemia, promyelocytic leukemia, eosinophilic leukemia, acute lymphoblastic leukemia (e.g., B-ALL), chronic lymphocytic leukemia (CLL), and chronic myeloid leukemia (CML)).

Analogues and Derivatives

One skilled in the art of cytotoxic agents will readily understand that each of the cytotoxic agents described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

All references cited herein and in the examples that follow are expressly incorporated by reference in their entireties.

EXAMPLES

Example 1

Preparation of DM-H (7) Stock Solution

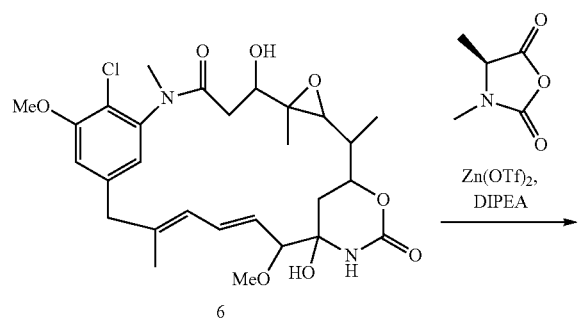

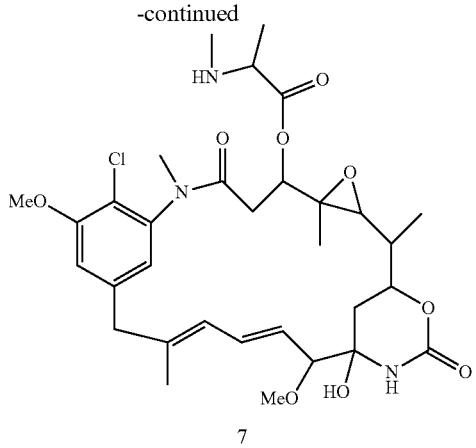

7

Maytansinol (5.0 g, 8.85 mmol) was dissolved in anhydrous DMF (125 mL) then cooled in an ice bath. The N-carboxy anhydride of N-methyl alanine (5.7 g, 44.25 mmol), anhydrous DIPEA (7.70 mL, 44.25 mmol) and zinc trifluoromethane sulfonate (22.5 g, 62 mmol) were then added with magnetic stirring under an argon atmosphere. The ice bath was removed and the reaction was allowed to warm with stirring. After 16 h, deionized water (10 mL) was added. After 30 min a 1:1 solution of saturated aqueous sodium bicarbonate: saturated aqueous sodium chloride (190 mL) and ethyl acetate (250 mL) were added with vigorous stirring. The mixture was transferred to a separatory funnel and the organic layer was retained. The aqueous layer was extracted with ethyl acetate (100 mL) then the organic layers were combined and washed with saturated aqueous sodium chloride (50 mL). The organic layer was concentrated to approximately ¼th its volume by rotary evaporation under vacuum without heating the evaporator bath, no purification was conducted. The concentration of the solution was estimated by dividing the mmoles of maytansinol used in the reaction (1.77 mmol) by the volume (150 mL) giving DM-H stock solution (0.06 mmol/mL). Aliqouts of the stock solution were immediately dispensed then used in reactions or stored in a −80 C freezer then thawed when needed.

Example 2

Synthesis of Thio-Peptide-Maytansinoids

Compounds of the type FMoc-Peptide-NH—CH$_2$—OAc were prepared as exemplified by FMoc-L-Ala-L-Ala-L-Ala-NH—CH$_2$—OAc.

FMoc-Peptide-OAc Compounds

FMoc-L-Ala-L-Ala-L-Ala-NH—CH$_2$—OAc (9a): FMoc-L-Ala-L-Ala-L-Ala-Gly-OH (500 mg, 0.979 mmol) was dissolved in DMF (2 mL), to which was added copper (II) acetate (17.8 mg, 0.098 mmol) and acetic acid (84 μL, 1.47 mmol) with magnetic stirring under argon. Once solids were dissolved, lead tetraacetate (434 mg, 0.979 mmol) was added. The reaction was allowed to proceed at 60° C. for 20 min then purified on a C18, 30 micron 450 g column cartridge, eluting with deionized water containing 0.1% formic acid and an linear acetonitrile gradient of 5% to 55% over 26 min at a flow rate of 125 mL/min Fractions containing pure desired product were frozen and lypholized to give 178 mg (34% yield) of a white solid. HRMS (M+Na)$^+$ calcd. 547.2163; found 547.2160. $^1$H NMR (400

MHz, DMSO-d6) δ 1.20 (qd, J=7.5, 6.9, 4.2 Hz, 9H), 1.91-2.05 (m, 3H), 3.26-3.38 (m, 1H), 4.05 (q, J=7.3 Hz, 1H), 4.23 (td, J=11.9, 10.7, 6.4 Hz, 5H), 5.07 (ddd, J=11.2, 6.9, 4.3 Hz, 2H), 7.32 (q, J=7.5 Hz, 2H), 7.41 (q, J=7.4 Hz, 2H), 7.52 (t, J=6.8 Hz, 1H), 7.71 (q, J=7.5, 7.0 Hz, 2H), 7.82-8.08 (m, 4H), 8.84 (q, J=7.1 Hz, 1H).

FMoc-D-Ala-L-Ala-L-Ala-NH—CH$_2$—OAc (9b): HRMS (M+Na)$^+$ calcd. 547.2163, found 547.2167. $^1$H NMR (400 MHz, DMSO-d6) δ 1.23 (dd, J=12.5, 7.4 Hz, 9H), 1.95 (s, 2H), 4.00-4.13 (m, 1H), 4.17-4.38 (m, 6H), 5.06 (q, J=8.8 Hz, 2H), 7.33 (t, J=7.3 Hz, 2H), 7.42 (t, J=7.4 Hz, 2H), 7.62 (d, J=6.8 Hz, 1H), 7.71 (t, J=8.6 Hz, 2H), 7.85-8.01 (m, 3H), 8.21 (d, J=7.0 Hz, 1H), 8.69 (d, J=6.9 Hz, 1H).

FMoc-L-Ala-D-Ala-L-Ala-NH—CH$_2$—OAc (9c): HRMS (M+Na)$^+$ calcd. 547.2163, found 547.2168. $^1$H NMR (400 MHz, DMSO-d6) δ 1.16-1.24 (m, 9H), 1.97 (s, 3H), 4.07 (q, J=7.0 Hz, 1H), 4.16-4.34 (m, 5H), 5.00-5.16 (m, 2H), 7.33 (td, J=7.4, 1.1 Hz, 2H), 7.42 (t, J=7.4 Hz, 2H), 7.58 (d, J=7.0 Hz, 1H), 7.72 (t, J=8.1 Hz, 2H), 7.90 (d, J=7.5 Hz, 2H), 8.03 (d, J=7.5 Hz, 1H), 8.14 (d, J=7.2 Hz, 1H), 8.85 (t, J=6.9 Hz, 1H).

FMoc-L-Ala-L-Ala-D-Ala-NH—CH$_2$—OAc (9d): HRMS (M+Na)$^+$ calcd. 547.2163, found 547.2167. $^1$H NMR (400 MHz, DMSO-d6) δ 1.18-1.25 (m, 9H), 1.97 (s, 3H), 3.96-4.15 (m, 1H), 4.17-4.36 (m, 5H), 5.09 (d, J=6.9 Hz, 2H), 7.34 (t, J=7.4 Hz, 2H), 7.42 (t, J=7.4 Hz, 2H), 7.57 (d, J=7.2 Hz, 1H), 7.71 (d, J=7.3 Hz, 2H), 7.90 (d, J=7.5 Hz, 2H), 8.07 (s, 2H), 8.86 (s, 1H).

FMoc-L-Ala-D-Ala-NH—CH$_2$—OAc (9f): HRMS (M+Na)$^+$ calcd. 476.1792, found 476.1786. $^1$H NMR (400 MHz, DMSO-d6) δ 1.13 (dd, J=7.1, 1.4 Hz, 6H), 1.89 (s, 3H), 3.99 (q, J=7.1 Hz, 1H), 4.10-4.29 (m, 4H), 4.95-5.08 (m, 2H), 7.26 (t, J=7.4, 1.3 Hz, 2H), 7.35 (t, J=7.4 Hz, 2H), 7.49 (d, J=7.2 Hz, 1H), 7.66 (t, J=7.6 Hz, 2H), 7.82 (d, J=7.5 Hz, 2H), 8.11 (d, J=7.7 Hz, 1H), 8.76 (t, J=7.0 Hz, 1H).

FMoc-D-Ala-L-Ala-NH—CH$_2$—OAc (9g): HRMS (M+Na)$^+$ calcd. 476.1792, found 476.1788. $^1$H NMR (400 MHz, DMSO-d6) δ 1.21 (dd, J=7.1, 1.4 Hz, 6H), 1.96 (s, 3H), 4.08 (t, J=7.1 Hz, 1H), 4.17-4.36 (m, 4H), 5.05-5.14 (m, 2H), 7.26-7.38 (m, 2H), 7.42 (t, J=7.4 Hz, 2H), 7.56 (d, J=7.3 Hz, 1H), 7.73 (t, J=7.6 Hz, 2H), 7.90 (d, J=7.6 Hz, 2H), 8.18 (d, J=7.8 Hz, 1H), 8.83 (t, J=6.9 Hz, 1H).

FMoc-D-Ala-D-Ala-NH—CH$_2$—OAc (9h): HRMS (M+H)$^+$ calcd. 455.4877, found 455.2051 $^1$H NMR (400 MHz, DMSO-d6) δ 1.14 (dd, J=7.1, 3.3 Hz, 6H), 1.21 (d, J=7.2 Hz, 1H), 1.81 (s, 1H), 1.91 (s, 2H), 4.01 (q, J=7.7 Hz, 1H), 4.09-4.27 (m, 5H), 4.95-5.10 (m, 1H), 7.26 (td, J=7.4, 1.2 Hz, 3H), 7.35 (t, J=7.4 Hz, 3H), 7.45 (d, J=7.6 Hz, 1H), 7.65 (t, J=7.1 Hz, 3H), 7.82 (d, J=6.4 Hz, 2H), 7.96 (d, J=7.4 Hz, 1H), 8.78 (t, J=7.0 Hz, 1H).

FMoc-Peptide-COOH Compounds

Compounds of the type FMoc-Peptide-NH—CH$_2$—S—(CH$_2$)$_n$—CO$_2$H were prepared as exemplified by FMoc-L-Ala-L-Ala-L-Ala-NH—CH$_2$—S—(CH$_2$)$_5$—CO$_2$H.

FMoc-L-Ala-L-Ala-L-Ala-NH—CH$_2$—S—(CH$_2$)$_5$—CO$_2$H (10a): 6-mercaptohexanoic acid (287 μL, 2.07 mmol) was dissolved in a solution of 1:4 TFA: dichloromethane (5 mL), then added to a vial containing FMoc-L-Ala-L-Ala-L-Ala-NH—CH$_2$—OAc (178 mg, 0.339 mmol). The reaction was allowed to proceed with magnetic stirring under an argon atmosphere at room temperature for 20 min. The crude material was concentrated en vacuo, redissolved in a minimum volume of DMF and purified on a C18.30 micron, 30 g cartridge eluting with deionized water containing 0.1% formic acid with a linear gradient of acetonitrile from 5% to 95% over 13 min at 35 mL/min. Fractions containing pure desired product were frozen and lypholized to give 200 mg (96% yield) of a white solid. HRMS (M+H)$^+$ calcd. 613.2686; found 613.2690. $^1$H NMR (400 MHz, DMSO-d6) δ 1.20 (dt, J=7.1, 4.9 Hz, 10H), 1.31 (tt, J=10.1, 6.0 Hz, 2H), 1.49 (dq, J=12.5, 7.4 Hz, 4H), 2.18 (t, J=7.3 Hz, 2H), 4.05 (t, J=7.3 Hz, 1H), 4.16-4.30 (m, 7H), 7.33 (td, J=7.4, 1.2 Hz, 2H), 7.42 (td, J=7.3, 1.1 Hz, 2H), 7.54 (d, J=7.4 Hz, 1H), 7.72 (t, J=7.0 Hz, 2H), 7.89 (d, J=7.5 Hz, 2H), 7.94-8.07 (m, 2H), 8.44 (t, J=6.1 Hz, 1H).

FMoc-D-Ala-L-Ala-L-Ala-NH—CH$_2$—S—(CH$_2$)$_5$—CO$_2$H (10b): HRMS (M+Na)$^+$ calcd. 635.2510, found 635.2515. $^1$H NMR (400 MHz, DMSO-d6) δ 1.15 (d, J=6.8 Hz, 3H), 1.18-1.25 (m, 10H), 2.18 (q, J=7.5 Hz, 4H), 2.40-2.48 (m, 1H), 2.70 (t, J=7.2 Hz, 1H), 4.15-4.30 (m, 6H), 6.29 (s, 2H), 7.34 (q, J=7.3 Hz, 3H), 7.42 (t, J=7.4 Hz, 3H), 7.63-7.78 (m, 1H), 7.85 (d, J=7.3 Hz, 2H), 7.89 (d, J=7.5 Hz, 3H), 8.37-8.46 (m, 1H).

FMoc-L-Ala-D-Ala-L-Ala-NH—CH$_2$—S—(CH$_2$)$_5$—CO$_2$H (10c): HRMS (M+Na)$^+$ calcd. 635.2510, found 635.2514. $^1$H NMR (400 MHz, DMSO-d6) δ 1.18-1.23 (m, 10H), 1.34 (q, J=3.4 Hz, 5H), 2.24 (s, 2H), 2.44 (s, 2H), 4.05 (t, J=7.1 Hz, 1H), 4.16-4.35 (m, 8H), 7.33 (t, J=7.4 Hz, 2H), 7.42 (t, J=7.5 Hz, 2H), 7.58 (d, J=7.0 Hz, 1H), 7.71 (t, J=8.4 Hz, 2H), 7.90 (s, 1H), 7.98 (d, J=7.5 Hz, 1H), 8.15 (d, J=7.3 Hz, 1H), 8.39 (t, J=6.2 Hz, 1H), 11.98 (s, 1H).

FMoc-L-Ala-L-Ala-D-Ala-NH—CH$_2$—S—(CH$_2$)$_5$—CO$_2$H (10d): HRMS (M+Na)$^+$ calcd. 635.2510, found 635.2510. $^1$H NMR (400 MHz, DMSO-d6) δ 1.15 (d, J=6.9 Hz, 3H), 1.21 (d, J=7.1 Hz, 9H), 1.28-1.38 (m, 3H), 1.44-1.60 (m, 5H), 2.13-2.22 (m, 3H), 3.33 (q, J=6.9 Hz, 1H), 4.20 (s, 2H), 6.29 (s, 2H), 7.29-7.40 (m, 3H), 7.38-7.47 (m, 3H), 7.85 (d, J=7.5 Hz, 2H), 7.89 (d, J=7.5 Hz, 2H), 8.26 (d, J=7.6 Hz, 1H), 8.48 (d, J=6.2 Hz, 1H).

FMoc-D-Ala-L-Ala-NH—CH$_2$—S—(CH$_2$)$_5$—CO$_2$H (10g): HRMS (M+H)$^+$ calcd. 542.2319, found 542.2316. $^1$H NMR (400 MHz, DMSO-d6) δ 1.13 (dd, J=7.1, 1.7 Hz, 6H), 1.16-1.25 (m, 2H), 1.32-1.47 (m, 4H), 2.08 (t, J=7.3 Hz, 2H), 3.25 (s, 2H), 3.99 (p, J=7.0 Hz, 1H), 4.07-4.27 (m, 6H), 7.26 (t, J=7.4, 1.2 Hz, 2H), 7.35 (t, J=7.4 Hz, 2H), 7.52 (d, J=7.0 Hz, 1H), 7.65 (t, J=7.3 Hz, 2H), 7.82 (d, J=7.5 Hz, 2H), 8.08 (d, J=7.7 Hz, 1H), 8.27 (t, J=6.2 Hz, 1H), 11.82 (s, 1H).

FMoc-L-Ala-D-Ala-NH—CH$_2$—S—(CH$_2$)$_5$—CO$_2$H (10f): HRMS (M+H)$^+$ calcd. 542.2319, found 542.2321. $^1$H NMR (400 MHz, DMSO-d6) δ 1.13 (dd, J=7.1, 1.8 Hz, 7H), 1.17-1.26 (m, 2H), 1.32-1.48 (m, 5H), 2.08 (t, J=7.3 Hz, 2H), 3.99 (p, J=7.1 Hz, 1H), 4.07-4.26 (m, 7H), 7.26 (t, J=7.4 Hz, 2H), 7.35 (t, J=7.4 Hz, 2H), 7.53 (d, J=7.1 Hz, 1H), 7.65 (t, J=7.3 Hz, 2H), 7.82 (d, J=7.4 Hz, 2H), 8.10 (d, J=7.7 Hz, 1H), 8.28 (t, J=6.3 Hz, 1H).

FMoc-D-Ala-D-Ala-NH—CH$_2$—S—(CH$_2$)$_5$—CO$_2$H (10h): (16.7 mg, 0.031 mmol, 70% yield). HRMS (M+H)$^+$ calcd. 542.2319, found 542.2318.

FMoc-L-Ala-D-Ala-L-Ala-NH—CH$_2$—S—(CH$_2$)$_3$—CO$_2$H (10j): HRMS (M+H)$^+$ calcd. 585.2377, found 585.2367. $^1$H NMR (400 MHz, DMSO-d6) δ 1.14-1.26 (m, 9H), 1.75 (p, J=7.3 Hz, 2H), 2.27 (t, J=7.3 Hz, 2H), 2.54 (d, J=7.7 Hz, 2H), 3.97-4.10 (m, 1H), 4.13-4.34 (m, 7H), 7.33 (t, J=7.5 Hz, 2H), 7.42 (t, J=7.5 Hz, 2H), 7.57 (d, J=6.9 Hz, 1H), 7.71 (t, J=8.4 Hz, 2H), 7.89 (d, J=7.6 Hz, 2H), 7.97 (d, J=7.5 Hz, 1H), 8.14 (d, J=7.0 Hz, 1H), 8.41 (s, 1H), 12.06 (s, 1H).

FMoc-D-Ala-L-Ala-NH—CH$_2$—S—(CH$_2$)$_2$—CO$_2$H (10i): HRMS (M+H)$^+$ calcd. 500.1850, found 500.1843. $^1$H NMR (400 MHz, DMSO-d6) δ 1.20 (dd, J=7.2, 1.9 Hz, 6H), 2.53 (d, J=7.1 Hz, 2H), 2.70 (t, J=7.1 Hz, 2H), 4.07 (q, J=7.0 Hz, 1H), 4.17-4.26 (m, 4H), 4.29 (d, J=6.8 Hz, 2H), 7.33 (t, J=7.4 Hz, 2H), 7.41 (t, J=7.5 Hz, 2H), 7.56 (d, J=7.1 Hz, 1H), 7.72 (t, J=7.7 Hz, 2H), 7.89 (d, J=7.5 Hz, 2H), 8.14 (d, J=7.6 Hz, 1H), 8.42 (t, J=6.3 Hz, 1H), 12.22 (s, 1H).

Synthesis of FMoc-L-Ala-D-Ala-L-Ala-NH—CH$_2$—OAc (9c):

(50 ml), washed with 10% aqueous citric acid (2×100 mL), water (100 mL), followed by brine (100 mL). The organic layer was dried over magnesium sulfate, filter and concentrate to yield crude FMoc-L-Ala-D-Ala-OtBu, assume 100% yield.

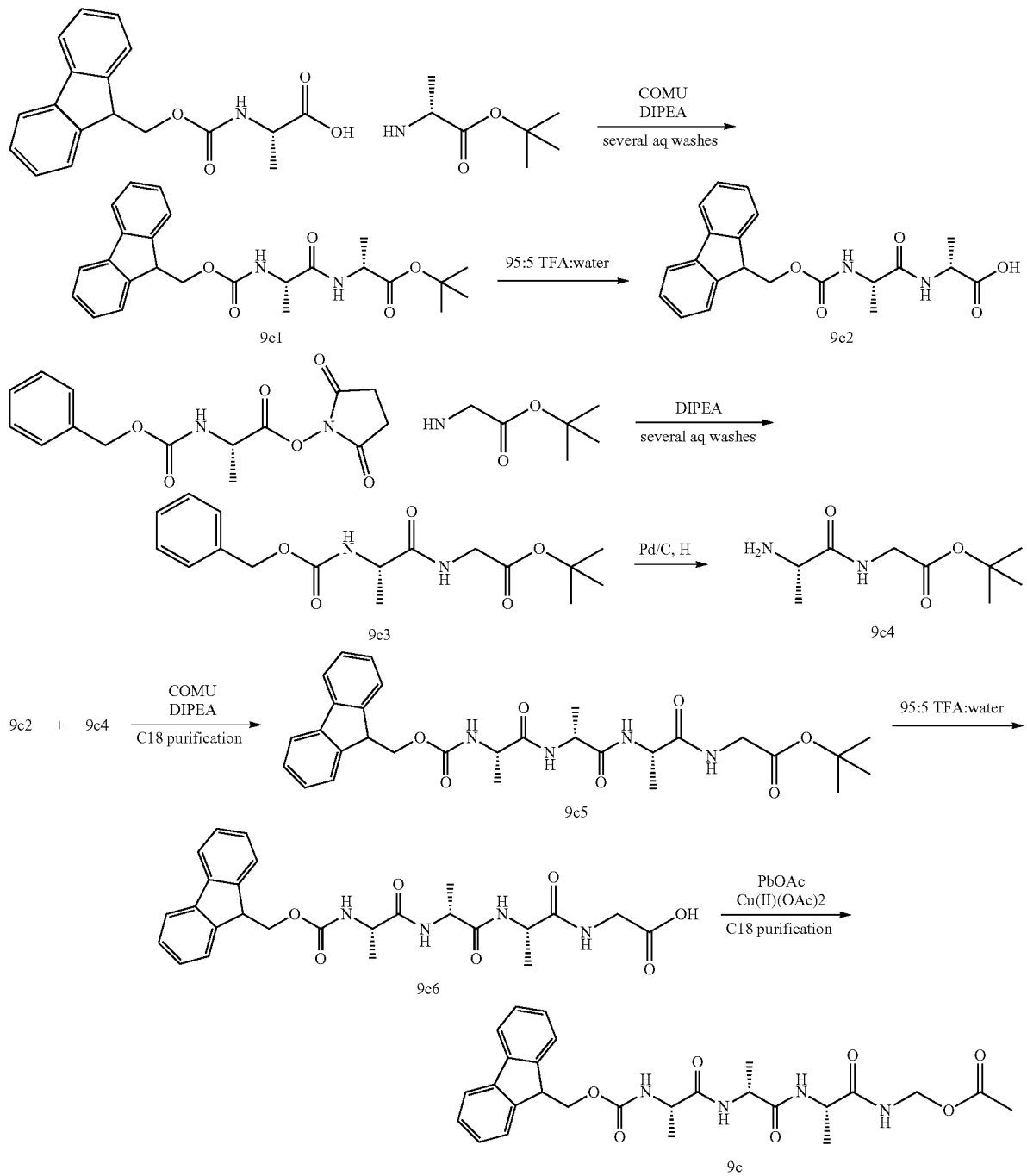

Step 1: FMoc-L-Ala-D-Ala-OtBu (9c1):

FMoc-L-alanine (10 g, 32.1 mmol) and D-Ala-OtBu, HCl (7.00 g, 38.5 mmol) were dissolved in CH2Cl2 (100 ml), treated with COMU (20.63 g, 48.2 mmol) and DIPEA (11.22 ml, 64.2 mmol). The reaction was allowed to proceed for under argon at room temperature. After 2 hours the reaction showed completion by UPLC, was diluted with 2-MeTHF Step 2: FMoc-L-Ala-D-Ala (9c2)

FMoc-LAla-DAla-OtBu (11.25 g, 25.7 mmol) was treated with TFA:Water (95:5) (50 ml). The reaction was allowed to proceed at room temperature under argon atmosphere. After 4 hours the reaction showed completion by UPLC, diluted with toluene (25 mL) and coevaporated 3× to yield FMoc-L-Ala-D-Ala, assume 100% yield.

Step 3: FMoc-L-Ala-Gly-OtBu (9c3)

Z-L-Ala-ONHS (10 g, 31.2 mmol) and tert-butyl glycinate, (6.28 g, 37.5 mmol) were dissolved in CH2Cl2 (100 ml), treated with DIPEA (10.91 ml, 62.4 mmol). The reaction was allowed to proceed under argon at room temperature. After 2 hours, UPLC showed completion, the reaction was diluted with 2-MeTHF (50 mL), awashed with 10% aqueous citric acid (100 mL), sat'd sodium bicarbonate (2×100 mL), water (100 mL), brine (100 mL). The organic layer dried over magnesium sulfate, filtered and concentrated to yield Z-L-Ala-Gly-OtBu, assume 100% yield.

Step 4. L-Ala-Gly-OtBu (9c4)

Z-Ala-Gly-OtBu (10.05 g, 29.9 mmol) was dissolved in 95:5 MeOH:Water (50 ml), transferred to hydrogenator flask, treated with Pd/C (1.272 g, 11.95 mmol). The hydrogenator flask was placed on the shaker, air was removed by vacuum while flask was shook. Hydrogen filled flask to 30 psi, flask was shaken for 2 minutes and hydrogen was removed by vacuum. This was repeated 2 additional times. Hydrogen was allowed to fill flask to 30 psi and was allowed to shake. After 4 hr, UPLC showed completion, reaction was filtered through a celite plug, en vucuo, redissolved in 2-MeTHF, concentrated to yield LAla-Gly-OtBu, assume 100% yield.

Step 5: FMoc-L-Ala-D-Ala-L-Ala-Gly-OtBu (9c5)

FMoc-LAla-D-ALa-OH (0.959 g, 2.508 mmol) and L-Ala-Gly-OtBu (0.718 g, 3.01 mmol) were dissolved in CH2Cl2 (10 ml), treated with COMU (1.181 g, 2.76 mmol) and DIPEA (0.876 ml, 5.02 mmol). The reaction was allowed to proceed under argon at room temperature. After 2 hours reaction showed completion. The reaction was concentrated to remove CH2Cl2, redissolved in 2 mL DMF and purified by C18 combiflash using a linear gradient, product was combined to yield FMoc-L-Ala-D-Ala-L-Ala-Gly-OtBu (660 mg, 46% yield).

Step 6. FMoc-L-Ala-D-Ala-L-Ala-Gly-OH (9c6)

FMoc-LAla-DAla-LAla-GlyOtBu (200 mg, 0.353 mmol) was treated with TFA:Water (95:5) (2 ml). The reaction was allowed to proceed under argon at room temperature. After 1 hr the reaction showed completion by UPLC, Diluted with toluene (1 mL), coevaporated 2× with toluene to yield FMoc-L-Ala-D-Ala-L-Ala-Gly-OH, assume 100% yield.

Step 7. FMoc-L-Ala-D-Ala-L-Ala-CH$_2$—OAc (9c7)

FMoc-L-Ala-D-Ala-L-Ala-Gly-OH (2.65 g, 5.19 mmol) was dissolved in DMF (20 mL), treated with copper (II) acetate (0.094 g, 0.519 mmol) and acetic acid (0.446 ml, 7.79 mmol) once all reagents were dissolved the reaction was treated lead tetraacetate (3.45 g, 7.785 mmol). The reaction was allowed to proceed under argon at 60° C. for 30 minutes. The crude reaction was purified via Combiflash Rf 200i using C18 450 g column with a flow rate of 125 mL/min with deionized water containing 0.1% formic acid and acetonitrile as solvents using a gradient as follows (time in minutes, percent acetonitrile) (0,5) (8,50) (26, 55). The desired product having a retention time of 11 minutes, product fractions were immediately froze and lyphorized to yield FMoc-L-Ala-D-Ala-L-Ala-CH2-OAc (843 mg, 1.607 mmol, 31.0% yield). HRMS (M+Na)$^+$ calcd 547.2163, found 547.2167. $^1$H NMR (400 MHz, DMSO-d6) δ 1.23 (dd, J=12.5, 7.4 Hz, 9H), 1.95 (s, 2H), 4.00-4.13 (m, 1H), 4.17-4.38 (m, 6H), 5.06 (q, J=8.8 Hz, 2H), 7.33 (t, J=7.3 Hz, 2H), 7.42 (t, J=7.4 Hz, 2H), 7.62 (d, J=6.8 Hz, 1H), 7.71 (t, J=8.6 Hz, 2H), 7.85-8.01 (m, 3H), 8.21 (d, J=7.0 Hz, 1H), 8.69 (d, J=6.9 Hz, 1H).

FMoc-Peptide-May-NMA Compounds

Compounds of the type FMoc-Peptide-NH—CH$_2$—S—(CH$_2$)$_n$—CO$_2$-DM were prepared as exemplified by FMoc-L-Ala-L-Ala-L-Ala-NH—CH$_2$—S—(CH$_2$)$_5$—CO—DM.

FMoc-L-Ala-L-Ala-L-Ala-NH—CH$_2$—S—(CH$_2$)$_5$—CO-DM (11a): To DM-H stock solution (8.2 mL, 0.49 mmol) was added FMoc-L-Ala-L-Ala-L-Ala-NH—CH$_2$—S—(CH$_2$)$_5$—COOH (300 mg, 0.49 mmol), EDC (94 mg, 0.490 mmol) and DIPEA (90 µL, 0.49 mmol). The reaction was allowed to proceed with magnetic stirring at room temperature under argon atmosphere for 2 h. The crude material was concentrated by rotary evaporation under vacuum and residue was taken up in a minimum volume of DMF then purified on a C18, 30 micron, 30 g cartridge eluting with deionized water containing 0.1% formic acid and a linear gradient of acetonitrile from 5% to 50% over 25 min. Fractions containing pure desired product were frozen and lyphorized to yield 151 mg, (37.2% yield) of white solid. HRMS (M+Na)$^+$ calcd. 1266.5170; found 1266.5141. $^1$H NMR (400 MHz, DMSO-d6) δ 0.77 (s, 3H), 1.12 (d, J=6.4 Hz, 3H), 1.14-1.22 (m, 12H), 1.22-1.30 (m, 3H), 1.35-1.49 (m, 4H), 1.50-1.55 (m, 1H), 1.59 (s, 3H), 2.00-2.07 (m, 1H), 2.14 (ddd, J=15.6, 8.7, 5.9 Hz, 1H), 2.40 (dtd, J=17.0, 7.9, 7.0, 4.9 Hz, 3H), 2.69 (s, 3H), 2.79 (d, J=9.6 Hz, 1H), 3.08 (s, 3H), 3.20 (d, J=12.6 Hz, 1H), 3.24 (s, 3H), 3.43 (d, J=12.4 Hz, 2H), 3.48 (d, J=8.9 Hz, 1H), 3.92 (s, 3H), 4.08 (ddd, J=20.8, 10.8, 5.0 Hz, 3H), 4.14-4.24 (m, 4H), 4.26 (d, J=6.0 Hz, 3H), 4.52 (dd, J=12.0, 2.8 Hz, 1H), 5.34 (q, J=6.7 Hz, 1H), 5.56 (dd, J=14.7, 9.0 Hz, 1H), 5.91 (s, 1H), 6.50-6.66 (m, 3H), 6.88 (s, 1H), 7.17 (d, J=1.8 Hz, 1H), 7.33 (td, J=7.5, 1.2 Hz, 2H), 7.41 (t, J=7.4 Hz, 2H), 7.53 (d, J=7.4 Hz, 1H), 7.72 (t, J=7.0 Hz, 2H), 7.89 (d, J=7.5 Hz, 3H), 7.99 (d, J=7.3 Hz, 1H), 8.36 (t, J=6.3 Hz, 1H).

FMoc-D-Ala-L-Ala-L-Ala-NH—CH$_2$—S—(CH$_2$)$_5$—CO-DM (11b): HRMS (M+Na)$^+$ calcd. 1266.5170, found 1266.5164. $^1$H NMR (400 MHz, DMSO-d6) δ 0.78 (s, 3H), 1.14 (dd, J=14.6, 6.5 Hz, 6H), 1.22 (t, J=6.8 Hz, 10H), 1.33-1.57 (m, 4H), 1.59 (s, 3H), 2.04 (d, J=13.5 Hz, 1H), 2.27-2.44 (m, 1H), 2.69 (s, 3H), 2.80 (d, J=9.7 Hz, 1H), 3.08 (s, 3H), 3.14-3.28 (m, 5H), 3.37-3.55 (m, 3H), 3.92 (s, 3H), 3.98-4.16 (m, 3H), 4.20 (dd, J=15.6, 7.6 Hz, 7H), 4.52 (d, J=12.7 Hz, 1H), 5.34 (d, J=6.9 Hz, 1H), 5.57 (dd, J=14.7, 9.0 Hz, 1H), 5.92 (s, 1H), 6.46-6.72 (m, 4H), 6.88 (s, 1H), 7.17 (s, 1H), 7.33 (t, J=7.5 Hz, 3H), 7.41 (t, J=7.4 Hz, 3H), 7.60-7.75 (m, 4H), 7.80-7.93 (m, 4H), 8.12 (t, 1H), 8.29 (d, J=6.9 Hz, 1H).

FMoc-L-Ala-D-Ala-L-Ala-NH—CH$_2$—S—(CH$_2$)$_5$—CO-DM (11c): HRMS (M+Na)$^+$ calcd. 1266.5170, found 1266.5170. $^1$H NMR (400 MHz, DMSO-d6) δ 0.71 (s, 3H), 0.96-1.16 (m, 10H), 1.16-1.51 (m, 10H), 1.52 (s, 4H), 1.82-2.16 (m, 1H), 2.17-2.56 (m, 11H), 2.62 (d, J=5.8 Hz, 4H), 2.68-2.87 (m, 3H), 2.92-3.04 (m, 4H), 3.09-3.22 (m, 7H), 3.24 (d, J=7.4 Hz, 1H), 3.33-3.50 (m, 2H), 3.73-3.89 (m, 4H), 3.92-4.07 (m, 2H), 4.07-4.25 (m, 2H), 4.45 (dd, J=12.0, 2.8 Hz, 1H), 5.27 (q, J=6.7 Hz, 1H), 5.40-5.55 (m, 1H), 5.85 (s, 1H), 6.33-6.66 (m, 4H), 6.81 (s, 2H), 7.03-7.19 (m, 1H), 7.19-7.43 (m, 2H), 7.62 (d, J=11.6 Hz, 1H), 7.73-7.85 (m, 1H).

FMoc-L-Ala-L-Ala-D-Ala-NH—CH$_2$—S—(CH$_2$)$_5$—CO-DM (11d): HRMS (M+Na)$^+$ calcd. 1266.5170, found 1266.5158. $^1$H NMR (400 MHz, DMSO-d6) δ 0.78 (s, 3H), 1.06-1.33 (m, 16H), 1.44 (d, J=10.3 Hz, 11H), 1.59 (s, 3H), 1.99-2.22 (m, 3H), 2.35-2.45 (m, 2H), 2.55 (d, J=1.8 Hz, 1H), 2.69 (s, 3H), 2.80 (d, J=9.6 Hz, 1H), 3.08 (s, 2H), 3.25 (s, 3H), 3.39-3.52 (m, 3H), 3.92 (s, 3H), 3.99-4.40 (m, 4H), 4.52 (d, J=11.1 Hz, 1H), 5.34 (d, J=6.8 Hz, 1H), 5.57 (dd, J=14.5, 9.2 Hz, 1H), 5.92 (s, 1H), 6.53-6.64 (m, 2H), 6.88

(s, 2H), 7.17 (d, J=1.9 Hz, 1H), 7.33 (t, J=7.3 Hz, 3H), 7.42 (t, J=7.4 Hz, 3H), 7.57 (d, J=7.4 Hz, 1H), 7.72 (s, 3H), 7.89 (d, J=7.6 Hz, 3H), 7.99 (d, J=7.6 Hz, 1H), 8.07 (s, 1H), 8.35 (s, 1H).

FMoc-D-Ala-L-Ala-NH—CH$_2$—S—(CH$_2$)$_5$—CO-DM (11g): HRMS (M+H)$^+$ calcd. 1173.4980, found 1173.4964. $^1$H NMR (400 MHz, DMSO-d6) δ 0.79 (s, 3H), 1.06-1.34 (m, 13H), 1.36-1.54 (m, 4H), 1.60 (s, 2H), 1.88-2.10 (m, 1H), 2.10-2.23 (m, 1H), 2.31-2.51 (m, 13H), 2.71 (s, 3H), 2.80 (d, J=9.6 Hz, 1H), 3.10 (s, 3H), 3.26 (s, 4H), 3.33-3.66 (m, 3H), 3.98-4.32 (m, 4H), 4.53 (dd, J=12.0, 2.8 Hz, 1H), 5.35 (q, J=6.7 Hz, 1H), 5.49-5.65 (m, 1H), 6.51-6.67 (m, 3H), 6.89 (s, 1H), 7.19 (d, J=1.8 Hz, 1H), 8.25 (s, 2H), 8.34 (d, J=7.1 Hz, 1H), 8.58 (t, J=6.3 Hz, 1H).

FMoc-L-Ala-D-Ala-NH—CH$_2$—S—(CH$_2$)$_5$—CO-DM (11f): HRMS (M+H)$^+$ calcd. 1173.4980, found 1173.4969.

FMoc-D-Ala-D-Ala-NH—CH$_2$—S—(CH$_2$)$_5$—CO-DM (11h): HRMS (M+Na)$^+$ calcd. 1195.4907, found 1195.4799. $^1$H NMR (400 MHz, DMSO-d$_6$) δ 0.71 (s, 3H), 1.00-1.22 (m, 13H), 1.28-1.45 (m, 2H), 1.52 (s, 3H), 1.91-2.14 (m, 1H), 2.26 (t, J=1.9 Hz, 5H), 2.48 (t, J=1.8 Hz, 2H), 2.62 (s, 3H), 2.66-2.77 (m, 2H), 3.01 (s, 2H), 3.10-3.21 (m, 5H), 3.28-3.47 (m, 2H), 3.86 (d, J=6.7 Hz, 4H), 3.93-4.25 (m, 10H), 4.37-4.54 (m, 1H), 5.27 (d, J=6.6 Hz, 1H), 5.40-5.56 (m, 1H), 5.85 (s, 1H), 6.31-6.66 (m, 3H), 6.81 (s, 1H), 7.11 (d, J=1.8 Hz, 1H), 7.26 (t, J=7.4 Hz, 2H), 7.35 (t, J=7.4 Hz, 2H), 7.45 (d, J=7.5 Hz, 1H), 7.65 (t, J=7.1 Hz, 2H), 7.82 (d, J=7.5 Hz, 2H), 7.89 (d, J=7.3 Hz, 1H).

FMoc-L-Ala-D-Ala-L-Ala-NH—CH$_2$—S—(CH$_2$)$_3$—CO-DM (11j): HRMS (M+H)$^+$ calcd. 1216.5038, found 1216.4999. $^1$H NMR (400 MHz, DMSO-d6) δ 0.78 (s, 3H), 0.95-1.29 (m, 16H), 1.37 (d, J=3.4 Hz, 1H), 1.46 (t, J=12.5 Hz, 2H), 1.59 (s, 3H), 1.62-1.90 (m, 1H), 1.99-2.07 (m, 1H), 2.08 (s, 2H), 2.18-2.43 (m, 1H), 2.50-2.59 (m, 1H), 2.69 (s, 3H), 2.73-2.83 (m, 1H), 3.10 (s, 2H), 3.25 (s, 3H), 3.38-3.55 (m, 2H), 3.91 (s, 3H), 3.99-4.13 (m, 4H), 4.12-4.35 (m, 7H), 4.52 (dd, J=12.0, 2.9 Hz, 1H), 5.34 (q, J=6.7 Hz, 1H), 5.48-5.65 (m, 1H), 5.92 (s, 1H), 6.48-6.70 (m, 3H), 6.88 (s, 1H), 7.17 (d, J=1.7 Hz, 1H), 7.33 (t, J=7.5 Hz, 2H), 7.41 (t, J=7.4 Hz, 2H), 7.58 (d, J=7.0 Hz, 1H), 7.71 (t, J=8.3 Hz, 2H), 7.89 (d, J=7.5 Hz, 3H), 7.95 (d, J=7.6 Hz, 1H), 8.15 (d, J=7.2 Hz, 1H), 8.29-8.38 (m, 1H), 8.41 (s, 1H).

FMoc-D-Ala-L-Ala-NH—CH$_2$—S—(CH$_2$)$_2$—CO-DM (11i): HRMS (M+H)$^+$ calcd. 1131.4510, found 1131.4507. $^1$H NMR (400 MHz, DMSO-d6) δ 0.76 (s, 3H), 1.08-1.21 (m, 12H), 1.24 (d, J=13.9 Hz, 1H), 1.38-1.52 (m, 2H), 1.58 (s, 3H), 1.99-2.09 (m, 1H), 2.33-2.44 (m, 1H), 2.68 (s, 3H), 2.80 (dd, J=14.4, 8.6 Hz, 1H), 3.08 (s, 3H), 3.17 (d, J=12.5 Hz, 1H), 3.23 (s, 3H), 3.46 (t, J=10.3 Hz, 2H), 3.91 (s, 3H), 4.00-4.13 (m, 3H), 4.13-4.34 (m, 5H), 4.52 (dd, J=12.0, 2.9 Hz, 1H), 5.30 (q, J=6.8 Hz, 1H), 5.55 (dd, J=13.4, 9.1 Hz, 1H), 5.91 (s, 1H), 6.55 (dd, J=7.4, 5.7 Hz, 3H), 6.87 (s, 1H), 7.16 (d, J=1.8 Hz, 1H), 7.32 (tt, J=7.4, 1.5 Hz, 2H), 7.41 (tt, J=7.5, 1.5 Hz, 2H), 7.57 (d, J=7.0 Hz, 1H), 7.71 (dd, J=10.5, 7.5 Hz, 2H), 7.88 (d, J=7.5 Hz, 2H), 8.14 (d, J=7.6 Hz, 1H), 8.37 (t, J=6.3 Hz, 1H).

Amino-Peptide-Maytansinoids

Compounds of the type H$_2$N-Peptide-NH—CH$_2$—S—(CH$_2$)$_n$—CO$_2$-DM were prepared as exemplified by H$_2$N-L-Ala-L-Ala-L-Ala-NH—CH$_2$—S—(CH$_2$)$_5$—CO-DM.

H$_2$N-L-Ala-L-Ala-L-Ala-NH—CH$_2$—S—(CH$_2$)$_5$—CO-DM (12a): FMoc-L-Ala-L-Ala-L-Ala-NH—CH$_2$—S—(CH$_2$)$_5$—CO-DM (151 mg, 0.121 mmol) was treated with 20% morpholine in DMF (2 mL). The reaction was allowed to proceed with magnetic stirring under argon at room temperature for 1 h. The crude material was purified on a C18, 30 micro, 150 g column cartridge eluting with deionized water containing 0.1% formic acid and a linear gradient of acetonitrile from 5% to 50% over 26 min Fractions containing desired product were immediately frozen and lypholized to give 46 mg (37.1% yield) of a colorless oil. HRMS (M+H)$^+$ calcd. 1022.4670; found 1022.4669. $^1$H NMR (400 MHz, DMSO-d6) δ 0.78 (s, 3H), 1.12 (d, J=6.3 Hz, 3H), 1.13-1.21 (m, 10H), 1.21-1.31 (m, 3H), 1.37-1.50 (m, 4H), 1.51-1.57 (m, 1H), 1.59 (s, 3H), 2.04 (dd, J=14.4, 2.8 Hz, 1H), 2.15 (ddd, J=15.9, 8.7, 6.0 Hz, 1H), 2.38 (td, J=7.0, 3.6 Hz, 2H), 2.70 (s, 3H), 2.79 (d, J=9.6 Hz, 1H), 3.09 (s, 3H), 3.21 (d, J=12.5 Hz, 1H), 3.25 (s, 3H), 3.33-3.55 (m, 8H), 3.93 (s, 3H), 4.01-4.33 (m, 5H), 4.52 (dd, J=12.0, 2.8 Hz, 1H), 5.34 (q, J=6.7 Hz, 1H), 5.57 (dd, J=14.6, 9.0 Hz, 1H), 5.95 (s, 1H), 6.48-6.65 (m, 3H), 6.89 (s, 1H), 7.18 (d, J=1.8 Hz, 1H), 8.07 (d, J=7.5 Hz, 1H), 8.13 (s, 1H), 8.31 (s, 1H), 8.40 (t, J=6.3 Hz, 1H).

H$_2$N-D-Ala-L-Ala-L-Ala-NH—CH$_2$—S—(CH$_2$)$_5$—CO-DM (12b): HRMS (M+H)$^+$ calcd. 1022.4670, found 1022.4675. $^1$H NMR (400 MHz, DMSO-d6) δ 0.71 (s, 3H), 1.05 (dd, J=6.7, 3.1 Hz, 7H), 1.08-1.16 (m, 10H), 1.19 (t, J=8.1 Hz, 3H), 1.30-1.50 (m, 6H), 1.52 (s, 3H), 1.97 (d, J=13.3 Hz, 1H), 2.01-2.21 (m, 2H), 2.34 (s, 3H), 2.63 (s, 3H), 2.73 (d, J=9.8 Hz, 1H), 3.02 (s, 3H), 3.14 (d, J=12.5 Hz, 1H), 3.33-3.48 (m, 2H), 3.86 (s, 3H), 3.95-4.23 (m, 7H), 4.45 (dd, J=13.1 Hz, 1H), 5.27 (q, J=6.8 Hz, 1H), 5.41-5.58 (m, 1H), 5.85 (s, 1H), 6.39-6.63 (m, 4H), 6.81 (s, 1H), 7.12 (d, J=1.8 Hz, 1H), 8.02 (s, 1H), 8.13 (d, J=7.7 Hz, 1H), 8.26 (s, 1H), 8.36 (t, J=6.2 Hz, 1H).

H$_2$N-L-Ala-D-Ala-L-Ala-NH—CH$_2$—S—(CH$_2$)$_5$—CO-DM (12c): HRMS (M+H)$^+$ calcd. 1022.4670, found 1022.4680. $^1$H NMR (400 MHz, DMSO-d6) δ 0.71 (s, 3H), 1.01-1.26 (m, 19H), 1.25-1.50 (m, 6H), 1.52 (s, 3H), 1.97 (d, J=13.7 Hz, 1H), 2.02-2.22 (m, 1H), 2.35 (dd, J=17.2, 9.5 Hz, 2H), 2.47 (d, J=11.5 Hz, 1H), 2.63 (s, 4H), 2.73 (d, J=9.6 Hz, 1H), 3.02 (s, 3H), 3.10-3.24 (m, 6H), 3.32-3.50 (m, 2H), 3.86 (s, 3H), 3.95-4.18 (m, 4H), 4.45 (dd, J=12.1, 2.6 Hz, 1H), 5.27 (q, J=6.9 Hz, 1H), 5.44-5.55 (m, 1H), 5.85 (s, 1H), 6.42-6.59 (m, 4H), 6.81 (s, 1H), 7.12 (d, J=1.7 Hz, 1H), 8.02 (s, 1H), 8.13 (d, J=7.7 Hz, 1H), 8.36 (t, J=6.3 Hz, 1H).

H$_2$N-L-Ala-L-Ala-D-Ala-NH—CH$_2$—S—(CH$_2$)$_5$—CO-DM (12d): HRMS (M+H)$^+$ calcd. 1022.4670, found 1022.4675. $^1$H NMR (400 MHz, DMSO-d6) δ 0.71 (s, 3H), 0.98-1.14 (m, 13H), 1.14-1.26 (m, 2H), 1.30-1.49 (m, 4H), 1.52 (s, 3H), 2.24-2.41 (m, 2H), 2.44 (d, J=1.8 Hz, 16H), 2.63 (s, 2H), 2.73 (d, J=9.6 Hz, 1H), 3.02 (s, 2H), 3.08-3.21 (m, 4H), 3.32-3.49 (m, 2H), 3.86 (s, 3H), 3.92-4.23 (m, 3H), 4.45 (d, J=11.8 Hz, 1H), 5.26 (t, J=6.7 Hz, 1H), 5.40-5.57 (m, 1H), 5.86 (s, 1H), 6.41-6.66 (m, 3H), 6.81 (s, 1H), 7.12 (d, J=1.7 Hz, 1H), 8.02 (s, 1H), 8.10 (d, J=7.7 Hz, 1H), 8.35 (t, J=6.3 Hz, 1H).

H$_2$N-D-Ala-L-Ala-NH—CH$_2$—S—(CH$_2$)$_5$—CO-DM (12g): HRMS (M+H)$^+$ calcd. 951.4299, found 951.4289. $^1$H NMR (400 MHz, DMSO-d6) δ 0.79 (s, 3H), 1.06-1.34 (m, 13H), 1.36-1.54 (m, 4H), 1.60 (s, 2H), 1.88-2.10 (m, 1H), 2.10-2.23 (m, 1H), 2.31-2.51 (m, 13H), 2.71 (s, 3H), 2.80 (d, J=9.6 Hz, 1H), 3.10 (s, 3H), 3.26 (s, 4H), 3.33-3.66 (m, 3H), 3.98-4.32 (m, 4H), 4.53 (dd, J=12.0, 2.8 Hz, 1H), 5.35 (q, J=6.7 Hz, 1H), 5.49-5.65 (m, 1H), 6.51-6.67 (m, 3H), 6.89 (s, 1H), 7.19 (d, J=1.8 Hz, 1H), 8.25 (s, 2H), 8.34 (d, J=7.1 Hz, 1H), 8.58 (t, J=6.3 Hz, 1H).

H$_2$N-L-Ala-D-Ala-NH—CH$_2$—S—(CH$_2$)$_5$—CO-DM (12f): HRMS (M+H)$^+$ calcd. 951.4226, found 951.1299. $^1$H NMR (400 MHz, DMSO-d6) δ 0.71 (s, 3H), 1.00-1.13 (m, 11H), 1.19 (t, J=8.9 Hz, 3H), 1.29-1.45 (m, 4H), 1.52 (s, 3H), 1.92-2.03 (m, 1H), 2.07 (dd, J=15.7, 8.7 Hz, 1H), 2.23-2.39 (m, 1H), 2.63 (s, 3H), 2.73 (d, J=9.7 Hz, 1H), 3.02 (s, 3H), 3.07-3.32 (m, 14H), 3.34-3.47 (m, 2H), 3.86 (s, 3H), 3.95-4.21 (m, 4H), 4.45 (dd, J=11.9, 2.8 Hz, 1H), 5.27 (q, J=6.8 Hz, 1H), 5.50 (dd, J=14.7, 9.0 Hz, 1H), 5.85 (s, 1H), 6.40-6.61 (m, 3H), 6.81 (s, 1H), 7.12 (d, J=1.8 Hz, 1H), 8.41 (t, J=6.1 Hz, 1H).

H$_2$N-D-Ala-D-Ala-NH—CH$_2$—S—(CH$_2$)$_5$—CO-DM (12h): HRMS (M+H)$^+$ calcd. 950.4226, found 951.4299. $^1$H NMR (400 MHz, DMSO-d6) δ 0.71 (s, 3H), 0.96-1.14 (m, 14H), 1.19 (t, J=8.9 Hz, 3H), 1.38 (q, J=10.5, 7.0 Hz, 5H), 1.52 (s, 3H), 1.88-2.02 (m, 1H), 2.02-2.18 (m, 1H), 2.22-2.41 (m, 2H), 2.48 (s, 1H), 2.63 (s, 3H), 2.73 (d, J=9.6 Hz, 1H), 3.02 (s, 3H), 3.08-3.22 (m, 4H), 3.34-3.48 (m, 2H), 3.86 (s, 4H), 3.95-4.23 (m, 5H), 4.45 (dd, J=11.9, 2.8 Hz, 1H), 5.27 (q, J=6.7 Hz, 1H), 5.41-5.60 (m, 1H), 5.85 (s, 1H), 6.40-6.65 (m, 4H), 6.81 (s, 1H), 7.12 (d, J=1.8 Hz, 1H), 8.44 (t, J=6.1 Hz, 1H).

H$_2$N-L-Ala-D-Ala-L-Ala-NH—CH$_2$—S—(CH$_2$)$_3$—CO-DM (12j): HRMS (M+H)$^+$ calcd. 994.4357, found 994.4330.

H$_2$N-D-Ala-L-Ala-NH—CH$_2$—S—(CH$_2$)$_2$—CO-DM (12i): HRMS (M+H)$^+$ calcd. 909.3830, found 909.3826. $^1$H NMR (400 MHz, DMSO-d6) δ 0.77 (s, 3H), 1.12 (d, J=6.7 Hz, 6H), 1.17 (dd, J=7.0, 5.2 Hz, 6H), 1.25 (d, J=13.3 Hz, 1H), 1.40-1.51 (m, 2H), 1.59 (s, 3H), 2.04 (dd, J=14.4, 2.9 Hz, 1H), 2.41 (ddt, J=18.6, 10.1, 5.4 Hz, 1H), 2.61-2.70 (m, 1H), 2.72 (s, 3H), 2.76-2.90 (m, 3H), 3.09 (s, 3H), 3.20 (d, J=12.4 Hz, 1H), 3.25 (s, 3H), 3.33 (q, J=6.9 Hz, 1H), 3.39-3.64 (m, 3H), 3.93 (s, 3H), 4.03-4.16 (m, 2H), 4.24 (dt, J=15.1, 7.6 Hz, 2H), 4.53 (dd, J=12.0, 2.9 Hz, 1H), 5.32 (q, J=6.8 Hz, 1H), 5.51-5.64 (m, 1H), 5.93 (s, 1H), 6.49-6.62 (m, 2H), 6.88 (s, 1H), 7.19 (d, J=1.8 Hz, 1H), 8.10 (s, 1H), 8.55 (t, J=6.3 Hz, 1H).

SPDB-Peptide-Maytansinoids

Compounds of the type SPDB-Peptide-NH—CH$_2$—S—(CH$_2$)$_n$—CO$_2$-DM were prepared as exemplified by SPDB-L-Ala-L-Ala-L-Ala-NH—CH$_2$—S—(CH$_2$)$_5$—CO-DM.

SPDB-L-Ala-L-Ala-L-Ala-NH—CH$_2$—S—(CH$_2$)$_5$—CO-DM (13a): H$_2$N-L-Ala-L-Ala-L-Ala-NH—CH$_2$—S—(CH$_2$)$_5$—CO-DM (46 mg, 0.045 mmol) was dissolved in DMF (2 mL), to which was added SPDB (14.7 mg, 0.045 mmol) and reacted at room temperature with magnetic stirring under an argon atmosphere for 1 h. The crude material was purified on a C18, 430 micro, 30 g cartridge eluting with deionized water containing 0.1% formic acid and a linear gradient of acetonitrile from 5% to 95% over 35 min. Fractions containing pure desired product were frozen and lypholized to give 38 mg, (68.5% yield) of white solid. HRMS (M+H)$^+$ calcd. 1233.4796; found 1233.4783. $^1$H NMR (400 MHz, DMSO-d6) δ 0.78 (s, 3H), 1.12 (d, J=6.4 Hz, 3H), 1.14-1.21 (m, 10H), 1.22-1.30 (m, 3H), 1.44 (qd, J=10.2, 4.5 Hz, 5H), 1.50-1.56 (m, 1H), 1.59 (s, 3H), 1.84 (p, J=7.3 Hz, 2H), 2.04 (dd, J=14.4, 2.7 Hz, 1H), 2.15 (ddd, J=15.8, 8.6, 5.9 Hz, 2H), 2.24 (t, J=7.2 Hz, 2H), 2.39 (dtdd, J=18.1, 13.2, 8.1, 4.7 Hz, 3H), 2.70 (s, 3H), 2.76-2.86 (m, 3H), 3.09 (s, 3H), 3.21 (d, J=12.5 Hz, 1H), 3.25 (s, 3H), 3.43 (d, J=12.4 Hz, 1H), 3.48 (d, J=9.0 Hz, 1H), 3.92 (s, 3H), 4.13 (s, 2H), 4.19 (h, J=6.6 Hz, 4H), 4.52 (dd, J=12.1, 2.8 Hz, 1H), 5.34 (q, J=6.8 Hz, 1H), 5.56 (dd, J=14.7, 9.0 Hz, 1H), 5.92 (s, 1H), 6.49-6.66 (m, 3H), 6.85-6.97 (m, 2H), 7.18 (d, J=1.8 Hz, 1H), 7.23 (ddd, J=7.3, 4.8, 1.2 Hz, 1H), 7.76 (dt, J=8.1, 1.2 Hz, 1H), 7.78-7.91 (m, 2H), 8.00 (d, J=7.1 Hz, 1H), 8.09 (d, J=7.0 Hz, 1H), 8.33 (t, J=6.3 Hz, 1H), 8.44 (dt, J=4.7, 1.3 Hz, 1H), 8.50 (s, 1H).

SPDB-D-Ala-L-Ala-L-Ala-NH—CH$_2$—S—(CH$_2$)$_5$—CO-DM (13b): HRMS (M+H)$^+$ calcd. 1233.4796, found 1233.4799. $^1$H NMR (400 MHz, DMSO-d6) δ 0.71 (s, 3H), 1.01-1.22 (m, 13H), 1.27-1.45 (m, 2H), 1.52 (s, 3H), 1.91-2.16 (m, 1H), 2.26 (d, J=7.4 Hz, 7H), 2.26 (t, J=1.9 Hz, 4H), 2.48 (t, J=1.8 Hz, 2H), 2.57-2.65 (m, 3H), 2.65-2.77 (m, 2H), 3.01 (s, 2H), 3.13 (d, J=12.2 Hz, 1H), 3.18 (s, 3H), 3.32-3.47 (m, 2H), 3.86 (d, J=6.7 Hz, 4H), 3.93-4.11 (m, 2H), 4.18 (t, J=11.2 Hz, 7H), 4.39-4.50 (m, 1H), 5.27 (q, J=6.7 Hz, 1H), 5.50 (dd, J=14.7, 8.8 Hz, 1H), 5.85 (s, 1H), 6.37-6.61 (m, 3H), 6.81 (s, 1H), 7.11 (d, J=1.8 Hz, 1H), 7.26 (t, J=7.4 Hz, 2H), 7.35 (t, J=7.4 Hz, 2H), 7.45 (d, J=7.5 Hz, 1H), 7.65 (t, J=7.1 Hz, 2H), 7.82 (d, J=7.5 Hz, 2H), 7.89 (d, J=7.3 Hz, 1H).

SPDB-L-Ala-D-Ala-L-Ala-NH—CH$_2$—S—(CH$_2$)$_5$—CO-DM (13c): HRMS (M+H)$^+$ calcd. 1233.4796, found 1233.4795. $^1$H NMR (400 MHz, DMSO-d6) δ 0.71 (s, 3H), 1.02-1.25 (m, 18H), 1.29-1.50 (m, 6H), 1.52 (s, 3H), 1.70-1.87 (m, 2H), 1.87-2.14 (m, 2H), 2.13-2.22 (m, 2H), 2.27-2.40 (m, 3H), 2.63 (s, 3H), 2.69-2.84 (m, 4H), 3.02 (s, 3H), 3.14 (d, J=12.3 Hz, 1H), 3.18 (s, 3H), 3.32-3.45 (m, 2H), 3.85 (s, 3H), 3.95-4.07 (m, 2H), 4.07-4.19 (m, 4H), 4.45 (dd, J=11.9, 2.7 Hz, 1H), 5.27 (q, J=6.7 Hz, 1H), 5.44-5.55 (m, 1H), 5.85 (s, 1H), 6.42-6.59 (m, 3H), 6.81 (s, 1H), 7.11 (s, 1H), 7.13-7.19 (m, 1H), 7.68 (d, J=8.2, 2.7 Hz, 1H), 7.72-7.80 (m, 1H), 7.88 (t, J=6.6 Hz, 1H), 8.04 (d, J=6.4 Hz, 1H), 8.09 (d, J=7.4 Hz, 1H), 8.25 (t, J=6.3 Hz, 1H), 8.37 (dd, J=5.0, 1.9 Hz, 1H).

SPDB-L-Ala-L-Ala-D-Ala-NH—CH$_2$—S—(CH$_2$)$_5$—CO-DM (13d): HRMS (M+H)$^+$ calcd. 1233.4796, found 1233.4797. $^1$H NMR (400 MHz, DMSO-d6) δ 0.72 (d, J=3.3 Hz, 3H), 0.98-1.28 (m, 22H), 1.30-1.46 (m, 3H), 1.53 (s, 3H), 1.78 (q, J=7.1 Hz, 2H), 1.86-2.16 (m, 2H), 2.19 (q, J=7.4, 5.6 Hz, 2H), 2.26-2.41 (m, 2H), 2.41-2.55 (m, 4H), 2.64 (d, J=3.2 Hz, 2H), 2.81-2.92 (m, 1H), 3.02 (s, 2H), 3.14 (d, J=12.0 Hz, 1H), 3.26 (s, 1H), 3.31-3.48 (m, 2H), 3.86 (s, 3H), 3.97-4.30 (m, 7H), 4.46 (dd, J=11.8, 3.2 Hz, 1H), 5.24-5.36 (m, 1H), 5.45-5.62 (m, 1H), 5.86 (s, 1H), 6.40-6.65 (m, 3H), 6.82 (d, J=3.4 Hz, 1H), 7.11 (d, J=3.2 Hz, 1H), 7.18 (d, J=12.1, 6.1, 4.9 Hz, 2H), 7.69 (d, J=8.1 Hz, 1H), 7.75 (t, J=7.6 Hz, 2H), 7.89 (d, J=7.8, 3.2 Hz, 1H), 7.95-8.04 (m, 2H), 8.26 (d, J=6.1 Hz, 1H), 8.33-8.47 (m, 1H).

SPDB-D-Ala-L-Ala-NH—CH$_2$—S—(CH$_2$)$_5$—CO-DM (13g): HRMS (M+H)$^+$ calcd. 1162.4425, found 1162.4405. $^1$H NMR (400 MHz, DMSO-d6) δ 0.71 (s, 3H), 1.08 (dt, J=13.9, 6.9 Hz, 15H), 1.15-1.25 (m, 3H), 1.28-1.44 (m, 5H), 1.52 (s, 3H), 1.77 (p, J=7.2 Hz, 2H), 1.91-2.02 (m, 1H), 2.02-2.13 (m, 1H), 2.17 (t, J=7.2 Hz, 2H), 2.22-2.40 (m, 2H), 2.63 (s, 3H), 2.68-2.80 (m, 3H), 3.02 (s, 3H), 3.13 (d, J=12.3 Hz, 1H), 3.18 (s, 3H), 3.33-3.45 (m, 2H), 3.85 (s, 3H), 3.95-4.16 (m, 5H), 4.45 (dd, J=12.1, 2.8 Hz, 1H), 5.27 (q, J=6.7 Hz, 1H), 5.44-5.56 (m, 1H), 5.85 (s, 1H), 6.43-6.60 (m, 3H), 6.82 (s, 1H), 7.11 (d, J=1.8 Hz, 1H), 7.12-7.18 (m, 1H), 7.65-7.79 (m, 2H), 8.06-8.16 (m, 2H), 8.30 (t, J=6.3 Hz, 1H), 8.35-8.40 (m, 1H).

SPDB-L-Ala-D-Ala-NH—CH$_2$—S—(CH$_2$)$_5$—CO-DM (13f): HRMS (M+H)$^+$ calcd. 1162.4399, found 1162.455. $^1$H NMR (400 MHz, DMSO-d6) δ 0.71 (s, 3H), 1.02-1.13 (m, 12H), 1.14-1.25 (m, 3H), 1.31-1.44 (m, 5H), 1.52 (s, 3H), 1.77 (p, J=7.3 Hz, 2H), 1.97 (d, J=14.3, 2.7 Hz, 1H), 2.02-2.13 (m, 1H), 2.17 (t, J=7.2 Hz, 2H), 2.28-2.40 (m, 3H), 2.43 (m, J=3.2 Hz, 3H), 2.63 (s, 3H), 2.69-2.80 (m, 3H), 3.02 (s, 3H), 3.13 (d, J=12.4 Hz, 1H), 3.18 (s, 3H), 3.39 (dd, J=21.0, 10.7 Hz, 2H), 3.85 (s, 3H), 3.96-4.18 (m, 5H), 4.45 (dd, J=12.1, 2.8 Hz, 1H), 5.27 (q, J=6.7 Hz, 1H), 5.45-5.55 (m, 1H), 5.85 (s, 1H), 6.43-6.60 (m, 3H), 6.81 (s, 1H), 7.10 (d, J=1.8 Hz, 1H), 7.16 (t, J=7.2, 4.9 Hz, 1H), 7.68 (d, J=8.1 Hz, 1H), 7.71-7.79 (m, 1H), 8.02-8.15 (m, 2H), 8.28 (t, J=6.3 Hz, 1H), 8.37 (d, J=4.8, 1.7 Hz, 1H).

SPDB-D-Ala-D-Ala-NH—CH$_2$—S—(CH$_2$)$_5$—CO-DM (13h): HRMS (M+H)$^+$ calcd. 1162.4399, found 1162.455. $^1$H NMR (400 MHz, DMSO-d6) δ 0.71 (s, 3H), 1.02-1.16

(m, 13H), 1.14-1.25 (m, 3H), 1.28-1.49 (m, 5H), 1.52 (s, 3H), 1.77 (p, J=7.2 Hz, 2H), 1.92-2.14 (m, 2H), 2.17 (t, J=7.2 Hz, 2H), 2.23-2.40 (m, 2H), 2.46-2.54 (m, 1H), 2.63 (s, 3H), 2.65-2.85 (m, 4H), 3.02 (s, 3H), 3.03-3.16 (m, 3H), 3.18 (s, 3H), 3.28-3.45 (m, 2H), 3.85 (s, 3H), 3.95-4.20 (m, 5H), 4.45 (dd, J=12.1, 2.8 Hz, 1H), 5.27 (q, J=6.7 Hz, 1H), 5.44-5.55 (m, 1H), 5.82-5.88 (m, 1H), 6.42-6.59 (m, 3H), 6.81 (s, 1H), 7.11 (d, J=1.9 Hz, 1H), 7.14-7.20 (m, 1H), 7.67-7.72 (m, 1H), 7.72-7.80 (m, 1H), 7.88 (d, J=7.6 Hz, 1H), 7.99 (d, J=7.1 Hz, 1H), 8.28 (t, J=6.3 Hz, 1H), 8.35-8.40 (m, 1H).

SPDB-L-Ala-D-Ala-L-Ala-NH—$CH_2$—S—$(CH_2)_3$—CO-DM (13j): HRMS $(M+H)^+$ calcd. 1203.4337, found 1203.4315. $^1$H NMR (400 MHz, DMSO-d6) δ 0.71 (s, 3H), 0.94-1.24 (m, 20H), 1.38 (s, 3H), 1.52 (s, 3H), 1.57-1.87 (m, 1H), 1.89-2.08 (m, 1H), 2.26 (t, J=15.1 Hz, 1H), 2.50 (d, J=5.2 Hz, 2H), 2.54-2.79 (m, 7H), 3.05 (d, J=3.8 Hz, 3H), 3.18 (s, 5H), 3.29-3.46 (m, 3H), 3.86 (d, J=6.1 Hz, 4H), 4.00 (s, 3H), 4.05-4.24 (m, 4H), 4.33-4.54 (m, 1H), 5.17-5.38 (m, 1H), 5.39-5.58 (m, 1H), 5.85 (s, 1H), 6.29-6.58 (m, 4H), 6.63 (s, 1H), 6.81 (s, 1H), 7.04-7.19 (m, 1H), 7.90 (s, 1H), 8.14-8.39 (m, 1H), 8.45 (s, 1H).

SPDB-D-Ala-L-Ala-NH—$CH_2$—S—$(CH_2)_2$—CO-DM (13i): HRMS $(M+H)^+$ calcd. 1120.3955, found 1120.3951. $^1$H NMR (400 MHz, DMSO-d6) δ 0.74-0.82 (m, 3H), 1.10-1.22 (m, 13H), 1.25 (d, J=14.1 Hz, 1H), 1.46 (t, J=10.9 Hz, 2H), 1.56-1.63 (m, 3H), 1.85 (ddd, J=14.4, 9.0, 5.1 Hz, 2H), 2.00 (ddd, J=14.7, 9.3, 5.4 Hz, 9H), 2.24 (dt, J=10.8, 5.0 Hz, 2H), 2.72 (d, J=3.6 Hz, 2H), 2.94 (dq, J=10.7, 7.2, 5.7 Hz, 9H), 3.10 (d, J=3.7 Hz, 3H), 3.20 (d, J=3.4 Hz, 1H), 3.25 (d, J=3.6 Hz, 3H), 3.32 (d, J=3.7 Hz, 1H), 3.47 (td, J=10.7, 10.0, 3.8 Hz, 2H), 3.93 (t, J=4.6 Hz, 3H), 4.02-4.25 (m, 6H), 4.49-4.57 (m, 1H), 5.28-5.37 (m, 1H), 5.53-5.62 (m, 1H), 5.92 (d, J=3.6 Hz, 1H), 6.57 (q, J=5.4, 4.5 Hz, 3H), 6.85-6.93 (m, 1H), 7.17 (d, J=3.3 Hz, 1H), 7.25 (dq, J=8.0, 4.9 Hz, 6H), 7.72-7.87 (m, 11H), 8.16 (dt, J=15.4, 4.9 Hz, 2H), 8.45 (t, J=9.9, 5.9 Hz, 6H).

Thio-Peptide-Maytansinoids

Compounds of the type HS—$(CH_2)_3$CO-Peptide-NH—$CH_2$—S—$(CH_2)_n$—$CO_2$-DM were prepared as exemplified by HS—$(CH_2)_3$CO-L-Ala-L-Ala-L-Ala-NH—$CH_2$—S—$(CH_2)_5$—CO-DM.

HS—$(CH_2)_3$CO-L-Ala-L-Ala-L-Ala-NH—$CH_2$—S—$(CH_2)_5$—CO-DM (14a): SPDB-L-Ala-L-Ala-L-Ala-NH—$CH_2$—S—$(CH_2)_5$—CO-DM (38 mg, 0.031 mmol) was dissolved in DMSO (1 mL) to which a solution of DTT (19 mg, 0.12 mmol) in 100 mM potassium phosphate, 2 mM EDTA pH 7.5 buffer (1 mL) was added. The reaction was allowed to proceed at room temperature with magnetic stirring under an argon for 1 h. The crude reaction was purified on a C18, 30 micron, 30 g cartridge eluting with deionized water containing 0.1% formic acid and a linear gradient of acetonitrile of 5% to 95% over 35 min. Fractions containing desired product were immediatley frozen and lypholized to give 18.2 mg, (52.5% yield) of a white solid. HRMS (M+H)+ calcd. 1124.4809; found 1124.4798. $^1$H NMR (400 MHz, DMSO-d6) δ 0.78 (s, 3H), 1.12 (d, J=6.4 Hz, 3H), 1.14-1.21 (m, 10H), 1.22-1.30 (m, 3H), 1.37-1.50 (m, 5H), 1.51-1.57 (m, 1H), 1.59 (s, 3H), 1.74 (p, J=7.2 Hz, 2H), 2.04 (dd, J=14.4, 2.8 Hz, 1H), 2.09-2.18 (m, 1H), 2.18-2.24 (m, 2H), 2.27 (t, J=7.6 Hz, 1H), 2.38 (td, J=7.1, 4.7 Hz, 2H), 2.44 (t, J=7.3 Hz, 2H), 2.70 (s, 3H), 2.79 (d, J=9.6 Hz, 1H), 3.09 (s, 3H), 3.21 (d, J=12.6 Hz, 1H), 3.25 (s, 3H), 3.43 (d, J=12.4 Hz, 1H), 3.49 (d, J=9.0 Hz, 1H), 3.93 (s, 3H), 4.08 (ddd, J=21.6, 11.4, 4.1 Hz, 2H), 4.13-4.28 (m, 4H), 4.52 (dd, J=12.1, 2.8 Hz, 1H), 5.34 (q, J=6.7 Hz, 1H), 5.56 (dd, J=14.7, 9.0 Hz, 1H), 5.91 (d, J=1.4 Hz, 1H), 6.48-6.66 (m, 3H), 6.88 (s, 1H), 7.18 (d, J=1.8 Hz, 1H), 7.86 (d, J=7.5 Hz, 1H), 7.96 (d, J=7.3 Hz, 1H), 8.05 (d, J=7.1 Hz, 1H), 8.33 (t, J=6.3 Hz, 1H).

HS—$(CH_2)_3$CO-D-Ala-L-Ala-L-Ala-NH—$CH_2$—S—$(CH_2)_5$—CO-DM (14b): HRMS $(M+Na)^+$ calcd. 1146.4629, found 1146.4591. $^1$H NMR (400 MHz, DMSO-d6) δ 0.71 (s, 3H), 1.03-1.25 (m, 19H), 1.30-1.45 (m, 6H), 1.52 (s, 4H), 1.65 (p, J=7.3 Hz, 2H), 1.91-2.02 (m, 1H), 2.02-2.13 (m, 1H), 2.12-2.19 (m, 4H), 2.29-2.39 (m, 4H), 2.63 (s, 3H), 2.73 (d, J=9.6 Hz, 1H), 3.02 (s, 3H), 3.14 (d, J=12.5 Hz, 1H), 3.33-3.47 (m, 2H), 3.86 (s, 3H), 4.01 (td, J=10.4, 9.7, 4.3 Hz, 2H), 4.04-4.16 (m, 5H), 4.45 (dd, J=12.0, 2.9 Hz, 1H), 5.27 (q, J=6.7 Hz, 1H), 5.43-5.56 (m, 1H), 5.85 (s, 1H), 6.38-6.61 (m, 4H), 6.81 (s, 1H), 7.11 (d, J=1.8 Hz, 1H), 7.82 (d, J=7.7 Hz, 1H), 7.97 (t, J=6.3 Hz, 1H), 8.10 (d, J=6.0 Hz, 1H), 8.25 (d, J=6.9 Hz, 1H).

HS—$(CH_2)_3$CO-L-Ala-D-Ala-L-Ala-NH—$CH_2$—S—$(CH_2)_5$—CO-DM (14c): HRMS $(M+Na)^+$ calcd. 1146.4629, found 1146.4553. $^1$H NMR (400 MHz, DMSO-d6) δ 0.71 (s, 3H), 0.99-1.26 (m, 21H), 1.31-1.45 (m, 5H), 1.52 (s, 3H), 1.67 (p, J=7.2 Hz, 2H), 1.89-2.02 (m, 1H), 2.02-2.24 (m, 4H), 2.25-2.46 (m, 3H), 2.63 (s, 3H), 2.73 (d, J=9.7 Hz, 1H), 3.02 (s, 3H), 3.18 (s, 3H), 3.32-3.51 (m, 2H), 3.86 (s, 3H), 3.96-4.18 (m, 7H), 4.45 (dd, J=12.0, 2.9 Hz, 1H), 5.27 (q, J=6.8 Hz, 1H), 5.44-5.63 (m, 1H), 5.85 (s, 1H), 6.37-6.59 (m, 4H), 6.81 (s, 1H), 7.11 (d, J=1.8 Hz, 1H), 7.89 (d, J=7.7 Hz, 1H), 8.03 (d, J=6.5 Hz, 1H), 8.08 (d, J=7.3 Hz, 1H), 8.27 (t, J=6.3 Hz, 1H).

HS—$(CH_2)_3$CO-L-Ala-L-Ala-D-Ala-NH—$CH_2$—S—$(CH_2)_5$—CO-DM (14d): HRMS $(M+Na)^+$ calcd. 1146.4629, found 1146.4519. $^1$H NMR (400 MHz, DMSO-d6) δ 0.71 (s, 3H), 0.95-1.24 (m, 20H), 1.27-1.45 (m, 5H), 1.52 (s, 3H), 1.67 (p, J=7.3 Hz, 2H), 1.93-2.01 (m, 1H), 2.02-2.22 (m, 4H), 2.22-2.41 (m, 5H), 2.63 (s, 3H), 2.73 (d, J=9.6 Hz, 1H), 3.02 (s, 3H), 3.18 (s, 4H), 3.39 (dd, J=21.4, 10.7 Hz, 2H), 3.86 (s, 3H), 3.94-4.24 (m, 6H), 4.45 (dd, J=12.0, 2.8 Hz, 1H), 5.27 (q, J=6.7 Hz, 1H), 5.44-5.57 (m, 1H), 5.85 (s, 1H), 6.37-6.65 (m, 3H), 6.81 (s, 1H), 7.11 (d, J=1.8 Hz, 1H), 7.89 (d, J=7.6 Hz, 1H), 7.93-8.05 (m, 2H), 8.26 (t, J=6.4 Hz, 1H).

HS—$(CH_2)_3$CO-D-Ala-L-Ala-NH—$CH_2$—S—$(CH_2)_5$—CO-DM (14g): HRMS $(M+H)^+$ calcd. 1053.4438, found 1053.4426. $^1$H NMR (400 MHz, DMSO-d6) δ 0.71 (s, 3H), 1.01-1.15 (m, 13H), 1.15-1.27 (m, 3H), 1.31-1.44 (m, 5H), 1.53 (s, 3H), 1.67 (p, J=7.1 Hz, 2H), 1.93-2.03 (m, 1H), 2.03-2.23 (m, 4H), 2.22-2.41 (m, 5H), 2.63 (s, 3H), 2.73 (d, J=9.7 Hz, 1H), 3.02 (s, 3H), 3.14 (d, J=12.5 Hz, 1H), 3.18 (s, 3H), 3.32-3.46 (m, 2H), 3.86 (s, 3H), 3.92-4.20 (m, 6H), 4.45 (dd, J=11.9, 2.8 Hz, 1H), 5.27 (q, J=6.7 Hz, 1H), 5.42-5.58 (m, 1H), 5.85 (s, 1H), 6.42-6.60 (m, 3H), 6.81 (s, 1H), 7.12 (d, J=1.8 Hz, 1H), 8.05 (d, J=6.5 Hz, 1H), 8.10 (d, J=7.8 Hz, 1H), 8.30 (t, J=6.3 Hz, 1H).

HS—$(CH_2)_3$CO-L-Ala-D-Ala-NH—$CH_2$—S—$(CH_2)_5$—CO-DM (14f): HRMS $(M+H)^+$ calcd. 1053.4366, found 1053.4438. $^1$H NMR (400 MHz, DMSO-d6) δ 0.71 (s, 3H), 1.02-1.14 (m, 13H), 1.19 (t, J=9.7 Hz, 3H), 1.31-1.43 (m, 6H), 1.53 (s, 3H), 1.67 (p, J=7.3 Hz, 2H), 1.91-2.02 (m, 1H), 2.02-2.22 (m, 4H), 2.34-2.39 (m, 4H), 2.63 (s, 3H), 2.73 (d, J=9.5 Hz, 1H), 3.02 (s, 3H), 3.19 (d, J=4.2 Hz, 4H), 3.30-3.47 (m, 2H), 3.86 (s, 3H), 3.94-4.20 (m, 6H), 4.45 (d, J=11.8, 2.8 Hz, 1H), 5.27 (q, J=6.7 Hz, 1H), 5.44-5.56 (m, 1H), 5.85 (s, 1H), 6.40-6.61 (m, 3H), 6.81 (s, 1H), 7.12 (s, 1H), 8.03 (d, J=6.5 Hz, 1H), 8.08 (d, J=7.8 Hz, 1H), 8.29 (t, J=6.2 Hz, 1H).

HS—$(CH_2)_3$CO-D-Ala-D-Ala-NH—$CH_2$—S—$(CH_2)_5$—CO-DM (14h): HRMS $(M+H)^+$ calcd. 1053.4366, found 1053.4438. $^1$H NMR (400 MHz, DMSFO-d6) δ 0.71 (s, 3H), 1.02-1.15 (m, 13H), 1.14-1.24 (m, 3H), 1.30-1.45

(m, 5H), 1.53 (s, 3H), 1.67 (p, J=7.1 Hz, 2H), 1.90-2.01 (m, 1H), 2.01-2.24 (m, 4H), 2.27-2.33 (m, 1H), 2.33-2.42 (m, 4H), 2.63 (s, 3H), 2.73 (d, J=9.7 Hz, 1H), 3.02 (s, 3H), 3.10-3.21 (m, 4H), 3.33-3.46 (m, 2H), 3.86 (s, 3H), 3.95-4.18 (m, 6H), 4.45 (dd, J=11.9, 2.8 Hz, 1H), 5.27 (q, J=6.7 Hz, 1H), 5.44-5.55 (m, 1H), 5.85 (s, 1H), 6.42-6.59 (m, 3H), 6.81 (s, 1H), 7.12 (d, J=1.8 Hz, 1H), 8.05 (d, J=6.5 Hz, 1H), 8.10 (d, J=7.8 Hz, 1H), 8.30 (t, J=6.3 Hz, 1H).

HS—$(CH_2)_3$CO-L-Ala-D-Ala-L-Ala-NH—$CH_2$—S—$(CH_2)_3$—CO-DM (14j): HRMS $(M+H)^+$ calcd. 1096.4496, found 1096.4464. 1H NMR (400 MHz, DMSO-d6) δ 0.78 (s, 3H), 1.02-1.31 (m, 19H), 1.35-1.55 (m, 2H), 1.60 (s, 3H), 1.74 (p, J=7.4 Hz, 3H), 1.78-1.93 (m, 1H), 2.14-2.33 (m, 4H), 2.41-2.49 (m, 2H), 2.71 (s, 3H), 2.80 (d, J=9.6 Hz, 1H), 3.12 (s, 3H), 3.22 (d, J=12.7 Hz, 1H), 3.26 (s, 3H), 3.47 (dd, J=21.3, 10.6 Hz, 2H), 3.93 (s, 4H), 4.03-4.13 (m, 3H), 4.13-4.25 (m, 3H), 4.52 (dd, J=12.0, 2.8 Hz, 1H), 5.35 (q, J=6.8 Hz, 1H), 5.50-5.64 (m, 1H), 5.92 (s, 1H), 6.47-6.69 (m, 4H), 6.88 (s, 1H), 7.18 (d, J=1.7 Hz, 1H), 7.94 (d, J=7.3 Hz, 1H), 8.09 (d, J=6.4 Hz, 1H), 8.15 (d, J=7.3 Hz, 1H), 8.32 (t, J=6.3 Hz, 1H).

HS—$(CH_2)_3$C0-$(CH_2)_3$—CO-D-Ala-L-Ala-NH—$CH_2$—S—$(CH_2)_2$—CO-DM (14i): HRMS $(M+H)^+$ calcd. 1011.3969, found 1011.3961. $^1$H NMR (400 MHz, DMSO-d6) δ 0.77 (s, 3H), 1.12 (d, J=6.4 Hz, 3H), 1.17 (dd, J=7.0, 5.1 Hz, 9H), 1.25 (d, J=13.0 Hz, 1H), 1.40-1.51 (m, 2H), 1.59 (s, 3H), 1.74 (q, J=7.2 Hz, 2H), 2.00-2.08 (m, 1H), 2.23 (dt, J=16.8, 7.6 Hz, 3H), 2.43 (q, J=7.4 Hz, 2H), 2.62-2.69 (m, 1H), 2.72 (s, 3H), 2.76-2.88 (m, 2H), 3.10 (s, 3H), 3.20 (d, J=12.6 Hz, 1H), 3.25 (s, 3H), 3.31 (s, 3H), 3.39-3.54 (m, 2H), 3.93 (s, 3H), 4.01-4.26 (m, 5H), 4.53 (dd, J=12.0, 2.8 Hz, 1H), 5.32 (q, J=6.8 Hz, 1H), 5.49-5.63 (m, 1H), 5.92 (d, J=1.4 Hz, 1H), 6.48-6.62 (m, 3H), 6.88 (s, 1H), 7.18 (d, J=1.8 Hz, 1H), 8.10 (d, J=6.5 Hz, 1H), 8.16 (d, J=7.7 Hz, 1H), 8.41 (t, J=6.3 Hz, 1H).

NHS-L-Ala-D-Ala-L-Ala-Imm-C6-May

Compounds of the type HOOC—$(CH_2)_3$CO-Peptide-NH—$CH_2$—S—$(CH_2)_n$—$CO_2$-DM were prepared as exemplified by HOOC—$(CH_2)_3$CO-L-Ala-D-Ala-L-Ala-NH—$CH_2$—S—$(CH_2)_5$—CO-DM.

HOOC—$(CH_2)_3$CO-L-Ala-D-Ala-L-Ala-NH—$CH_2$—S—$(CH_2)_3$—CO-DM (19a): L-Ala-D-Ala-L-Ala-NH—$CH_2$—S—$(CH_2)_5$—CO-DM (17.25 mg, 0.017 mmol) was treated with glutaric anhydride (38.5 mg, 0.337 mmol) and reacted at room temperature with magnetic stirring under argon overnight. The crude reaction was purified by HPLC using a XDB-C18, 21.2×5 mm, 5 micron column eluting with deionized water containing 0.1% formic acid and a linear gradient of acetonitrile from 5% to 95% over 30 min at 20 ml/min Fractions containing pure desired product were immediately combined, frozen and lypholized to give 3 mg, (15% yield) of white solid. HRMS $(M+H)^+$ calcd. 1136.4987, found 1136.4954. $^1$H NMR (400 MHz, DMSO-d6) δ 0.71 (s, 3H), 0.92-1.27 (m, 20H), 1.26-1.48 (m, 5H), 1.52 (s, 3H), 1.63 (q, J=7.1 Hz, 2H), 1.83-2.20 (m, 7H), 2.23-2.41 (m, 5H), 2.63 (s, 4H), 2.73 (d, J=9.5 Hz, 1H), 3.02 (s, 3H), 3.36-3.50 (m, 2H), 3.86 (s, 3H), 3.91-4.24 (m, 7H), 4.45 (d, J=11.8 Hz, 1H), 5.27 (q, J=6.7 Hz, 1H), 5.41-5.57 (m, 1H), 5.86 (s, 1H), 6.32-6.66 (m, 3H), 6.81 (s, 1H), 7.12 (s, 1H), 8.06 (t, J=9.1 Hz, 2H), 8.35 (d, J=11.6 Hz, 1H), 8.62 (s, 1H).

HOOC—$(CH_2)_3$CO-D-Ala-L-Ala-NH—$CH_2$—S—$(CH_2)_5$—CO-DM (19g): HRMS $(M+H)^+$ calcd. 1136.4987, found 1136.4962. $^1$H NMR (400 MHz, DMSO-d6) δ 0.71 (s, 3H), 0.97-1.14 (m, 13H), 1.14-1.26 (m, 3H), 1.28-1.45 (m, 5H), 1.52 (s, 3H), 1.62 (p, J=7.5 Hz, 2H), 1.93-2.00 (m, 1H), 2.08 (dt, J=13.1, 7.4 Hz, 6H), 2.25-2.41 (m, 3H), 2.63 (s, 3H), 2.73 (d, J=9.5 Hz, 1H), 3.02 (s, 3H), 3.18 (s, 3H), 3.31-3.48 (m, 2H), 3.86 (s, 3H), 3.93-4.19 (m, 6H), 4.45 (dd, J=12.0, 2.8 Hz, 1H), 5.27 (q, J=6.8 Hz, 1H), 5.43-5.58 (m, 1H), 5.85 (s, 1H), 6.40-6.61 (m, 3H), 6.81 (s, 1H), 7.11 (d, J=1.8 Hz, 1H), 8.03 (d, J=6.5 Hz, 1H), 8.13 (d, J=7.8 Hz, 1H), 8.34 (t, J=6.3 Hz, 1H), 11.94 (s, 1H).

HOOC—$(CH_2)_3$—CO-L-Ala-D-Ala-L-Ala-NH—$CH_2$—S—$(CH_2)_3$—CO-DM (19i): HRMS $(M+H)^+$ calcd. 1108.4674, found 1108.4634. $^1$H NMR (400 MHz, DMSO-d6) δ 0.78 (s, 3H), 1.04-1.32 (m, 16H), 1.45 (d, J=12.6 Hz, 2H), 1.60 (s, 3H), 1.69 (p, J=7.2 Hz, 3H), 1.77-1.95 (m, 1H), 1.99-2.07 (m, 1H), 2.11-2.20 (m, 4H), 2.20-2.39 (m, 1H), 2.55 (s, 1H), 2.71 (s, 3H), 2.80 (d, J=9.5 Hz, 1H), 3.12 (s, 3H), 3.40 (d, J=21.0 Hz, 8H), 3.49 (d, J=9.1 Hz, 1H), 3.93 (s, 3H), 4.02-4.27 (m, 6H), 4.48-4.61 (m, 1H), 5.34 (q, J=6.6 Hz, 1H), 5.48-5.65 (m, 1H), 5.92 (s, 1H), 6.50-6.71 (m, 3H), 6.88 (s, 1H), 7.18 (s, 1H), 7.99 (d, J=7.6 Hz, 1H), 8.08 (d, J=6.5 Hz, 1H), 8.22 (d, J=7.4 Hz, 1H), 8.30 (s, 1H), 8.42 (s, 1H).

Compounds of the type NHS—OOC—$(CH_2)_3$CO-Peptide-NH—$CH_2$—S—$(CH_2)_n$—$CO_2$-DM were prepared as exemplified by NHS—OOC—$(CH_2)_3$—CO-D-Ala-L-Ala-NH—$CH_2$—S—$(CH_2)_5$—CO-DM.

NHS—OOC—$(CH_2)_3$—CO-D-Ala-L-Ala-NH—$CH_2$—S—$(CH_2)_5$—CO-DM (20g): HOOC—$(CH_2)_3$CO-D-Ala-L-Ala-NH—$CH_2$—S—$(CH_2)_5$—CO-DM (8 mg 7.5 μmol) was dissolved in DMSO (1 mL), treated with NHS (0.9 mg, 7.51 μmol) and EDC (1.4 mg, 7.51 μmol). The reaction was allowed to proceed at room temperature with magnetic stirring under an argon atmosphere for 2 hours. The crude material was purified via HPLC using a XDB-C18, 21.2×5 mm, 5 μm column eluting with deionized water containing 0.1% formic acid and a linear gradient of acetonitrile from 5% to 95% over 30 min at 20 ml/min Fractions containing desired product were combined and immediately frozen then lypholized to give 6.5 mg (74% yield) of white solid. $^1$H NMR (400 MHz, DMSO-d6) δ 0.71 (s, 3H), 1.00-1.14 (m, 13H), 1.14-1.25 (m, 3H), 1.29-1.46 (m, 5H), 1.52 (s, 3H), 1.75 (p, J=7.5 Hz, 2H), 1.92-2.12 (m, 2H), 2.16 (t, J=7.3 Hz, 2H), 2.22-2.39 (m, 3H), 2.62 (d, J=10.8 Hz, 5H), 2.73 (d, J=10.5 Hz, 5H), 3.02 (s, 3H), 3.18 (s, 3H), 3.32-3.47 (m, 2H), 3.86 (s, 3H), 3.95-4.19 (m, 6H), 4.45 (dd, J=12.0, 2.8 Hz, 1H), 5.27 (q, J=6.8 Hz, 1H), 5.42-5.57 (m, 1H), 5.82-5.87 (m, 1H), 6.41-6.60 (m, 4H), 6.81 (s, 1H), 7.11 (d, J=1.7 Hz, 1H), 8.05 (d, J=6.5 Hz, 1H), 8.10 (d, J=7.7 Hz, 1H), 8.20 (d, J=4.8 Hz, 1H), 8.29 (t, J=6.3 Hz, 1H).

NHS—OOC—$(CH_2)_3$—CO -L-Ala-D-Ala-L-Ala-NH—$CH_2$—S—$(CH_2)_5$—CO-DM (20g): HRMS $(M+H)^+$ calcd. 1233.5151, found 1233.5135.

NHS—OOC—$(CH_2)_3$—CO -L-Ala-D-Ala-L-Ala-NH—$CH_2$—S—$(CH_2)_3$—CO-DM (20i): HRMS $(M+H)^+$ calcd. 1205.4838, found 1205.4808.

Compounds of the type $H_2N$—O—$CH_2$—CO-Peptide-NH—$CH_2$—S—$(CH_2)_n$—$CO_2$-DM were prepared as exemplified by $H_2N$—O—$CH_2$—CO-L-Ala-D-Ala-L-Ala-NH—$CH_2$—S—$(CH_2)_5$—CO-DM. $H_2N$—O—$CH_2$—CO-L-Ala-D-Ala-L-Ala-NH—$CH_2$—S—$(CH_2)_5$—CO-DM (22c):

$H_2N$-L-Ala-D-Ala-L-Ala-$CH_2$—S—$(CH_2)_5$—CO-DM (23 mg, 0.022 mmol) was dissolved in DMF (1 mL), treated with FMoc-aminoxyacetic acid (14.09 mg, 0.045 mmol), and EDC (8.62 mg, 0.045 mmol. The reaction was allowed to proceed at room temperature with magnetic stirring under an argron atmosphere for 3 h. The crude material was treated with 20% morpholine in DMF (1 mL) and allowed to proceed for 2 h. The crude material was purified via semi-prep HPLC using a XDB-C18, 21.2×5 mm, 5 μm eluting with deionized water containing 0.1% formic acid and a linear gradient of acetonitrile from 5% to 95% over 30 min at 20 ml/min Fractions containing desired product were pooled and immediately froze then lypholized to give 5.5 mg (22% yield) of white solid. HRMS (M+H)+ calcd. 1095.4834, found 1095.4795. $^1$H NMR (400 MHz, DMSO-$d_6$) δ 0.71 (s, 3H), 1.00-1.14 (m, 13H), 1.14-1.25 (m, 6H), 1.31-1.43 (m, 4H), 1.52 (s, 3H), 1.92-2.02 (m, 1H), 2.02-2.14 (m, 1H), 2.23-2.39 (m, 3H), 2.63 (s, 3H), 2.73 (d, J=9.6 Hz, 1H), 3.02 (s, 3H), 3.14 (d, J=12.5 Hz, 1H), 3.18 (s, 3H), 3.29-3.46 (m, 3H), 3.86 (s, 3H), 3.90 (d, J=2.0 Hz, 2H), 3.95-4.20 (m, 6H), 4.25 (p, J=7.7, 7.2 Hz, 1H), 4.45 (dd, J=12.0, 2.8 Hz, 1H), 5.27 (q, J=6.8 Hz, 1H), 5.44-5.58 (m, 1H), 5.85 (s, 1H), 6.30 (s, 2H), 6.43-6.60 (m, 3H), 6.81 (s, 1H), 7.12 (d, J=1.7 Hz, 1H), 7.82 (d, J=7.4 Hz, 1H), 7.97 (d, J=7.6 Hz, 1H), 8.10 (d, J=7.2 Hz, 1H), 8.29 (t, J=6.3 Hz, 1H).

H$_2$N—O—CH$_2$CO-L-Ala-D-Ala-L-Ala-NH—CH$_2$—S—(CH$_2$)$_3$—CO-DM (22i): HRMS (M+H)+ calcd. 1067.4521, found 1067.4484. $^1$H NMR (400 MHz, DMSO-$d_6$) δ 0.71 (s, 3H), 1.01-1.26 (m, 18H), 1.30-1.46 (m, 2H), 1.52 (s, 3H), 1.55-1.69 (m, 1H), 1.69-1.84 (m, 1H), 1.97 (d, J=14.4, 2.8 Hz, 1H), 2.15-2.31 (m, 1H), 2.56-2.61 (m, 1H), 2.63 (s, 3H), 2.73 (d, J=9.6 Hz, 1H), 3.04 (s, 3H), 3.14 (d, J=12.6 Hz, 1H), 3.18 (s, 3H), 3.36 (d, J=12.3 Hz, 1H), 3.42 (dd, J=9.1, 3.3 Hz, 1H), 3.85 (s, 3H), 3.90 (d, J=2.3 Hz, 2H), 3.95-4.05 (m, 3H), 4.06-4.17 (m, 2H), 4.15-4.35 (m, 2H), 4.45 (dd, J=12.0, 2.8 Hz, 1H), 5.27 (q, J=6.7 Hz, 1H), 5.44-5.56 (m, 1H), 5.85 (s, 1H), 6.30 (s, 2H), 6.42-6.61 (m, 3H), 6.81 (s, 1H), 7.11 (d, J=1.7 Hz, 1H), 7.82 (d, J=7.3 Hz, 1H), 7.96 (d, J=7.6 Hz, 1H), 8.11 (d, J=7.2 Hz, 1H), 8.22-8.40 (m, 1H).

Mal-(CH$_2$)$_3$—CO-L-Ala-D-Ala-L-Ala-NH—CH$_2$—S—(CH$_2$)$_5$—CO-DM (23c): H$_2$N-L-Ala-D-Ala-L-Ala-CH$_2$—S—(CH$_2$)$_5$—CO-DM (8 mg, 7.82 µmol), was dissolved in DMF (2 mL), treated with 3-maleimidopropanoic acid (1.32 mg, 7.82 µmol), EDC (2.25 mg, 0.012 mmol) and HOBt (1.198 mg, 7.82 µmol). The reaction was allowed to proceed at room temperature with magnetic stirring under an argron atmosphere for 2 h. The crude material was purified via semi-prep HPLC using a XDB-C18, 21.2×5 mm, 5 µm eluting with deionized water containing 0.1% formic acid and a linear gradient of acetonitrile from 5% to 95% over 30 min at 20 ml/min Fractions containing desired product were immediately combined and frozen then lypholized to give 1.8 mg (19.60% yield) of white solid. HRMS (M+H)+ calcd. 1173.4940, found 1173.4931. $^1$H NMR (400 MHz, DMSO-d6) δ 0.71 (s, 3H), 1.02-1.14 (m, 15H), 1.16-1.25 (m, 3H), 1.30-1.44 (m, 5H), 1.52 (s, 3H), 1.92-2.03 (m, 1H), 2.03-2.17 (m, 1H), 2.23-2.39 (m, 4H), 2.63 (s, 3H), 2.73 (d, J=9.6 Hz, 1H), 3.02 (s, 3H), 3.18 (s, 4H), 3.33-3.46 (m, 2H), 3.52 (t, J=7.3 Hz, 2H), 3.86 (s, 3H), 3.95-4.17 (m, 7H), 4.45 (dd, J=12.0, 2.9 Hz, 1H), 5.27 (q, J=6.7 Hz, 1H), 5.44-5.56 (m, 1H), 5.85 (s, 1H), 6.39-6.64 (m, 3H), 6.81 (s, 1H), 6.86 (s, 1H), 6.92 (s, 2H), 7.11 (d, J=1.7 Hz, 1H), 7.89 (d, J=7.4 Hz, 1H), 8.10 (d, J=7.3 Hz, 1H), 8.17 (d, J=6.7 Hz, 1H), 8.28 (t, J=6.3 Hz, 1H), 8.43 (s, 1H).

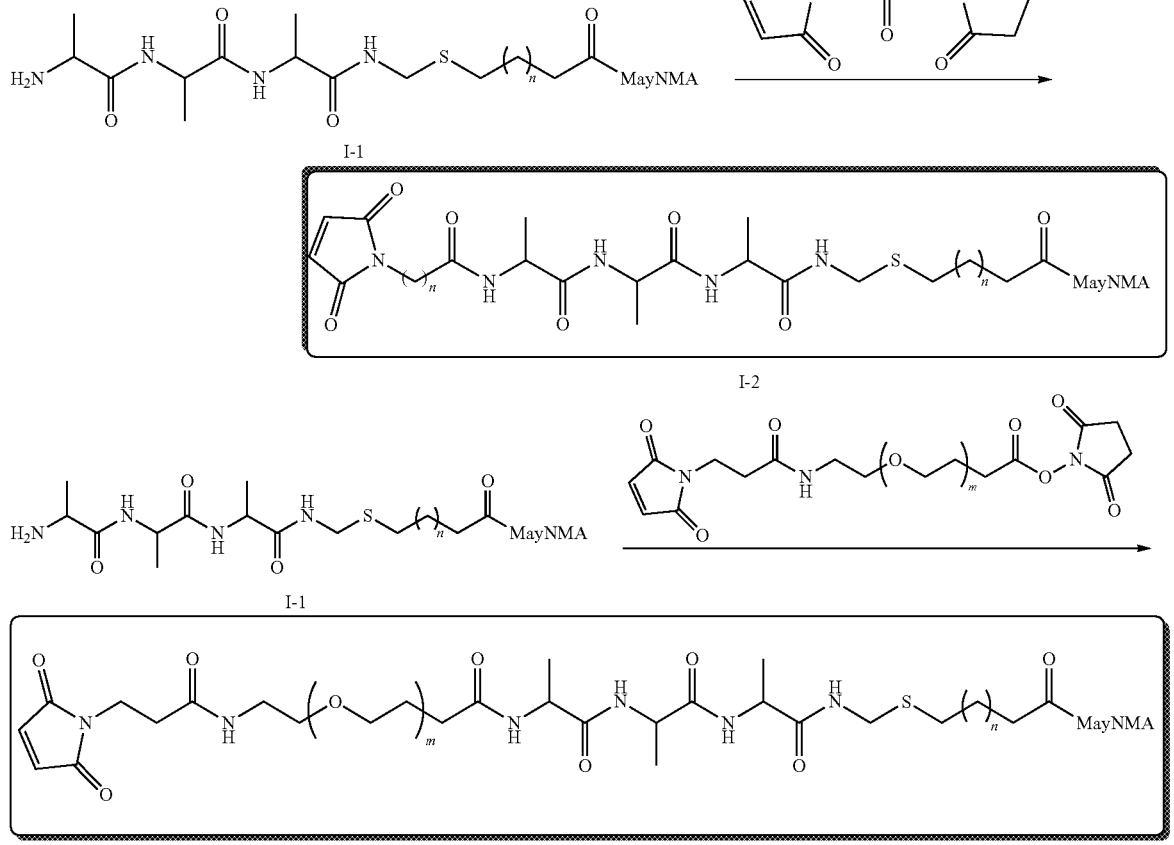

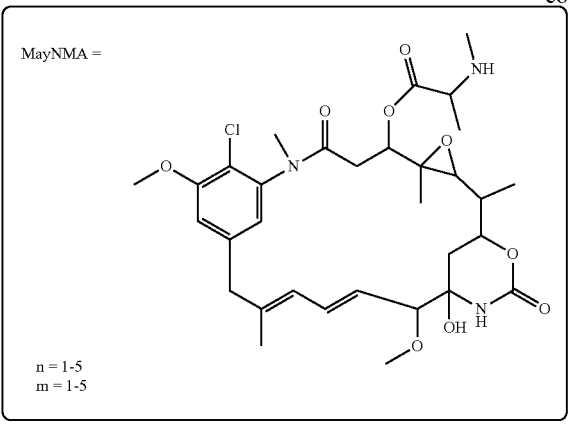

n = 1-5
m = 1-5

Mal2-LAla-D-Ala-L-Ala-Imm-C6-May

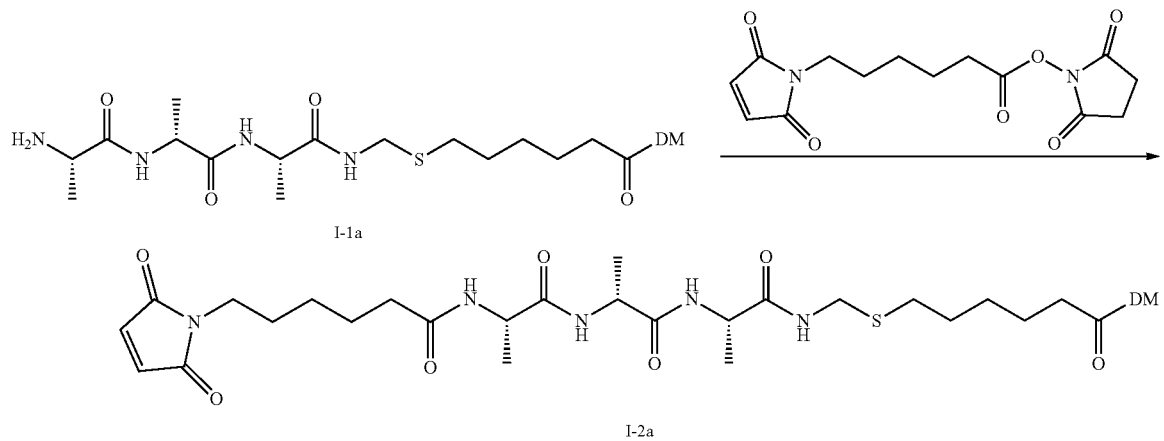

Mal-C5-L-Ala-D-Ala-L-Ala-Imm-C6-May: Reaction between L-Ala-D-Ala-L-Ala-CH$_2$—S—(CH$_2$)$_5$—CO-MayNMA (compound I-1a) (25 mg, 0.024 mmol), and 2,5-dioxopyrrolidin-1-yl 6-(2,5-dioxo-2,5-dihydro-1H-pyrrol-1-yl)hexanoate (7.54 mg, 0.024 mmol) yielded Mal-C5-L-Ala-D-Ala-L-Ala-Imm-C6-May (compound I-2a) (20.8 mg, 0.017 mmol, 70.0% yield). LRMS (M+H)$^+$ calcd 1215.52, found 1216.4. $^1$H NMR (400 MHz, DMSO-d6) δ 0.71 (s, 3H), 1.05 (d, J=6.4 Hz, 3H), 1.07-1.14 (m, 14H), 1.15-1.25 (m, 3H), 1.39 (t, J=9.2 Hz, 10H), 1.52 (s, 3H), 2.01 (t, J=7.6 Hz, 3H), 2.26 (t, J=1.9 Hz, 1H), 2.28-2.38 (m, 2H), 2.57-2.62 (m, 1H), 2.63 (s, 3H), 2.73 (d, J=9.6 Hz, 1H), 3.02 (s, 3H), 3.14 (d, J=12.5 Hz, 1H), 3.18 (s, 3H), 3.29 (t, J=7.1 Hz, 2H), 3.36 (d, J=12.5 Hz, 1H), 3.42 (d, J=9.0 Hz, 1H), 3.86 (s, 3H), 3.96-4.05 (m, 1H), 4.04-4.15 (m, 4H), 4.41-4.48 (m, 1H), 5.27 (q, J=6.7 Hz, 1H), 5.46-5.54 (m, 1H), 5.82-5.88 (m, 1H), 6.47-6.50 (m, 2H), 6.54 (t, J=11.4 Hz, 2H), 6.82 (s, 1H), 6.92 (s, 2H), 7.11 (d, J=1.8 Hz, 1H), 7.86-7.93 (m, 2H), 7.95 (s, 1H), 8.05 (d, J=7.4 Hz, 1H), 8.24 (t, J=6.2 Hz, 1H).

Mal-(CH$_2$)$_2$-PEG$_2$-CO-L-Ala-D-Ala-L-ALa-NH—CH2-S—(CH2)5-CO-MayNMA

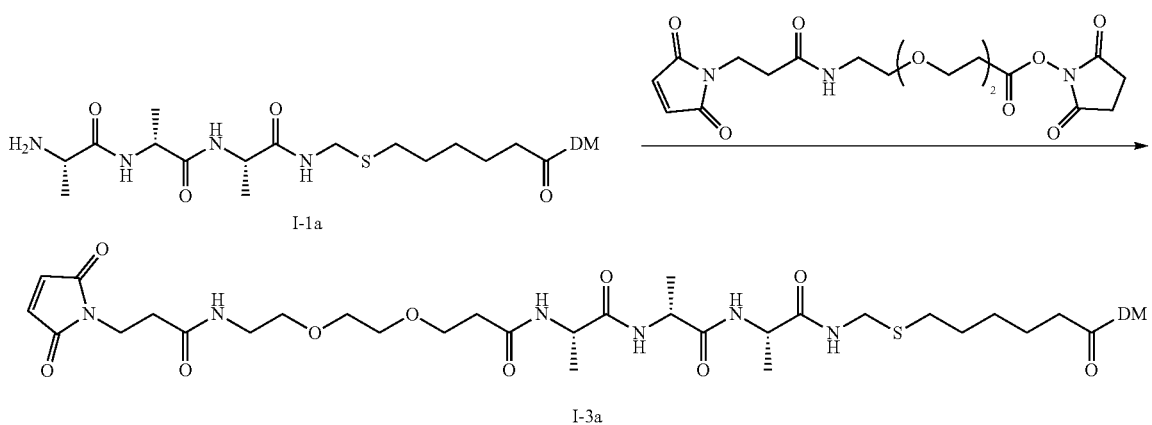

Mal-(CH$_2$)$_2$-PEG$_2$-CO-L-Ala-D-Ala-L-ALa-NH—CH$_2$—S—(CH$_2$)$_5$—CO-MayNMA:

Reaction between L-Ala-D-Ala-L-Ala-NH—CH$_2$—S—(CH$_2$)$_5$—CO-MayNMA (compound I-1a) (25 mg, 0.024 mmol) and Mal-amido-PEG$_2$-NHS (10.40 mg, 0.024 mmol) yielded Mal-(CH2)$_2$-PEG$_2$-CO2-L-Ala-D-Ala-L-ALa-NH—CH$_2$—S—(CH$_2$)$_5$—CO-MayNMA (compound I-3a) (14.1 mg, 10.58 μmol, 43.3% yield).

LRMS (M+H)$^+$ calcd 1332.58, found 1332.95.

$^1$H NMR (400 MHz, DMSO-d6) δ 0.71 (s, 4H), 1.05 (d, J=6.3 Hz, 4H), 1.07-1.14 (m, 15H), 1.18 (d, J=9.0 Hz, 2H), 1.37 (d, J=11.8 Hz, 6H), 1.52 (s, 3H), 2.23-2.38 (m, 5H), 2.63 (s, 4H), 2.72 (d, J=9.7 Hz, 1H), 3.02 (s, 3H), 3.07 (q, J=5.7 Hz, 2H), 3.18 (s, 3H), 3.39 (s, 4H), 3.41 (d, J=9.9 Hz, 2H), 3.47-3.56 (m, 4H), 3.86 (s, 4H), 3.95-4.08 (m, 2H), 4.08-4.19 (m, 3H), 4.41-4.51 (m, 1H), 5.23-5.31 (m, 1H), 5.44-5.54 (m, 1H), 5.85 (s, 1H), 6.46-6.50 (m, 2H), 6.54 (t, J=11.3 Hz, 2H), 6.83 (s, 1H), 6.93 (s, 2H), 7.12 (s, 1H), 7.88-8.00 (m, 2H), 8.01-8.08 (m, 2H), 8.27 (t, J=6.2 Hz, 1H).

Mal-(CH$_2$)$_2$-PEG-$_4$-CO-L-Ala-D-Ala-L-ALa-NH—CH$_2$—S—(CH$_2$)$_5$—CO-MayNMA mmol) and DIPEA (17.5 μL, 0.100 mmol) with magnetic stirring at room temperature for 10 min. Then 6-mercaptohexanoic acid (13.8 μL, 0.100 mmol) was added. After 30 min the crude material was purified via semi-prep HPLC using a XDB-C18, 21.2×5 mm, 5 μm eluting with deionized water containing 0.1% formic acid and a linear gradient of acetonitrile from 5% to 95% over 30 min at 20 ml/min Fractions containing desired product were immediately combined and frozen then lypholized to give 12 mg (15% yield) of white solid. HRMS (M+H)$^+$ calcd. 780.3291, found 780.3281. $^1$H NMR (400 MHz, DMSO-d6) δ 0.79 (s, 3H), 1.06-1.21 (m, 5H), 1.21-1.57 (m, 6H), 1.60 (s, 2H), 2.00-2.12 (m, 2H), 2.12-2.27 (m, 2H), 2.27-2.37 (m, 2H), 2.50 (s, 4H), 2.70 (s, 3H), 2.74-2.91 (m, 2H), 2.91-3.09 (m, 1H), 3.10 (s, 2H), 3.19-3.24 (m, 2H), 3.26 (s, 3H), 3.39-3.53 (m, 2H), 3.94 (s, 3H), 4.03-4.11 (m, 1H), 4.52 (dd, J=12.0, 2.9 Hz, 1H), 5.35 (q, J=6.8 Hz, 1H), 5.52-5.62 (m, 1H), 5.93 (d, J=1.3 Hz, 1H), 6.49-6.67 (m, 3H), 6.89 (s, 1H), 7.20 (d, J=1.8 Hz, 1H).

DM-CO—(CH$_2$)$_5$—SMe (25a): DM-CO—(CH$_2$)$_5$—SH (12 mg, 0.015 mmol) was dissolved in DMF (2 mL), treated with DIPEA (24 μL, 0.139 mmol) and iodomethane (2.88

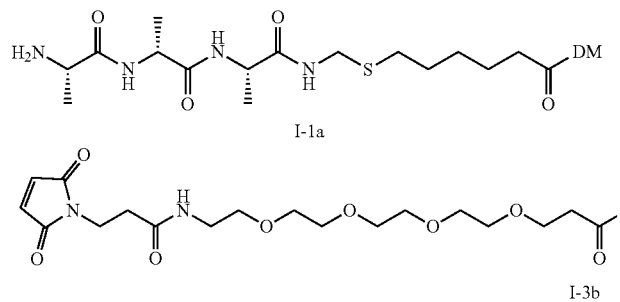

I-1a

I-3b

Mal-(CH$_2$)$_2$-PEG$_4$-CO$_2$-L-Ala-D-Ala-L-ALa-NH—CH$_2$—S—(CH$_2$)$_5$—CO-MayNMA:

Reaction between L-Ala-D-Ala-L-Ala-NH—CH$_2$—S—(CH$_2$)$_5$—CO-MayNMA (compound I-1a) (25 mg, 0.024 mmol) and Mal-amido-PEG4-NHS (12.55 mg, 0.024 mmol) yielded Mal-(CH$_2$)$_2$-PEG$_4$-CO2-L-Ala-D-Ala-L-ALa-NH—CH$_2$—S—(CH$_2$)$_5$—CO-MayNMA Mal-PEG4-CO2-C6-LDL-DM (compound I-3b) (22.3 mg, 0.016 mmol, 64.2% yield).

LRMS (M+H)$^+$ calcd 1420.63, found 1420.06

$^1$H NMR (400 MHz, DMSO-d6) δ 0.71 (s, 4H), 1.05 (d, J=6.4 Hz, 3H), 1.07-1.16 (m, 14H), 1.19 (t, J=8.1 Hz, 2H), 1.31-1.50 (m, 2H), 1.52 (s, 4H), 1.98 (s, 1H), 2.02-2.17 (m, 2H), 2.20-2.40 (m, 7H), 2.63 (s, 4H), 2.73 (d, J=9.6 Hz, 1H), 3.02 (s, 3H), 3.05-3.12 (m, 2H), 3.18 (s, 3H), 3.28-3.36 (m, 1H), 3.37-3.45 (m, 15H), 3.47-3.57 (m, 4H), 3.86 (s, 4H), 3.94-4.08 (m, 2H), 4.12 (ddt, J=14.5, 7.3, 3.6 Hz, 4H), 4.41-4.49 (m, 1H), 5.27 (q, J=6.7 Hz, 1H), 5.45-5.55 (m, 1H), 5.86 (s, 1H), 6.42-6.60 (m, 4H), 6.83 (s, 1H), 6.94 (s, 1H), 7.12 (d, J=1.8 Hz, 1H), 7.89-8.00 (m, 2H), 8.00-8.09 (m, 2H), 8.26 (t, J=6.2 Hz, 1H).

Example 3

Synthesis of the Metabolites

DM-CO—(CH$_2$)$_5$—SH (24a): To DM-H stock solution (1.5 mL, 0.100 mmol), was added EDC (29 mg, 0.150

μL, 0.046 mmol) was allowed to proceed under argon at room temperature for 2 h. The crude material was purified via a XDB-C18, 21.2×5 mm, 5 μm column with a flow rate 20 ml/min Using deionized water with 0.1% formic acid and linear gradient of acetonitrile from 5% to 95% over 30 min at 20 ml/min. Fractions containing desired product were combined, frozen then lypholized to give 2 mg (16% yield) of white solid. HRMS (M+H)$^+$ calcd. 794.3448, found 794.3440. $^1$H NMR (400 MHz, DMSO-d6) δ 0.71 (s, 3H), 1.01-1.13 (m, 6H), 1.13-1.27 (m, 3H), 1.27-1.50 (m, 6H), 1.53 (s, 3H), 1.87 (s, 2H), 1.93-2.04 (m, 2H), 2.04-2.15 (m, 1H), 2.15-2.27 (m, 2H), 2.27-2.41 (m, 1H), 2.63 (s, 3H), 2.73 (d, J=9.6 Hz, 1H), 3.02 (s, 3H), 3.10-3.22 (m, 5H), 3.33-3.49 (m, 2H), 3.86 (s, 3H), 3.94-4.06 (m, 1H), 4.45 (dd, J=12.1, 2.8 Hz, 1H), 5.28 (q, J=6.7 Hz, 1H), 5.44-5.56 (m, 1H), 5.85 (s, 1H), 6.42-6.62 (m, 3H), 6.81 (s, 1H), 7.13 (d, J=1.7 Hz, 1H).

DM-CO—(CH$_2$)$_3$—SSPy (26): DM-CO—(CH$_2$)$_3$—SSPy (3267-50-R1): SPDB (30.1 mg, 0.092 mmol) was added to DM-H stock solution (0.81 mL, 0.046 mmol) at room temperature with magnetic stirring. After 30 min the solution was purified on a XDB-C18, 21.2×5 mm, 5 μm column with a flow rate 20 ml/min Using deionized water with 0.1% formic acid and linear gradient of acetonitrile from 5% to 95% over 30 min at 20 ml/min. Fractions containing desired product were combined, frozen then lypholized to give 6 mg (15% yield) of a white solid. HRMS (M+H)$^+$ calcd. 861.2964, found 861.2963. $^1$H NMR (400 MHz, DMSO-d6) δ 0.70 (s, 3H), 1.02-1.12 (m, 7H), 1.13-1.21 (m, 1H), 1.31-1.45 (m, 3H), 1.52 (s, 3H), 1.70-1.90 (m, 2H), 1.96 (dd, J=14.2, 2.9 Hz, 1H), 2.19-2.31 (m, 1H), 2.62 (s, 3H), 2.68-2.81 (m, 4H), 3.00 (s, 2H), 3.18 (s, 4H), 3.34 (d, J=12.4 Hz, 1H), 3.41 (d, J=9.1 Hz, 1H), 3.87 (s, 3H), 4.00 (t, J=11.2 Hz, 1H), 4.44 (dd, J=12.0, 2.9 Hz, 1H), 5.25 (q, J=6.8 Hz, 1H), 5.41-5.52 (m, 1H), 5.85 (s, 1H), 6.43-6.53 (m, 3H), 6.81 (s, 1H), 7.09 (d, J=1.8 Hz, 1H), 7.12-7.19 (m, 1H), 7.50-7.61 (m, 1H), 7.66-7.76 (m, 1H), 8.31-8.39 (m, 1H).

DM-CO—(CH$_2$)$_3$—SH (24b): DM-CO—(CH$_2$)$_3$—SSPy (6 mg, 6.96 μmol) was added to a solution of DTT (1.1 mg, 6.96 μmol) in 2:1 DMSO: potassium phosphate 2 mM EDTA pH 7.5 buffer (0.5 mL) and magnetically stirred at room temperature for 20 min Crude solution was purified on a XDB-C18, 21.2×5 mm, 5 μm column with a flow rate 20 ml/min Using deionized water with 0.1% formic acid and linear gradient of acetonitrile from 5% to 95% over 30 min at 20 ml/min. Fractions containing desired product were combined, frozen then lypholized to give 5 mg (95% yield) of white solid. HRMS (M+H)$^+$ calcd. 752.2978, found 752.2962. $^1$H NMR (400 MHz, DMSO-d6) δ 0.71 (d, J=1.9 Hz, 3H), 1.08 (dd, J=18.6, 6.6 Hz, 7H), 1.18 (d, J=12.4 Hz, 2H), 1.27-1.49 (m, 3H), 1.52 (d, J=2.7 Hz, 4H), 1.55-1.68 (m, 1H), 1.77 (J=14.2, 8.5, 6.5 Hz, 1H), 1.91-2.05 (m, 1H), 2.15 (t, J=7.9 Hz, 1H), 2.38 (s, 2H), 2.44-2.60 (m, 1H), 2.64 (s, 2H), 2.66-2.84 (m, 1H), 3.03 (d, J=12.6 Hz, 3H), 3.09-3.18 (m, 1H), 3.18 (s, 3H), 3.36 (d, J=12.2 Hz, 1H), 3.42 (d, J=9.0 Hz, 1H), 3.86 (s, 2H), 3.93-4.08 (m, 1H), 4.45 (dd, J=12.0, 2.8 Hz, 1H), 5.27 (q, 1H), 5.42-5.58 (m, 1H), 5.85 (d, J=1.3 Hz, 1H), 6.40-6.61 (m, 4H), 6.81 (s, 1H), 7.12 (d, J=1.8 Hz, 1H).

DM-CO—(CH$_2$)$_3$—SMe (25b): DM-CO—(CH$_2$)$_3$—SH (5 mg, 6.65 μmol), was dissolved in anhydrous DMF (0.3 mL) to which was added DIPEA (3.57 μL, 0.020 mmol) and iodomethane (1.2 μL, 0.020 mmol) with magnetic stirring at room temperature. After 1 h the crude solution was purified on a XDB-C18, 21.2×5 mm, 5 μm column with a flow rate 20 ml/min Using deionized water with 0.1% formic acid and linear gradient of acetonitrile from 5% to 95% over 30 min at 20 ml/min Fractions containing desired product were combined, frozen then lypholized to give 1 mg (19% yield) of a white solid. HRMS (M+H)$^+$ calcd. 766.3135, found 766.3121. $^1$H NMR (400 MHz, DMSO-d6) δ 0.71 (s, 3H), 1.08 (dd, J=18.1, 6.6 Hz, 7H), 1.18 (d, J=12.9 Hz, 1H), 1.30-1.47 (m, 2H), 1.53 (s, 3H), 1.56-1.68 (m, 1H), 1.68-1.78 (m, 1H), 1.78 (s, 3H), 1.91-2.05 (m, 1H), 2.18-2.31 (m, 1H), 2.33-2.41 (m, 2H), 2.63 (s, 3H), 2.73 (d, J=9.7 Hz, 1H), 3.05 (s, 3H), 3.18 (s, 4H), 3.33-3.48 (m, 2H), 3.86 (s, 3H), 4.00 (t, J=11.5 Hz, 1H), 4.45 (dd, J=12.1, 2.8 Hz, 1H), 5.28 (q, J=6.7 Hz, 1H), 5.43-5.57 (m, 1H), 5.85 (s, 1H), 6.41-6.62 (m, 3H), 6.81 (s, 1H), 7.12 (d, J=1.8 Hz, 1H), 8.47 (s, 1H).

Example 4

Preparation of ADCs (16a-16i, 17a-17i, 18a-18i)

Preparation of Maytansinoid Solutions for the Preparation of ADCs (16a-16i, 17a-17i, 18a-18i)

Sulfo-GMBS and one of the thiol-bearing compounds (14a-14j) were dissolved in a solution of 3:7 (50 mM sodium succinate, pH 5.0: DMA) to give a concentration of 1.5 mM and 1.9 mM of each respectively. The solution was gently stirred at room temperature for 30 min then excess thiol was quenched by bringing the solution to 0.5 mM in N-ethyl maleimide (NEM) with gentle stirring for 10 min.

Preparation of ADCs (16a-16i, 17a-17i, 18a-18i)

To a solution of the antibody (2.5 mg/mL) in 60 mM EPPS containing 15% by volume N,N-dimethyl acetamide (DMA), pH 8.0 was added 6.5 mole eq. of maytansinoid solution. After 16 h the reaction mixture was purified using a NAP-G25 column that was pre-equilibrated and run with 10 mM sodium succinate, pH 5.5, 250 mM glycine, 0.5% sucrose, and 0.01% Tween-20 buffer. The purified conjugate was analyzed to determine the maytansinoid per antibody ratio (MAR), percent aggregated conjugate, free maytansinoid levels and endotoxin units (EU) as previously described by Widdison W. et. al. J Med Chem (2006) 49, 4392-408. Protein aggregate levels in all conjugates were below 3%, free maytansinoid levels were below 1% and endotoxin levels were below 0.2 EU/mg.

ADCs 1a-1d and 4a-4c were used as comparators to evaluate the conjugates of the invention. The ADCs 1a-1d and 4a-4c prepared as described by Widdison W., et. al., Bioconjugate Chem., (2015), 26, 2261-2278.

Preparation of C242-sGMBS-LDL-DM (ADC 18c)

Figure 3:
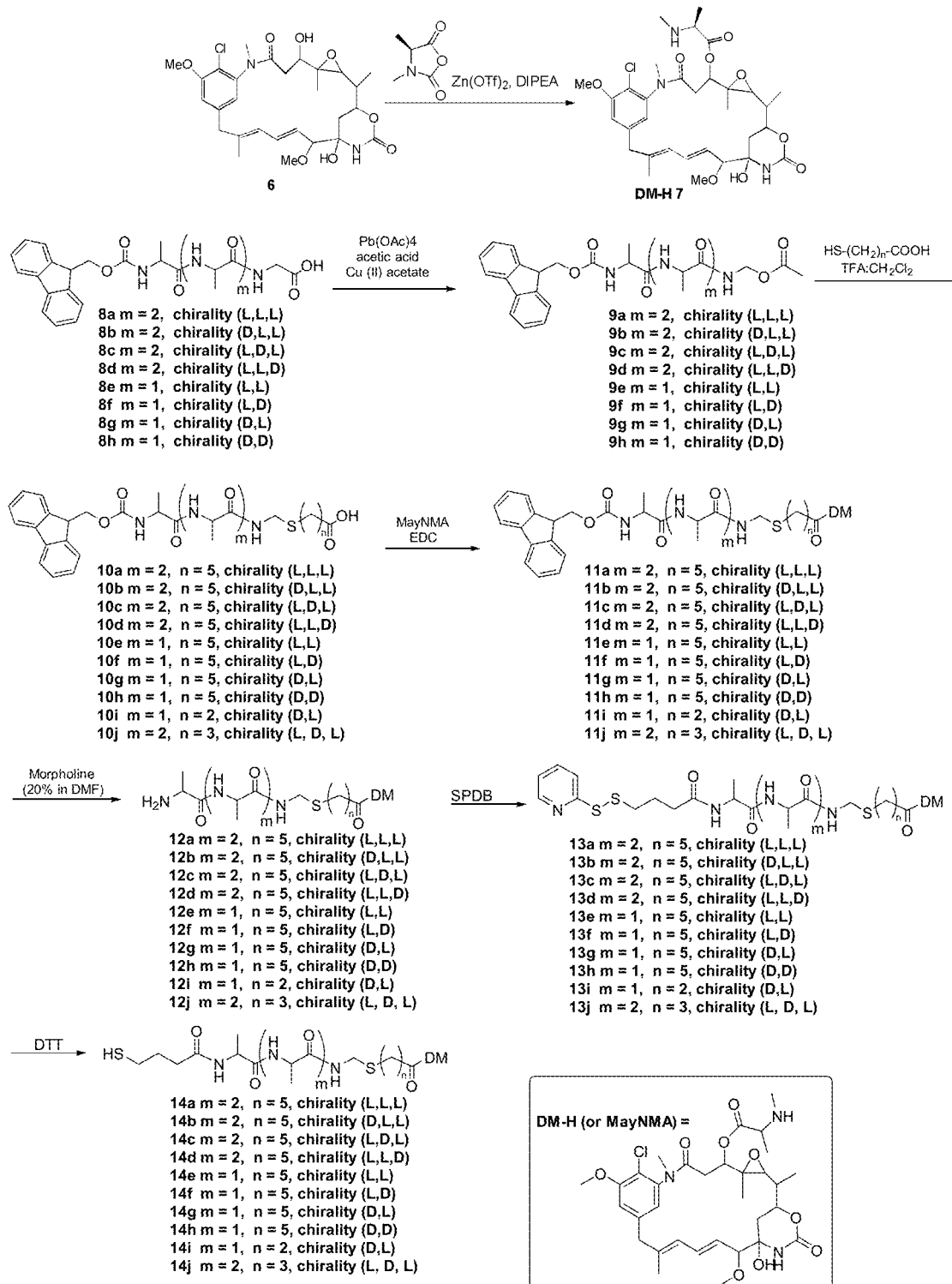
FIG. 3 depicts synthetic schemes for preparing representative maytansinoid compounds of the present invention having self-immolative peptide linkers.
Figure 4:
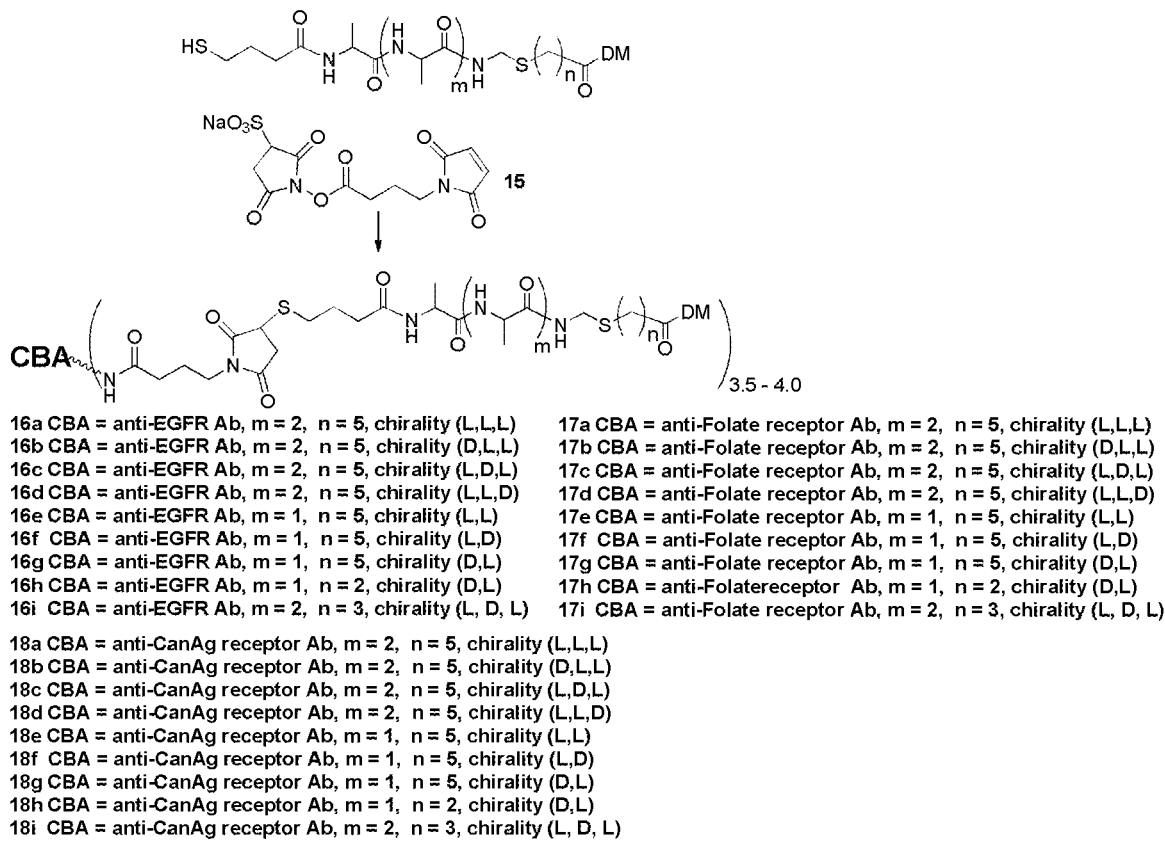
FIG. 4 depicts synthetic scheme for preparing a representative conjugate of the present invention.
Figure 5:
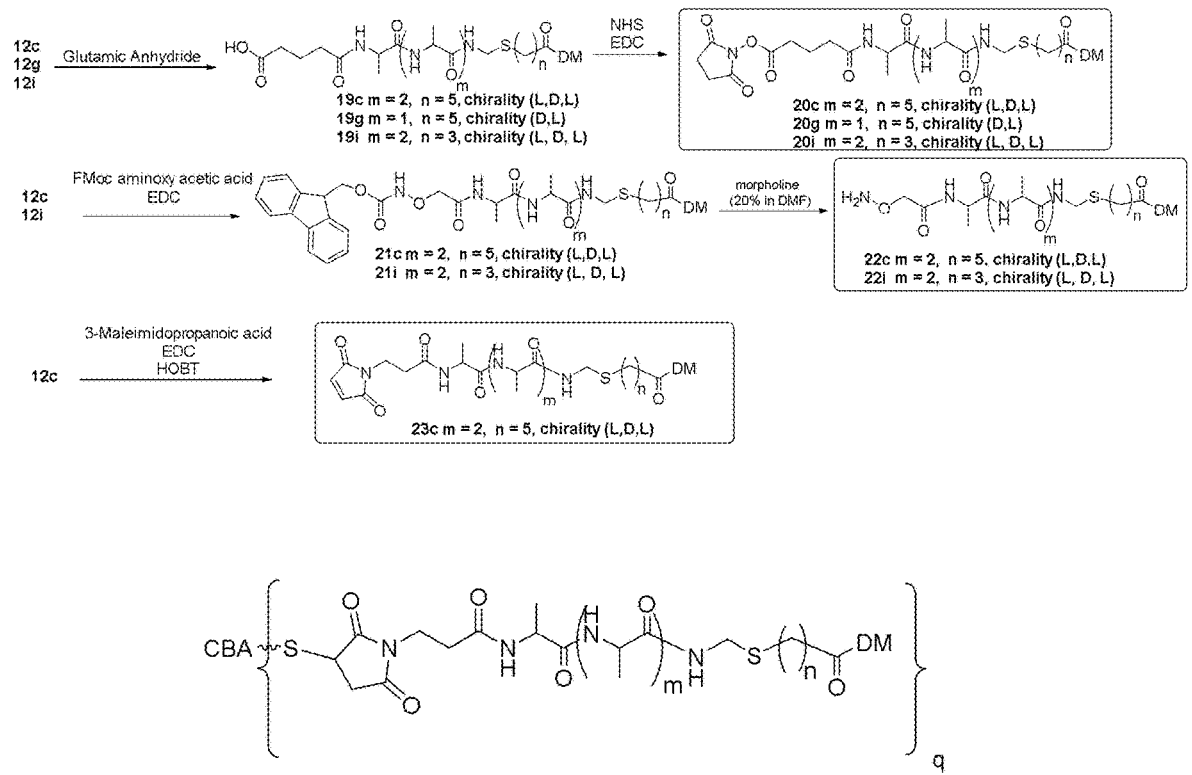
FIG. 5 depicts synthetic schemes for preparing representative maytansinoid compounds of the present invention having self-immolative peptide linkers.
Figure 6:
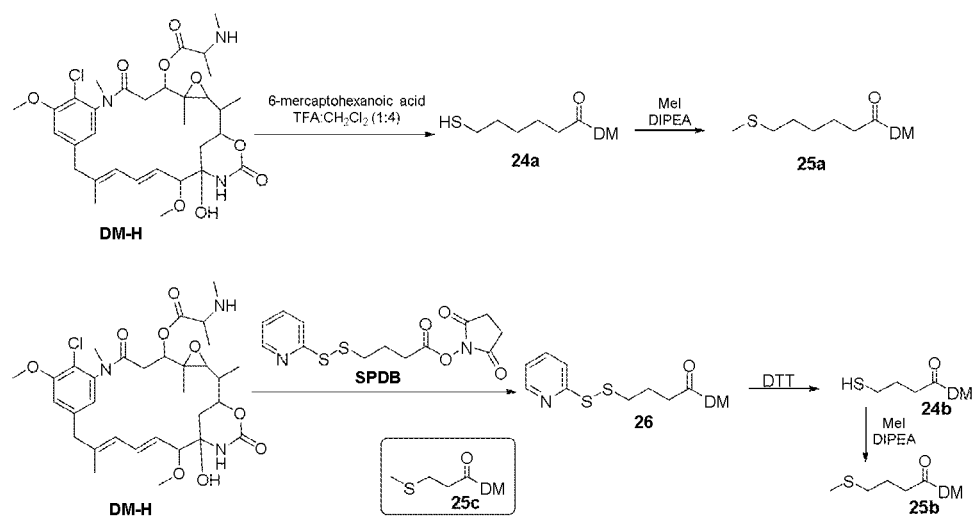
FIG. 6 depicts synthetic schemes for preparing S-methylated metabolite of the conjugates of the present invention.

Prior to conjugation, sGMBS-LDL-DM was prepared by mixing a stock solution of sulfo-GMBS (compound 15 in FIG. 4) in N—N-dimethylacetamide (DMA, SAFC) with a stock solution of LDL-DM (compound 14c in FIG. 3) in DMA in presence of succinate buffer pH 5.0 to obtain a 60/40 organic/aqueous solution and final concentrations of 1.5 mM sulfo-GMBS and 1.95 mM LDL-DM. The reaction was incubated for 10 min at 25° C. The crude sGMBS-LDL-DM mixture was added to a solution containing C242 antibody in phosphate buffered saline (PBS) pH 7.4 spiked with 5× solution of 300 mM 4-(2-Hydroxyethyl)-1-piperazinepropanesulfonic acid (EPPS) pH 8.0 and 15% DMA (v/v) to a final ratio of 7.5 mol sulfo-GMBS-LDL-DM to 1 mol of C242 antibody. The reaction was incubated overnight at 25° C.

The reaction was purified into 10 mM Succinate, 250 mM Glycine, 0.5% Sucrose, 0.01% Tween20, pH 5.5 formulation buffer using NAP desalting columns (GE Healthcare) and filtered through a syringe filter with a 0.22 μm PVDF membrane.

Figure 20:
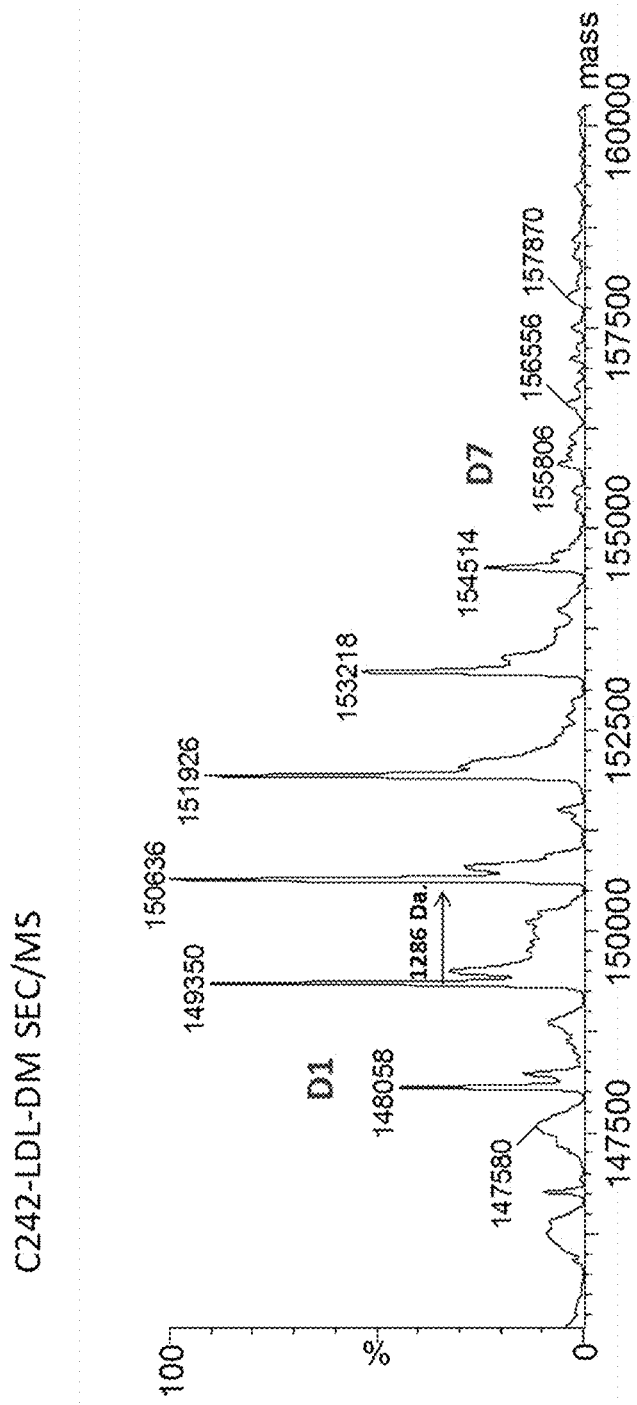
FIG. 20 shows SEC/MS spectrum of conjugate 18c.

The purified conjugate was found to have 3.8 mol LDL-DM/mol antibody by UV-Vis, 95% monomer by SEC, and below 1% free drug by HPLC Hisep column analysis. The SEC/MS spectrum for C242-sGMBS-LDL-DM is shown in FIG. 20.

Preparation of ML66-sGMBS-LDL-DM (ADC 16c)

Prior to conjugation, sGMBS-LDL-DM was prepared by mixing a stock solution of sulfo-GMBS (compound 15 in FIG. 4) in N-N-dimethylacetamide (DMA, SAFC) with a stock solution of LDL-DM (compound 14c in FIG. 3) in DMA in presence of succinate buffer pH 5.0 to obtain a 60/40 organic/aqueous solution and final concentrations of 1.5 mM sulfo-GMBS and 1.95 mM LDL-DM. The reaction was incubated for 10 min at 25° C. The crude sGMBS-LDL-DM mixture was added to a solution containing ML66 antibody in phosphate buffered saline (PBS) pH 7.4 spiked with 5× solution of 300 mM 4-(2-Hydroxyethyl)-1-piperazinepropanesulfonic acid (EPPS) pH 8.0 and 15% DMA (v/v) to a final ratio of 8.0 mol sulfo-GMBS-LDL-DM to 1 mol of ML66 antibody. The reaction was incubated overnight at 25° C.

The reaction was purified into 10 mM Succinate, 250 mM Glycine, 0.5% Sucrose, 0.01% Tween20, pH 5.5 formulation buffer using NAP desalting columns (GE Healthcare) and filtered through a syringe filter with a 0.22 μm PVDF membrane.

Figure 21:
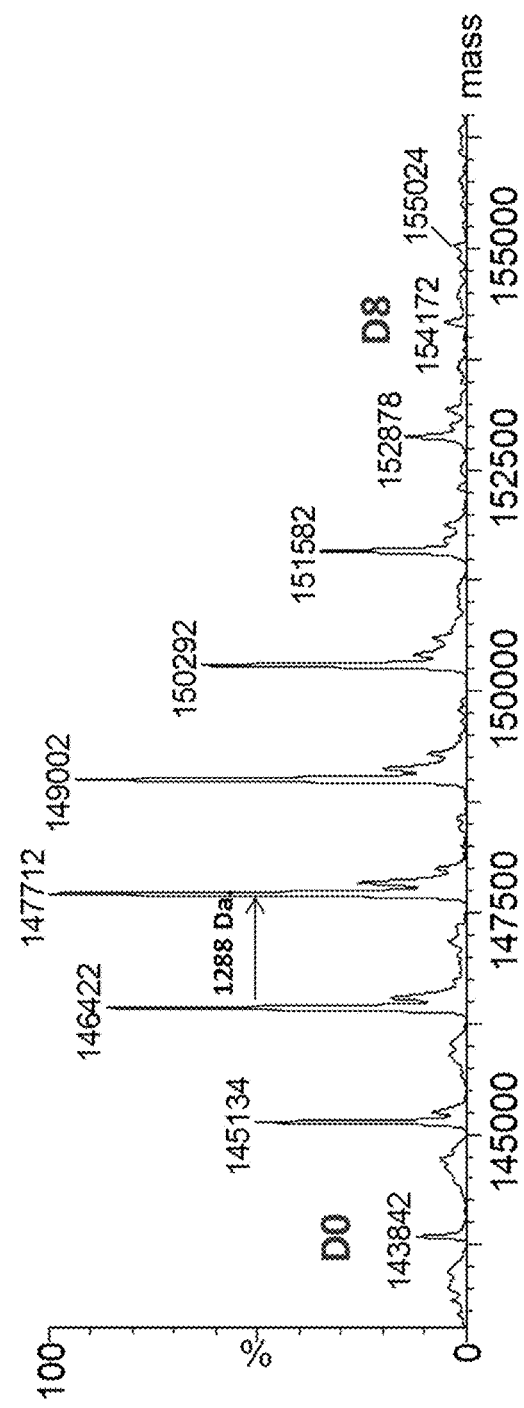
FIG. 21 shows SEC/MS spectrum of conjugate 16c.

The purified conjugate was found to have 3.7 mol LDL-DM/mol antibody by UV-Vis, 98% monomer by SEC, and below 1% free drug by HPLC Hisep column analysis. The SEC/MS spectrum for C242-sGMBS-LDL-DM is shown in FIG. 21.

Preparation of M9346A-sGMBS-LDL-DM (Conjugate 17c)

Prior to conjugation, sGMBS-LDL-DM (compound 15 in FIG. 4) was prepared by mixing a stock solution of sulfo-GMBS in N-N-dimethylacetamide (DMA, SAFC) with a stock solution of LDL-DM (compound 14c in FIG. 3) in DMA in presence of succinate buffer pH 5.0 to obtain a 60/40 organic/aqueous solution and final concentrations of 3 mM sulfo-GMBS and 3.9 mM LDL-DM. The reaction was incubated for 2 h at 25° C. The crude sGMBS-LDL-DM mixture was added to a solution containing M9346A antibody in phosphate buffered saline (PBS) pH 7.4 spiked with 5× solution of 300 mM 4-(2-Hydroxyethyl)-1-piperazinepropanesulfonic acid (EPPS) pH 8.5 and 10% DMA (v/v) to a final ratio of 9.5 mol sulfo-GMBS-LDL-DM to 1 mol of M9346A antibody. The reaction was incubated overnight at 25° C.

The reaction was purified into 10 mM Succinate, 250 mM Glycine, 0.5% Sucrose, 0.01% Tween20, pH 5.5 formulation buffer using NAP desalting columns (GE Healthcare) and filtered through a syringe filter with a 0.22 μm PVDF membrane.

Figure 22:
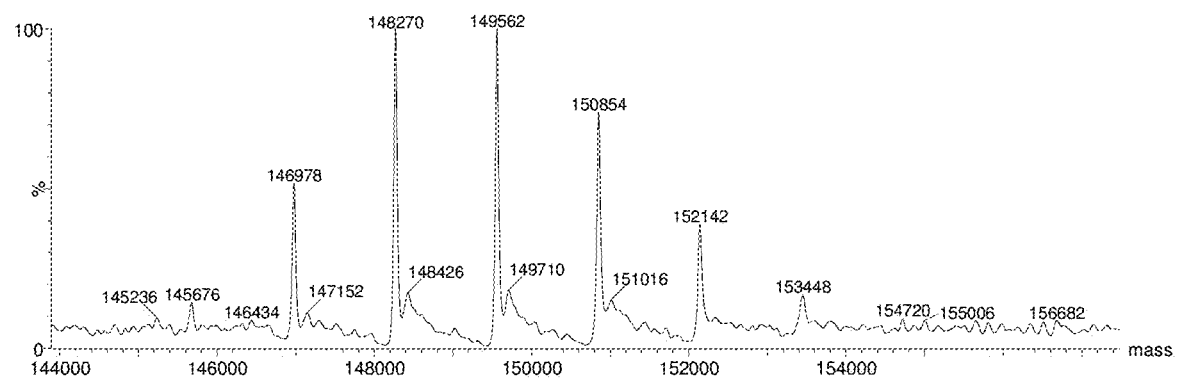
FIG. 22 shows SEC/MS spectrum of conjugate 17c.

The purified conjugate was found to have 3.7 mol LDL-DM/mol antibody by UV-Vis, 99% monomer by SEC, and below 1% free drug by SEC/reverse-phase HPLC dual column analysis. The SEC/MS spectrum for C242-sGMBS-LDL-DM is shown in FIG. 22.

Preparation of M9346A-C442-MalC5-LDL-DM (Conjugate 26c)

M9346A-C442 (anti-Folate antibody with engineered Cys at 442 position) in phosphate buffered saline (PBS) pH 7.4 (Life Technologies) was treated with 50 molar equivalents of tris(2-carboxyethyl)phosphine (TCEP, Sigma-Aldrich) and incubated for 1 h at 37° C. TCEP was removed by NAP desalting columns (GE Healthcare) and 100 molar equivalents of dehydroascorbic acid (Sigma-Aldrich) were added to the purified reduced M9346A-C442 in PBS pH 7.4, 2 mM EDTA (Sigma-Aldrich) and incubated for 90 minutes to 4 hours at 25° C.

The reduced and re-oxidized antibody solution was used immediately for conjugation to MalC5-LDL-DM (compound I-2a shown above).

The re-oxidized M9346A-C442 antibody was spiked with PBS pH 6.0, 2 mM EDTA and the conjugation was carried out in 90% aqueous solution with 10% N-N-dimethylacetamide (DMA, SAFC) and 5 equivalents of MalC5-LDL-DM. The reaction was incubated over night at 25° C.

Post-reaction, the conjugate was purified into 10 mM Acetate, 9% sucrose, 0.01% Tween-20, pH 5.0 formulation buffer using NAP desalting columns (GE Healthcare) and filtered through a syringe filter with a 0.22 μm PVDF membrane.

Figure 23:
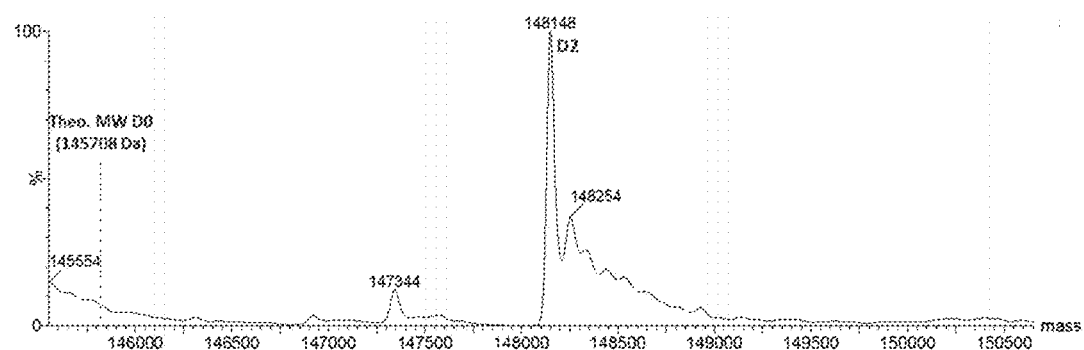
FIG. 23 shows SEC/MS spectrum of conjugate 26c.

The purified conjugate was found to have 2 mol LDL-DM/mol antibody by UV-Vis, 97% monomer by SEC, and below 3% free drug by SEC/reverse-phase HPLC dual column analysis. The SEC/MS spectrum for C242-sGMBS-LDL-DM is shown in FIG. 23.

Example 5

Cell Binding Assay

The binding of naked antibodies or ADCs to antigen positive cells was evaluated by an indirect immunofluorescence assay using flow cytometry. Cells (5×104 per well) were plated in a round-bottomed 96-well plate and incubated at 4° C. for 3 h with serial dilutions of test article in 0.2 mL of alpha-MEM supplemented with 2% (v/v) normal goat serum (Sigma, St., Louis, Mo.). Each sample was assayed in triplicate. Control wells lacked test article. The cells were then washed with 0.2-mL cold (4° C.) medium and stained with fluorescein labeled goat anti-human immunoglobulin G (IgG) antibody for 1 h at 4° C. The cells were again washed with medium, fixed in 1% formaldehyde/PBS solution, and analyzed using a FACS Calibur flow cytometer (BD Biosciences, San Jose, Calif.).

Figure 7:
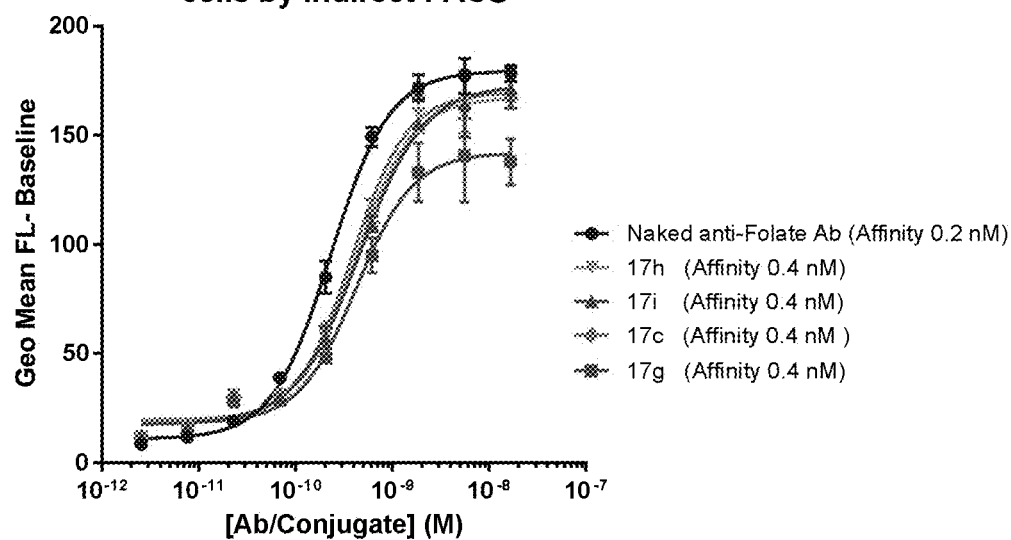
FIG. 7 shows binding affinity of the representative conjugates of the present invention for target antigen on T47D cells.

As shown in FIG. 7, conjugation only moderately affected the binding affinities of the naked antibody.

Example 6

In Vitro Cytotoxicity Assays for ADCs and Metabolites

Assays were performed in flat bottom 96-well plates in triplicate for each data point. Test articles were first diluted in complete cell culture media using 5-fold dilution series and 100 μL were added into each well. The final concentrations typically ranged from $3 \times 10^{-8}$ M to $8 \times 10^{-14}$ M. The target cells were then added to the test articles at 1,500 to 3,000 cells per well in 100 μL of complete culture media. The mixtures were incubated at 37° C. in a humidified 5% $CO_2$ incubator for 5 days. Viability of the remaining cells was determined by the WST-8 (Tetrazolium salt-8; 2-(2-methoxy-4-nitrophenyl)-3-(4-nitrophenyl)-5-(2,4-disulfophenyl)-2H-tetrazolium) based colorimetric assay using the Cell Counting Kit-8 (Dojindo Molecular Technologies, Inc., Rockville, Md.). The WST-8 is reduced by dehydrogenases in live cells to give a yellow-colored formazan product that is soluble in tissue culture media. The amount of formazan dye is directly proportional to the number of live cells. The WST-8 was added to a final volume of 10% and plates were incubated at 37° C. in a humidified 5% $CO_2$ incubator for an additional 4 h. The WST-8 signals were then measured using a microplate plate reader at optical density of 450 nm. The surviving fraction was calculated by dividing the value of each treated sample by the average value of untreated controls, and plotted against the test article concentrations in a semi-log plot for each treatment. $IC_{50}$ values were determined using nonlinear regression (curve fit) with GraphPad Prism v5 program (GraphPad Software, La Jolla, Calif.).

Figure 8:
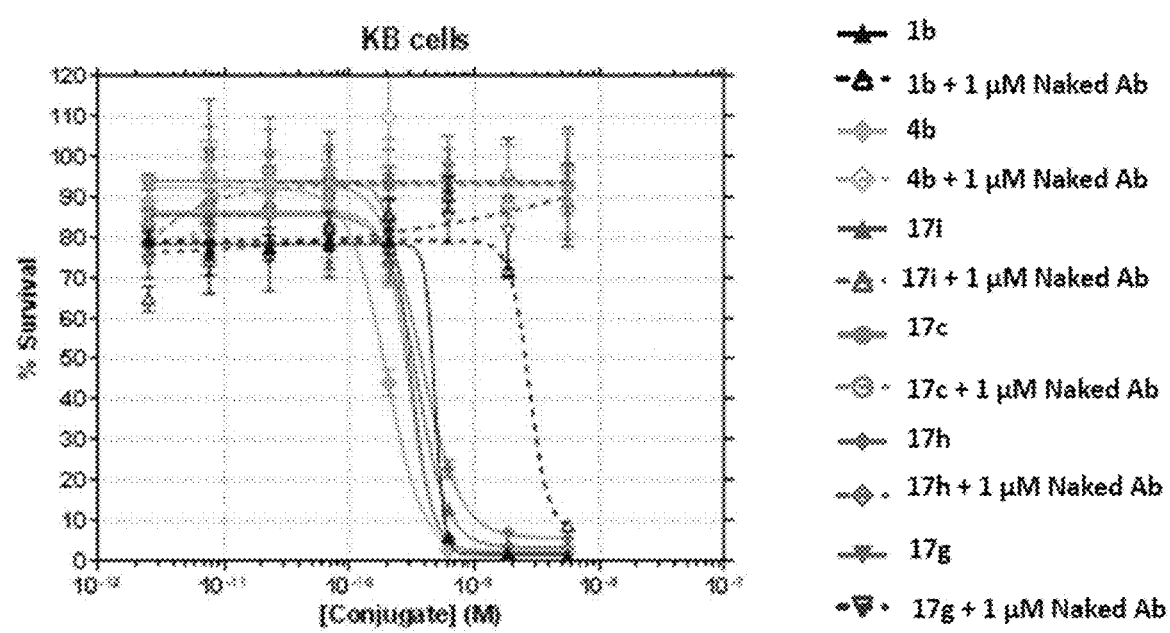
FIG. 8 shows in vitro cytotoxicity of the representative conjugates of the present invention against KB cells.

As shown in FIG. 8, the conjugates of the present invention are highly potent against KB cells and the in vitro cytotoxicity is antigen-specific as the addition of the naked antibody significantly reduced the cytotoxicity of the conjugates.

The in vitro cytotoxicity of the conjugates of the present invention was compared with Ab-sSPDB-DM4 conjugate having a cleavable disulfide linker and the peptide anilino maytansinoid conjugate (Table 1). As shown in Table 1, the conjugates of the present invention are generally more cytotoxic than the Ab-sSPDB-DM4 conjugate. In addition, the length of the alkyl chain in the spacer $L_1$ group has little effect on cytotoxicity to antigen-positive cells.

TABLE 1

| | KB | | Igrov-1 | | Jeg-3 | | SKOV-6 | |
|---|---|---|---|---|---|---|---|---|
| | ADC | +Block | ADC | +Block | ADC | +Block | ADC | +Block |
| 1b | 0.5 | 3 | 2 | 8 | 5 | 9 | 3 | 7 |
| 4b | 0.2 | >50 | 0.3 | 20 | 0.2 | 10 | 0.9 | 10 |
| 17h | 0.4 | >50 | 30 | >50 | 0.5 | >50 | >10 | >50 |
| 17i | 0.3 | >50 | 50 | >50 | 0.7 | >50 | >10 | >50 |
| 17g | 0.3 | >50 | 3 | >50 | 0.5 | >50 | >10 | >50 |
| 17c | 0.3 | >50 | 7 | >50 | 0.6 | >50 | >10 | >50 |

Figure 14:
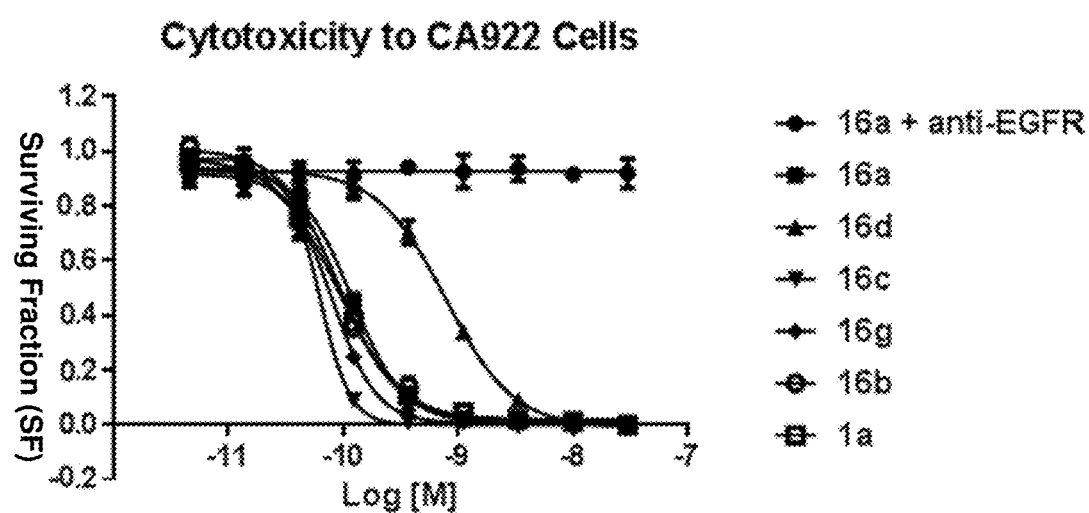
FIG. 14 shows in vitro cytotoxicity of the representative conjugates of the present invention compared to 1a against CA922 cells.

In vitro cytotoxicity of the conjugate of the present invention was also tested against CA922 cells. As shown in FIG. 14, the D-Ala in the peptide linker of the conjugate is detrimental to the cytotoxicity if attached directly to the immolating nitrogen in —NH—$CR^1R^2$—S— portion of the conjugate of formula (I).

Figure 15:
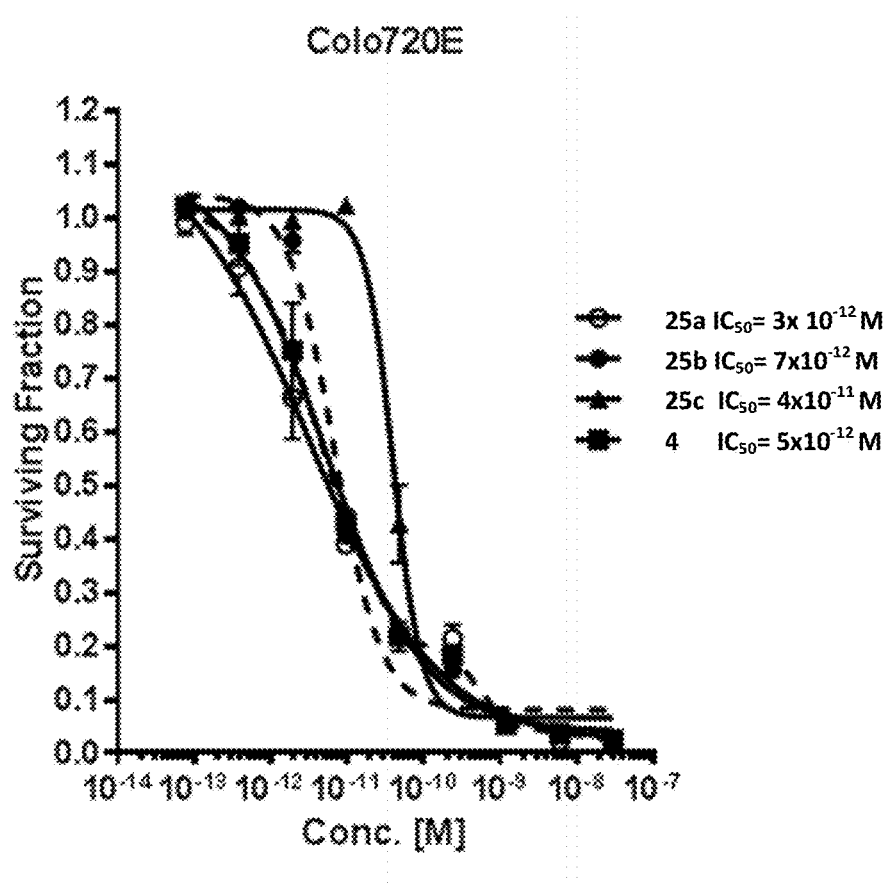
FIG. 15 shows in vitro cytoxicity of metabolites of 25a, 25b and 25c as compared to the metabolite species 3 of the conjugate Ab-sSPDB-DM4.

In vitro cytotoxicity of the predominant ADC metabolites was tested against Colo720E, H1703, H1975 and COLO704 cells and the data are shown in FIG. 15 and Table 2 below. The data suggest that increasing metabolite hydrophobicity (longer alkyl chain in the $L_1$ spacer) increases metabolite cytotoxicity.

TABLE 2

In vitro cytotoxicity of predominant ADC metabolites on H1703, H1975 and COL0704 Cells

| | $IC_{50}$ (M) | | |
|---|---|---|---|
| Metabolite | H1703 Cells | H1975 Cells | COLO704 Cells |
| 25a | $2.27 \times 10^{-12}$ | $8.93 \times 10^{-13}$ | $3.04 \times 10^{-12}$ |
| 25b | $5.92 \times 10^{-12}$ | $5.60 \times 10^{-12}$ | $6.88 \times 10^{-12}$ |
| 25c | $5.02 \times 10^{-11}$ | $4.78 \times 10^{-11}$ | $3.99 \times 10^{-11}$ |
| 3 | $3.70 \times 10^{-12}$ | $1.78 \times 10^{-12}$ | $5.06 \times 10^{-12}$ |

Example 7

In Vivo Efficacy Studies

The in vivo efficacy of ADCs were evaluated in mice bearing established xenograft (H1703 250 mm³), HT-29 (100 mm³) or NCI—H2110 (100 mm³). Female SCID mice were inoculated subcutaneously in the right flank with the desired cell type in serum-free medium/matrigel. Tumors were grown to the designated size. The animals were then randomly divided into groups (6 animals per group). Control mice were treated with phosphate-buffered saline. Mice were dosed with ADC at mg/kg levels indicated in the studies. All dosings in xenograft models was based on the weight of the antibody component of the conjugate. All treatments were administered by tail vein intravenous injection. Tumor sizes were measured twice weekly in three dimensions using a caliper with tumor volumes expressed in mm³ and calculated using the formula V=½ (length×width×height). Body weight was also measured twice per week.

Figure 13:
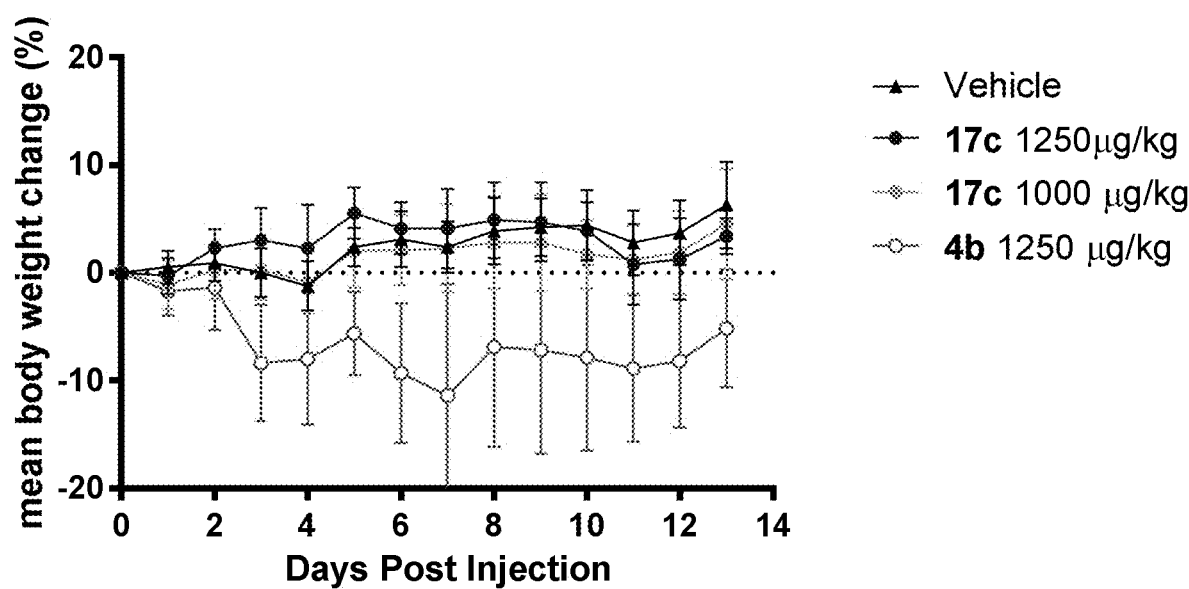
FIG. 13 shows body weight changes for mice treated with a representative conjugate of the present invention as compared to mice treated with conjugate 4b.

As shown in FIGS. 10, 11A, 11B and 12, the conjugates of the present invention are highly active against the H1703 (FIG. 10), HT-29 (FIGS. 11A and 11B), NCI—H2110 (FIG. 12) xenograft tumors in the in vivo mouse model. The conjugate 17c is well tolerated as compared to the peptide anilino maytansinoid conjugate (see FIG. 13).

Figure 18:
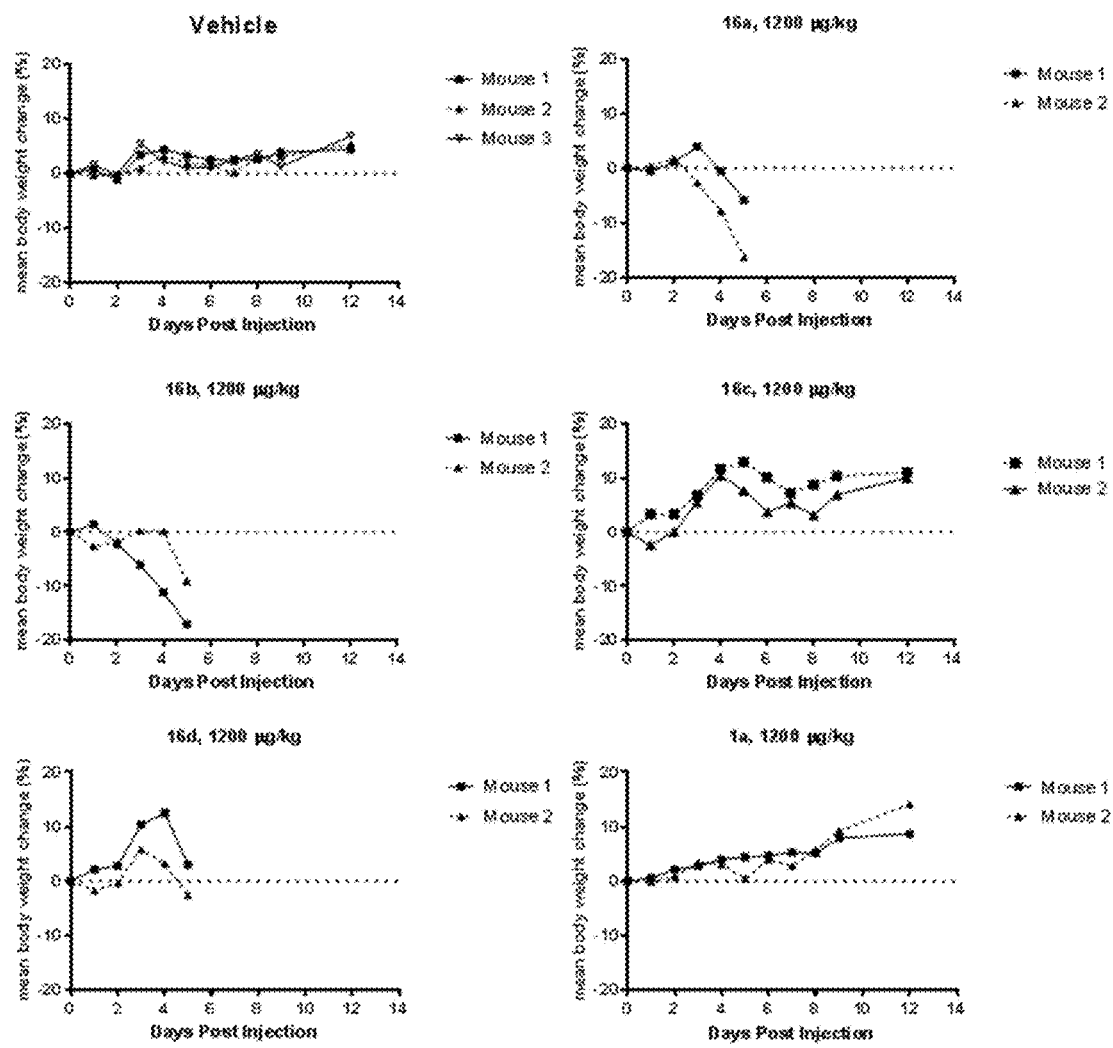

Mouse tolerability studies for the conjugates of the present invention with different peptide linker (i.e. A in formula (I)) were also carried out. The body weight of the mice dosed with the conjugates was measured. As shown in FIG. 18, mouse tolerability decreases if the peptide linker contains consecutive L-alanines.

Example 8

In Vitro Bystander Killing Assays

Bystander killing assays in which the number of antigen-negative cells are held constant in the presence of varying numbers of antigen-positive cells were conducted as described previously using the ratio of antigen-positive to antigen-negative cells designated in the relevant figures. A variation on this assay in which antigen-negative and antigen-positive cells were held constant was perform as follows: 3000 EGFR+ Ca9-22 cells were mixed with 2000 EGFR-MCF7 cells and the cell mixture was incubated with 0.66 nM of the indicated ADCs for 4 days. The viable cells were quantified using the WST-8 assay. In the same assay, the cytotoxic potency of the ADCs against Ca9-22 or MCF7 cells was also assessed; all ADCs killed the EGFR+ Ca9-22 cells at a similar level but had no impact on the EGFR-MCF7 cells unless antigen-positive cells were added.

In another experiment, various ratios of FRα(+)/FRα(−) cells were mixed in low adherence U-bottomed wells and exposed to 2 nM of the conjugate of the present invention that is not toxic for FRα(−) cells (Namalwa, 1000 cells seeded) but kills all FRα(+) cells (JEG-3, 150K FRα ABC). The survival of FRα(−) cells was measured by Cell Titer Glo assay (Promega) after 4 days. The data are shown in FIG. 9C. Specifically, the bystander killing for the conjugate of the present invention was compared to the peptide aniline maytansinoid conjugate and the data is shown in Table 3 below.

TABLE 3

| Conjugate | # Jeg-3 cells required to kill 100% FRα (—) cells |
|---|---|
| 4b | 3000 |
| 17c | 1000 |

Figure 9A:
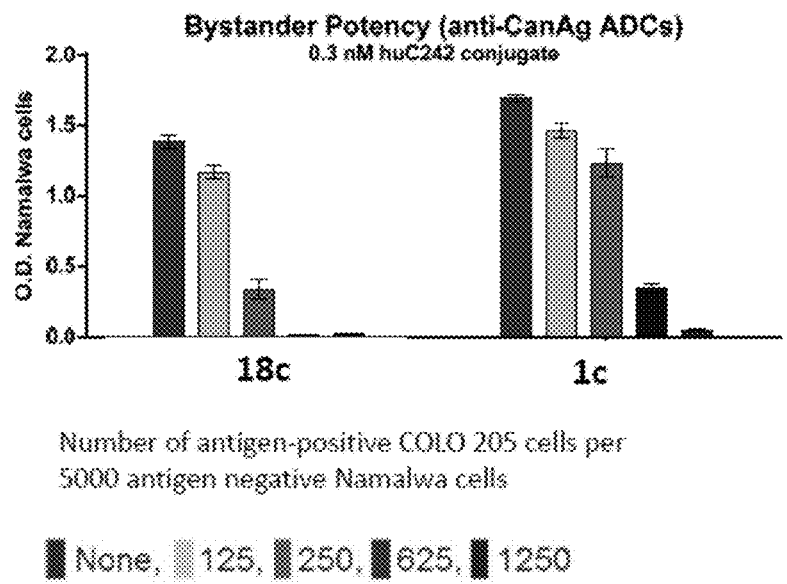
FIGS. 9A, 9B, 9C and 9D show bystander killing effects of the representative conjugates of the present invention.
Figure 9B:
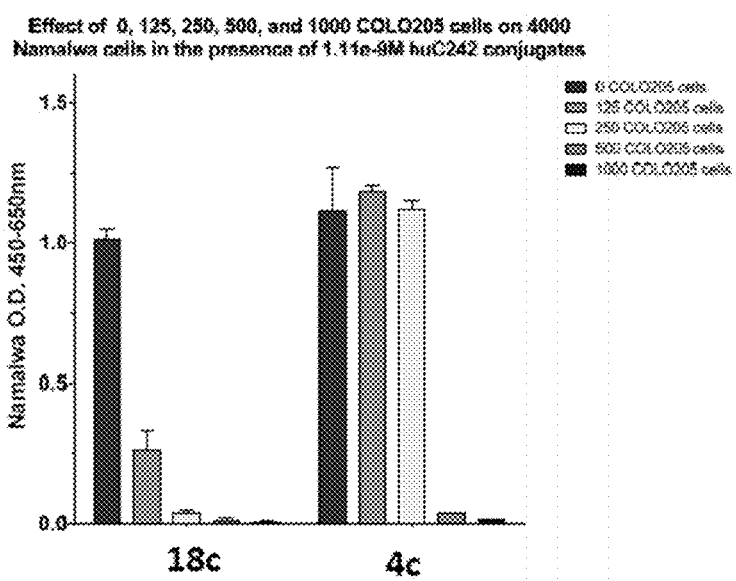
Figure 9C:
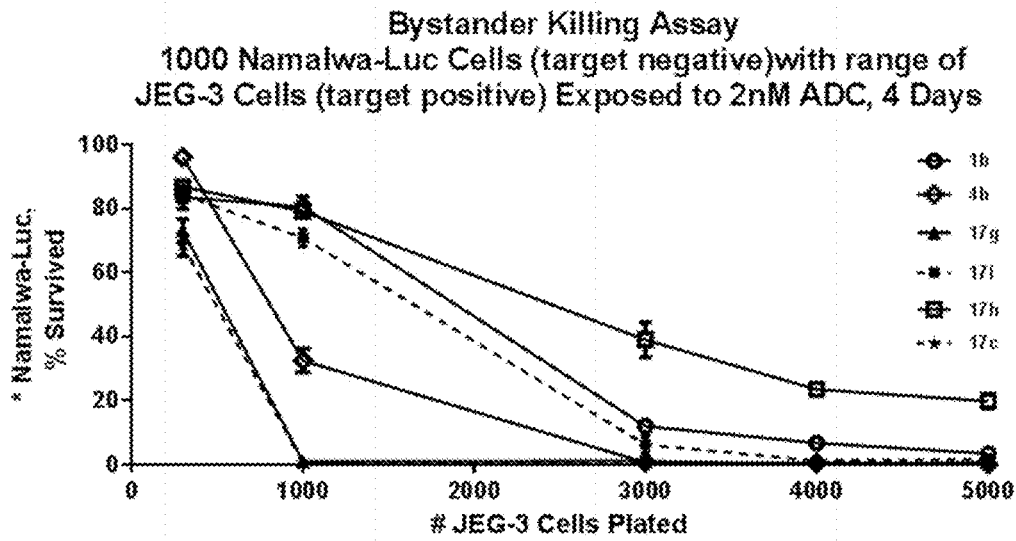

As shown in FIGS. 9A, 9B and 9C, the conjugate of the present invention has higher bystander killing effect than the Ab-sSPDB-DM4 conjugate having a cleavable disulfide linker and the peptide anilino maytansinoid conjugate. In addition, when other factors are held constant, increasing metabolite hydrophobicity increases metabolite cytotoxicity, which increases the bystander killing of the corresponding conjugates. Further, the data seem to show that the conjugate of the present invention differ from the Ab-sSPDB-DM4 conjugate and the peptide aniline maytansinoid conjugate in the types of metabolites released and release efficiencies. The bystander killing effect of the conjugate of the present invention is greater than the peptide anilino maytansinoid conjugate, which is in turn greater than Ab-sSPDB-DM4 (17g>4b>1b).

Figure 9D:
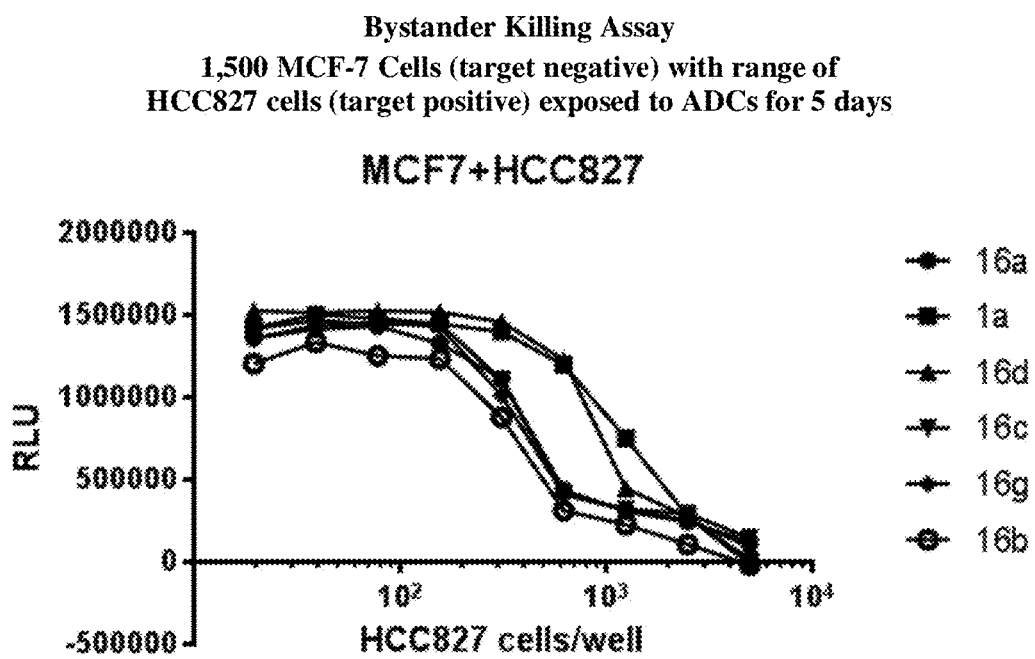
Figure 10:
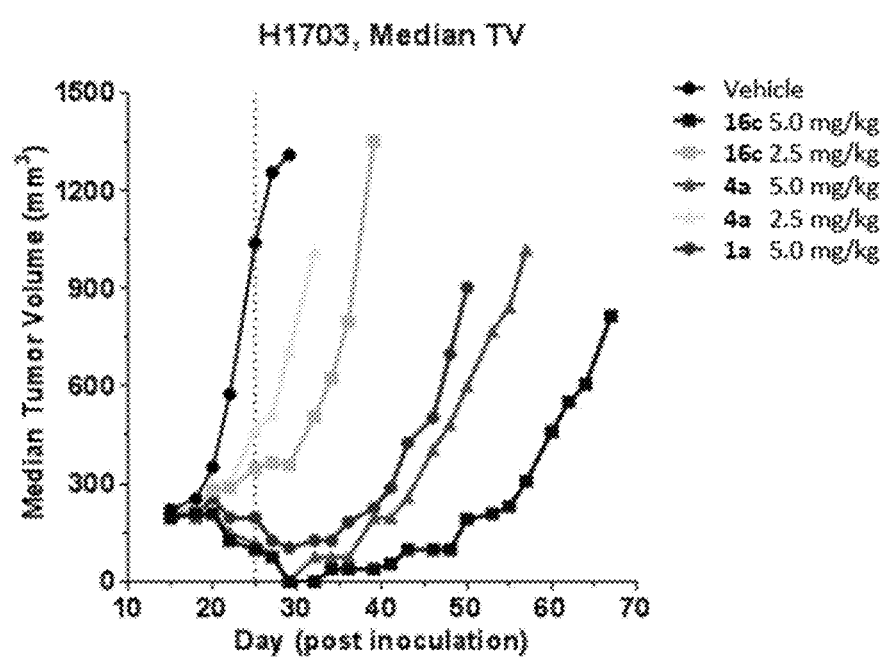
FIG. 10 shows in vivo antitumor activity of a representative conjugate of the present invention in mice bearing large 250 mm$^2$ EGFR receptor positive xenografts.
Figure 11A:
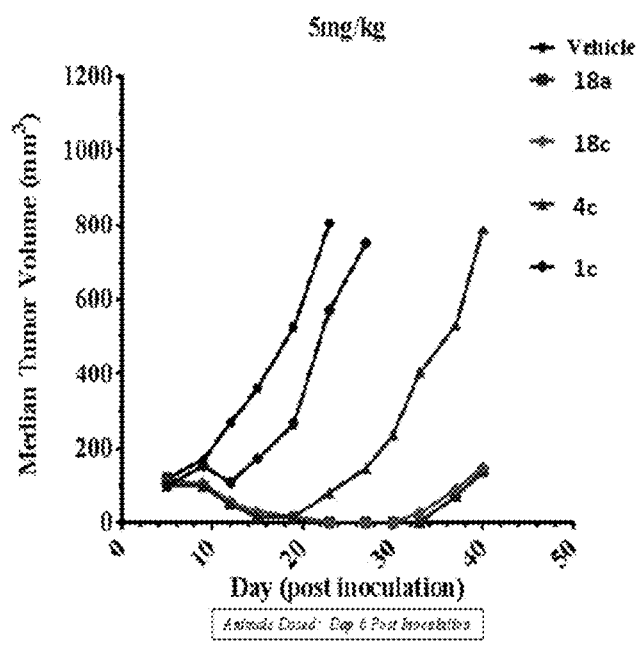
FIGS. 11A and 11B show in vivo antitumor activities of representative conjugates of the present invention in mice bearing CanAg+ HT-29 xenografts at 5 mg/kg (FIG. 11A) and 2.5 mg/kg (FIG. 11B) doses.
Figure 11B:
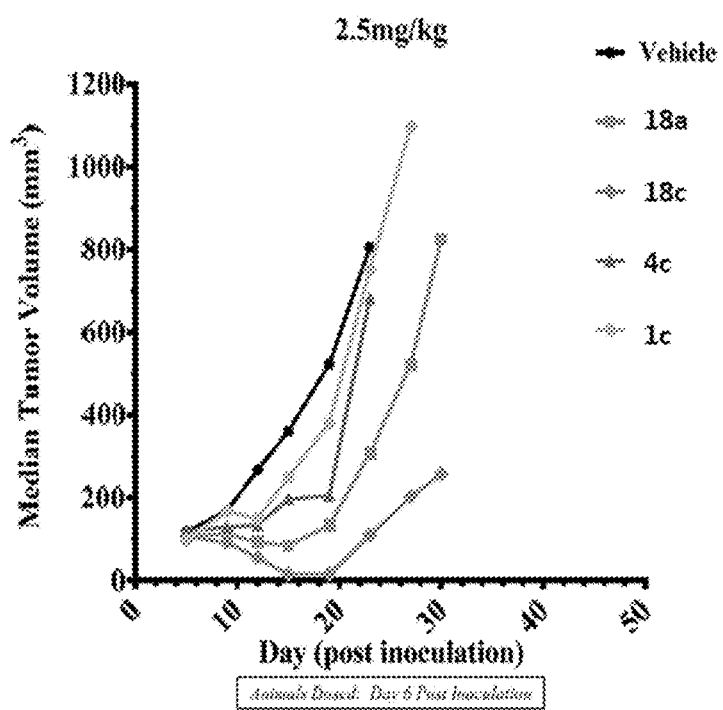
Figure 12:
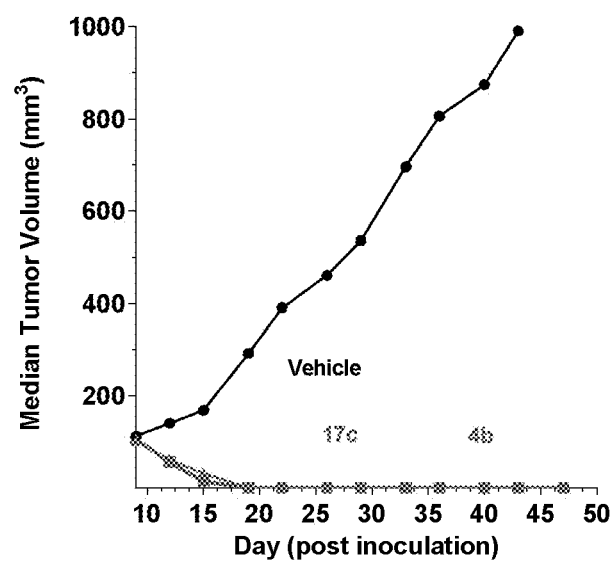
FIG. 12 shows in vivo antitumor activity of a representative conjugate of the present invention in mice bearing NCI-H2110 folate receptor positive xenografts. The mice were dosed with conjugates 17c or 4b at 3 mg/kg doses.

As shown in FIG. 9D, the D-Ala in the peptide linker of the conjugate is detrimental to the bystander killing if attached directly to the immolating nitrogen in —NH—$CR^1R^2$—S-portion of the conjugate of formula (I).

Example 9

In Vitro Metabolism Study

FRα-expressing KB cells were treated with a saturating amount of 17c conjugate for 24 hours. Catabolite-containing media was incubated with 5 mM NEM to cap any free thiol present and then captured by pre-bound protein A-anti-maytansinoid antibody complex. The catabolites were released by acetone extraction, and analyzed by UHPLC/HRMS.

Figure 16:
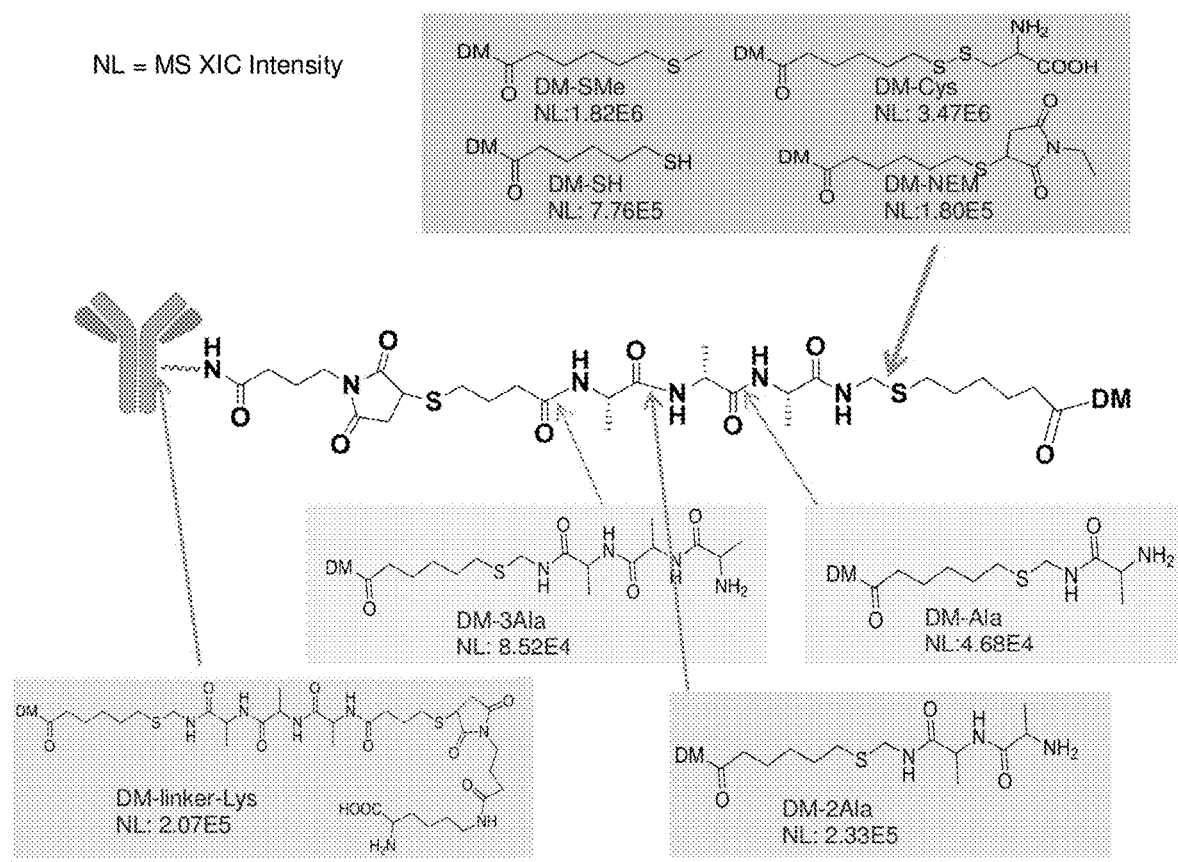
FIG. 16 shows metabolite species detected from the in vitro metabolism study of the conjugate 17c and proposed cleavage sites.

The detected metabolites and proposed cleavage sites are shown in FIG. 16. The major effluxed catabolites identified in cell culture media were DM-SMe (25a) and DM-SH species.

Figure 19:
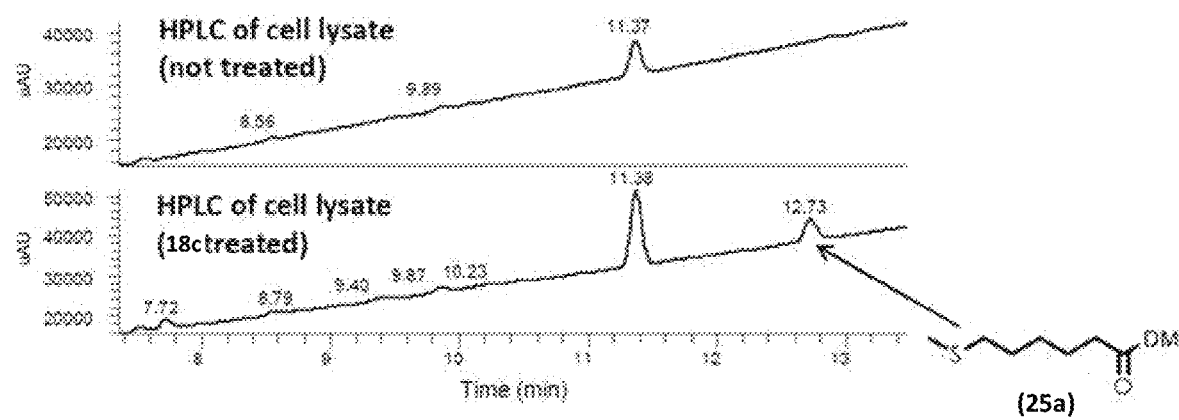
FIG. 19 shows UPLC traces for the DTT and NEM treated cell lysate from COLO205 cells that were not exposed to any conjugate (top) and COLO205 cells that were exposed to conjugate 18c.

In another experiment, conjugate 18c (anti-CanAg-LDL-DM) was incubated with COLO205 cells followed by cell lysis and reduction of any disulfide bonds and capping of resulting thiols with N-ethyl maleimide by a previously described method (see Erickson H K, Park P U, Widdison W C, Kovtun Y V, Garrett L M, Hoffman K, et al. Antibody-maytansinoid conjugates are activated in targeted cancer cells by lysosomal degradation and linker-dependent intracellular processing. Cancer Res 2006; 66(8):4426-33). A non-treated control was also performed where COL0205 cells, not treated with conjugate, were lysed and disulfide bonds reduced then the resulting thiols were capped with N-ethyl Maleimide. Both samples were analyzed by UPLC/MS using a Thermo Q-Exactive Mass spectrometer set for Pos, Neg, DDA Top-10 MS/MS detection was in series with a Dionex UltiMate 3000 UPLC that was equipped with a Waters UPLC BEH C8, 1.8 micrometer, 100×2.1 mm column. The column compartment set to 30 degrees C. and the uv detector was set to 252 nm. The injection volume was 40 μL. The column was eluted with deionized water containing 0.1% formic acid with a linear gradient of acetonitrile containing 0.1% formic acid of 20% to 100% over 20 min at a flow rate of 0.35 mL/min followed by a flush of 100% acetonitrile containing 0.1% formic acid for 10 min. As shown in FIG. 19, The top UPLC trace is of the DTT and NEM treated cell lysate from COLO205 cells that were not exposed to any conjugate. The bottom UPLC trace is of the DTT and NEM treated cell lysate from COLO0205 cells that were treated with conjugate 18c. The 12.73 min retention time peak had the same retention time and mass spectrum as $CH_3S(CH_2)_5CO$-DM compound (compound 25a) made in the laboratory.

In a similar experiment, 100 nM of C242-sGMBS-LDL-DM (18c) was added the Colo205 cell culture and incubate at 37° C. for 24 hrs. Cell and media were separated and catabolites were extracted with affinity capture and reconstituted with 20% acetonitrile. The catabolites were analyzed by UHPLC/HRMS. The major catabolite species identified in cell media include DM-SMe, oxidized DM-SMe and acid-form free drug (see structures below)

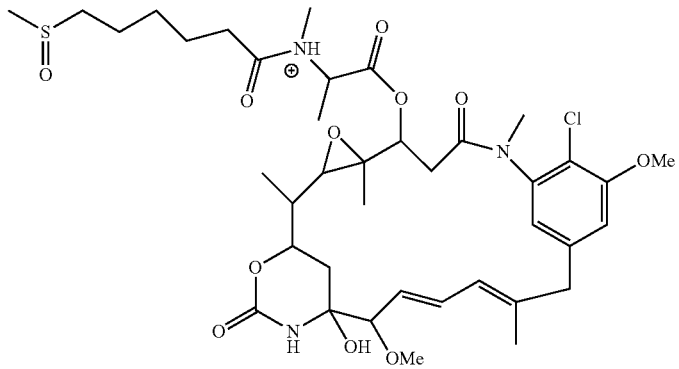

Chemical Formula: $C_{39}H_{57}ClN_3O_{11}S^+$
Exact Mass: 810.34
oxidized DM-SMe

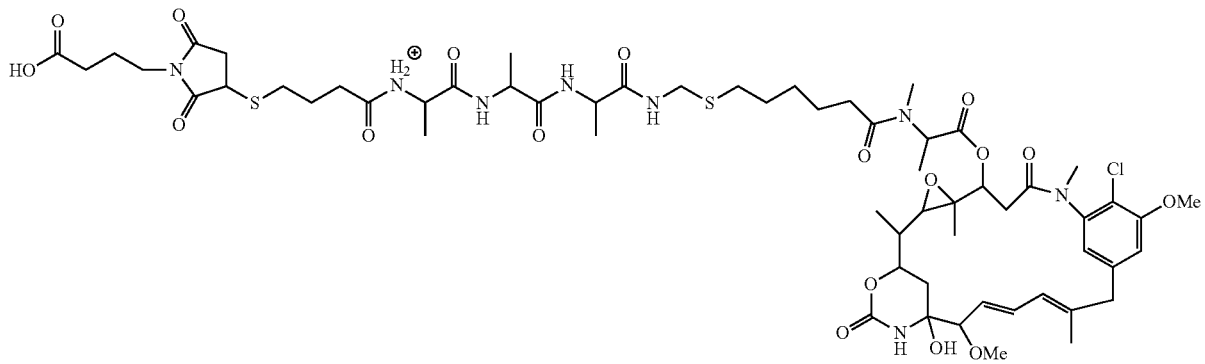

Chemical Formula: $C_{60}H_{88}ClN_8O_{18}S_2^+$
Exact Mass: 1307.53
acid-form free drug

Example 10

In Vivo Efficacy in OV-90 Ovarian Model

The in vivo efficacy of a conjugate of the present invention was evaluated in mice bearing OV-90 xenograft using similar procedures described in Example 7.

Figure 17A:
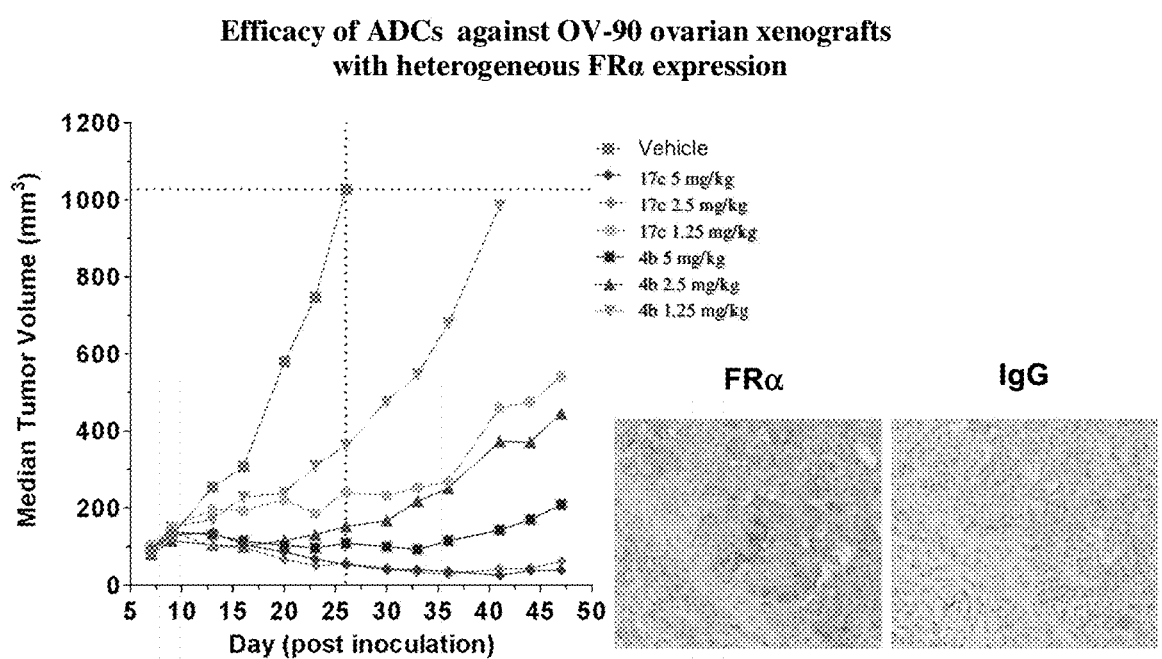
FIGS. 17A and 17B shows in vivo antitumor activity of a representative conjugate of the present invention in mice bearing OV-90 ovarian xenografts with heterogenous FRα expression. Mice were dosed with conjugate 17c or conjugate 4b at 1.25 mg/kg, 2.5 mg/kg or 5 mg/kg doses.
Figure 17B:
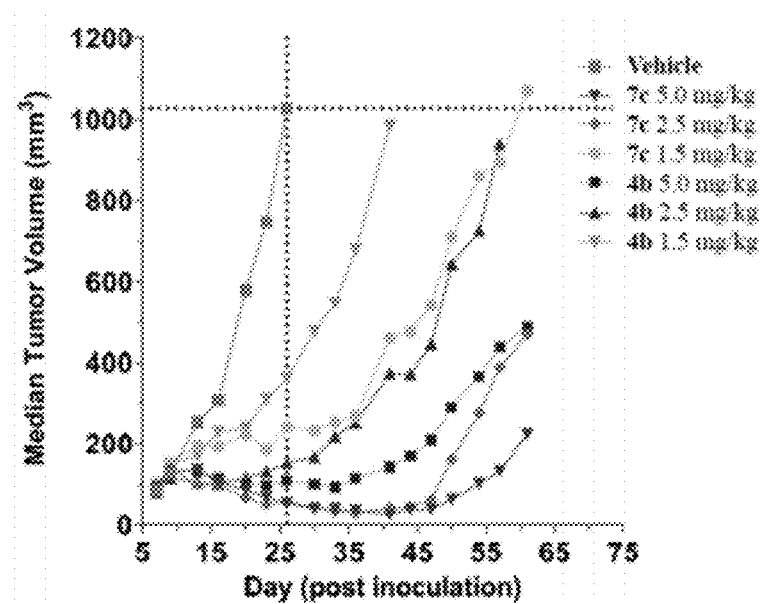

As shown in FIGS. 17A and 17B and Table 4, the conjugate of the present invention exhibits enhanced activity against heterogenous ovarian tumor xenograft model with relatively low FRα expression level (H-score 35) as compared to the peptide anilino maytansinoid conjugate.

TABLE 4

| Group | Ab Dose (mg/kg) | % T/C | PR | CR | Result |
|---|---|---|---|---|---|
| 17c | 5 | 5 | 5/6 | 0/6 | Highly Active |
|  | 2.5 | 5 | 5/6 | 0/6 | Highly Active |
|  | 1.25 | 24 | 0/6 | 0/6 | Active |
| 4b | 5 | 11 | 2/6 | 0/6 | Active |
|  | 2.5 | 15 | 0/6 | 0/6 | Active |
|  | 1.25 | 35 | 0/6 | 0/6 | Active |

Example 11

Mouse Tolerability Study a. The tolerability of 1200 μg/kg huML66-GMBS-LAlaLAlaLAla-Immol-DM (16a), huML66-GMBS-DAlaLAla-LAla-Immol-DM (16b), huML66-GMBS-LAlaDAla-LAla-Immol-DM (16c), huML66-GMBS-LAlaLAlaDAla-Immol-DM (16d), and huML66-sSPDB-DM4 (1a) was tested in female CD-1 mice.

Materials:

| huML66-GMBS-LAlaLAlaLAla-Immol-DM (16a) |
|---|
| Concentration of DM1: 83.39 μg/mL |
| Antibody Concentration: 4.3 mg/mL |
| Ratio of Drug to Antibody: 3.8 DM/Ab |
| Endotoxin: 0.37 EU/mg |
| Monomer: 99.0% |
| Free Drug: None detected |
| huML66-LAlaDAlaLAla-Immol-DM (16c) |
| Concentration of DM1: 70.27 μg/ml |
| Antibody Concentration: 3.6 mg/ml |
| Ratio of Drug to Antibody: 3.8 DM/Ab |
| Endotoxin: 0.27 EU/mg |
| Monomer: 98.7% |
| Free Drug: None detected |
| huML66-s-SPDB-DM4 (1a) |
| Concentration of DM1: 84.35 μg/ml |
| Antibody Concentration: 4.6 mg/ml |
| Ratio of Drug to Antibody: 3.4 DM/Ab |
| Endotoxin: 0.46 EU/mg |
| Monomer: 99.2% |
| Free Drug: None detected |
| huML66-GMBS-DAlaLAlaLAla-Immol-DM (16b) |
| Concentration of DM1: 60.36 μg/ml |
| Antibody Concentration: 3.4 mg/ml |
| Ratio of Drug to Antibody: 3.5 DM/Ab |
| Endotoxin: 0.29 EU/mg |
| Monomer: 97.9% |
| Free Drug: None detected |
| huML66-LAlaLAlaDAla-Immol-DM (16d) |
| Concentration of DM1: 69.52 μg/ml |
| Antibody Concentration: 3.7 mg/ml |
| Ratio of Drug to Antibody: 3.6 DM/Ab |
| Endotoxin: 0.33 EU/mg |
| Monomer: 98.1% |
| Free Drug: None detected |

Groups and Treatments: (2 Mice/Group)
1. Vehicle control
2. huML66-GMBS-LAlaLAlaLAla-Immol-DM (16a), 1200 μg/kg
3. huML66-GMBS-DAlaLAlaLAla-Immol-DM (16b), 1200 μg/kg
4. huML66-GMBS-LAlaDAlaLAla-Immol-DM (16c), 1200 μg/kg
5. huML66-GMBS-LAlaLAlaDAla-Immol-DM (16d), 1200 μg/kg
6. huML66-sSPDB-DM4 (1a), 1200 μg/kg Study Specific Design:

Thirty mice were randomized into 6 groups (2 mice per group) by body weight. The body weights ranged from 24.4 to 27.5 grams (26.2±0.96, Mean±SD). Mice in each group were identified by a colored mark on the fur. Treatment was started on day 15 post arrival. The mice were dosed with conjugate based on individual body weight. Administration of all conjugates or PBS was carried out intravenously with a 1.0 ml syringe fitted with a 27 gauge, ½ inch needle. Due to the given doses, treatments were divided into 2 injections, 2 hours apart. Mice are not allowed more than 350 μl per injection.

Figure 24A:
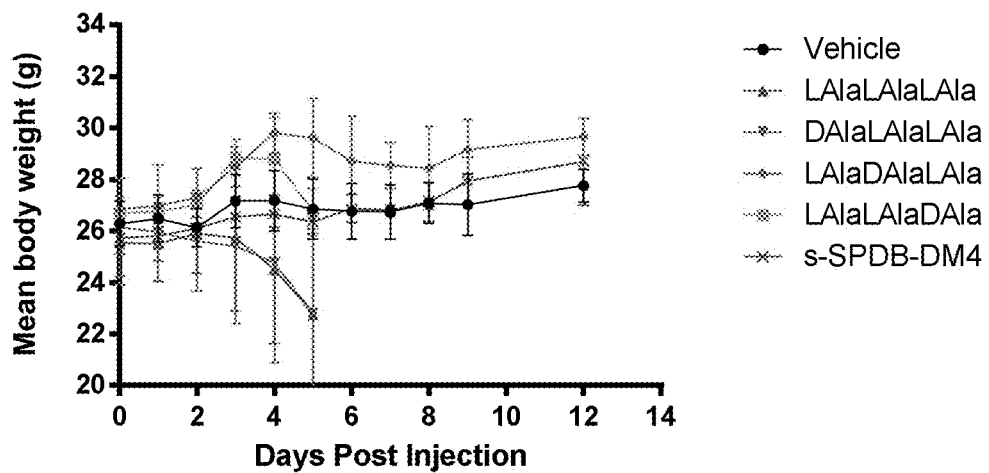
FIG. 24A shows body weights (Mean±SD, g) of CD-1 mice dosed with 1200 µg/kg huML66-GMBS-Ala3-Immol-DM (conjugates 16a, 16b, 16c and 16d) or huML66-s-SPDB-DM4 (conjugate 1a).
Figure 24B:
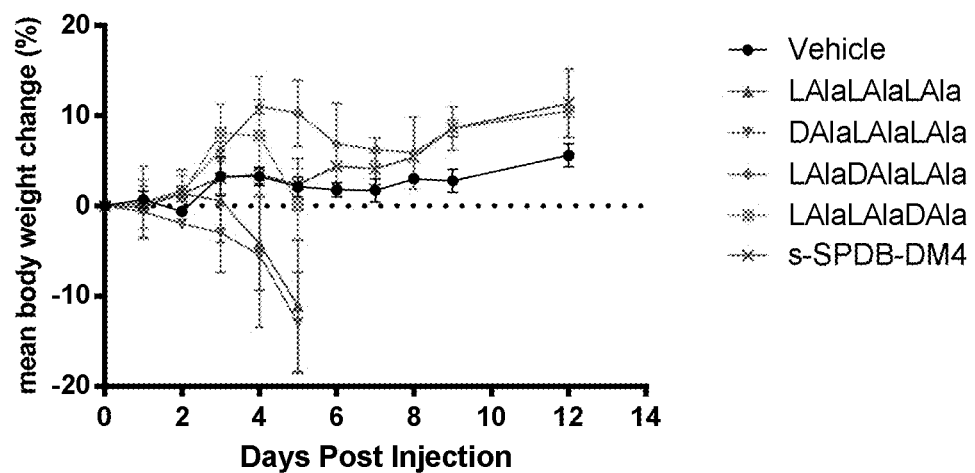
FIG. 24B shows body weight change (Mean±SD, g) of CD-1 mice dosed with 1200 µg/kg huML66-GMBS-Ala3-Immol-DM (conjugates 16a, 16b, 16c and 16d) or huML66-s-SPDB-DM4 (conjugate 1a).
Figure 25A:
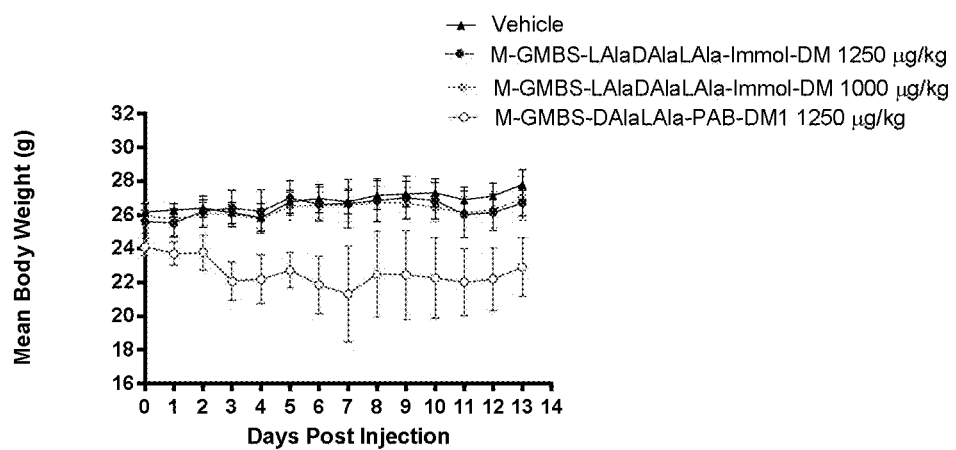
FIG. 25A shows body weights (Mean±SD, g) of CD-1 mice dosed with 1000 or 1250 µg/kg Mov19v1.6-GMBS-1AladAlalAla-Immol-DM (conjugate 17c) or 1250 µg/kg Mov19v1.6-GMBS-dAlalAla-PAB-DM1 (conjugate 4b).
Figure 25B:
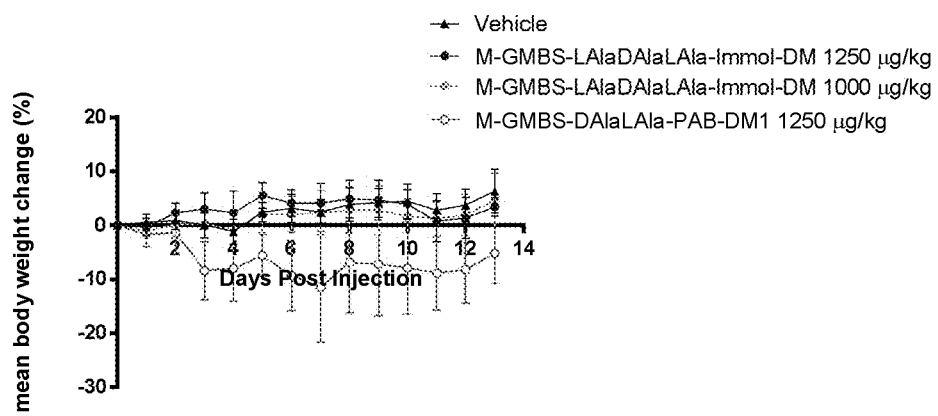
FIG. 25B shows body weight change (Mean±SD, g) of CD-1 mice dosed with 1000 or 1250 µg/kg Mov19v1.6-GMBS-1AladAlalAla-Immol-DM (conjugate 17c) or 1250 µg/kg Mov19v1.6-GMBS-dAlalAla-PAB-DM1 (conjugate 4b).

The body weight of the mice dosed with the conjugates was measured and shown in FIGS. 24A and 24B.

b. The tolerability of 1000 μg/kg and 1250 μg/kg Mov19v1.6-GMBS-1AladAlalAla-Immol-DM (17c) and 1250 μg/kg Mov19v1.6-GMBS-dAlalAla-PAB-DM1 (4b) was tested in female CD-1 mice.

Materials:

| Mov19v1.6-GMBS-1AladAlalAla-Immol-DM |
|---|
| Concentration of DM1: 63.18 μg/mL |
| Antibody Concentration: 3.5 mg/ml |
| Ratio of Drug to Antibody: 3.6 DM/Ab |
| Endotoxin: <0.14 EU/mg |
| Monomer: 98.7% |
| Free Drug: None detected |
| Mov19v1.6-GMBS-dAlalAla-PAB-DM1 |
| Concentration of DM1: 40.01 μg/ml |
| Antibody Concentration: 2.5 mg/ml |
| Ratio of Drug to Antibody: 3.5 DM/Ab |
| Endotoxin: 0.67 EU/mg |
| Monomer: 98.3% |
| Free Drug: None detected |

Groups and Treatments: (8 Mice/Group)
1. Vehicle control
2. Mov19v1.6-GMBS-1AladAlalAla-Immol-DM, 1250 μg/kg
3. Mov19v1.6-GMBS-1AladAlalAla-Immol-DM, 1000 μg/kg
4. Mov19v1.6-GMBS-dAlalAla-PAB-DM1, 1250 μg/kg Study Specific Design:

Thirty-two mice were randomized into 4 groups (8 mice per group) by body weight. The body weights ranged from 23.4 to 27.3 grams (25.5±1.02, Mean±SD). Mice in each group were identified by ear notching. Treatment was started on day 8 post arrival. The mice were dosed with conjugate based on individual body weight. Administration of all conjugates or PBS was carried out intravenously with a 1.0 ml syringe fitted with a 27 gauge, ½ inch needle. Due to the given doses, treatments were divided into 2 injections, 2 hours apart. Mice were not allowed more than 350 µl per injection.

The body weight of the mice dosed with the conjugates was measured and shown in FIGS. 25A-25D.

Example 12

Pharmacokinetic Studies

1. Conjugate 17c

Figure 26:
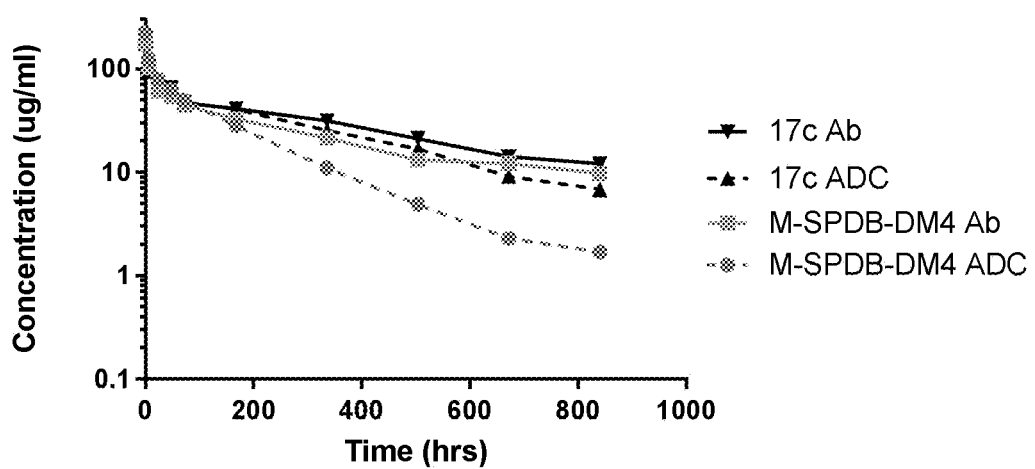
FIG. 26 shows pharmacokinetic profiles of conjugate 17c and M-SPDB-DM4 conjugate in mice.
Figure 26:
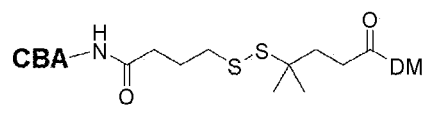

The pharmacokinetics of M-LDL-IMM-DM (conjugate 17c) and M-SPDB-DM4 were evaluated in female CD-1 mice. The mice were randomly distributed based on body weight into 2 groups of six mice. Mice in Group A received a single intravenous injection via tail vein of 10 mg/kg M-LDL-IMM-DM. Mice in Group B received a single intravenous injection via tail vein of 10 mg/kg M-SPDB-DM4. Blood was collected at 2 minutes, 6, 24, 48, 72, 168, 336, 504, 672 and 840 hours. Mice were bled in turn to assure that no mouse was bled more than two times in a 24 hour period. Serum was separated from the blood and samples were frozen at −80° C. until analysis by ELISA. Total antibody and ADC ELISAs were performed on the samples and concentration versus time plots are shown in FIG. 26. The total antibody ELISA quantitates antibody bearing at least one maytansinoid as well as antibody with no attached maytansinoids. The concentration is determined by capturing with an anti-human IgG antibody, then quantitated using an enzyme-labeled anti-human IgG antibody. The ADC ELISA involves the capture of conjugate bearing at least one attached maytansinoid using an anti-maytansinoid antibody then the antibody component of the conjugate is captured and detected with an enzyme labeled anti-human FC antibody. In order to be detected a conjugate must contain at least one covalently linked maytansinoid.

PK parameters were derived using the standard algorithms of the noncompartmental pharmacokinetic analysis program, Phoenix WinNonlin, Professional v 6.1 (Certara, Princeton, N.J.) and are shown in Table 5.

TABLE 5

| ADC/ELISA | $C_{Max}$ (µg/ml) | $T_{1/2}$ (h) | $AUC_{0-\infty}$ (h * µg/ml) | Cl (ml/h/kg) | $V_{SS}$ (ml/kg) |
|---|---|---|---|---|---|
| 17c Ab ELISA | 153.8 | 366.4 | 31,341 | 0.32 | 162 |
| 17c ADC ELISA | 188.1 | 261.2 | 24,454 | 0.41 | 145 |
| M-SPDB-DM4 Ab ELISA | 173.4 | 305.5 | 24,256 | 0.41 | 184 |
| M-SPDB-DM4 ADC ELISA | 224.4 | 142.4 | 15,535 | 0.64 | 112 |

2. Conjugate 26c

Figure 27:
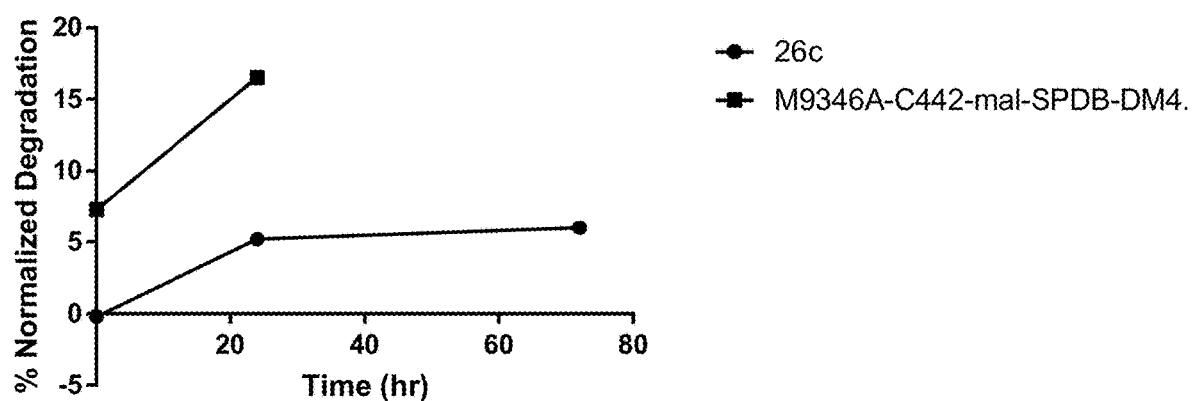
FIG. 27 shows normalized percent degradation versus time for conjugate 26c and M9346A-C442-mal-SPDB-DM4.
Figure 27:
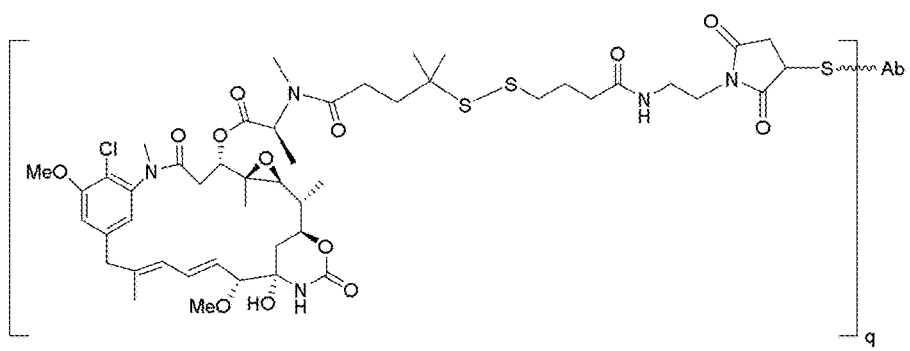

CD-1 mice were injected with a single 10 mg/kg dose of 26c or M9346A-C442-mal-SPDB-DM4. Blood was collected at 2 minutes, 24 hours and 72 hours post injection. The ADCs were purified from plasma using affinity capture with a folate receptor α-Fc fusion protein and samples were analyzed by size exclusion chromatography (SEC) and mass spectrometry (MS). Loss of DM or DM4 was measured as normalized percent degradation versus time and is plotted in FIG. 27. The in vivo stability of 26c is greater than M9346A-C442-mal-SPDB-DM4 as demonstrated by less observed degradation at the 2 minute (−0.2 vs 7.3%) and 24 hour time-points (5.2 vs 16.5%). The 72 hour sample concentration for M9346A-C442-mal-SPDB-DM4 was too dilute to be able to get a normalized percent degradation value.

What is claimed is:

1. A cell-binding agent-cytotoxic agent conjugate represented by the following formula:

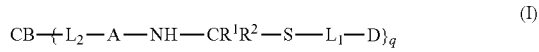
(I)

or a pharmaceutically acceptable salt thereof, wherein:

CB is a cell-binding agent;

$L_2$ is represented by one of the following formulas:

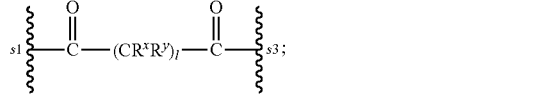
(L2a)

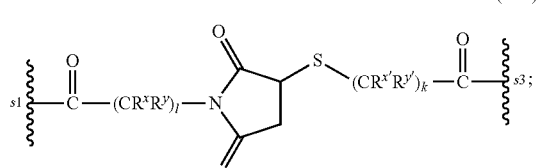
(L2b)

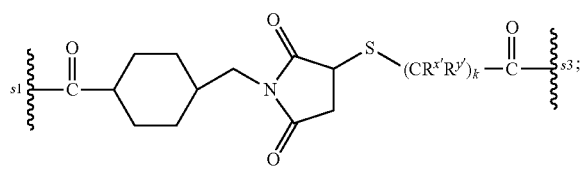
(L2c)

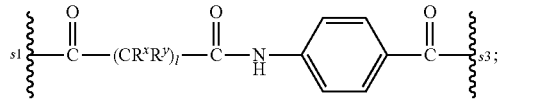
(L2e)

wherein:

$R^x$, $R^y$, $R^{x'}$ and $R^{y'}$ are all H;

l and k are each independently an integer an integer from 2 to 6; and s1 indicates the site connected to the cell-binding agent CB and s3 indicates the site connected to the A group;

A is a peptide comprising 2 to 20 amino acid residues, wherein the peptide is cleavable by a protease;

$R^1$ and $R^2$ are each independently H or a $C_{1-3}$alkyl;

$L_1$ is $CR^3R^4$—$(CH_2)_{1-8}$—$C(=O)$—, wherein $R^3$ and $R^4$ are each independently H or Me;

D is represented by the following formula:

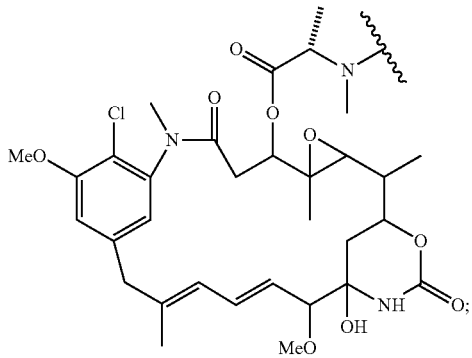 [SMILES: *N(C)[C@@H](C)C(=O)OC1CC(=O)N(C)c2cc(cc(OC)c2Cl)C/C(C)=C/C=C/C(OC)C2(O)CC(OC(=O)N2)C(C)C2OC12C]

and q is an integer from 1 to 20.

2. The conjugate of claim 1, wherein one of $R^1$ and $R^2$ is H, and the other one is Me; or $R^1$ and $R^2$ are both H.

3. The conjugate of claim 1, wherein $L_2$ is represented by the following structural formula:

(L2b)

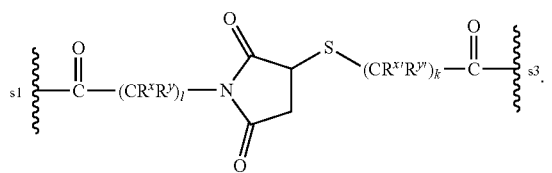

4. The conjugate of claim 1, wherein A is selected from the group consisting of Gly-Gly-Gly, Ala-Val, Val-Ala, D-Val-Ala, Val-Cit, D-Val-Cit, Val-Lys, Phe-Lys, Lys-Lys, Ala-Lys, Phe-Cit, Leu-Cit, Ile-Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Ala-Ala, D-Ala-Ala-Ala, Ala-D-Ala-Ala, Ala-Ala-D-Ala, Ala-Leu-Ala-Leu (SEQ ID NO: 1), β-Ala-Leu-Ala-Leu (SEQ ID NO: 2), Gly-Phe-Leu-Gly (SEQ ID NO: 3), Val-Arg, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, Gln-Val, Asn-Ala, Gln-Phe, Gln-Ala, D-Ala-Pro, and D-Ala-tBu-Gly, wherein the first amino acid in each peptide is connected to $L_2$ group and the last amino acid in each peptide is connected to —NH—$CR^1R^2$—S-$L_1$-D.

5. The conjugate of claim 1, wherein D is represented by the following formula:

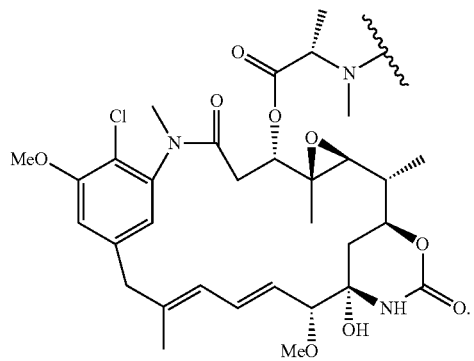 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

6. The conjugate of claim 1, wherein the conjugate is represented by the following formula:

or a pharmaceutically acceptable salt thereof, wherein:

is the cell-binding agent connected to the $L_2$ group through a Lys amine group;

$R^3$ and $R^4$ are each independently H or Me;

$D_1$ is represented by the following formula:

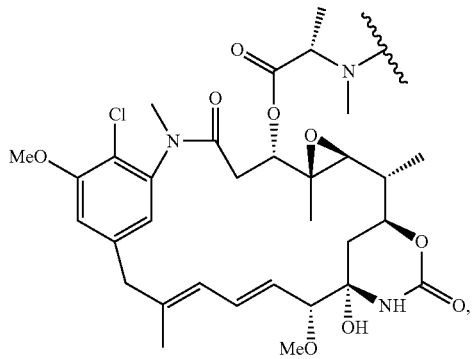 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

A is Ala-Ala-Ala, Ala-D-Ala-Ala, Ala-Ala, D-Ala-Ala, Val-Ala, D-Val-Ala, D-Ala-Pro, or D-Ala-tBu-Gly; and m1, p1, n1 and m3 are each independently an integer from 2 to 4; and m2, n2 and p2 are each independently an integer from 3 to 5.

7. The conjugate of claim 6, wherein the conjugate is represented by the following formula:

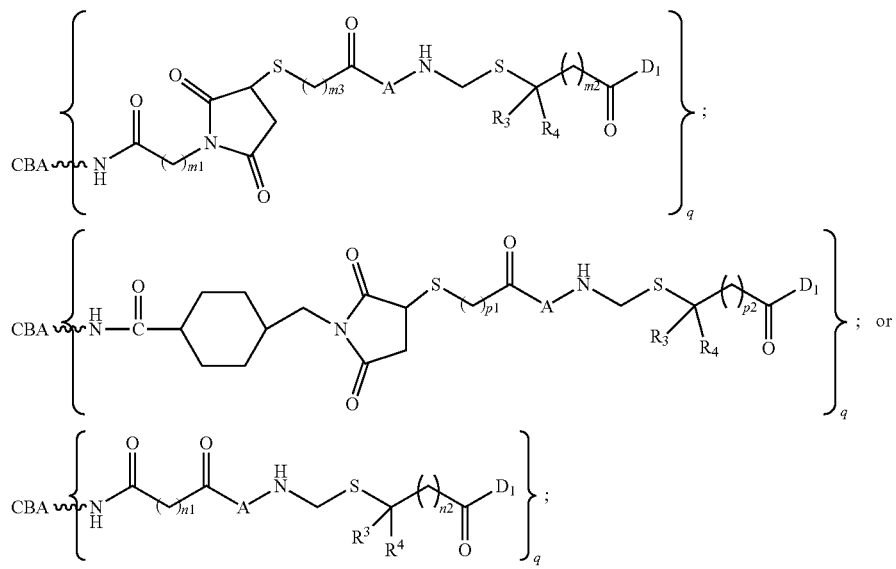

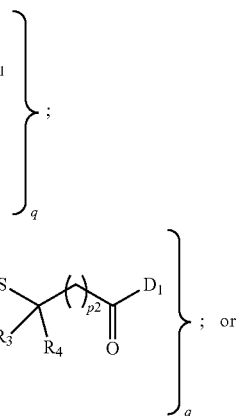

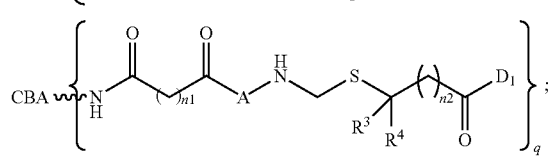

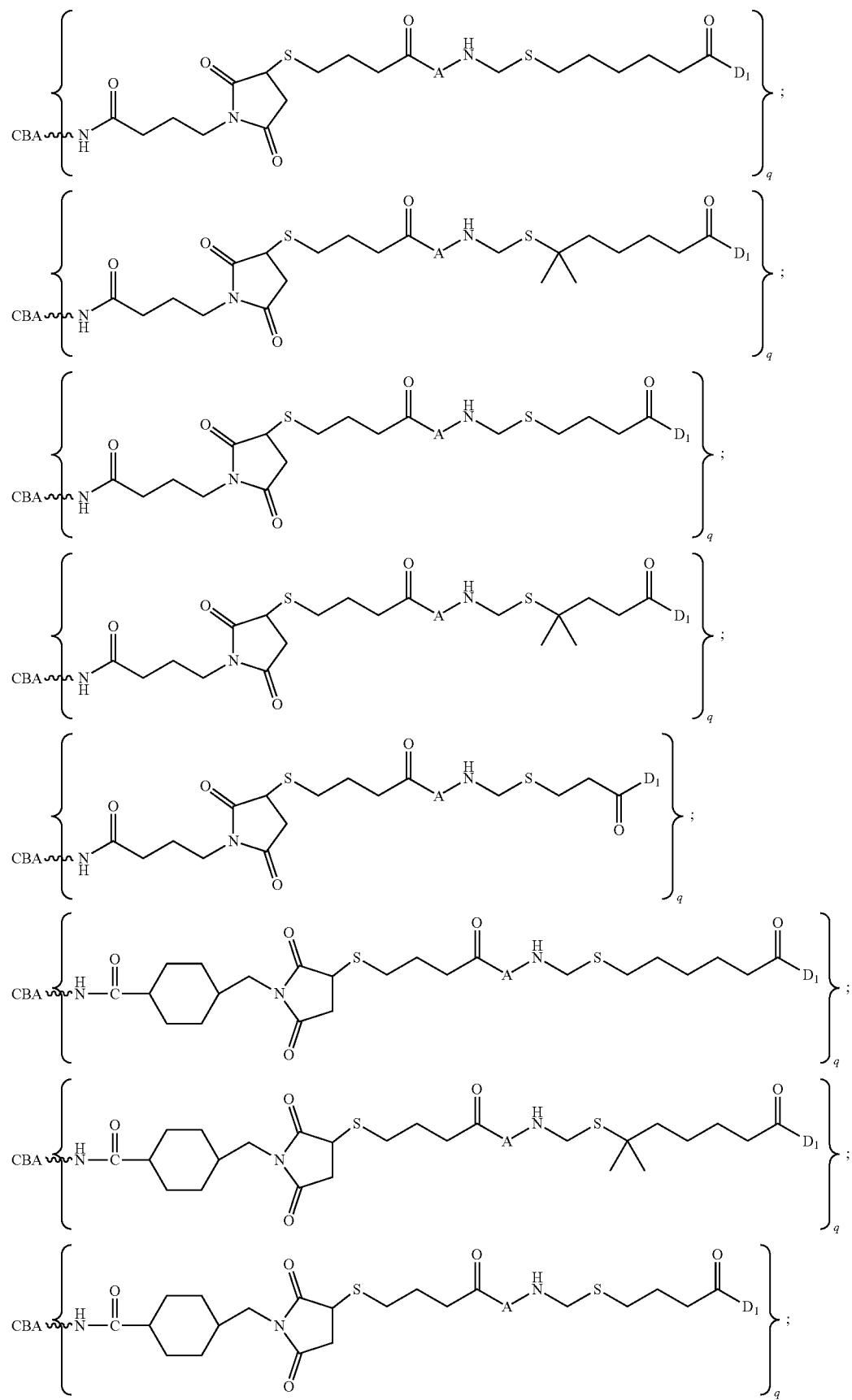

-continued
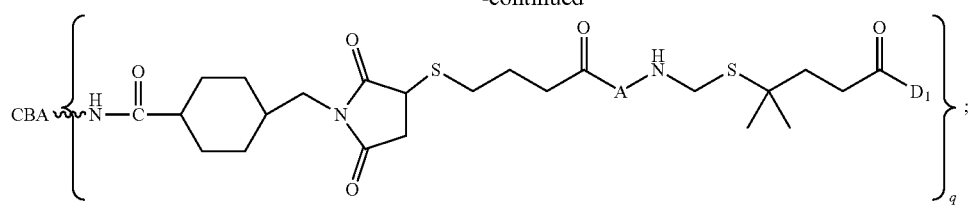
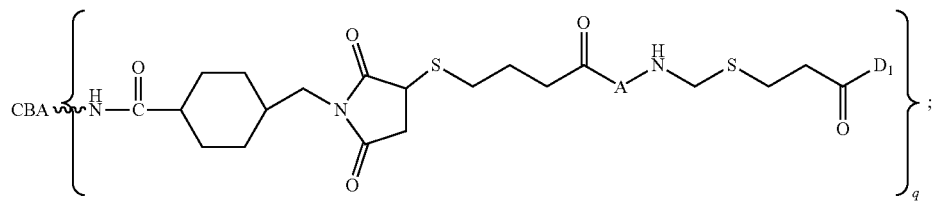
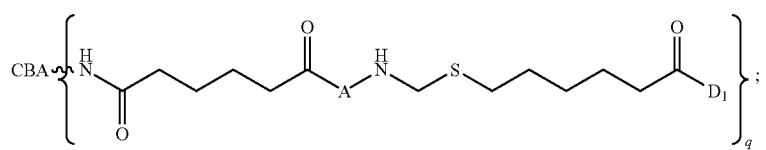
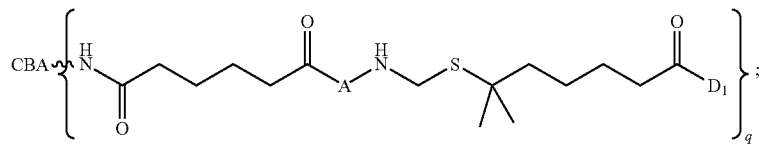
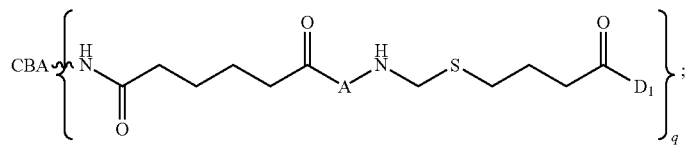
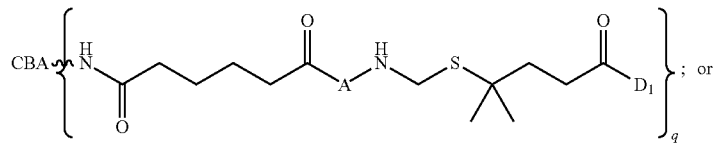; or
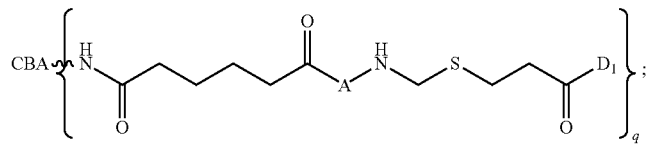;

or a pharmaceutically acceptable salt thereof, wherein:
A is Ala-Ala-Ala, Ala-D-Ala-Ala, Ala-Ala, D-Ala-Ala, Val-Ala, D-Val-Ala, D-Ala-Pro, or D-Ala-tBu-Gly, and
$D_1$ is represented by the following formula:

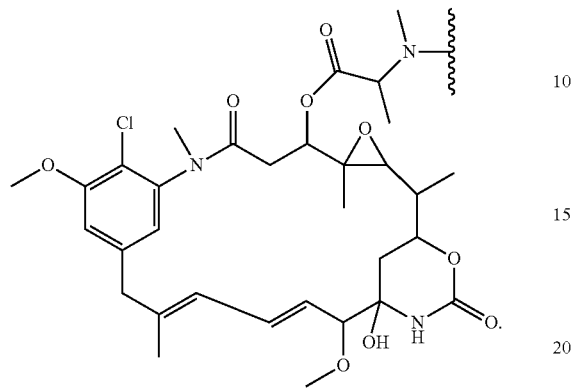

8. The conjugate of claim 7, wherein the conjugate is represented by the following formula:

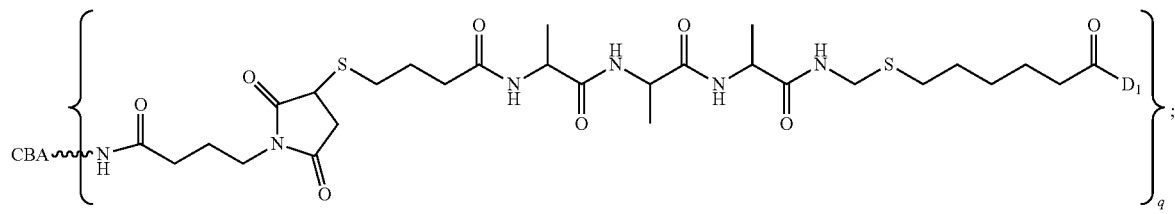

or

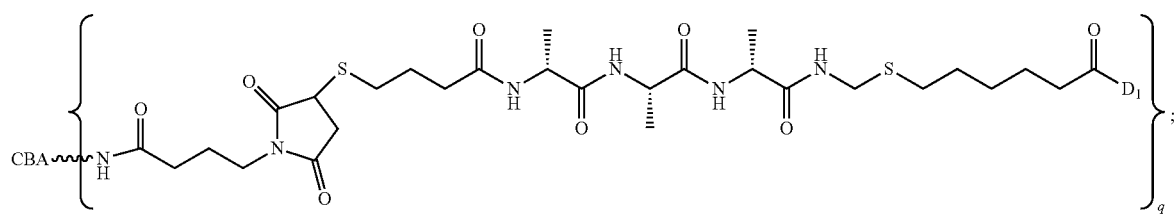

or a pharmaceutically acceptable salt thereof, wherein $D_1$ is represented by the following formula:

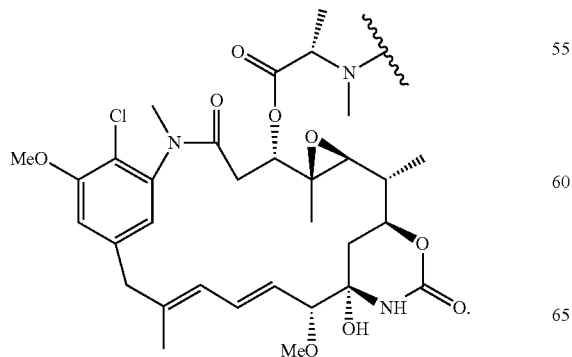

9. The conjugate of claim 1, wherein the cell-binding agent is an antibody or an antigen-binding fragment thereof, a resurfaced antibody or a resurfaced antibody fragment thereof, a monoclonal antibody or a monoclonal antibody fragment thereof, a humanized antibody or a humanized antibody fragment thereof, a chimeric antibody or a chimeric antibody fragment thereof.

10. The conjugate of claim 9, wherein the cell-binding agent is an anti-folate receptor antibody or antibody fragment thereof.

11. The conjugate of claim 10, wherein the anti-folate receptor antibody or antibody fragment thereof comprises (a) a heavy chain CDR1 having the amino acid sequence of SEQ ID NO: 4; a heavy chain CDR2 having the amino acid sequence of SEQ ID NO: 5; and a heavy chain CDR3 having the amino acid sequence of SEQ ID NO: 6; and (b) a light chain CDR1 having the amino acid sequence of SEQ ID NO: 7; a light chain CDR2 having the amino acid sequence of SEQ ID NO: 8; and a light chain CDR3 having the amino acid sequence of SEQ ID NO: 9.

12. The conjugate of claim 10, wherein the anti-folate receptor antibody comprises a heavy chain variable domain having the amino acid sequence of SEQ ID NO: 14, and a light chain variable domain having the amino acid sequence of SEQ ID NO: 15 or SEQ ID NO: 16.

13. The conjugate of claim 10, wherein the anti-folate receptor antibody comprises the heavy chain having the amino acid sequence of SEQ ID NO: 11, and the light chain having the amino acid sequence of SEQ ID NO: 12 or SEQ ID NO: 13.

14. The conjugate of claim 10, wherein the anti-folate receptor antibody comprises the heavy chain having the amino acid sequence of SEQ ID NO: 11 and the light chain having the amino acid sequence of SEQ ID NO: 13.

15. A cell-binding agent-cytotoxic agent conjugate represented by the following formula:

wherein:
Ab is an anti-folate receptor antibody or antibody fragment thereof; and
$D_1$ is represented by the following formula:

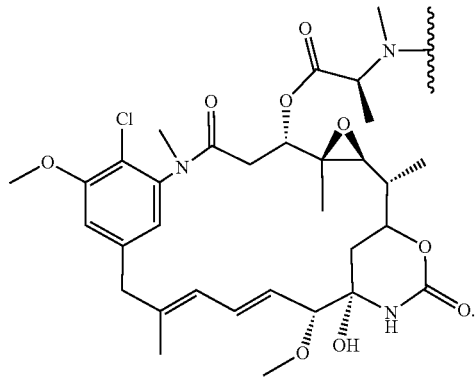

16. The conjugate of claim 15, wherein the anti-folate receptor antibody or antibody fragment thereof comprises (a) a heavy chain CDR1 having the amino acid sequence of SEQ ID NO: 4; a heavy chain CDR2 having the amino acid sequence of SEQ ID NO: 10; and a heavy chain CDR3 having the amino acid sequence of SEQ ID NO: 6; and (b) a light chain CDR1 having the amino acid sequence of SEQ ID NO: 7; a light chain CDR2 having the amino acid sequence of SEQ ID NO: 8; and a light chain CDR3 having the amino acid sequence of SEQ ID NO: 9.

17. The conjugate of claim 15, wherein the anti-folate receptor antibody comprises a heavy chain variable domain having the amino acid sequence of SEQ ID NO: 14, and a light chain variable domain having the amino acid sequence of SEQ ID NO: 15 or SEQ ID NO: 16.

18. The conjugate of claim 15, wherein the anti-folate receptor antibody comprises the heavy chain having the amino acid sequence of SEQ ID NO: 11, and the light chain having the amino acid sequence of SEQ ID NO: 12 or SEQ ID NO: 13.

19. The conjugate of claim 15, wherein the anti-folate receptor antibody comprises the heavy chain having the amino acid sequence of SEQ ID NO: 11 and the light chain having the amino acid sequence of SEQ ID NO: 13.

20. The conjugate of claim 1, wherein the conjugate is represented by the following formula:

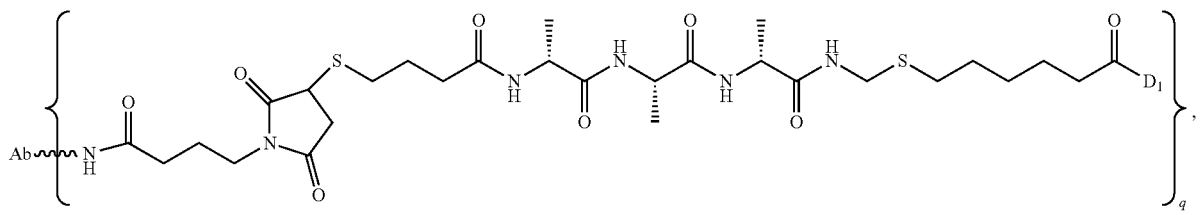

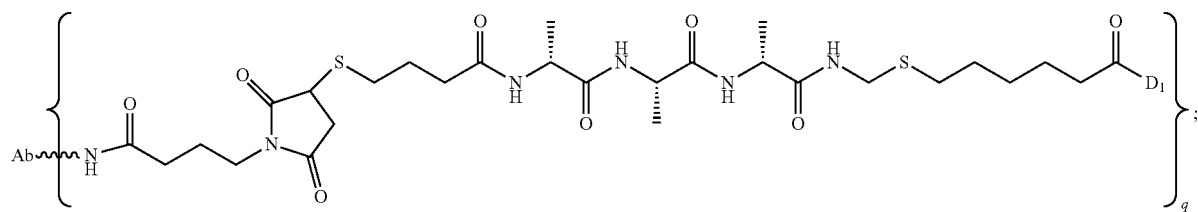

wherein:
Ab is an antibody or an antigen-binding fragment thereof; and
$D_1$ is represented by the following formula:

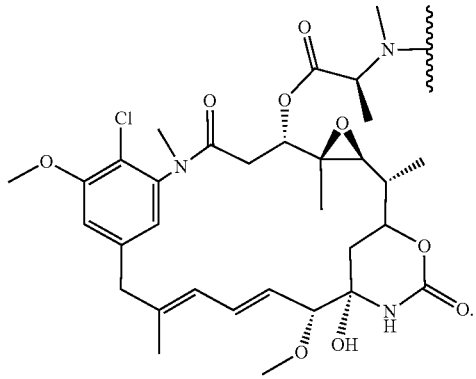 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)CC(OC(=O)N2)[C@@H](C)[C@@H]2O[C@@]12C]

21. The conjugate of claim 11, wherein the anti-folate receptor antibody or antibody fragment thereof comprises a heavy chain CDR2 having the amino acid sequence of SEQ ID NO: 10.

22. A pharmaceutical composition comprising the conjugate of claim 1 and a pharmaceutically acceptable carrier.

23. A method of inhibiting abnormal cell growth or treating a proliferative disorder in a mammal comprising administering to said mammal a therapeutically effective amount of the conjugate of claim 1.

* * * * *